United States Patent
Rossi et al.

(10) Patent No.: US 10,669,528 B2
(45) Date of Patent: Jun. 2, 2020

(54) METHODS AND COMPOSITIONS RELATING TO HEMATOPOIETIC STEM CELL EXPANSION, ENRICHMENT, AND MAINTENANCE

(71) Applicants: CHILDREN'S MEDICAL CENTER CORPORATION, Boston, MA (US); PRESIDENT AND FELLOWS OF HARVARD COLLEGE, Cambridge, MA (US)

(72) Inventors: Derrick J. Rossi, Newton, MA (US); Wataru Ebina, Boston, MA (US); Morag Stewart, Boston, MA (US); Paula Gutierrez-Martinez, Brookline, MA (US); Lee L. Rubin, Wellesley, MA (US); Lance Davidow, Lexington, MA (US)

(73) Assignees: CHILDREN'S MEDICAL CENTER CORPORATION, Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 137 days.

(21) Appl. No.: 15/738,638

(22) PCT Filed: Jun. 24, 2016

(86) PCT No.: PCT/US2016/039303
§ 371 (c)(1),
(2) Date: Dec. 21, 2017

(87) PCT Pub. No.: WO2016/210292
PCT Pub. Date: Dec. 29, 2016

(65) Prior Publication Data
US 2018/0187156 A1    Jul. 5, 2018

Related U.S. Application Data

(60) Provisional application No. 62/184,599, filed on Jun. 25, 2015, provisional application No. 62/207,136, filed on Aug. 19, 2015.

(51) Int. Cl.
*C12N 5/0789* (2010.01)
*A61K 35/28* (2015.01)
*A61K 38/19* (2006.01)
*C12N 15/86* (2006.01)
*C07K 14/495* (2006.01)

(52) U.S. Cl.
CPC ............ *C12N 5/0647* (2013.01); *A61K 35/28* (2013.01); *A61K 38/193* (2013.01); *C12N 15/86* (2013.01); *C07K 14/495* (2013.01); *C12N 2500/02* (2013.01); *C12N 2500/38* (2013.01); *C12N 2500/62* (2013.01); *C12N 2500/99* (2013.01); *C12N 2501/065* (2013.01); *C12N 2501/115* (2013.01); *C12N 2501/125* (2013.01); *C12N 2501/145* (2013.01); *C12N 2501/15* (2013.01); *C12N 2501/155* (2013.01); *C12N 2501/2303* (2013.01); *C12N 2501/2312* (2013.01); *C12N 2501/26* (2013.01); *C12N 2501/415* (2013.01); *C12N 2501/727* (2013.01); *C12N 2501/998* (2013.01); *C12N 2501/999* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 2011/0041807 A1 | 2/2011 | Cooke | |
| 2012/0028351 A1 | 2/2012 | Li et al. | |
| 2013/0171110 A1* | 7/2013 | Woods | C12N 5/0635 424/93.7 |
| 2014/0057353 A1* | 2/2014 | Nishino | C12N 5/0647 435/455 |
| 2014/0248696 A1 | 9/2014 | Zhang et al. | |
| 2014/0369973 A1 | 12/2014 | Bernstein et al. | |
| 2015/0164952 A1 | 6/2015 | Mahmud | |
| 2015/0250824 A1 | 9/2015 | Ma | |
| 2017/0173083 A1* | 6/2017 | Federation | A61K 35/28 |

FOREIGN PATENT DOCUMENTS

| | | |
|---|---|---|
| WO | 2014/153069 A2 | 9/2014 |
| WO | 2014/153115 A2 | 9/2014 |

(Continued)

OTHER PUBLICATIONS

Chotinantakil et al., "Hematopoietic stem cell development, niches, and signaling pathways." Bone Marrow Research 18(55):1-17 (2012).
Schuster et al., "Expansion of hematopoietic stem cells for transplantation: current perspectives." Experimental Hematology & Oncology 1(1):1-6 (2012).
Cui et al. "The LSD1 inhibitor RN-1 induces fetal hemoglobin synthesis and reduces disease pathology in sickle cell mice." Blood 126(3):386-396 (2015).
Fares et al. "Pyrimidoindole derivatives are agonists of human hematopoietic stem cell self-renewal." Science 345(6203)1509-1512 (2014).

(Continued)

*Primary Examiner* — Daniel C Gamett
(74) *Attorney, Agent, or Firm* — Nixon Peabody LLP; David S. Resnick; Nicole D. Kling

(57) ABSTRACT

The methods and compositions described herein relate to producing, expanding, enriching, and/or maintaining hematopoietic stem cells ex vivo by treating the cells with an agent(s) that exhibits two or more activities selected from modulation of histone methylation; inhibition of TGFβ signaling; inhibition of p38 signaling; activation of canonical Wnt signaling; and modulation of histone acetylation. In some embodiments, the technology described herein relates to transplantation of hematopoietic stem cells.

21 Claims, 57 Drawing Sheets

Specification includes a Sequence Listing.

(56) References Cited

FOREIGN PATENT DOCUMENTS

WO    2015/148716 A1    10/2015
WO     2016210292 A1    12/2016

OTHER PUBLICATIONS

Malinge et al. "Ikaros inhibits megakaryopoiesis through functional interaction with GATA-1 and NOTCH signaling." Blood 121(13):2440-2451 (2013).
Ng et al. "Genome-wide lineage-specific transcriptional networks underscore Ikaros-dependent lymphoid priming in hematopoietic stem cells." Immunity 30(4):493-507 (2009).
Sen et al., "Homocysteine-induced myofibroblast differentiation in mouse aortic endothelial cells." Journal of Cellular Physiology 209(3):767-774 (2006).
Verhelle et al. "Lenalidomide and CC-4047 inhibit the proliferation of malignant B cells while expanding normal CD34+ progenitor cells." Cancer Research 67(2):746-755 (2007).
Ebina et al. "Cominatorial Pathway Modulation toward Ex Vivo Maintenance and Propagation of Hematopoietic Stem Cells." Doctoral Disseration, Harvard University, Graduate School of Arts and Sciences <http://nrs.harvard.edu/urn-3:HUL.InstRepos:33493367> (2016).
Moutouh-De Parseval et al. "Pomalidomide and lenalidomide regulate erythropoiesis and fetal hemoglobin production in human CD34+ cells." The Journal of Clinical Investigation 118(1): 248-258 (2008).
Yoshida et al. "Ikaros fingers on lymphocyte differentiation." International Journal of Hematology 100(3): 220-229 (2014).

\* cited by examiner cKit enriched Fgd5-ZsGreen bone marrow

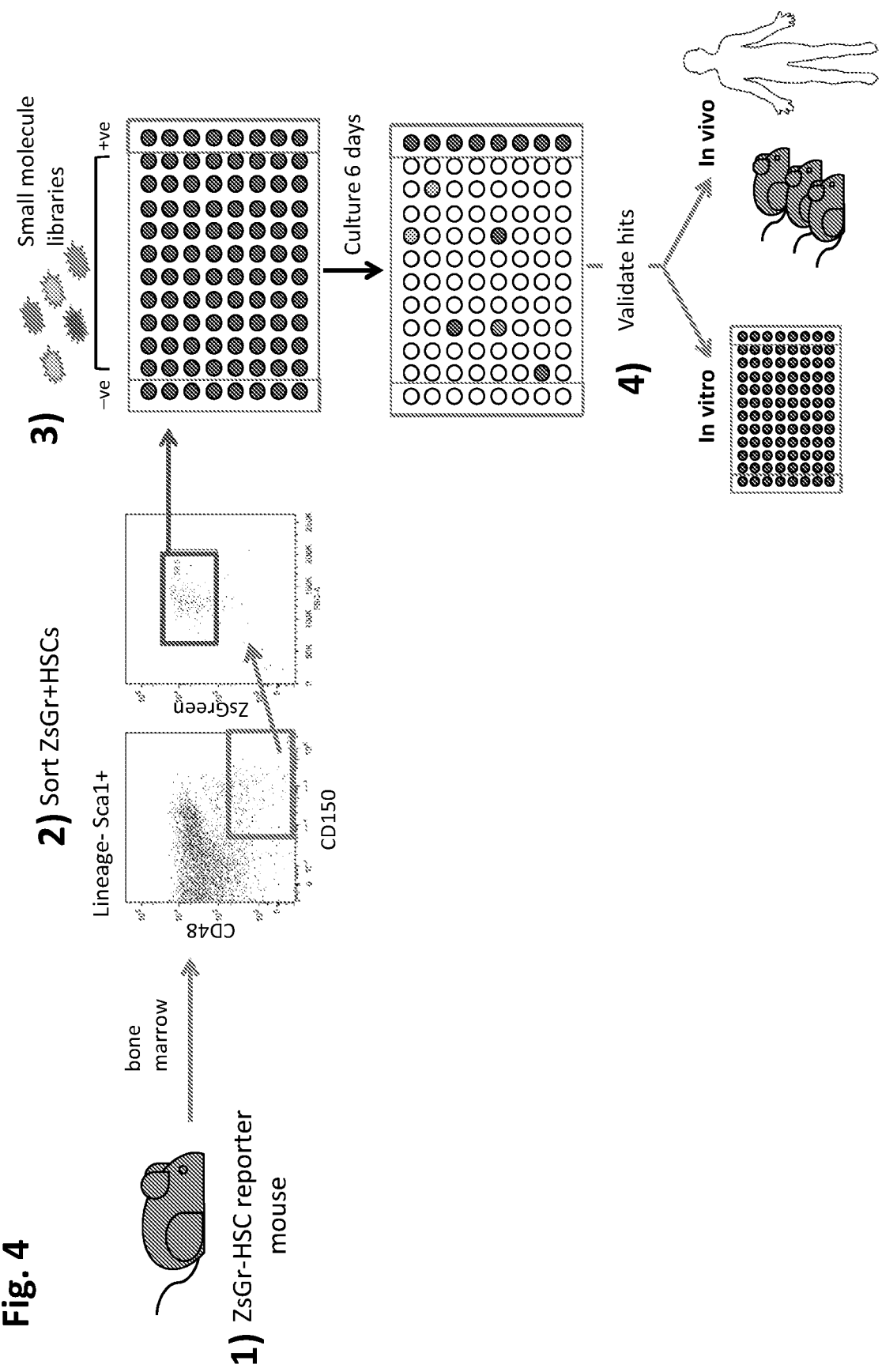

Fig. 6
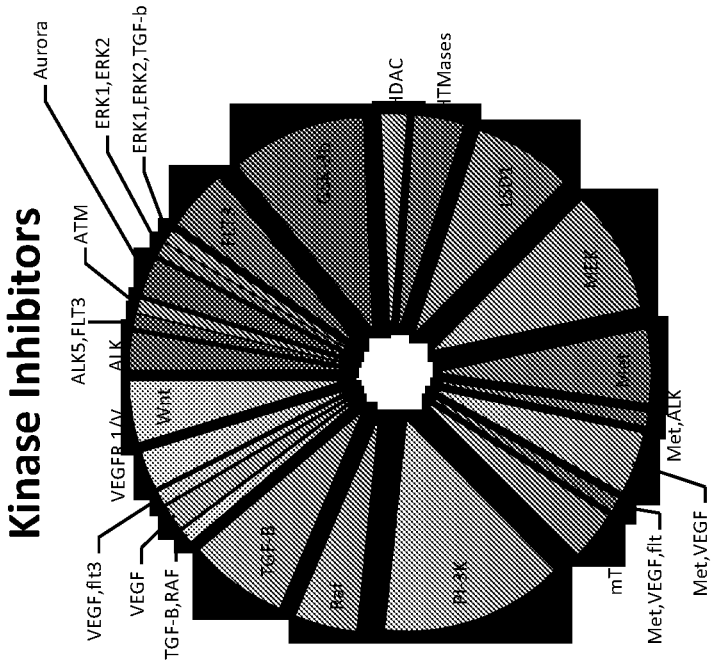
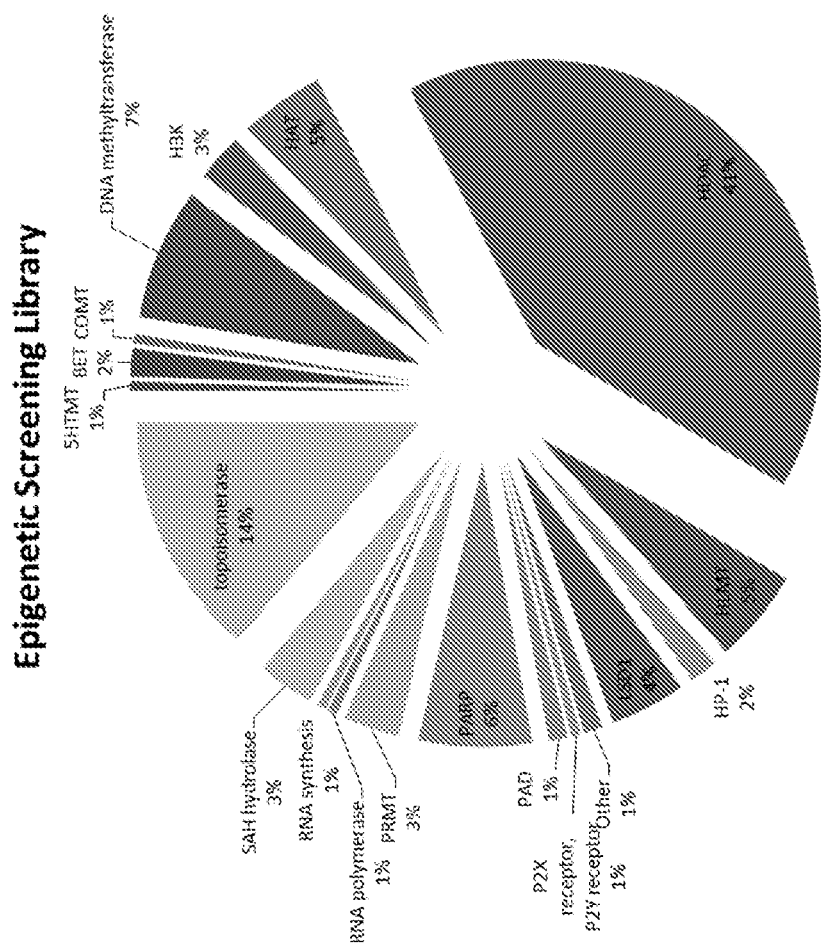

A)

B)

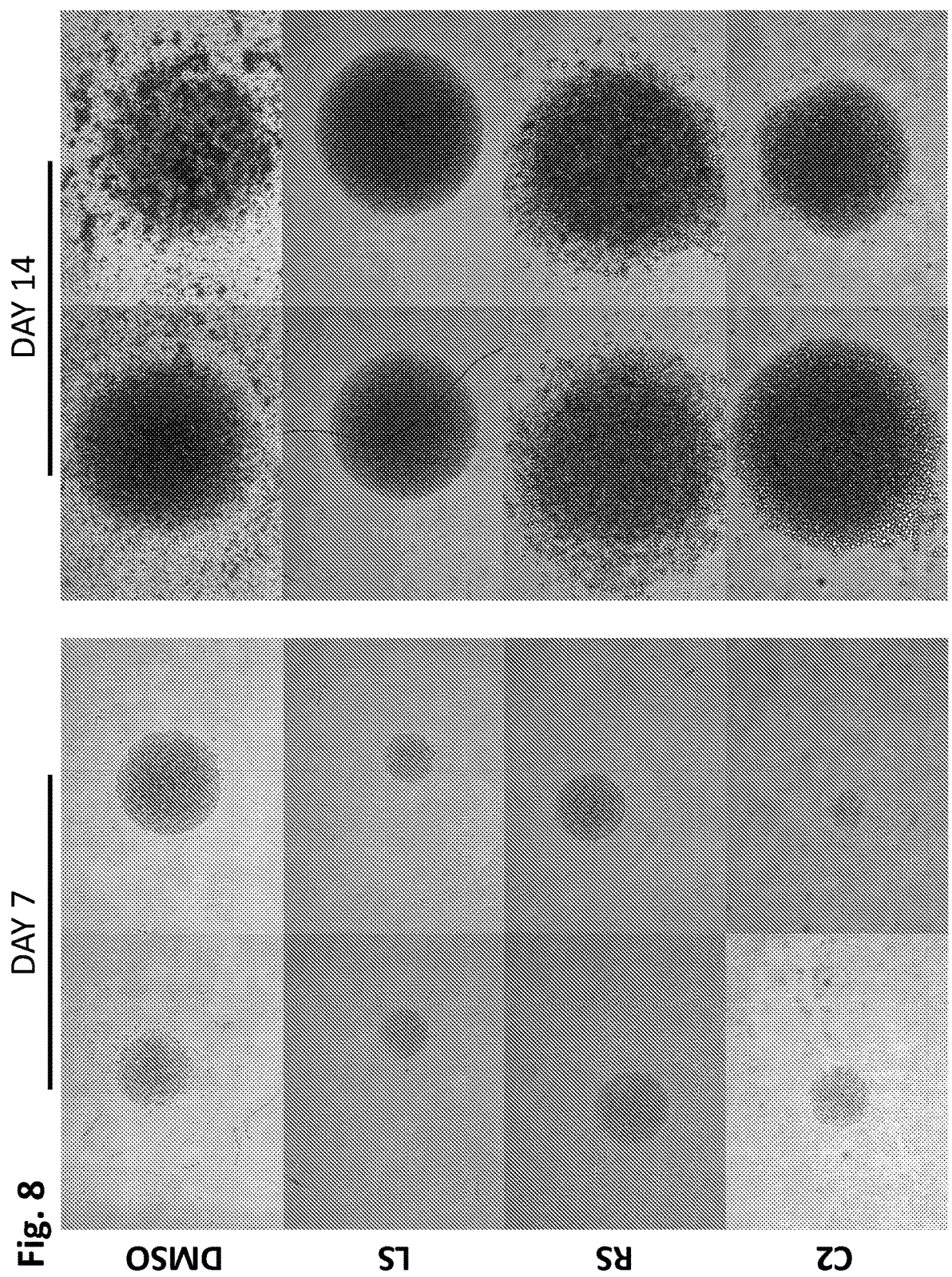

Figs. 18A-18B A)

| Morphogenetic Signals | Intestinal Crypt | Bone Marrow | HSC proliferative maintenance |
|---|---|---|---|
| BMP | - | ? | - |
| Cannonical Wnt | + | + | + |
| Tgf-b | - | - | - |
| Notch | + | + | + |
| Retinoic Acid | ? | - | - |

B)

| Morphogenetic Signals | HSC proliferative maintenance | Modulator |
|---|---|---|
| BMP | - | DMH1 (BMP inhibitor) |
| Cannonical Wnt | + | CHIR99021 (GSK3beta inhibitor) |
| Tgf-b | - | A83-01 (Tgfbeta inhibitor) |
| Notch | + | Trichostatin A (HDAC inhibitor), Tranylcypromine (LSD1 inhibitor) |
| Retinoic Acid | - | RA free medium |

| Additional Signals | HSC proliferative maintenance | Modulator |
|---|---|---|
| P38 MAP Kinase | - | SB203580 (p38 inhibitor) |
| Metabolic fuel | + | Sodium acetate (energy substrate) |

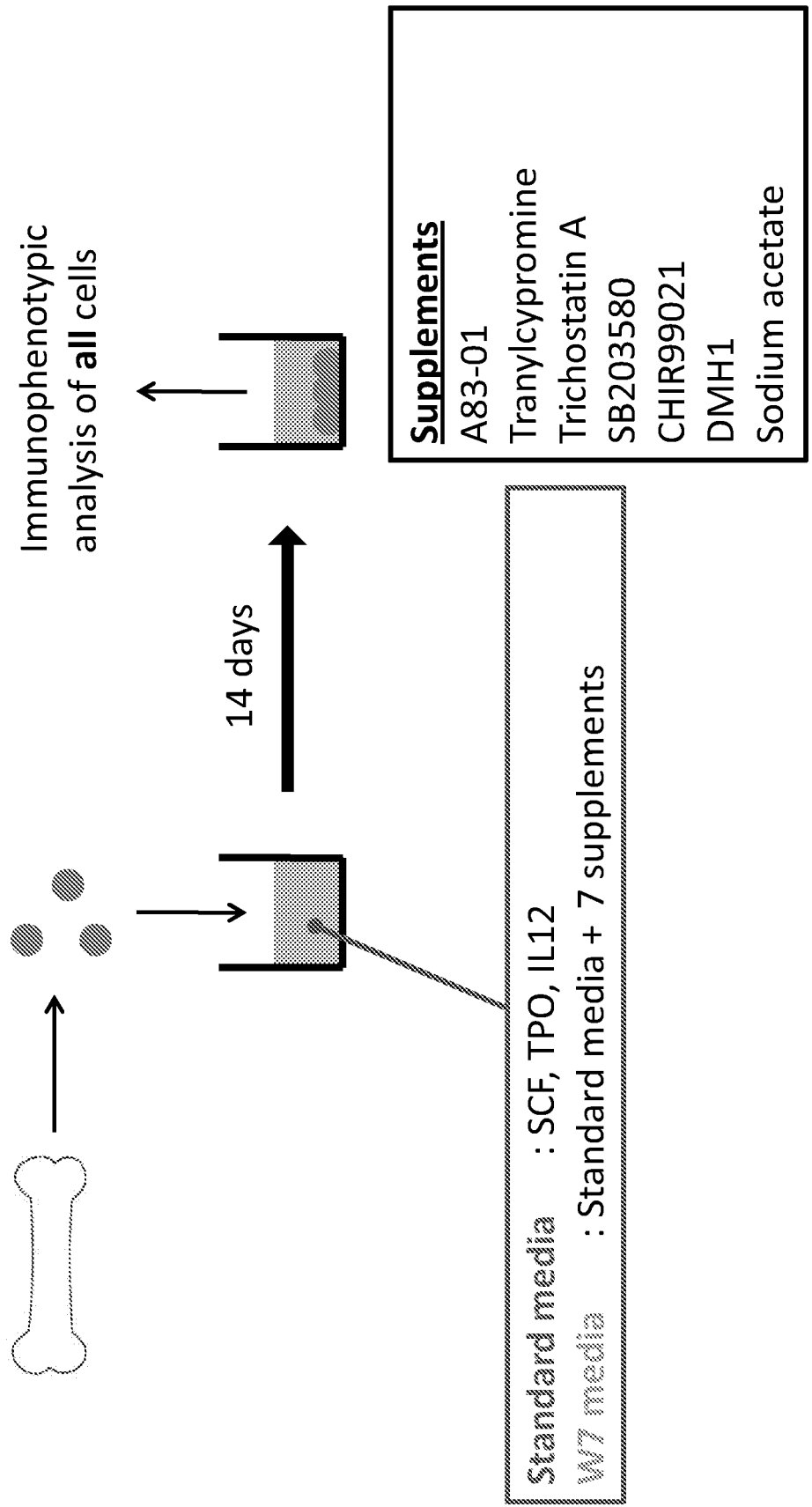

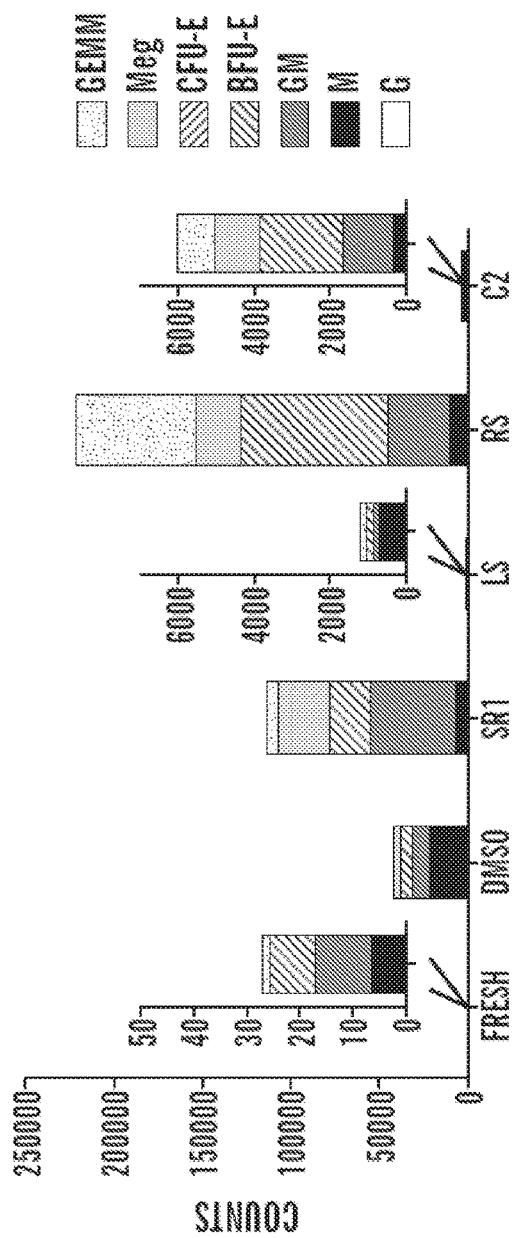
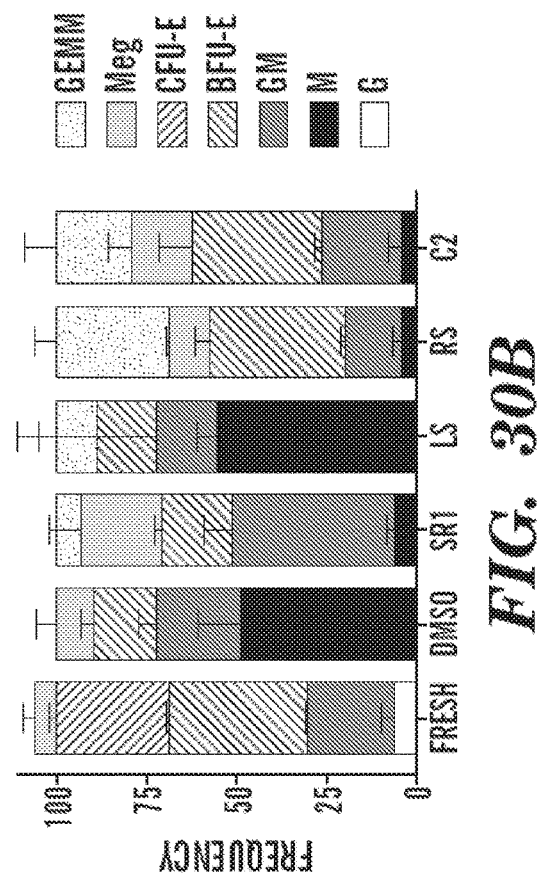
FIG. 30A
FIG. 30B

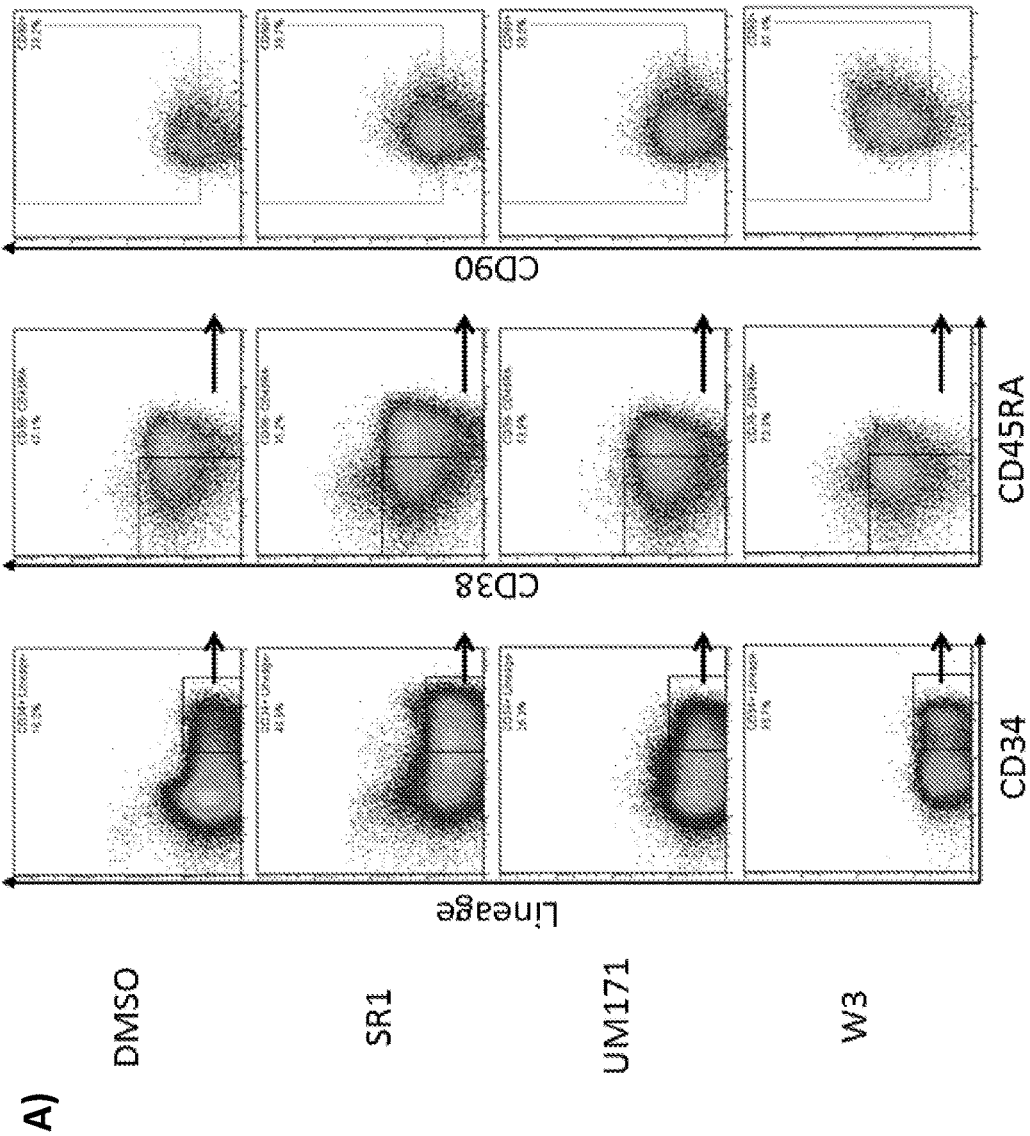

Figs. 37B-37C
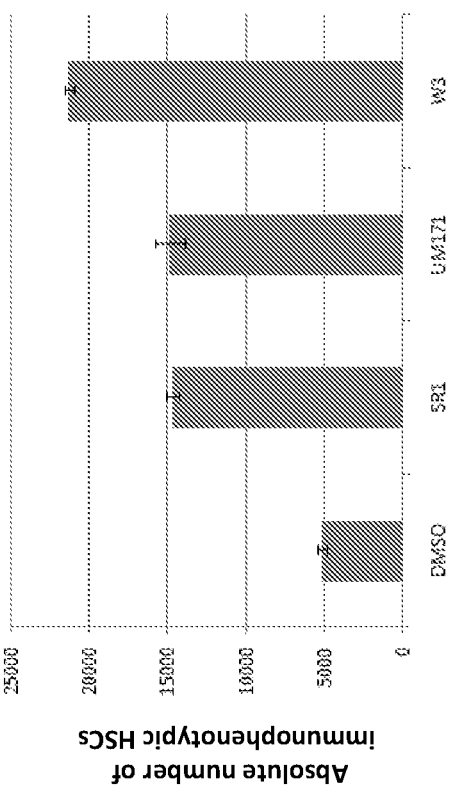
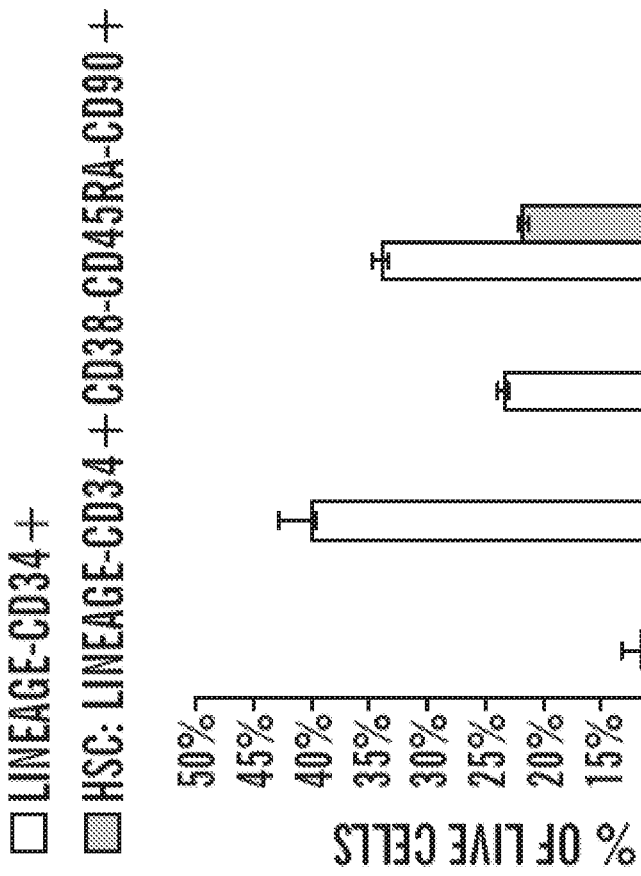
FIG. 37B

Figs. 38B-38C
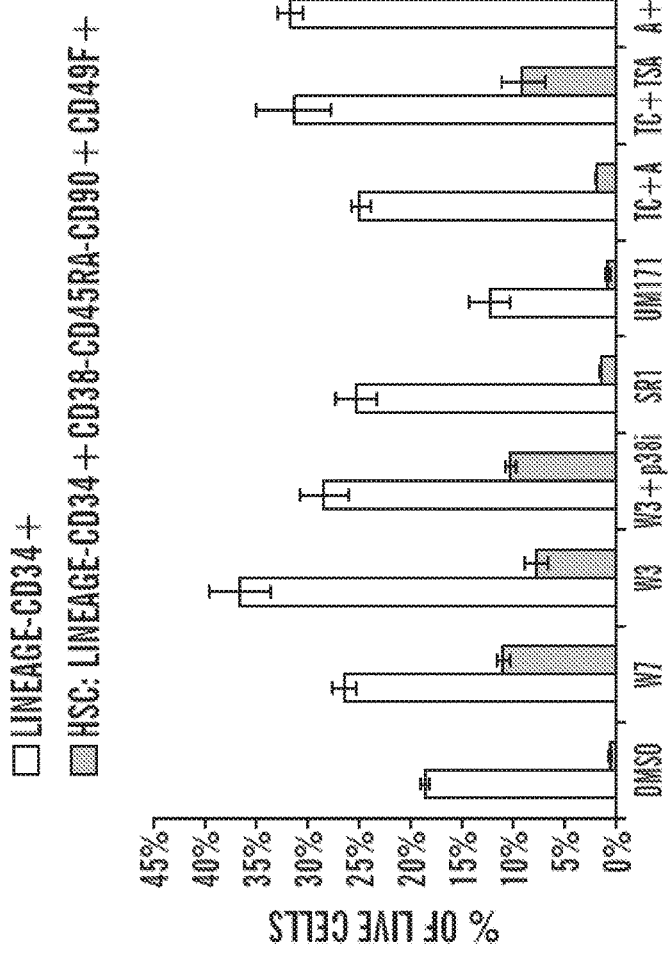
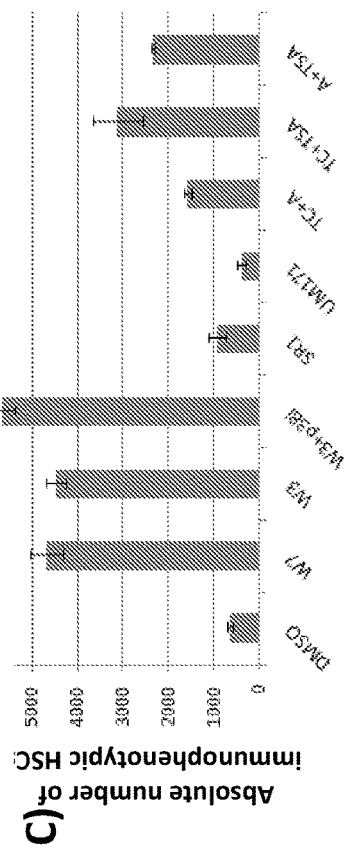
FIG. 38B
FIG. 38C

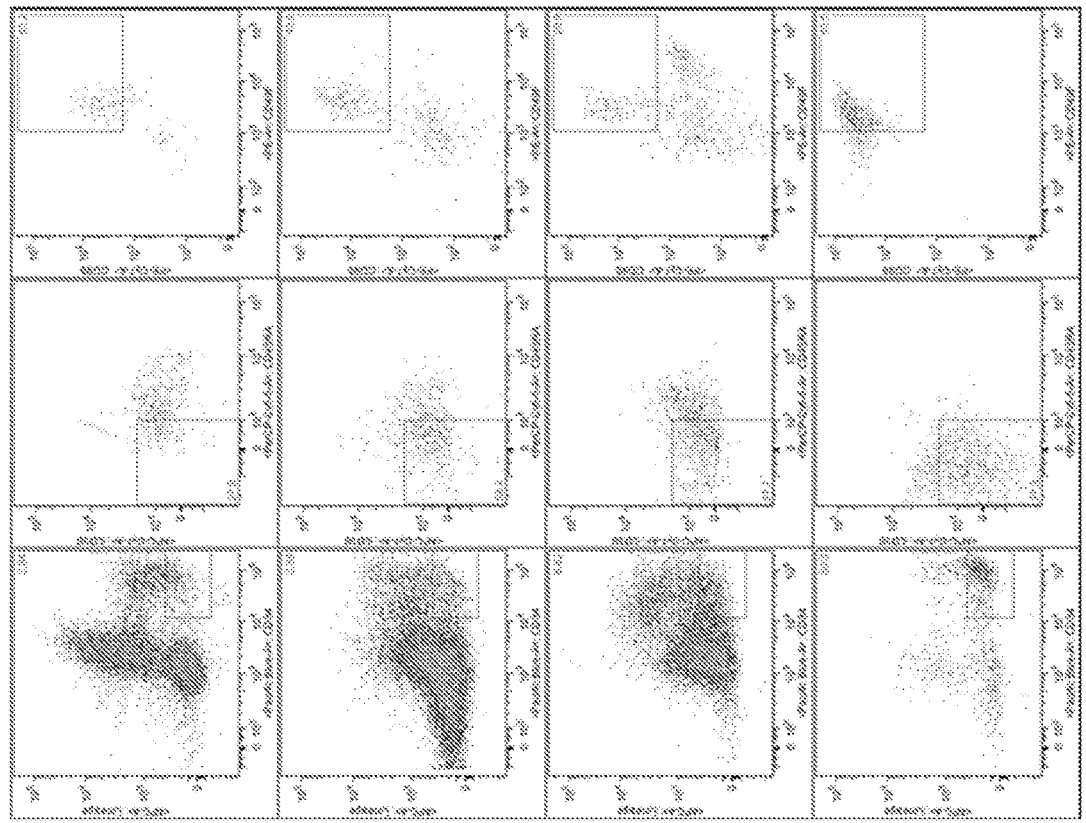

Figs. 40B-40C
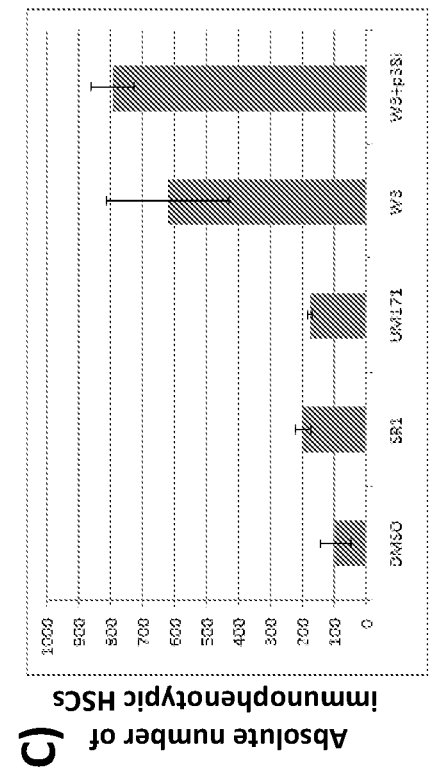
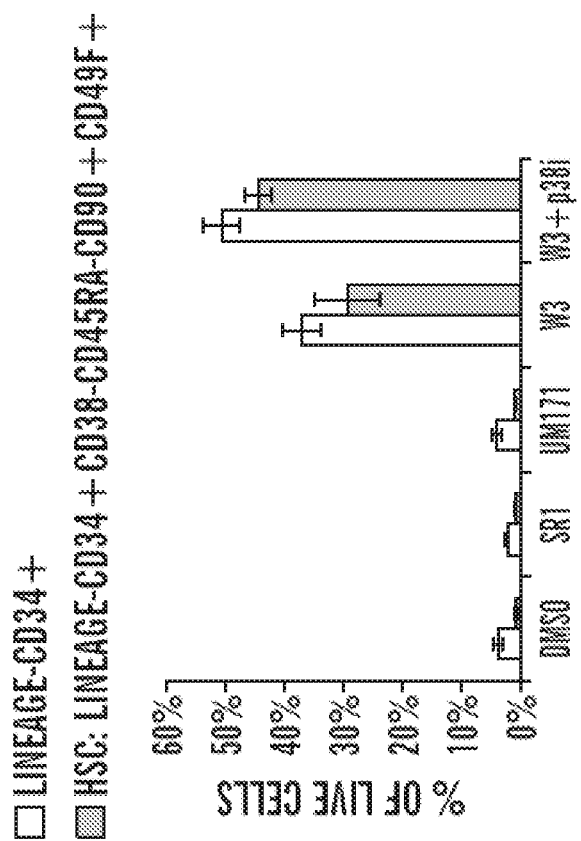
FIG. 40B

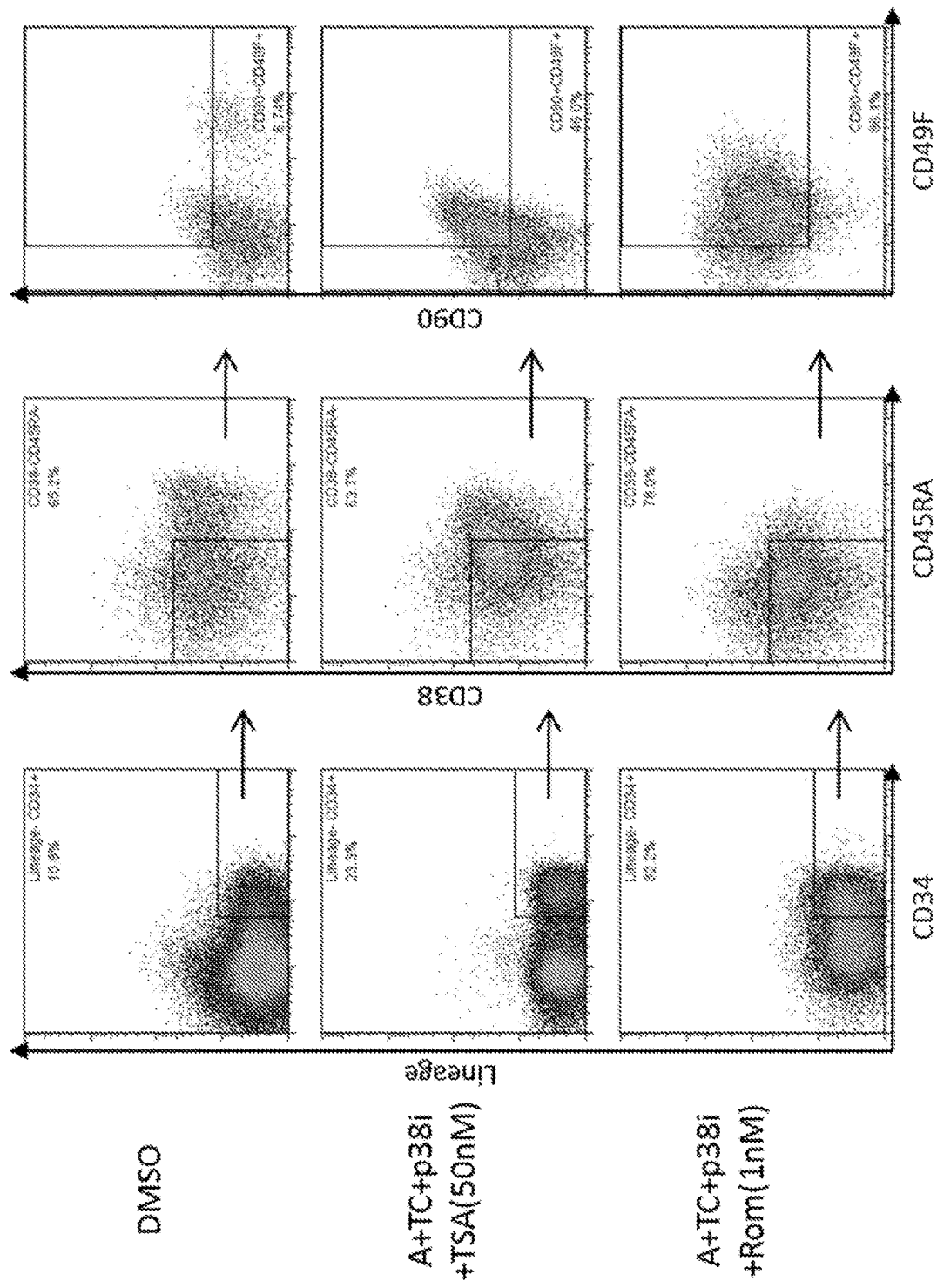

Figs. 41B-41C
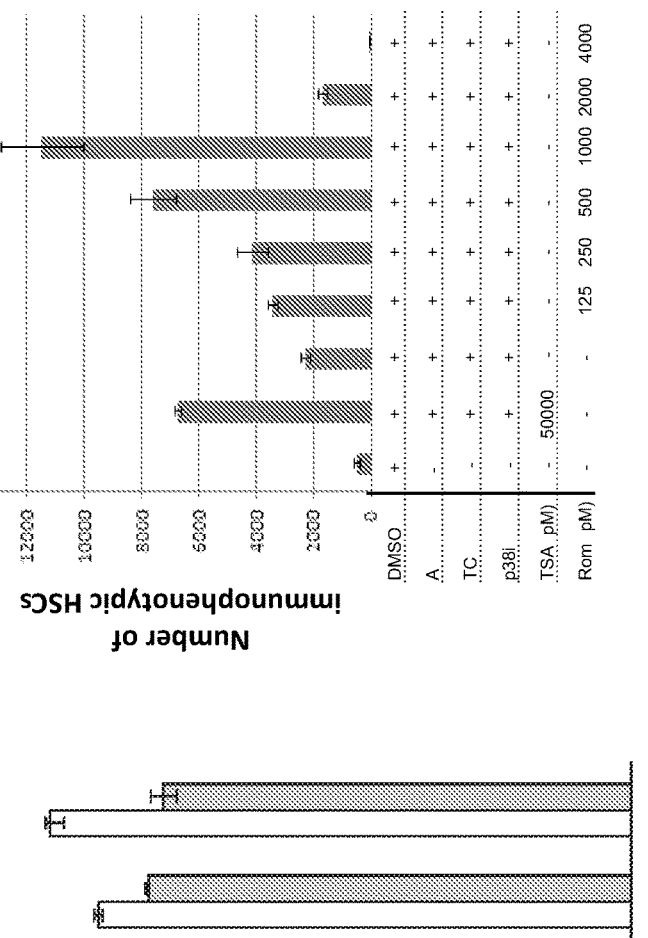
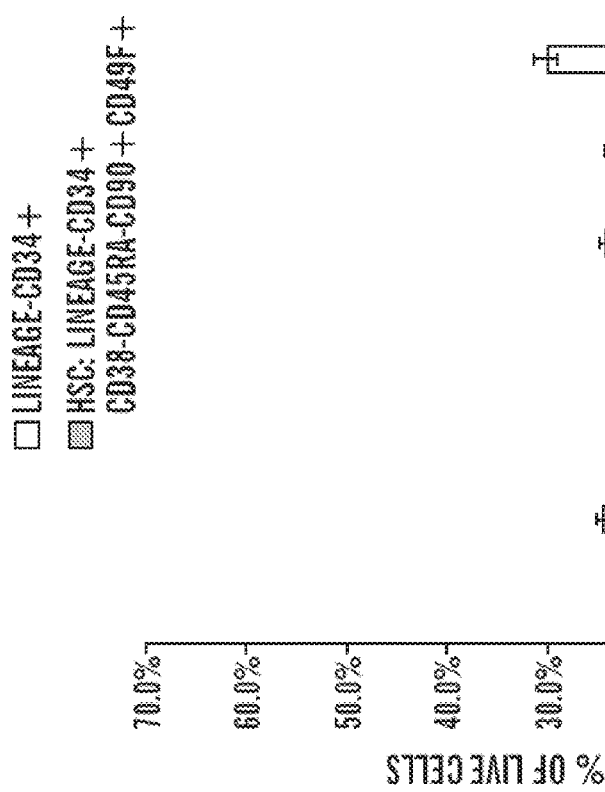
FIG. 41B

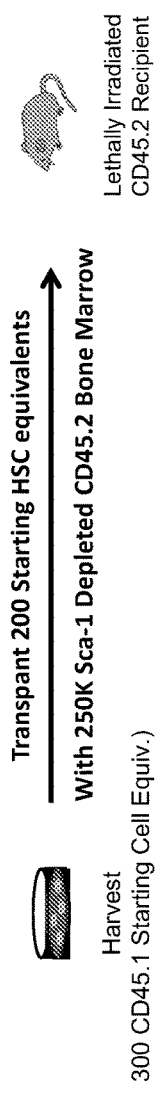
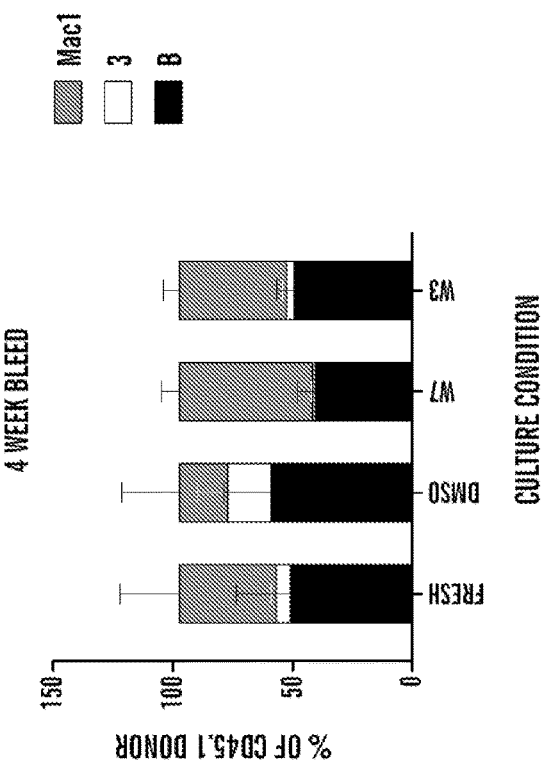
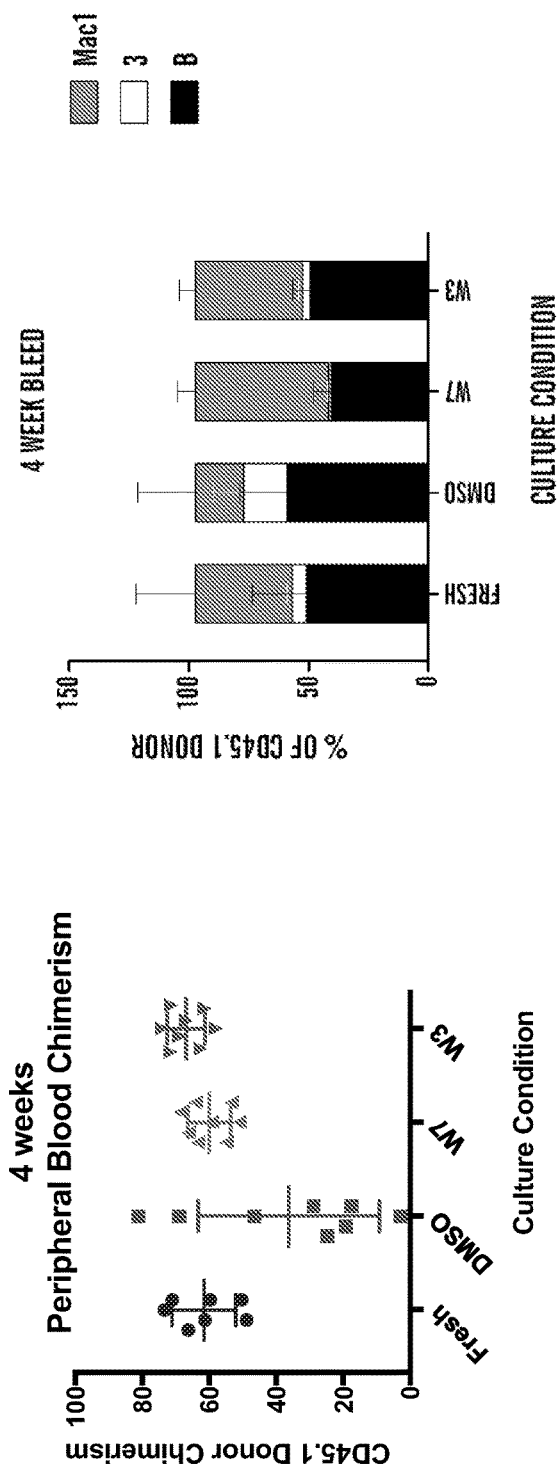

SEQUENCE LISTING

```
<160> NUMBER OF SEQ ID NOS: 13

<210> SEQ ID NO 1
<211> LENGTH: 21
<212> TYPE: DNA
<213> ORGANISM: Homo sapiens

<400> SEQUENCE: 1
aatcctgcat gagcaactgc a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
```
uccugcauga gcaacugcat t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ugcaguugcu caugcaggat t                                              21

<210> SEQ ID NO 4
<211> LENGTH: 21
<212> TYPE: DNA
<213> ORGANISM: Homo sapiens

<400> SEQUENCE: 4
aaggccaagc tgaagcagaa c                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ggccaagcug aagcagaact t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
guucugcuuc agcuuggcct t                                              21

<210> SEQ ID NO 7
<211> LENGTH: 20
<212> TYPE: DNA
<213> ORGANISM: Homo sapiens

<400> SEQUENCE: 7
agcatgagaa catactccag                                                20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 8
gcaugagaac auacuccagt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
cuggaguaug uucucaugct t                                              21

<210> SEQ ID NO 10
<211> LENGTH: 21
<212> TYPE: DNA
<213> ORGANISM: Homo sapiens

<400> SEQUENCE: 10
aagacgcgga agctcatgga g                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
gacgcggaag cucauggagt t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
cuccaugagc uuccgcguct t                                              21

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (3)..(10)
```

```
<223> OTHER INFORMATION: Cross-link between residues
<220> FEATURE:
<223> OTHER INFORMATION: C-term NH2

<400> SEQUENCE: 13

Pro Gln Arg Ile Leu Asp Gln His Val Ser Arg Val Met Lys
1               5                   10
```

METHODS AND COMPOSITIONS RELATING TO HEMATOPOIETIC STEM CELL EXPANSION, ENRICHMENT, AND MAINTENANCE

CROSS-REFERENCE TO RELATED APPLICATIONS

This application is a 35 U.S.C. § 371 National Phase Entry Application of International Application No. PCT/US2016/039303 filed Jun. 24, 2016, which designates the U.S. and claims benefit under 35 U.S.C. § 119(e) of U.S. Provisional Application No. 62/184,599 filed Jun. 25, 2015 and 62/207,136 filed Aug. 19, 2015, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 13, 2016, is named 701039-084082-PCT_SL.txt and is 3,946 bytes in size.

TECHNICAL FIELD

The technology described herein relates to compositions and methods for the ex vivo expansion, enrichment, and maintenance of hematopoietic stem cells.

BACKGROUND

While hematopoietic stem cells have significant therapeutic potential, a limitation that has hindered their use in the clinic has been the difficulty associated with obtaining sufficient numbers of these cells. In particular, hematopoietic stem cells are resistant to maintenance, propagation, and expansion ex vivo. Another challenge to be overcome in order to further develop the use of hematopoietic stem cells (HSCs) as a therapeutic modality is the loss of multi-potency that can occur when these cells are cultured ex vivo. There is currently a need for compositions and methods for the ex vivo maintenance, propagation, and expansion of HSCs that preserve the multi-potency and hematopoietic functionality of these cells. Described herein is the inventors' discovery of a number of compounds that permit hematopoietic stem cell ex vivo maintenance, propagation, expansion and enrichment. The compositions and methods of the invention address the challenges posed by conventional HSC therapies by providing strategies for maintaining, propagating and expanding these cells and also enriching heterogeneous cell populations with HSCs while preserving the ability of the ex vivo cultured cells to self-renew and differentiate into a multitude of different blood cell types both in vitro and upon transplantation into a recipient.

SUMMARY OF THE INVENTION

The present invention is directed to compositions and methods for the expansion, enrichment, and maintenance of hematopoietic stem cells during ex vivo culturing. The compositions and methods of the invention can be used to produce expanded populations of hematopoietic stem cells that have retained the ability to differentiate into a multitude of cell types within the hematopoietic lineage. The invention additionally provides methods for introducing and modulating the expression of polynucleotides within hematopoietic stem cells during ex vivo propagation. Hematopoietic stem cells or progeny thereof produced according to the compositions and methods of the invention or cells derived from these hematopoietic stem cells can be infused into a recipient, such as a human patient, in order to treat a variety of pathologies. The present invention also provides media for culturing hematopoietic stem cells that contain agents useful for the expansion, enrichment, and maintenance of these cells. Additionally, the invention provides kits containing compositions of the invention described herein.

In a first aspect, the invention provides a method of producing an expanded population of hematopoietic stem cells ex vivo, the method including contacting a population of hematopoietic stem cells with one or more agents that together exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation.

such that the one or more agents are present in amounts that are sufficient to produce an expanded population of hematopoietic stem cells. In some embodiments, the one or more agents together exhibit two or more activities selected from the above group.

In a second aspect, the invention provides a method of enriching a population of cells with hematopoietic stem cells ex vivo, the method including contacting a population of hematopoietic cells that contains one or more hematopoietic stem cells with one or more agents that together exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation.

such that the one or more agents are present in amounts that are sufficient to produce a population of cells enriched with hematopoietic stem cells. In some embodiments, the one or more agents together exhibit two or more activities selected from the above group.

In an additional aspect, the invention relates to a method of maintaining the hematopoietic stem cell functional potential of a population of hematopoietic stem cells ex vivo for at least two days by contacting a first population of hematopoietic stem cells with one or more agents that together exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation.

such that the population of hematopoietic stem cells contacted with the agents exhibit a hematopoietic stem cell functional potential after two or more days that is greater than that of a control population of hematopoietic stem cells cultured under the same conditions and for the same time as the first population of hematopoietic stem cells but not contacted with the one or more agents. In some embodiments, the one or more agents together exhibit two or more activities selected from the above group.

In embodiments of the above aspects of the invention, the modulation of histone methylation is activation of histone methylation, maintenance of histone methylation, or inhibition of histone demethylation. In additional embodiments, the modulation of histone acetylation is activation of histone acetylation, maintenance of histone acetylation, or inhibition of histone deacetylation. In particular embodiments of the invention, the one or more agents include a compound that activates histone methylation, maintains histone methylation, or inhibits histone demethylation and a compound that inhibits TGFβ signaling.

In some embodiments, the method includes contacting the population of hematopoietic stem cells with one or more compounds selected from UM171, structural analogs thereof, and the compounds listed in Table 11. In some embodiments, the one or more compounds listed in Table 11 includes UM171.

In certain embodiments of the invention, the compound that activates histone methylation, maintains histone methylation, or inhibits histone demethylation is a histone demethylase inhibitor and the compound that inhibits TGFβ signaling is a TGFβ receptor inhibitor. The one or more agents that inhibit TGFβ signaling may include a TGFβ receptor inhibitor. In some embodiments, the TGFβ receptor inhibitor is selected from the group consisting of ALK5 inhibitor II, LY364947, DMH1, and A83-01. In some embodiments, the TGFβ receptor inhibitor is A83-01.

In particular cases, the histone demethylase inhibitor is a LSD1 inhibitor. For instance, the LSD1 inhibitor may be LSD1 inhibitor IV RN-1 or tranylcypromine, and the TGFβ receptor inhibitor may be ALK5 inhibitor II (E-616452). In some embodiments, the method includes contacting the population of hematopoietic stem cells with one or more agents that modulate histone methylation. In some embodiments, the one or more agents that modulate histone methylation activate histone methylation, maintain histone methylation, or inhibit histone demethylation. For instance, the one or more agents that modulate histone methylation may include a histone demethylase inhibitor. In some embodiments, the histone demethylase inhibitor is a LSD1 inhibitor, such as a LSD1 inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine. In some embodiments, the LSD1 inhibitor is Tranylcypromine.

In a further aspect, the present invention provides a method of producing an expanded population of hematopoietic stem cells ex vivo by contacting a population of hematopoietic stem cells with one or more agents that together inhibit the activity of one or more proteins selected from the group consisting of:
  a. a histone demethylase;
  b. a protein that propagates TGFβ signaling;
  c. a protein that propagates p38 signaling;
  d. a protein that promotes β-catenin degradation; and
  e. a histone deacetylase.

such that the one or more agents are present in amounts that are sufficient to produce an expanded population of hematopoietic stem cells. In some embodiments, the one or more agents together inhibit the activity of two or more proteins selected from the above group.

An additional aspect of the invention relates to a method of enriching a population of cells with hematopoietic stem cells ex vivo by contacting a population of hematopoietic cells that contains one or more hematopoietic stem cells with one or more agents that together inhibit the activity of one or more proteins selected from the group consisting of:
  a. a histone demethylase;
  b. a protein that propagates TGFβ signaling;
  c. a protein that propagates p38 signaling;
  d. a protein that promotes β-catenin degradation; and
  e. a histone deacetylase.

such that the one or more agents are present in amounts that are sufficient to produce a population of cells enriched with hematopoietic stem cells. In some embodiments, the one or more agents together inhibit the activity of two or more proteins selected from the above group.

In another aspect, the invention provides a method of maintaining the hematopoietic stem cell functional potential of a population of hematopoietic stem cells ex vivo for at least two days by contacting a first population of hematopoietic stem cells with one or more agents that together inhibit the activity of one or more proteins selected from the group consisting of:
  a. a histone demethylase;
  b. a protein that propagates TGFβ signaling;
  c. a protein that propagates p38 signaling;
  d. a protein that promotes β-catenin degradation; and
  e. a histone deacetylase.

such that the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the one or more agents. In some embodiments, the one or more agents together inhibit the activity of two or more proteins selected from the above group.

In some embodiments, the method includes contacting the population of hematopoietic stem cells with one or more agents that modulate histone acetylation. In some embodiments, the one or more agents that modulate histone acetylation activate histone acetylation, maintain histone acetylation, or inhibit histone deacetylation. In some embodiments, the one or more agents that that modulate histone acetylation include a histone deacetylation inhibitor, such as a histone deacetylase inhibitor selected from the group consisting of Trichostatin A, valproic acid, butyrylhydroxamic acid, and istodax. In some embodiments, the histone deacetylase inhibitor is Trichostatin A.

In certain embodiments of the above aspects of the invention, the one or more agents include a combination of agents selected from the combination of agents of Table 1, Table 2, Table 3, Table 4, Table 5, and Table 6.

In particular embodiments of the above aspects of the invention, the histone demethylase is LSD1. In additional embodiments, the one or more agents include a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine. In some cases, the protein that propagates TGFβ signaling is a TGFβ receptor. In additional embodiments, the one or more agents include a compound that inhibits a protein that propagates TGFβ signaling selected from the group consisting of ALK5 inhibitor II (E-616452), LY364947, A83-01, and DMH1. In certain cases, the one or more agents include a compound that inhibits a protein that propagates p38 signaling, and wherein the compound is SB203580. Additionally or alternatively, the one or more agents include a compound that inhibits a protein that promotes β-catenin degradation selected from the group consisting of CHIR99021, lithium chloride, BIO, and FGF2 (also referred to as FGF basic, e.g., recombinant mouse FGF2). In still further cases, the one or more agents include a compound that inhibits a histone deacetylase are selected from the group consisting of Trichostatin A, valproic acid, butyrylhydroxamic acid, and istodax (romidepsin). In other embodiments, the one or more agents together inhibit the activity of a histone demethylase and a protein that propagates TGFβ signaling. In certain embodiments, the histone demethylase is LSD1. In additional embodiments, the protein that propagates TGFβ signaling is a TGFβ receptor. In particular cases, the one or more agents include LSD1 inhibitor IV RN-1 and ALK5 inhibitor II (E-616452). In further embodiments, the one or more agents include a compound that inhibits p38 signaling. In still other cases, the one or more agents include a compound that inhibits a histone deacetylase. In other embodiments, the one or more agents further include a compound that inhibits BMP signaling. In certain embodiments, the one or more agents include a combination of inhibitors or other agents specified in any one of Tables 1-10.

In an additional aspect, the invention provides a method of producing an expanded population of hematopoietic stem cells ex vivo by contacting a population of hematopoietic stem cells with (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II (E-616452), LY364947, A83-01, Trichostatin A, SB203580, CHIR99021, DMH1, sodium acetate, and istodax (romidepsin).

In another aspect, the invention relates to a method of enriching a population of cells with hematopoietic stem cells ex vivo by contacting a population of hematopoietic cells that contains one or more hematopoietic stem cells with (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II (E-616452), LY364947, A83-01, Trichostatin A, SB203580, CHIR99021, DMH1, sodium acetate, and istodax (romidepsin).

In another aspect, the invention provides a method of maintaining the hematopoietic stem cell functional potential of a population of hematopoietic stem cells ex vivo for at least two days by contacting a first population of hematopoietic stem cells with (a) a first agent selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II (E-616452), LY364947, A83-01, Trichostatin A, SB203580, CHIR99021, DMH1, sodium acetate, and istodax (romidepsin), wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the first and second agents.

In embodiments of any of the above-described aspects of the invention, the one or more agents may be a combination of agents selected from the combination of agents of Table 7, Table 8, Table 9, and Table 10. In certain embodiments of the above aspects of the invention, the one or more agents are present in amounts that are sufficient to stimulate expansion of the population of hematopoietic stem cells by 10% or more relative to a population of hematopoietic stem cells not contacted with the one or more agents after seven or more days of culture (e.g., after seven, ten, twelve, fourteen, fifteen, twenty, or more days of culture). In additional embodiments, the one or more agents are present in amounts that are sufficient to stimulate expansion of the population of hematopoietic stem cells by 10% or more relative to a population of hematopoietic stem cells that have been contacted with a substance that inhibits aryl hydrocarbon receptor signaling (such as StemRegenin 1, also referred to as SR1, or an analog thereof), UM171 or an analog thereof, a prostaglandin, an agonist of Notch signaling, or an inhibitor of SIRT1, such as nicotinamide, cambinol, or an analog thereof, after seven or more days of culture (e.g., after seven, ten, twelve, fourteen, fifteen, twenty, or more days of culture). In certain cases, the one or more agents are present in amounts that are sufficient to enrich the population of cells with hematopoietic stem cells by 10% or more relative to a population of hematopoietic stem cells not contacted with the one or more agents after seven or more days of culture (e.g., after seven, ten, twelve, fourteen, fifteen, twenty, or more days of culture). In still other embodiments, the one or more agents are present in amounts that are sufficient to enrich the population of cells with hematopoietic stem cells by 10% or more relative to a population of hematopoietic stem cells that have been contacted with a substance that inhibits aryl hydrocarbon receptor signaling (such as SR1 or an analog thereof), UM171 or an analog thereof, a prostaglandin, an agonist of Notch signaling, or an inhibitor of SIRT1, such as nicotinamide, cambinol, or an analog thereof, after seven or more days of culture (e.g., after seven, ten, twelve, fourteen, fifteen, twenty, or more days of culture).

In some embodiments, the method includes contacting the population of hematopoietic stem cells with one or more compounds selected from UM171, structural analogs thereof, and the compounds listed in Table 11. In some embodiments, the one or more compounds listed in Table 11 includes UM171.

In some embodiments, the method further includes contacting the population of hematopoietic stem cells with one or more agents that inhibit TGFβ signaling. The one or more agents that inhibit TGFβ signaling may include a TGFβ receptor inhibitor. In some embodiments, the TGFβ receptor inhibitor is selected from the group consisting of ALK5 inhibitor II, LY364947, DMH1, and A83-01. In some embodiments, the TGFβ receptor inhibitor is A83-01.

In some embodiments, the method includes contacting the population of hematopoietic stem cells with one or more agents that modulate histone methylation. In some embodiments, the one or more agents that modulate histone methylation activate histone methylation, maintain histone methylation, or inhibit histone demethylation. For instance, the one or more agents that modulate histone methylation may include a histone demethylase inhibitor. In some embodiments, the histone demethylase inhibitor is a LSD1 inhibitor, such as a LSD1 inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine. In some embodiments, the LSD1 inhibitor is Tranylcypromine.

In some embodiments, the method includes contacting the population of hematopoietic stem cells with one or more agents that modulate histone acetylation. In some embodiments, the one or more agents that modulate histone acetylation activate histone acetylation, maintain histone acetylation, or inhibit histone deacetylation. In some embodiments, the one or more agents that that modulate histone acetylation include a histone deacetylation inhibitor, such as a histone deacetylase inhibitor selected from the group consisting of Trichostatin A, valproic acid, butyrylhydroxamic acid, and istodax. In some embodiments, the histone deacetylase inhibitor is Trichostatin A.

In some embodiments, the method includes contacting the population of hematopoietic stem cells with one or more agents that exhibit one or more activities selected from the group consisting of:
  a. inhibition of p38 signaling; and
  b. activation of canonical Wnt signaling.

In some embodiments, the method includes contacting the population of hematopoietic stem cells with one or more agents that inhibit aryl hydrocarbon receptor signaling, such as SR1.

In another aspect, the invention provides a method of producing an expanded population of hematopoietic stem cells ex vivo, the method including contacting a population of hematopoietic stem cells with one or more compounds listed in Table 11 and one or more agents that exhibit one or more activities selected from the group consisting of:
  a. modulation of histone methylation;
  b. inhibition of TGFβ signaling;
  c. inhibition of p38 signaling;
  d. activation of canonical Wnt signaling;
  e. modulation of histone acetylation; and
  f. inhibition of aryl hydrocarbon receptor signaling,
wherein the one or more compounds and one or more agents are present in amounts that are sufficient to produce an expanded population of hematopoietic stem cells.

In another aspect, the invention provides a method of enriching a population of cells with hematopoietic stem cells ex vivo, the method including contacting a population of hematopoietic cells that contains one or more hematopoietic stem cells with one or more compounds listed in Table 11 and one or more agents that exhibit one or more activities selected from the group consisting of:
  a. modulation of histone methylation;
  b. inhibition of TGFβ signaling;
  c. inhibition of p38 signaling;
  d. activation of canonical Wnt signaling;
  e. modulation of histone acetylation; and
  f. inhibition of aryl hydrocarbon receptor signaling,
wherein the one or more compounds and one or more agents are present in amounts that are sufficient to produce a population of cells enriched with hematopoietic stem cells.

In another aspect, the invention provides a method of maintaining the hematopoietic stem cell functional potential of a population of hematopoietic stem cells ex vivo for at least two days, the method including contacting a first population of hematopoietic stem cells with one or more compounds listed in Table 11 and one or more agents that exhibit one or more activities selected from the group consisting of:
  a. modulation of histone methylation;
  b. inhibition of TGFβ signaling;
  c. inhibition of p38 signaling;
  d. activation of canonical Wnt signaling;
  e. modulation of histone acetylation; and
  f. inhibition of aryl hydrocarbon receptor signaling,
wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the one or more compounds and one or more agents.

In another aspect, the invention provides a method of producing an expanded population of hematopoietic stem cells ex vivo, the method including contacting a population of hematopoietic stem cells with one or more agents that inhibit aryl hydrocarbon receptor signaling and one or more agents that exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation,
wherein the one or more agents are present in amounts that are sufficient to produce an expanded population of hematopoietic stem cells.

In another aspect, the invention provides a method of enriching a population of cells with hematopoietic stem cells ex vivo, the method including contacting a population of hematopoietic cells that contains one or more hematopoietic stem cells with one or more agents that inhibit aryl hydrocarbon receptor signaling and one or more agents that exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation,
wherein the one or more agents are present in amounts that are sufficient to produce a population of cells enriched with hematopoietic stem cells.

In another aspect, the invention provides a method of maintaining the hematopoietic stem cell functional potential of a population of hematopoietic stem cells ex vivo for at least two days, the method including contacting a first population of hematopoietic stem cells with one or more agents that inhibit aryl hydrocarbon receptor signaling and one or more agents that exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation,
wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the one or more agents.

In some embodiments, the method includes contacting the population of hematopoietic stem cells with one or more compounds selected from UM171, structural analogs thereof, and the compounds listed in Table 11.

In some embodiments, the method includes contacting the population of hematopoietic stem cells with a TGFβ receptor inhibitor selected from the group consisting of ALK5 inhibitor II, LY364947, DMH1, and A83-01.

In some embodiments, the method includes contacting the population of hematopoietic stem cells with a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine.

In some embodiments, the method includes contacting the population of hematopoietic stem cells with a histone deacetylase inhibitor selected from the group consisting of Trichostatin A, valproic acid, butyrylhydroxamic acid, and istodax.

In some embodiments, the method includes contacting the population of hematopoietic stem cells with one or more agents selected from the group consisting of:
- a. a compound that inhibits a protein that propagates p38 signaling including SB203580; and
- b. a compound that inhibits a protein that promotes β-catenin degradation selected from the group consisting of CHIR99021, lithium chloride, BIO, and FGF2.

In some embodiments, the method includes contacting the population of hematopoietic stem cells with one or more agents that inhibit aryl hydrocarbon receptor, such as SR1.

In some embodiments, the method includes contacting the population of hematopoietic stem cells with a compound that inhibits BMP signaling.

In another aspect, the invention provides a method of producing an expanded population of hematopoietic stem cells ex vivo, the method including contacting a population of hematopoietic stem cells with one or more compounds listed in Table 11 and one or more agents that inhibit the activity of one or more proteins selected from the group consisting of:
- a. a histone demethylase;
- b. a protein that propagates TGFβ signaling;
- c. a protein that propagates p38 signaling;
- d. a protein that promotes β-catenin degradation;
- e. a histone deacetylase; and
- f. aryl hydrocarbon receptor, wherein the one or more compounds and one or more agents are present in amounts that are sufficient to produce an expanded population of hematopoietic stem cells.

In another aspect, the invention provides a method of enriching a population of cells with hematopoietic stem cells ex vivo, the method including contacting a population of hematopoietic cells that contains one or more hematopoietic stem cells with one or more compounds listed in Table 11 and one or more agents that inhibit the activity of one or more proteins selected from the group consisting of:
- a. a histone demethylase;
- b. a protein that propagates TGFβ signaling;
- c. a protein that propagates p38 signaling;
- d. a protein that promotes β-catenin degradation;
- e. a histone deacetylase; and
- f. aryl hydrocarbon receptor, wherein the one or more compounds and one or more agents are present in amounts that are sufficient to produce a population of cells enriched with hematopoietic stem cells.

In another aspect, the invention provides a method of maintaining the hematopoietic stem cell functional potential of a population of hematopoietic stem cells ex vivo for at least two days, the method including contacting a first population of hematopoietic stem cells with one or more compounds listed in Table 11 and one or more agents that inhibit the activity of one or more proteins selected from the group consisting of:
- a. a histone demethylase;
- b. a protein that propagates TGFβ signaling;
- c. a protein that propagates p38 signaling;
- d. a protein that promotes β-catenin degradation;
- e. a histone deacetylase; and
- f. aryl hydrocarbon receptor, wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the one or more compounds and one or more agents.

In another aspect, the invention provides a method of producing an expanded population of hematopoietic stem cells ex vivo, the method including contacting a population of hematopoietic stem cells with one or more agents that inhibit aryl hydrocarbon receptor and one or more agents that inhibit the activity of one or more proteins selected from the group consisting of:
- a. modulation of histone methylation;
- b. inhibition of TGFβ signaling;
- c. inhibition of p38 signaling;
- d. activation of canonical Wnt signaling; and
- e. modulation of histone acetylation, wherein the one or more agents are present in amounts that are sufficient to produce an expanded population of hematopoietic stem cells.

In another aspect, the invention provides a method of enriching a population of cells with hematopoietic stem cells ex vivo, the method including contacting a population of hematopoietic cells that contains one or more hematopoietic stem cells with one or more agents that inhibit aryl hydrocarbon receptor and one or more agents that inhibit the activity of one or more proteins selected from the group consisting of:
- a. modulation of histone methylation;
- b. inhibition of TGFβ signaling;
- c. inhibition of p38 signaling;
- d. activation of canonical Wnt signaling; and
- e. modulation of histone acetylation, wherein the one or more agents are present in amounts that are sufficient to produce a population of cells enriched with hematopoietic stem cells.

In another aspect, the invention provides a method of maintaining the hematopoietic stem cell functional potential of a population of hematopoietic stem cells ex vivo for at least two days, the method including contacting a first population of hematopoietic stem cells with one or more agents that inhibit aryl hydrocarbon receptor and one or more agents that inhibit the activity of one or more proteins selected from the group consisting of:
- a. modulation of histone methylation;
- b. inhibition of TGFβ signaling;
- c. inhibition of p38 signaling;
- d. activation of canonical Wnt signaling; and
- e. modulation of histone acetylation, wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the one or more agents.

In some embodiments, the method further includes contacting the population of hematopoietic stem cells with one or more compounds selected from UM171, structural analogs thereof, and the compounds listed in Table 11.

In some embodiments, the method further including contacting the population of hematopoietic stem cells with a TGFβ receptor inhibitor selected from the group consisting of ALK5 inhibitor II, LY364947, DMH1, and A83-01.

In some embodiments, the method includes contacting the population of hematopoietic stem cells with a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine.

In some embodiments, the method includes contacting the population of hematopoietic stem cells with a histone deacetylase inhibitor selected from the group consisting of Trichostatin A, valproic acid, butyrylhydroxamic acid, and istodax.

In some embodiments, the method includes contacting the population of hematopoietic stem cells with one or more compounds selected from the group consisting of:
  a. a compound that inhibits a protein that propagates p38 signaling including SB203580; and
  b. a compound that inhibits a protein that promotes β-catenin degradation selected from the group consisting of CHIR99021, lithium chloride, BIO, and FGF2.

In some embodiments, the method includes contacting the population of hematopoietic stem cells with SR1.

In another aspect, the invention provides a method of producing an expanded population of hematopoietic stem cells ex vivo, the method including contacting a population of hematopoietic stem cells with one or more compounds selected from UM171, structural analogs thereof, and the compounds listed in Table 11; and one or more agents selected from the group consisting of:
  a. a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine;
  b. a TGFβ receptor inhibitor selected from the group consisting of ALK5 inhibitor II, LY364947, DMH1, and A83-01;
  c. a compound that inhibits a protein that propagates p38 signaling comprising SB203580;
  d. a compound that inhibits a protein that promotes β-catenin degradation selected from the group consisting of CHIR99021, lithium chloride, BIO, and FGF2;
  e. a histone deacetylase inhibitor selected from the group consisting of Trichostatin A, valproic acid, butyrylhydroxamic acid, and istodax; and
  f. an aryl hydrocarbon receptor inhibitor comprising SR1,
wherein the one or more compounds selected from UM171, structural analogs thereof, and the compounds listed in Table 11 and the one or more agents are present in amounts that are sufficient to produce an expanded population of hematopoietic stem cells.

In another aspect, the invention provides a method of enriching a population of cells with hematopoietic stem cells ex vivo, the method including contacting a population of hematopoietic cells that contains one or more hematopoietic stem cells with UM171 and one or more agents selected from the group consisting of:
  a. a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine;
  b. a TGFβ receptor inhibitor selected from the group consisting of ALK5 inhibitor II, LY364947, DMH1, and A83-01;
  c. a compound that inhibits a protein that propagates p38 signaling comprising SB203580;
  d. a compound that inhibits a protein that promotes β-catenin degradation selected from the group consisting of CHIR99021, lithium chloride, BIO, and FGF2;
  e. a histone deacetylase inhibitor selected from the group consisting of Trichostatin A, valproic acid, butyrylhydroxamic acid, and istodax; and
  f. an aryl hydrocarbon receptor inhibitor comprising SR1,
wherein the UM171 and the one or more agents are present in amounts that are sufficient to produce a population of cells enriched with hematopoietic stem cells.

In another aspect, the invention provides method of maintaining the hematopoietic stem cell functional potential of a population of hematopoietic stem cells ex vivo for at least two days, the method including contacting a first population of hematopoietic stem cells with one or more compounds selected from UM171, structural analogs thereof, and the compounds listed in Table 11 and one or more agents selected from the group consisting of:
  a. a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine;
  b. a TGFβ receptor inhibitor selected from the group consisting of ALK5 inhibitor II, LY364947, DMH1, and A83-01;
  c. a compound that inhibits a protein that propagates p38 signaling comprising SB203580;
  d. a compound that inhibits a protein that promotes β-catenin degradation selected from the group consisting of CHIR99021, lithium chloride, BIO, and FGF2;
  e. a histone deacetylase inhibitor selected from the group consisting of Trichostatin A, valproic acid, butyrylhydroxamic acid, and istodax; and
  f. an aryl hydrocarbon receptor inhibitor comprising SR1,
wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the UM171 and the one or more agents.

In another aspect, the invention provides a method of producing an expanded population of hematopoietic stem cells ex vivo, the method including contacting a population of hematopoietic stem cells with SR1 and one or more agents selected from the group consisting of:
  a. a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine;
  b. a TGFβ receptor inhibitor selected from the group consisting of ALK5 inhibitor II, LY364947, DMH1, and A83-01;
  c. a compound that inhibits a protein that propagates p38 signaling comprising SB203580;
  d. a compound that inhibits a protein that promotes β-catenin degradation selected from the group consisting of CHIR99021, lithium chloride, BIO, and FGF2; and
  e. a histone deacetylase inhibitor selected from the group consisting of Trichostatin A, valproic acid, butyrylhydroxamic acid, and istodax,
wherein the SR1 and the one or more agents are present in amounts that are sufficient to produce an expanded population of hematopoietic stem cells.

In another aspect, the invention provides a method of enriching a population of cells with hematopoietic stem cells ex vivo, the method including contacting a population of hematopoietic cells that contains one or more hematopoietic stem cells with SR1 and one or more agents selected from the group consisting of:
  a. a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine;
b. a TGFβ receptor inhibitor selected from the group consisting of ALK5 inhibitor II, LY364947, DMH1, and A83-01;
c. a compound that inhibits a protein that propagates p38 signaling comprising SB203580;
d. a compound that inhibits a protein that promotes β-catenin degradation selected from the group consisting of CHIR99021, lithium chloride, BIO, and FGF2; and
e. a histone deacetylase inhibitor selected from the group consisting of Trichostatin A, valproic acid, butyrylhydroxamic acid, and istodax, wherein the SR1 and the one or more agents are present in amounts that are sufficient to produce a population of cells enriched with hematopoietic stem cells.

In another aspect, the invention provides a method of maintaining the hematopoietic stem cell functional potential of a population of hematopoietic stem cells ex vivo for at least two days, the method including contacting a first population of hematopoietic stem cells with SR1 and one or more agents selected from the group consisting of:
a. a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine;
b. a TGFβ receptor inhibitor selected from the group consisting of ALK5 inhibitor II, LY364947, DMH1, and A83-01;
c. a compound that inhibits a protein that propagates p38 signaling comprising SB203580;
d. a compound that inhibits a protein that promotes β-catenin degradation selected from the group consisting of CHIR99021, lithium chloride, BIO, and FGF2; and
e. a histone deacetylase inhibitor selected from the group consisting of Trichostatin A, valproic acid, butyrylhydroxamic acid, and istodax, wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the SR1 and the one or more agents.

In some embodiments, the one or more agents or compounds are present in amounts that are sufficient to stimulate expansion of the population of cells by 10% or more relative to a population of hematopoietic stem cells not contacted with the one or more agents or compounds after seven or more days of culture (e.g., after seven, ten, twelve, fourteen, fifteen, twenty, or more days of culture).

In some embodiments, the one or more agents or compounds are present in amounts that are sufficient to stimulate expansion of the population of cells by 10% or more relative to a population of hematopoietic stem cells that have been contacted with a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

In some embodiments, the one or more agents or compounds are present in amounts that are sufficient to enrich the population of cells with hematopoietic stem cells by 10% or more relative to a population of hematopoietic stem cells not contacted with the one or more agents or compounds after seven or more days of culture (e.g., after seven, ten, twelve, fourteen, fifteen, twenty, or more days of culture).

In some embodiments, the one or more agents or compounds are present in amounts that are sufficient to enrich the population of cells with hematopoietic stem cells by 10% or more relative to a population of hematopoietic stem cells that have been contacted with a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

In some embodiments, the first population of hematopoietic stem cells exhibits a hematopoietic stem cell functional potential after three or more days of culture (e.g., three, five, seven, ten, twelve, fourteen, fifteen, twenty, or more days) that is greater than that of the control population of hematopoietic stem cells.

In some embodiments, the hematopoietic stem cells are mammalian cells, such as human cells. In some embodiments, the hematopoietic stem cells are CD34+ cells. In some embodiments, at least 10% of the CD34+ cells are CD34+, CD34+CD38−, CD34+CD38-CD90+, CD34+CD38-CD90+CD45RA−, or CD34+CD38-CD90+CD45RA-CD49F+ cells. In some embodiments, the hematopoietic stem cells are from human cord blood. In some embodiments, the hematopoietic stem cells are from human mobilized peripheral blood. In some embodiments, the hematopoietic stem cells are from human bone marrow. In some embodiments, the hematopoietic stem cells are freshly isolated from the human. In some embodiments, the hematopoietic stem cells have been previously cryopreserved. In some embodiments, the mammalian cells are murine cells.

In embodiments of the above-described methods of maintaining the hematopoietic stem cell functional potential of a population of hematopoietic stem cells, the population of hematopoietic stem cells exhibits a hematopoietic stem cell functional potential after two or more days of culture (e.g., three, five, seven, ten, twelve, fourteen, fifteen, twenty, or more days) that is greater than that of the control population of hematopoietic stem cells.

In embodiments of any of the above-described aspects of the invention, the hematopoietic stem cells are mammalian cells. In certain cases, the mammalian cells are human cells. In particular embodiments, the human cells are CD34+ cells. In certain cases, at least 10% of the CD34+ cells are CD34+CD38−, CD34+CD38-CD90+, CD34+CD38-CD90+CD45RA−, or CD34+CD38-CD90+CD45RA-CD49F+ cells. In certain embodiments, the hematopoietic stem cells are from human cord blood. In other embodiments, hematopoietic stem cells are from human mobilized peripheral blood. In alternative embodiments, the hematopoietic stem cells are from human bone marrow. In certain cases, the hematopoietic stem cells are freshly isolated from the human. In other cases, the hematopoietic stem cells have been previously cryopreserved. In particular embodiments of the invention, the mammalian cells are murine cells.

In further embodiments of any of the above-described methods of the invention, the hematopoietic stem cells are cultured for two or more days (e.g., three, five, seven, ten, twelve, fourteen, fifteen, twenty or more days). In certain cases, the hematopoietic stem cells contact the one or more agents for two or more days (e.g., three, five, seven, ten, twelve, fourteen, fifteen, twenty, or more days). In some cases, the hematopoietic stem cells are contacted with the one or more agents simultaneously. In other embodiments, the hematopoietic stem cells are contacted with the one or more agents at different times.

In certain embodiments of the above-described methods of the invention, the hematopoietic stem cells maintain hematopoietic stem cell functional potential after two days (e.g., three, five, seven, ten, twelve, fourteen, fifteen, twenty, or more days) in culture. In particular cases, the hematopoietic stem cells maintain hematopoietic stem cell functional potential following transplantation after two or more days (e.g., three, five, seven, ten, twelve, fourteen, fifteen, twenty or more days) in culture. In other embodiments, the hematopoietic stem cells maintain long term engraftment potential after two or more days (e.g., three, five, seven, ten, twelve, fourteen, fifteen, twenty, or more days) in culture. In certain cases, upon transplantation into a patient, the hematopoietic stem cells give rise to recovery of a population of cells selected from the group consisting of neutrophils, platelets, red blood cells, monocytes, macrophages, antigen-presenting cells, microglia, osteoclasts, dendritic cells, and lymphocytes. In particular embodiments, the lymphocytes are selected from the group consisting of natural killer (NK) cells, T cells (e.g., CD4+ or CD8+ cells), and B cells. In certain cases, the hematopoietic stem cells are capable of localizing to hematopoietic tissue to reestablish productive hematopoiesis in a transplanted recipient.

In additional embodiments of the invention, the hematopoietic stem cells are cultured on a plastic surface or on a substrate including vitronectin, fibronectin, or matrigel. In certain cases, the hematopoietic stem cells are cultured in the presence of 2-20% oxygen, 2-12% oxygen, or about 5% oxygen. In some embodiments, the hematopoietic stem cells are cultured in the presence of 2-12% oxygen. In some embodiments, the hematopoietic stem cells are cultured in the presence of about 5% oxygen.

In further embodiments of the invention, the hematopoietic stem cells are originally within a mononuclear cell fraction prior to treatment with the one or more agents. In certain cases, the hematopoietic stem cells are originally within a CD34+, CD34+CD38-, CD34+CD38-CD90+, CD34+CD38-CD90+CD45RA-, or CD34+CD38-CD90+ CD45RA-CD49F+ enriched cell fraction prior to contacting the one or more agents. In some embodiments, the hematopoietic stem cells are originally within a CD34+, CD34+CD38-, CD34+CD38-CD90+, CD34+CD38-CD90+ CD45RA-, or CD34+CD38-CD90+CD45RA-CD49F+, or CD34+CD38-CD90+CD45RA-CD49F+EPCR+ enriched cell fraction prior to contacting the one or more agents or compounds. In particular cases, the hematopoietic stem cells are originally within an un-enriched cell fraction prior to contacting the one or more agents.

In an additional aspect, the invention provides a method of introducing and/or modulating the expression of one or more polynucleotides in a population of hematopoietic stem cells, the method including the steps of:
  a. inserting one or more polynucleotides into the population of hematopoietic stem cells; and
  b. expanding or maintaining the population of hematopoietic stem cells according to the above-described methods of the invention.

In certain cases, (a) precedes (b). In other embodiments, (b) precedes (a).

In another aspect, the invention provides a method of introducing a polynucleotide into a population of hematopoietic stem cells, the method including:
  a. inserting the polynucleotide into the population of hematopoietic stem cells; and
  b. expanding the population of hematopoietic stem cells according to the method of any one of the above embodiments, or maintaining the hematopoietic stem cell functional potential of the population of hematopoietic stem cells according to the method of any one of the above embodiments.

In some embodiments, step (a) above precedes step (b). In some embodiments, step (b) precedes step (a).

In additional embodiments, the method further includes introducing one or more reagents that cleave a nucleic acid in the cells. In certain cases, the one or more reagents that cleave a nucleic acid in the cells include a zinc finger nuclease (ZFN), a transcription activator-like effector nuclease (TALEN), a CRISPR-associated protein, or a meganuclease.

In certain embodiments of the invention, the one or more polynucleotides are introduced into the hematopoietic stem cells by contacting the cells with a viral vector (such as a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including herpesvirus (e.g., Herpes Simplex virus types 1 and 2, Epstein-Barr virus, cytomegalovirus), and poxvirus (e.g., vaccinia, modified vaccinia Ankara, fowlpox and canarypox)). In other cases, the one or more polynucleotides are introduced into the hematopoietic stem cells by contacting the cells with a vector that encodes a transposable element (such as the piggybac transposon or the sleeping beauty transposon).

In some embodiments, the method includes contacting the hematopoietic stem cells with a vector selected from the group consisting of a viral vector (such as retrovirus, adenovirus, parvovirus, coronavirus, rhabdovirus, paramyxovirus, picornavirus, alphavirus, herpes virus, or poxvirus) and a transposable element (such as a piggybac transposon or sleeping beauty transposon).

In certain embodiments of the invention, the one or more polynucleotides are introduced into the hematopoietic stem cells by electroporation, Nucleofection™, or squeeze-poration.

In some embodiments, the method includes contacting the cells with a transformation agent selected from the group consisting of a cationic polymer (e.g., diethylaminoethyl-dextran), a cationic lipid, calcium phosphate, an activated dendrimer, and a magnetic bead.

In some embodiments, the method includes introducing the polynucleotide into the hematopoietic stem cells by microinjection or laserfection.

In some embodiments, the polynucleotide includes a regulatory sequence selected from the group consisting of a promoter, enhancer, or silencer sequence.

In some embodiments, the polynucleotide encodes a molecule selected from the group consisting of a protein and a RNA (mRNA, tRNA, siRNA, miRNA, shRNA). In some embodiments, the polynucleotide is a chemically modified RNA.

In certain embodiments of the invention, the one or more polynucleotides are introduced into the hematopoietic stem cells by contacting the hematopoietic stem cells with cationic lipids, cationic polymers such as diethylaminoethyl (DEAE)-dextran, calcium phosphate, activated dendrimers, magnetic beads, or by microinjection, or laserfection of the hematopoietic stem cells.

In further embodiments, the one or more polynucleotides are introduced into the hematopoietic stem cells by contacting the cells with nanoparticles including the one or more polynucleotides. In certain embodiments, the one or more polynucleotides are introduced into the hematopoietic stem cells by contacting the cells with one or more VSV-G induced microvesicles (also referred to as Gesicles).

In particular cases, the one or more polynucleotides introduced into the population of hematopoietic stem cells contain a gene regulation element, such as a promoter, enhancer, or silencer. In other cases, the one or more polynucleotides encode a protein or RNA molecule (such as mRNA, tRNA, siRNA, miRNA, or shRNA). In certain embodiments, the one or more polynucleotides introduced into the population of hematopoietic stem cells are chemically modified RNA molecules.

In additional embodiments, the method further includes introducing into a recipient the population of expanded hematopoietic stem cells into which a polynucleotide has been inserted or progeny thereof.

In another aspect, the invention provides a method of treating a recipient with hematopoietic stem cells or progeny thereof, the method including the steps of:
 a. providing a population of hematopoietic stem cells;
 b. expanding the population of hematopoietic stem cells according to the above-described methods of the invention;
 c. optionally differentiating the hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, lymphocytes, NK cells, B-cells and/or T-cells; and
 d. introducing the population of expanded hematopoietic stem cells or progeny thereof into the recipient.

In an additional aspect, the invention relates to a method of treating a recipient with hematopoietic stem cells or progeny thereof, the method including the steps of:
 a. providing a population of hematopoietic stem cells;
 b. enriching the population of hematopoietic stem cells according to the above-described methods of the invention;
 c. optionally differentiating the hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, lymphocytes, NK cells, B-cells and and/or T-cells; and
 d. introducing the population of cells enriched with hematopoietic stem cells or progeny thereof into the recipient.

In another aspect, the invention provides a method of treating a recipient with hematopoietic stem cells or progeny thereof, the method including the steps of:
 a. providing a population of hematopoietic stem cells;
 b. maintaining the hematopoietic stem cell functional potential of the population of hematopoietic stem cells according to the above-described methods of the invention;
 c. optionally differentiating the hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, such as NK cells, B-cells and/or T-cells; and
 d. introducing the population of hematopoietic stem cells or progeny thereof into the recipient.

In a further aspect, the invention provides a method of treating a recipient with hematopoietic stem cells or progeny thereof, the method including the steps of:
 a. providing a population of hematopoietic stem cells produced by the above-described methods of the invention;
 b. optionally differentiating the hematopoietic stem cells to into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, lymphocytes, NK cells, B-cells and/or T-cells; and
 c. introducing the population of hematopoietic stem cells or progeny thereof into the recipient.

In some embodiments of the above aspects of the invention, the recipient is a human. In particular embodiments, the hematopoietic stem cells are derived from one or more hematopoietic stem cells isolated from a human donor. In certain cases, the hematopoietic stem cells are from mobilized peripheral blood of the donor. In additional embodiments, the donor has been previously administered one or more mobilizing agents selected from the group consisting of a CXCR4 antagonist (e.g., AMD3100), GCSF, and GROβ.

In some embodiments of any of the above-described methods of the invention, the hematopoietic stem cells are additionally contacted with a substance that inhibits aryl hydrocarbon receptor signaling. For instance, the substance that inhibits aryl hydrocarbon receptor signaling may be SR1 or an analog thereof. In further embodiments of the invention, the hematopoietic stem cells are additionally contacted with UM171 or an analog thereof. In still other embodiments, the hematopoietic stem cells are additionally contacted with a prostaglandin, such as dmPGE2 or an analog thereof. In certain cases, the hematopoietic stem cells may be contacted with an agonist of Notch signaling. In additional embodiments, the hematopoietic stem cells may be contacted with an inhibitor of SIRT1, such as nicotinamide, cambinol, or an analog thereof.

In some embodiments, the hematopoietic stem cells are additionally contacted with an agonist of Notch signaling.

In some embodiments, the hematopoietic stem cells are additionally contacted with an inhibitor of SIRT1. In some embodiments, the inhibitor or SIRT1 is selected from the group consisting of nicotinamide, cambinol, and analogs thereof.

In some embodiments of the methods of the invention, the recipient is a human patient suffering from a disease selected from the group consisting of Acute Lymphoblastic Leukemia (ALL), Acute Myelogenous Leukemia (AML), Chronic Myelogenous Leukemia (CML), Chronic Lymphocytic Leukemia (CLL), Hodgkin Lymphoma (HL), Non-Hodgkin Lymphoma (NHL), Myelodysplastic Syndrome (MDS), Multiple myeloma, Aplastic anemia, Bone marrow failure, Myeloproliferative disorders such as Myelofibrosis, Essential thrombocytopenia or Polycythemia vera, Fanconi anemia, Dyskeratosis congenita, Common variable immune deficiency (CVID, such as CVID 1, CVID 2, CVID 3, CVID 4, CVID 5, and CVID 6), Human immunodeficiency virus (HIV), Hemophagocytic lymphohistiocystosis, Amyloidosis, Solid tumors such as Neuroblastoma, Germ cell tumors, Breast cancer, Wilms' tumor, Medulloblastoma, and Neuroectodermal tumors, Autoimmune diseases such as Scleroderma, Multiple sclerosis, Ulcerative colitis, Systemic lupus erythematosus and Type I diabetes, or protein deficiencies such as Adrenoleukodystrophy (ALD), Metachromatic leukodystrophy (MLD), Hemophilia A & B, Hurler syndrome, Hunter syndrome, Fabry disease, Gaucher disease, Epidermolysis bullosa, Globoid Cell Leukodystrophy, Sanfillipo syndrome, and Morquio syndrome.

In some embodiments, the recipient is a human patient suffering from a genetic blood disease selected from the group consisting of Sickle cell anemia, Alpha thalassemia, Beta thalassemia, Delta thalassemia, Hemoglobin E/thalassemia, Hemoglobin S/thalassemia, Hemoglobin C/thalassemia, Hemoglobin D/thalassemia, Chronic granulomatous disease (X-linked Chronic granulomatous disease, autosomal recessive (AR) chronic granulomatous disease, chronic granulomatous disease AR I NCF1, Chronic granulomatous disease AR CYBA, Chronic granulomatous disease AR II NCF2, Chronic granulomatous disease AR III NCF4), X-linked Severe Combined Immune Deficiency (SCID), ADA SCID, IL7-RA SCID, CD3 SCID, Rag1/Rag2 SCID, Artemis SCID, CD45 SCID, Jak3 SCID, Congenital agranulocytosis, Congenital agranulocytosis-congenital neutropenia-SCN1, Congenital agranulocytosis-congenital neutropenia-SCN2, Familial hemophagocytic lymphohistiocystosis (FHL), Familial hemophagocytic lymphohistiocytosis type 2 (FHL2, perforin mutation), Agammaglobulinemia (X-linked Agammaglobulinemia), Wiskott-Aldrich syndrome, Chediak-Higashi syndrome, Hemolytic anemia due to red cell pyruvate kinase deficiency, Paroxysmal nocturnal hemoglobinuria, X-linked Adrenoleukodystrophy (X-ALD), X-linked lymphoproliferative disease, Unicentric Castleman's Disease, Multicentric Castleman's Disease, Congenital amegakaryocytic thrombocytopenia (CAMT) type I, Reticular dysgenesis, Fanconi anemia, Acquired idiopathic sideroblastic anemia, Systemic mastocytosis, Von willebrand disease (VWD), Congenital dyserythropoietic anemia type 2, Cartilage-hair hypoplasia syndrome, Hereditary spherocytosis, Blackfan-Diamond syndrome, Shwachman-Diamond syndrome, Thrombocytopenia-absent radius syndrome, Osteopetrosis, Infantile osteopetrosis, Mucopolysaccharidoses, Lesch-Nyhan syndrome, Glycogen storage disease, Congenital mastocytosis, Omenn syndrome, X-linked Immunodysregulation, polyendocrinopathy, and enteropathy (IPEX), IPEX characterized by mutations in FOXP3, X-linked syndrome of polyendocrinopathy, immune dysfunction, and diarrhea (XPID), X-Linked Autoimmunity-Allergic Dysregulation Syndrome (XLAAD), IPEX-like syndrome, Hyper IgM type 1, Hyper IgM type 2, Hyper IgM type 3, Hyper IgM type 4, Hyper IgM type 5, X linked hyperimmunoglobulin M, Bare lymphocyte Syndrome type I, and Bare lymphocyte Syndrome type II (Bare lymphocyte Syndrome type II, MHC class I deficiency; Bare lymphocyte Syndrome type II, complementation group A; Bare lymphocyte Syndrome type II, complementation group C; Bare lymphocyte Syndrome type II complementation group D; Bare lymphocyte Syndrome type II, complementation group E).

In some embodiments, the recipient is a human patient suffering from a hematolymphoid malignancy, a non-hematolymphoid malignancy, or a protein deficiency, or a tissue or cell transplantation recipient (e.g., to induce tolerance to transplanted tissue or cells).

Populations of hematopoietic stem cells expanded, enriched, or maintained by the compositions and/or methods of the invention, as well as progeny thereof, can also be used to treat a patient (e.g., a human patient) suffering from a hematolymphoid malignancy, a non-hematolymphoid malignancy, or a protein deficiency. In other embodiments, the patient may be the recipient of a tissue or cell transplant, and the hematopoietic stem cells or progeny thereof are administered in order to induce tolerance to the transplanted tissue or cells.

In some embodiments of the above-described methods of treating a patient with hematopoietic stem cells or progeny thereof, the hematopoietic stem cells are autologous or syngeneic. Alternatively, the hematopoietic stem cells may be allogeneic.

In an additional aspect, the invention provides a composition including one or more agents that together exhibit one or more activities selected from the group consisting of:

a. modulation of histone methylation;
b. inhibition of TGFβ signaling;
c. inhibition of p38 signaling;
d. activation of canonical Wnt signaling; and
e. modulation of histone acetylation.

In some embodiments, the one or more agents together exhibit two or more activities selected from the above group.

In another aspect, the invention provides a composition including:

a. one or more compounds listed in Table 11; and one or more of
b. one or more agents that inhibit TGFβ signaling;
c. one or more agents that modulate histone methylation;
d. one or more agents that modulate histone acetylation; and
e. one or more agents that inhibit aryl hydrocarbon receptor signaling.

In another aspect, the invention provides a composition including:

a. one or more agents that inhibit aryl hydrocarbon receptor signaling; and one or more of
b. one or more agents that inhibit TGFβ signaling;
c. one or more agents that modulate histone methylation; and
d. one or more agents that modulate histone acetylation.

In some embodiments, the compound listed in Table 11 is UM171.

In embodiments, the modulation of histone methylation is activation of histone methylation, maintenance of histone methylation, or inhibition of histone demethylation. In additional embodiments, the modulation of histone acetylation is activation of histone acetylation, maintenance of histone acetylation, or inhibition of histone deacetylation. In particular embodiments, the one or more agents include a compound that activates histone methylation, maintains histone methylation, or inhibits histone demethylation and a compound that inhibits TGFβ signaling. In certain cases, the compound that activates histone methylation, maintains histone methylation, or inhibits histone demethylation is a histone demethylase inhibitor and the compound that inhibits TGFβ signaling is a TGFβ receptor inhibitor. In particular embodiments, the histone demethylase inhibitor is a LSD1 inhibitor. In additional embodiments, the LSD1 inhibitor is LSD1 inhibitor IV RN-1 and the TGFβ receptor inhibitor is ALK5 inhibitor II (E-616452).

In some embodiments, the aryl hydrocarbon receptor inhibitor is SR1.

In some embodiments, the composition includes a compound that inhibits BMP signaling.

In another aspect, the invention provides a composition including one or more agents that together inhibit the activity of one or more proteins selected from the group consisting of:
  a. a histone demethylase;
  b. a protein that propagates TGFβ signaling;
  c. a protein that propagates p38 signaling;
  d. a protein that promotes β-catenin degradation; and
  e. a histone deacetylase.

In some embodiments, the one or more agents together inhibit the activity of two or more proteins selected from the above group.

In some embodiments of this aspect of the invention, the histone demethylase is LSD1. In additional embodiments, the one or more agents include a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine. In particular cases, the protein that propagates TGFβ signaling is a TGFβ receptor. In some embodiments, the one or more agents include a compound that inhibits a protein that propagates TGFβ signaling selected from the group consisting of ALK5 inhibitor II (E-616452), LY364947, A83-01, and DMH1. In certain cases, the one or more agents include a compound that inhibits a protein that propagates p38 signaling, and wherein the compound is SB203580. In additional embodiments, the one or more agents include a compound that inhibits a protein that promotes β-catenin degradation selected from the group consisting of CHIR99021, lithium chloride, BIO, and FGF2 (e.g., recombinant mouse FGF2). In still other embodiments, the one or more agents include a compound that inhibits a histone deacetylase selected from the group consisting of Trichostatin A, valproic acid, butyrylhydroxamic acid, and istodax (romidepsin). In particular cases, the one or more agents together inhibit the activity of a histone demethylase and a protein that propagates TGFβ signaling. In certain embodiments, the histone demethylase is LSD1. In additional embodiments, the protein that propagates TGFβ signaling is a TGFβ receptor. In certain cases, the one or more agents include LSD1 inhibitor IV RN-1 and ALK5 inhibitor II (E-616452). In additional embodiments, the one or more agents include a compound that inhibits p38 signaling. In other embodiments, the one or more agents include a compound that inhibits a histone deacetylase. In certain cases, the one or more agents include a compound that inhibits BMP signaling.

In another aspect, the invention provides a composition including:
  a. a compound listed in Table 11; and one or more of
  b. a TGFβ receptor inhibitor;
  c. a histone demethylase inhibitor;
  d. a histone deacetylase inhibitor; and
  e. an aryl hydrocarbon receptor inhibitor.

In another aspect, the invention provides a composition including:
  a. an aryl hydrocarbon receptor inhibitor; and one or more of
  b. a TGFβ receptor inhibitor;
  c. a compound listed in Table 11;
  d. a histone demethylase inhibitor; and
  e. a histone deacetylase inhibitor.

In some embodiments, the composition includes one or more agents selected from the group consisting of:
  a. a compound that inhibits a protein that propagates p38 signaling including SB203580; and
  b. a compound that inhibits a protein that promotes β-catenin degradation selected from the group consisting of CHIR99021, lithium chloride, BIO, and FGF2.

In another aspect, the invention provides a composition including:
  a. UM171, a structural analog thereof, or a compound listed in Table 11; and one or more of
  b. a TGFβ receptor inhibitor selected from the group consisting of ALK5 inhibitor II, LY364947, DMH1, and A83-01;
  c. a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine;
  d. a histone deacetylase inhibitor selected from the group consisting of Trichostatin A, valproic acid, butyrylhydroxamic acid, and istodax; and
  e. SR1.

In another aspect, the invention provides a composition including
  a. SR1; and one or more of
  b. a TGFβ receptor inhibitor selected from the group consisting of ALK5 inhibitor II, LY364947, DMH1, and A83-01;
  c. a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine; and
  d. a histone deacetylase inhibitor selected from the group consisting of Trichostatin A, valproic acid, butyrylhydroxamic acid, and istodax.

In another aspect, the invention provides a composition including (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II (E-616452), LY364947, A83-01, Trichostatin A, SB203580, CHIR99021, DMH1, sodium acetate, and istodax (romidepsin). In certain cases, the one or more agents are present in amounts that are sufficient to produce an expanded population of hematopoietic stem cells. In additional embodiments, the one or more agents are present in amounts that are sufficient to produce a population of cells enriched with hematopoietic stem cells. In still other embodiments, the one or more agents are present in amounts sufficient to maintain hematopoietic stem cell functional potential of the population of hematopoietic stem cells for at least two days. In particular embodiments, the one or more agents are present in an aqueous solution. In other embodiments, the one or more agents are present as a lyophilized solid.

In some embodiments of the above-described compositions of the invention, the one or more agents are present in amounts that are sufficient to stimulate expansion of the population of cells by 10% or more relative to a population of hematopoietic stem cells that have been contacted with a substance that inhibits aryl hydrocarbon receptor signaling (such as SR1 or an analog thereof), UM171 or an analog thereof, a prostaglandin, an agonist of Notch signaling, or an inhibitor of SIRT1, such as nicotinamide, cambinol, or an analog thereof, after seven or more days of culture (e.g., after seven, ten, twelve, fourteen, fifteen, twenty, or more days of culture). In certain cases, the one or more agents are present in amounts that are sufficient to enrich the population of cells with hematopoietic stem cells by 10% or more relative to a population of hematopoietic stem cells that have been contacted with a substance that inhibits aryl hydrocarbon receptor signaling (such as SR1 or an analog thereof), UM171 or an analog thereof, a prostaglandin, an agonist of Notch signaling, or an inhibitor of SIRT1, such as nicotinamide, cambinol, or an analog thereof, after seven or more days of culture (e.g., after seven, ten, twelve, fourteen, fifteen, twenty, or more days of culture). In particular embodiments, the one or more agents are present in amounts that are sufficient to maintain long term engraftment potential of the hematopoietic stem cells post-transplantation after having contacted the cells in culture for two or more days (e.g., three, five, seven, ten, twelve, fourteen, fifteen, twenty, or more days).

In an additional aspect, the invention provides a composition including a multi-component combination specified in any one of Tables 1-10.

In another aspect, the invention provides a cell culture medium including any of the above-described compositions of the invention. In certain cases, the cell culture medium is substantially free of serum. In some embodiments, cytokines may be added to the cell culture media of the invention, e.g., in order to further stimulate the proliferation of hematopoietic stem cells or to induce the differentiation of hematopoietic stem cells into a desired population of blood cells.

In embodiments of the above-described compositions of the invention, the composition may additionally include a population of hematopoietic stem cells in contact with the one or more agents. In certain cases, the hematopoietic stem cells have been cultured in the presence of the one or more agents for two or more days (e.g., three, five, seven, ten, twelve, fourteen, fifteen, twenty, or more days).

In additional aspects, the invention provides a method of producing an expanded population of hematopoietic stem cells ex vivo by contacting a population of hematopoietic stem cells with one or more agents that together exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation.

and wherein the cells are additionally contacted with one or more substances selected from the group consisting of a substance that inhibits aryl hydrocarbon receptor signaling such as SR1 or an analog thereof, UM171 or an analog thereof, a prostaglandin, an agonist of Notch signaling, or an inhibitor of SIRT1 such as nicotinamide, cambinol, or an analog thereof, such that the one or more agents and one or more substances are present in amounts that together are sufficient to produce an expanded population of hematopoietic stem cells.

In a further aspect, the invention provides a method of enriching a population of cells with hematopoietic stem cells ex vivo by contacting a population of hematopoietic cells that contains one or more hematopoietic stem cells with one or more agents that together exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation.

and wherein the cells are additionally contacted with one or more substances selected from the group consisting of a substance that inhibits aryl hydrocarbon receptor signaling such as SR1 or an analog thereof, UM171 or an analog thereof, a prostaglandin, an agonist of Notch signaling, or an inhibitor of SIRT1 such as nicotinamide, cambinol, or an analog thereof, such that the one or more agents and one or more substances are present in amounts that together are sufficient to produce a population of cells enriched with hematopoietic stem cells.

In an additional aspect, the invention relates to a method of maintaining the hematopoietic stem cell functional potential of a population of hematopoietic stem cells ex vivo for at least two days by contacting a first population of hematopoietic stem cells with one or more agents that together exhibit one or more activities selected from the group consisting of:
  a. modulation of histone methylation;
  b. inhibition of TGFβ signaling;
  c. inhibition of p38 signaling;
  d. activation of canonical Wnt signaling; and
  e. modulation of histone acetylation.

wherein the first population of hematopoietic stem cells are additionally contacted with one or more substances selected from the group consisting of a substance that inhibits aryl hydrocarbon receptor signaling such as SR1 or an analog thereof, UM171 or an analog thereof, a prostaglandin, an agonist of Notch signaling, or an inhibitor of SIRT1 such as nicotinamide, cambinol, or an analog thereof, and wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the one or more agents and the one or more substances.

In yet another aspect, the invention provides a population of hematopoietic stem cells produced by any of the above-described methods of the invention. In other cases the invention provides a population of cells derived from the hematopoietic stem cells produced by any of the above-described methods of the invention.

In an additional aspect, the invention provides a kit including any of the above-described compositions of the invention, in addition to a package insert. In certain cases, the package insert instructs a user of the kit to expand, enrich, or maintain a population of hematopoietic stem cells ex vivo. In other cases, the package insert instructs the user to express a polynucleotide in the hematopoietic stem cells. In additional embodiments, the package insert instructs the user to administer the hematopoietic stem cells to a recipient.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used herein, the term "expanded population" of hematopoietic stem cells or hematopoietic progenitor cells refers to a population of cells comprising at least one more hematopoietic stem cell, such that the quantity of hematopoietic stem cells in the population is greater (e.g., at least 10% greater, at least 20% greater, at least 30% greater) than the number of HSCs prior to administration of one or more agents as described herein (e.g., one or more agents that together exhibit two or more activities selected from the group consisting of modulation of histone methylation, inhibition of TGFβ signaling, inhibition of p38 signaling, activation of canonical Wnt signaling, and modulation of histone acetylation). In some embodiments, the one or more agents modulate TGFβ signaling, modulate lysine methylation, modulate p38 signaling, modulate canonical Wnt signaling, modulate histone methylation, or modulate histone acetylation.

As used herein, an agent that inhibits histone demethylation refers to a substance or composition (e.g., a small molecule, protein, interfering RNA, messenger RNA, or other natural or synthetic compound, or a composition such as a virus or other material composed of multiple substances) capable of attenuating or preventing the activity of a histone demethylase or other enzyme that catalyzes the formation of an intermediate that leads to histone demethylation. Inhibition can occur by direct interaction or via indirect means, such as by causing a reduction in the quantity of histone demethylase produced in a cell or by inhibition of the interaction between a histone demethylase and a methylated histone substrate. Histone demethylases include lysine-specific demethylases, such as LSD1 and LSD2, as well as other FAD-dependent histone demethylases. Histone demethylases also include dioxygenases that utilize divalent iron ($Fe^{2+}$) to catalyze oxidative demethylation of histone residues, such as AlkB, and Jumonji C (JmjC) domain-containing histone demethylases, such as JHDM1, JHDM2, and members of the JMJD2 superfamily of histone demethylases. Other enzymes that convert methylated histone residues into reactive intermediates that subsequently undergo oxidative demethylation include monoamine oxidases. Histone demethylation inhibitors may directly bind a histone demethylase and compete with a methylated histone substrate for binding at the enzyme active site. Alternatively, an agent that inhibits histone demethylation may bind a histone demethylase at a location remote from the active site and disrupt or prevent the interaction between the enzyme and a methylated histone substrate, e.g., by inducing a conformational change in the enzyme, or disrupt or prevent the catalytic cycle, e.g., by inactivating or displacing enzymatic cofactors.

An agent that inhibits histone demethylation is capable of attenuating or preventing the formation of a demethylated histone residue with a half-maximal inhibitory concentration ($IC_{50}$) of 100 μM or below (e.g., between 1 nM and 100 μM) as determined from a histone demethylation assay known in the art or described herein. Exemplary assays that can be used to elucidate the biological activity of a histone demethylation inhibitor include, without limitation, cell-based growth inhibition assays and dissociation-enhanced lanthanide fluorescence assays as described in U.S. Pat. No. 8,735,622, time-resolved fluorescence resonance energy transfer assays as described in WO 2014/151945, as well as mass spectrometry-based assays and coupled-enzyme formaldehyde dehydrogenase assays as described in WO 2010/043866, among others.

As used herein, an agent that inhibits the TGFβ signaling pathway refers to a substance or composition (e.g., a small molecule, protein, interfering RNA, messenger RNA, or other natural or synthetic compound, or a composition such as a virus or other material composed of multiple substances) that can attenuate or prevent the transcription of one or more genes that are transcribed due to the activity of a SMAD transcription co-activator protein. An agent that inhibits the TGFβ signaling pathway may disrupt the signal transduction cascade that leads to SMAD-induced gene transcription at one or more points within the pathway. For instance, a TGFβ signaling pathway inhibitor may disrupt or prevent TGFβ or a TGFβ superfamily ligand, such as Activin, Nodal, bone morphogenetic protein (BMP), growth and differentiation factor (GDF), or Mullerian inhibitory factor (MIF), from binding to its endogenous receptor, thus inhibiting the phosphorylation and activation of the receptor-associated SMAD proteins. A TGFβ signaling pathway inhibitor may function by preventing the translocation of one or more SMAD proteins to the nucleus, for example, by binding a SMAD protein and preventing or disrupting the interaction between the SMAD protein and the nucleoporins. A TGFβ signaling pathway inhibitor may stabilize the interaction between one or more SMAD proteins and SMAD Anchor for Receptor Activation (SARA), which sequesters SMAD proteins in the cytoplasm and prevents their translocation into the nucleus. Other examples of TGFβ signaling pathway inhibitors include substances, such as neurogenin, that bind SMAD proteins and sequester them from DNA-bound transcription factors, thus preventing transcription of a target gene. Alternative inhibitors of the TGFβ signaling pathway include substances that promote the ubiquitination of one or more SMAD proteins, thereby marking the protein for degradation by the proteasome and preventing target gene transcription.

Exemplary assays that can be used to determine the inhibitory activity of a TGFβ signaling pathway inhibitor include, without limitation, electrophoretic mobility shift assays, antibody supershift assays, as well as TGFβ-inducible gene reporter assays, as described in WO 2006/012954, among others.

As used herein, an agent that inhibits the p38 signaling pathway refers to a substance or composition (e.g., a small molecule, protein, interfering RNA, messenger RNA, or other natural or synthetic compound, or a composition such as a virus or other material composed of multiple substances) that can attenuate or prevent the activity of the p38 mitogen activated protein kinases (MAPKs, e.g., p38α, p38β, p38γ, or p38δ) or any protein that is involved, either directly or indirectly, in activating one or more of these enzymes. An agent that inhibits the p38 signaling pathway may include a substance, such as a monoclonal antibody, that binds to a cytokine receptor, such as IL-1R, and prevents the receptor-mediated activation of p38 MAP kinases. Alternatively, a p38 signaling pathway inhibitor may bind a p38 protein directly and attenuate or prevent the phosphorylation of the p38 activation loop by a MAP kinase. An agent that inhibits the p38 signaling pathway may alternatively disrupt the formation of poly-ubiquitin chains at lysine residues of TNF receptor associated factor (TRAF), which serve as scaffolds for MAPK complexes. Other inhibitors of the p38 signaling pathway include those that promote the phosphorylation of MAP kinases at sites remote from the activation loop and prevent their association with p38, as well as those that acetylate MAP kinases within the activation loop and thus prevent phosphorylation and concomitant activation of the MAP kinase.

Exemplary assays that can be used to determine the inhibitory activity of an agent that inhibits the p38 signaling pathway include, without limitation, fluorescence anisotropy competitive binding assays, as well as time-resolved fluorescence resonance energy transfer assays, as described in WO 2006/012954, among others.

As used herein, an agent that inhibits histone deacetylation refers to a substance or composition (e.g., a small molecule, protein, interfering RNA, messenger RNA, or other natural or synthetic compound, or a composition such as a virus or other material composed of multiple substances) capable of attenuating or preventing the activity of histone deacetylase, more particularly its enzymatic activity either via direct interaction or via indirect means such as by causing a reduction in the quantity of a histone deacetylase produced in a cell or by inhibition of the interaction between a histone deacetylase and an acetylated histone substrate. Inhibiting histone deacetylase enzymatic activity means reducing the ability of a histone deacetylase to catalyze the removal of an acetyl group from a histone residue (e.g., a mono-, di-, or tri-methylated lysine residue; a monomethylated arginine residue, or a symmetric/asymmetric dimethylated arginine residue, within a histone protein). Preferably, such inhibition is specific, such that the an agent that inhibits histone deacetylation reduces the ability of a histone deacetylase to remove an acetyl group from a histone residue at a concentration that is lower than the concentration of the inhibitor that is required to produce another, unrelated biological effect.

As used herein, the terms "histone deacetylase" and "HDAC" refer to any one of a family of enzymes that catalyze the removal of acetyl groups from the ε-amino groups of lysine residues at the N-terminus of a histone. Unless otherwise indicated by context, the term "histone" is meant to refer to any histone protein, including HI, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9, HDAC-10, and HDAC-11.

As used herein, an agent that inhibits a protein that promotes β-catenin degradation include those agents that inhibit β-catenin phosphorylation or ubiquitination. These agents may be any substance (e.g., a small molecule, protein, interfering RNA, messenger RNA, or other natural or synthetic compound, or a composition such as a virus or other material composed of multiple substances) that can reduce the rate or extent of β-catenin degradation, e.g., by attenuating the catalysis of phosphorylation of serine and/or threonine residues that would otherwise render β-catenin a substrate for ubiquitination and proteasome-mediated degradation (for example, at residues Ser33, Ser37 and/or at Thr41). By extending the half life of functional β-catenin, these agents promote a concomitant increase in the rate or extent of transcription of a gene that is transcribed due to the activity of the β-catenin transcription co-activator. Exemplary agents that inhibit β-catenin phosphorylation include agonists of the canonical β-catenin/Wnt signaling pathway, a signal transduction cascade that orchestrates the inhibition of glycogen synthase kinase 3 (GSK3) by providing substrates that compete with β-catenin for phosphorylation.

As used herein, a "Wnt signaling agonist" refers to an agonist of the canonical Wnt signaling pathway. Agonists of this pathway further include Wnt proteins or other compounds that bind directly to the Frizzled and LRP5/6 co-receptor proteins in a manner that promotes an increase in the concentration of β-catenin in the nucleus of a mammalian cell. Alternatively, a β-catenin/Wnt pathway agonist may function by inhibiting one or more secreted Frizzled-related proteins (SFRPs) or Wnt inhibitory protein (WIF), which bind and sequester Wnt proteins from the endogenous Wnt co-receptors.

Exemplary methods that can be used to determine the activity of a β-catenin/Wnt pathway agonist include, without limitation, monitoring the expression of a reporter gene under the control of a TCF/LEF family transcription factor, as well as TOPFlash luciferase reporter assays, as described in US 2014/0044763.

As used herein, a compound that inhibits aryl hydrocarbon receptor signaling include agents that inhibit the signal transduction cascade that is propagated by the binding of the aryl hydrocarbon receptor to an activating ligand thereof. The aryl hydrocarbon receptor is a cytosolic, ligand-inducible transcription factor that, upon binding to an agonistic ligand, translocates into the nucleus and promotes the transcription of target genes containing the distinct sequence motifs, such as the gene encoding cytochrome P450A1 enzyme that contains an upstream dioxin-responsive element. Examples of agents that inhibit aryl hydrocarbon receptor signaling include aryl hydrocarbon receptor inhibitors, which may include compounds, such as SR1, that bind the aryl hydrocarbon receptor directly and thus compete with aryl hydrocarbon receptor ligands for binding to the receptor. Additional examples of agents that inhibit aryl hydrocarbon receptor signaling include agents that interfere with the translocation of the active aryl hydrocarbon receptor to the nucleus, and agents that inhibit the interaction of the aryl hydrocarbon receptor with the DNA (e.g., the promoter regions containing XRE sites) of target genes.

As used herein, an agonist of Notch signaling is an agent that promotes activation of Notch pathway function. The term "Notch pathway function" as used herein refers to a function mediated by the Notch signal transduction pathway including, but not limited to, nuclear translocation of the intracellular domain of Notch, nuclear translocation of RBP-Jκ or its Drosophila homolog Suppressor of Hairless; activation of bHLH genes of the Enhancer of Split complex, e.g., Mastermind; activation of the HES-1 gene or the KBF2 (also referred to as CBF1) gene; inhibition of Drosophila neuroblast segregation; and binding of Notch to a Delta protein, a Jagged/Serrate protein, Fringe, Deltex or RBP-Jκ/Suppressor of Hairless, or homologs or analogs thereof. The Notch signal transduction cascade and the phenotypes effected by Notch signaling are described, e.g., in Kopan et al., Cell 137:216 (2009) and Jarriault, et al., Mol. Cell. Biol. 18:7423 (1998), the disclosures of each of which are incorporated herein by reference. Examples of Notch agonists are described, e.g., in US 2014/0369973 and in U.S. Pat. No. 7,399,633, the disclosures of each of which are incorporated herein by reference. Exemplary Notch agonists include, without limitation, Notch proteins, as well as analogs, derivatives, and fragments thereof; other proteins that propagate the Notch signaling pathway, as well as analogs, derivatives, and fragments thereof; activating antibodies that stimulate Notch receptor activity and antigen-binding fragments thereof that retain agonistic activity; nucleic acids encoding proteins that potentiate Notch signaling; as well as proteins, derivatives, and analogs thereof which bind to or otherwise interact with Notch proteins or other proteins in the Notch pathway such that Notch pathway activity is promoted. Such agonists include, but are not limited to, Notch proteins and derivatives thereof containing the Notch intracellular domain, Notch nucleic acids encoding the foregoing, and proteins contacting the Notch-interacting domain of Notch ligands (e.g., the extracellular domain of Delta or Serrate). Other agonists include but are not limited to RBPJκ/Suppressor of Hairless or Deltex. Fringe can additionally be used to enhance Notch activity, for example in conjunction with Delta protein. These proteins, fragments, and derivatives thereof can be recombinantly expressed and isolated or can be chemically synthesized using peptide and protein synthesis techniques known in the art.

As used herein, the term "inhibitor" refers to any compound, natural or synthetic, which can reduce the activity of a target protein or signaling pathway. An inhibitor can be, for example, a peptide, a protein, an antibody, a peptidomimetic, an amino acid, an amino acid analog, a polynucleotide, a polynucleotide analog, an aptamer, a nucleotide, a nucleotide analog, an organic or inorganic compound. An inhibitor may attenuate or prevent the activity of a target protein either directly or indirectly. Direct inhibition can be obtained, for instance, by binding to a protein and preventing the protein from interacting with an endogenous molecule, such as an enzyme, a substrate, or other binding partner, thereby diminishing the activity of the protein. For instance, an inhibitor may bind an enzyme active site and sterically preclude binding of an endogenous substrate at this location, thus decreasing the enzymatic activity of the protein. Alternatively, indirect inhibition can be obtained, for instance, by binding to a protein that promotes the activity of a target protein by inducing a conformational change or catalyzing a chemical modification of the target protein. For instance, indirect inhibition of a target protein may be achieved by binding and inactivating a kinase that catalyzes the phosphorylation of, and thus activates, the target protein.

As used herein, the term "hematopoietic stem cells" (or "HSCs") refer to immature blood cells having the capacity to self-renew and to differentiate into mature blood cells comprising diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). It is known in the art that such cells may or may not include $CD34^+$ cells. $CD34^+$ cells are immature cells that express the CD34 cell surface marker. In humans, CD34+ cells are believed to include a subpopulation of cells with the stem cell properties defined above, whereas in mice, HSCs are CD34−. In addition, HSCs also refer to long term repopulating HSC (LT-HSC) and short term repopulating HSC (ST-HSC). LT-HSC and ST-HSC are differentiated, based on functional potential and on cell surface marker expression. For example, human HSC are a CD34+, CD38−, CD45RA−, CD90+, CD49F+, and lin− (negative for mature lineage markers including CD2, CD3, CD4, CD7, CD8, CD10, CD11B, CD19, CD20, CD56, CD235A). In mice, bone marrow LT-HSC are CD34−, SCA-1+, C-kit+, CD135−, Slamfl/CD150+, CD48−, and lin− (negative for mature lineage markers including Ter119, CD11b, Gr1, CD3, CD4, CD8, B220, IL7ra), whereas ST-HSC are CD34+, SCA-1+, C-kit+, CD135−, Slamfl/CD150+, and lin− (negative for mature lineage markers including Ter119, CD11b, Gr1, CD3, CD4, CD8, B220, IL7ra). In addition, ST-HSC are less quiescent (i.e., more active) and more proliferative than LT-HSC under homeostatic conditions. However, LT-HSC have greater self renewal potential (i.e., they survive throughout adulthood, and can be serially transplanted through successive recipients), whereas ST-HSC have limited self renewal (i.e., they survive for only a limited period of time, and do not possess serial transplantation potential). Any of these HSCs can be used in any of the methods described herein. Optionally, ST-HSCs are useful because they are highly proliferative and thus, can more quickly give rise to differentiated progeny.

As used herein, the phrase "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

Hematopoietic stem cells are optionally obtained from blood products. A blood product includes a product obtained from the body or an organ of the body containing cells of hematopoietic origin. Such sources include unfractionated bone marrow, umbilical cord, placenta, peripheral blood, or mobilized-peripheral blood. All of the aforementioned crude or unfractionated blood products can be enriched for cells having hematopoietic stem cell characteristics in a number of ways. For example, the more mature, differentiated cells are selected against, via cell surface molecules they express. Optionally, the blood product is fractionated by positively selecting for $CD34^+$ cells. $CD34^+$ cells include a subpopulation of hematopoietic stem cells capable of self-renewal, multi-potency, and that can be reintroduced into a transplant recipient whereupon they home to the hematopoietic stem cell niche and re-establish productive and sustained hematopoiesis. Such selection is accomplished using, for example, commercially available magnetic anti-CD34 beads (Dynal, Lake Success, N.Y.). Unfractionated blood products are optionally obtained directly from a donor or retrieved from cryopreservative storage. Hematopoietic stem cells can also be optionally obtained from differentiated embryonic stem cells, differentiated induced pluripotent stem cells or from other reprogrammed mature cells types.

The terms "stem cell" or "undifferentiated cell" as used herein, refer to a cell in an undifferentiated or partially differentiated state that has the property of self-renewal and has the developmental potential to differentiate into multiple cell types. A stem cell is capable of proliferation and giving rise to more such stem cells while maintaining its functional potential. Stem cells can divide asymmetrically, which is known as obligatory asymmetrical differentiation, with one daughter cell retaining the functional potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. Alternatively, some of the stem cells in a population can divide symmetrically into two stem cells. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity may be natural or may be induced artificially upon treatment with various factors. Cells that begin as stem cells might proceed toward a differentiated phenotype, but then can be induced to "reverse" and re-express the stem cell phenotype, a term often referred to as "dedifferentiation" or "reprogramming" or "retrodifferentiation" by persons of ordinary skill in the art.

As used herein, "homing potential" refers to the capability of a stem cell to localize to sites in vivo that can support productive hematopoiesis such as the bone marrow.

As used herein, a cell population that is "enriched" in a particular cell type refers to a population in which the relative proportion of cells of a particular type has increased in comparison with a previous population of cells (for example, in comparison with a population of cells prior to treatment with one or more agents that together exhibit two or more activities selected from the group consisting of modulation of histone methylation, inhibition of TGFβ signaling, inhibition of p38 signaling, activation of canonical Wnt signaling, and modulation of histone acetylation).

The term "multipotent" when used in reference to a "multipotent cell" refers to a cell that has the developmental potential to differentiate into multiple different hematopoietic cell types. Hematopoietic stem cells are multi-potent and can form the many different types of blood cells (red, white, platelets, etc.), but it cannot form neurons.

As used herein, the phrases "preserve multi-potency" or "maintain multi-potency" refer to a process by which the degree of multi-potency of a population of cells is preserved over a period of time. The degree of multi-potency of a population of cells describes the number and identity of differentiated cell types into which a population of cells can differentiate. For example, a population of cells exhibiting multi-potency that has been maintained over a period of two days ex vivo (e.g., in culture) is capable of differentiating into at least the same number of different cell types as the population was capable of differentiating into at the beginning of the cell culture period.

As used herein, a "mobilizing agent" is an agent capable of inducing the migration of hematopoietic stem cells from the bone marrow of a subject to the peripheral blood. Exemplary mobilizing agents include CXCR4 antagonists, such as AMD3100, as well as GCSF and GROβ.

As used herein, "contacting" a population of cells with one or more agents can be achieved in a variety of ways. For instance, a population of hematopoietic stem cells may be contacted with one or more agents that together exhibit two or more activities selected from the group consisting of modulation of histone methylation, inhibition of TGFβ signaling, inhibition of p38 signaling, activation of canonical Wnt signaling, and modulation of histone acetylation (e.g., LSD1 inhibitor IV RN-1; LSD1 inhibitor II S2101; LSD1 inhibitor LSD1-C76; LSD1 inhibitor III CBB1007; LSD1 inhibitor I; ALK5 inhibitor II (E-616452); LY364947; A83-01; Trichostatin A; Tranylcypromine; SB203580; CHIR99021; DMH1; sodium acetate; and istodax) by culturing the hematopoietic stem cells in the presence of these agents for a period of time, such as for two or more days. When more than once agent is contacted with a population of cells, the agents can be present in the cell culture medium together, such that the cells are exposed to the one or more agents simultaneously. Alternatively, the one or more agents may be added to the cell culture medium sequentially. For instance, the one or more agents may be added to a population of cells in culture according to a particular regimen, e.g., such that different agents are added to the culture media at different times during a culture period.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. In one embodiment, engraftment is determined by measuring white blood cell counts in peripheral blood during a post-transplant period. Alternatively, engraftment can be assessed by measuring recovery of marrow cells by donor cells in a bone marrow aspirate sample.

As used herein, the term "self-renewal" refers to the ability of a stem cell to produce daughter stem cells with the same phenotype, characteristics and functional potential as the original stem cell. In particular, self-renewal, as used herein, is defined as the ability to continue proliferation while maintaining an undifferentiated multi-potent stem cell state.

As used herein, a population of cells that has been "freshly isolated" from a donor refers to a population of cells that has been isolated from a donor without having been cryopreserved and thawed prior to infusion. A population of cells may be isolated from a donor and separated into two intermediate populations, one of which may be infused into a patient and the other of which may be cryopreserved. In this instance, the intermediate population that is infused into the patient is considered freshly isolated. A population of cells is considered to be freshly isolated from a donor if the population is cultured ex vivo prior to infusion in the patient. For example, this culturing step may be performed in order to expand, enrich, and/or maintain the population of hematopoietic stem cells prior to administration of the resulting cells to a patient. In these instances, the resulting cells are considered to be freshly isolated from the donor, to the extent that the cells that are administered to the patient have not been cryopreserved and thawed prior to infusion into the patient.

As used herein, the term "ZsGr" refers to the fluorescent cassette ZsGreen, and references to "Fdg5·ZsGr" indicate that the fluorescent ZsGreen reporter cassette is knocked in frame into the endogenous Fgd5 locus. In these cases, ZsGreen expression is under the control of the Fgd5 promoter. The inventors have previously shown that Fgd5 is exclusively expressed in hematopoietic stem cells in the murine hematopoietic system. The inventors have further shown that highly pure hematopoietic stem cells can be isolated based on single color ZsGreen fluorescence when using Fdg5·ZsGreen mice. Hematopoietic stem cells isolated from such mice are referred to as ZsGr+, or Fgd5·ZsGr+. This reporter construct is described in further detail in Gazit R, Mandal P K, Ebina W, Ben-Zvi A, Nombela-Arrieta C, Silberstein L E, Rossi D J. Journal of Experimental Medicine. 211(7):1315-31 (2014), the disclosure of which is incorporated herein by reference.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

As used herein, "CRU (competitive repopulating unit)" refers to a unit of measure of long-term engrafting stem cells, which can be detected after in-vivo transplantation.

As used herein, the term "modulate" means to change or induce an alteration in a particular biological activity. Modulation includes, but is not limited to, stimulating or inhibiting an activity (e.g., by activating a receptor so as to initiate a signal transduction cascade, to inhibit a receptor from propagating a signaling pathway, by activating an endogenous inhibitor that attenuates a biological activity, or by inhibiting the activity of a protein that inhibits a particular biological function. Modulation of a protein that propagates a particular signaling pathway may result in an increase or a decrease in activity (e.g., in histone methylation, TGFβ signaling, p38 signaling, Wnt signaling, or histone acetylation), a change in the affinity of one protein in a pathway for another, or another change in the structural, functional, or immunological properties associated with the activity of a pathway or protein within a pathway.

The terms "increased", "increase", "enhance", or "activate" are all used herein to mean an increase by a statistically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker, an "increase" is a statistically significant increase in such level.

As used herein, a "subject" means a human or animal Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

As used herein, a "recipient" is a patient that receives a transplant, such as a transplant containing a population of hematopoietic stem cells or a population of differentiated cells. The transplanted cells administered to a recipient may be, e.g., autologous, syngeneic, or allogeneic cells.

As used herein, a "donor" is a human or animal from which one or more cells are isolated prior to administration of the cells, or progeny thereof, into a recipient. The one or more cells may be, e.g., a population of hematopoietic stem cells to be expanded, enriched, or maintained according to the methods of the invention prior to administration of the cells or the progeny thereof into a recipient.

Preferably, the subject is a mammal. The mammal can be a human, non-human primate, mouse, rat, dog, cat, horse, or cow, but is not limited to these examples. Mammals other than humans can be advantageously used as subjects that represent animal models of disease and/or treatment. A subject can be male or female.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "polynucleotide", "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. In another aspect, the nucleic acid can be chemically modified-RNA. For instance, the nucleic acid can be chemically modified messenger RNA. In another aspect, the nucleic acid can be RNA synthesized with naturally occurring or synthetic nucleotide analogs. Suitable nucleic acid molecules are DNA, including genomic DNA or cDNA. Other suitable nucleic acid molecules are RNA, including mRNA, tRNA, siRNA, miRNA, or shRNA.

A used herein, the term "siRNA" refers to a double stranded nucleic acid molecule capable of RNA interference or "RNAi", as disclosed, for example, in Bass, Nature 411: 428-429 (2001); Elbashir et al., Nature 411: 494-498 (2001); WO 2000/044895; WO 2001/036646; WO 1999/032619; WO 2000/001846; WO 2001/029058; WO 1999/007409; and WO 2000/044914, the disclosures of each of which are incorporated herein by reference. As used herein, siRNA molecules are not limited to those molecules containing only RNA, but further encompass chemically modified nucleotides and non-nucleotides having RNAi capacity or activity.

As used herein, the term "miRNA" refers to a class of small, non-coding, single-stranded RNA, typically between 18-23 nucleotides in length. miRNA molecules are capable of regulating gene expression by modulating the stability and translation of mRNA encoding specific proteins. miRNA also influence other nuclear processes, such as heterochromatin formation and genome rearrangement.

As used herein, the term "shRNA" (small hairpin RNA) refers to an RNA duplex containing siRNA, part of which is in the form of a hairpin structure. In addition to the duplex portion, the hairpin structure may contain a loop portion positioned between the two sequences that form the duplex. The loop can vary in length. For instance, the loop may be 5, 6, 7, 8, 9, 10, 11, 12 or 13 nucleotides in length. The hairpin structure can also contain 3' or 5' overhang portions. For example, the overhang may be a 3' or a 5' overhang and may be 0, 1, 2, 3, 4 or 5 nucleotides in length.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound, cell, or population of cells as disclosed herein into a subject by a method or route which results in at least partial delivery of the agent at a desired site. Pharmaceutical compositions comprising the compounds or cells disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." As used herein, the term "about" indicates a deviation of ±10%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, "LSD1 inhibitor II S2101" refers to a compound having the structure of Formula I or a pharmaceutically acceptable salt thereof. The synthesis of LSD1 inhibitor II S2101 as well as the structure and synthesis of related compounds, e.g., derivatives, including those with similar biological activity are known in the art, see, e.g. WO 1998/009625; WO 2003/016309; WO 2004/087646; WO 2005/033066; WO 2006/034769; WO 2007/068330; WO 2009/147217; WO 2014/194280; US 2013/0178520; U.S. Pat. No. 5,426,196; EP 764640; and EP 764632, the disclosures of each of which are incorporated herein by reference.

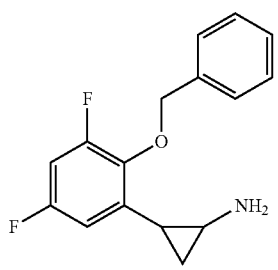

Formula I

As used herein, "LSD1 inhibitor IV RN-1" refers to a compound having the structure of Formula II or a pharmaceutically acceptable salt thereof. The synthesis of LSD1 inhibitor IV RN-1 as well as the structure and synthesis of related compounds, e.g., derivatives, including those with similar biological activity are known in the art, see, e.g. WO 2015/003643; WO 2014/205266; WO 2014/19428; WO 2012/122405; WO 2014/018375; WO 2009/147217; WO 2007/068330; WO 2006/034769; WO 2005/033066; WO 2004/087646; WO 2003/016309; WO 1998/009625; WO 1997/010822; WO 1997/010825; WO 1995/017408; and US 2013/0178520, each of which is incorporated by reference herein in its entirety.

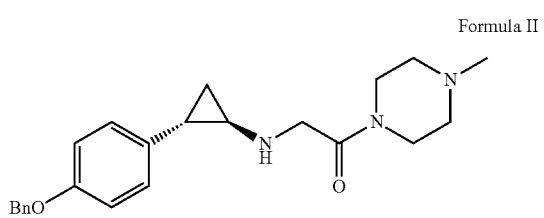 [SMILES: CN1CCN(C(=O)CN[C@@H]2C[C@H]2c2ccc(OCc3ccccc3)cc2)CC1]

Formula II

As used herein, "LSD1 inhibitor LSD1-C76" refers to a compound having the structure of Formula III or a pharmaceutically acceptable salt thereof. The synthesis of LSD1 inhibitor LSD1-C76 as well as the structure and synthesis of related compounds, e.g., derivatives, including those with similar biological activity are known in the art.

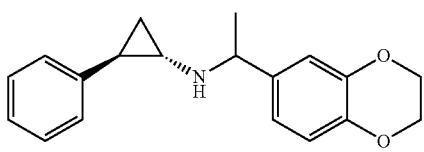

Formula III

As used herein, "LSD1 inhibitor III CBB1007" refers to a compound having the structure of Formula IV or a pharmaceutically acceptable salt thereof. The synthesis of LSD1 inhibitor III CBB1007 as well as the structure and synthesis of related compounds, e.g., derivatives, including those with similar biological activity are known in the art.

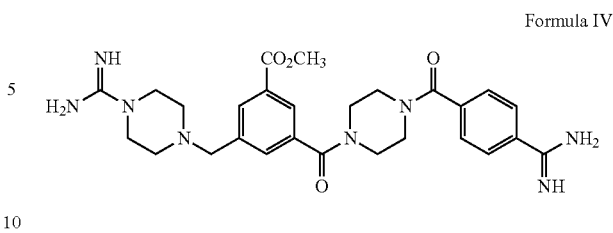

Formula IV

As used herein, "LSD1 inhibitor I" refers to a compound having the structure of Formula V or a pharmaceutically acceptable salt thereof. LSD1 inhibitor I is also referred to in the art as BHC110 Inhibitor I, Histone Lysine Demethylase Inhibitor III, and/or KDM1 Inhibitor I. The synthesis of LSD1 inhibitor I as well as the structure and synthesis of related compounds, e.g., derivatives, including those with similar biological activity are known in the art.

Formula V

As used herein, "ALK5 inhibitor II" (also referred to as "RepSox" or "E-616452" refers to a compound having the structure of Formula VI or a pharmaceutically acceptable salt thereof. ALK5 inhibitor II (E-616452) is also referred to in the art as Transforming Growth Factor-b Type I Receptor Kinase Inhibitor II or Repsox.

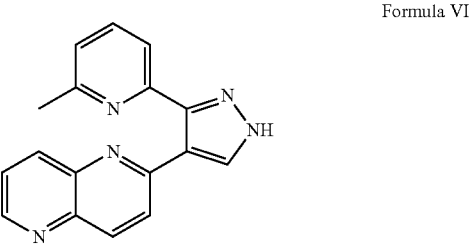 [SMILES: Cc1cccc(-c2n[nH]cc2-c2ccc3ncccc3n2)n1]

Formula VI

As used herein, "LY364947" refers to a compound having the structure of Formula VII or a pharmaceutically acceptable salt thereof. LY364947 is also referred to in the art as ALK5 Inhibitor I TbR-I Inhibitor Transforming Growth Factor-b Type I Receptor Kinase Inhibitor. The synthesis of LY364947 and ALK5 inhibitor II as well as the structure and synthesis of related compounds, e.g., derivatives, including those with similar biological activity are known in the art, see, e.g. U.S. Pat. No. 6,028,072; WO 2002/062794; WO 2004/026302; WO 2004/026306; WO 2004/072033; WO 2007/088651; WO 2007/070866; WO 2007/039151; and WO 2007/052943, each of which is incorporated by reference herein in its entirety.

Formula VII

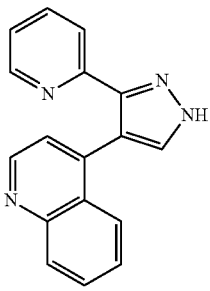

As used herein, "A83-01" refers to a compound having the structure of Formula VIII or a pharmaceutically acceptable salt thereof. The synthesis of A83-01 as well as the structure and synthesis of related compounds, e.g., derivatives, including those with similar biological activity are known in the art, see, e.g., US 2003/0064997; US 2003/0064997; US 2003/0064997; U.S. Pat. Nos. 5,777,097; 5,871,934; GB 2306108; WO 1993/014081; WO 1995/003297; WO 1997/33883; WO 1997/35855; and WO 1993/014081; each of which is incorporated by reference herein in its entirety.

Formula VIII

As used herein, "trichostatin A" refers to a compound having the structure of Formula IX or a pharmaceutically acceptable salt thereof. The synthesis of trichostatin A as well as the structure and synthesis of related compounds, e.g., derivatives, including those with similar biological activity are known in the art, see, e.g. U.S. Pat. Nos. 4,690,918; 4,946,999; EP 0827946; JP 07206670; and JP 60149520; each of which is incorporated by reference herein in its entirety.

Formula IX

As used herein, "tranylcypromine" refers to a compound having the structure of Formula X or a pharmaceutically acceptable salt thereof. The synthesis of tranylcypromine as well as the structure and synthesis of related compounds, e.g., derivatives, including those with similar biological activity are known in the art, see, e.g. U.S. Pat. Nos. 2,993,931; 2,997,422; 3,011,945; 3,079,403; 3,134,676; and 3,244,596, each of which is incorporated by reference herein in its entirety.

Formula X

As used herein, "SB203580" refers to a compound having the structure of Formula XI or a pharmaceutically acceptable salt thereof. The synthesis of SB203580 as well as the structure and synthesis of related compounds, e.g., derivatives, including those with similar biological activity are known in the art, see, e.g., WO 2007/070866; WO 2008/022182; WO 2010/065917; WO 2010/077955; and WO 2010/102267; each of which is incorporated by reference herein in its entirety.

Formula XI

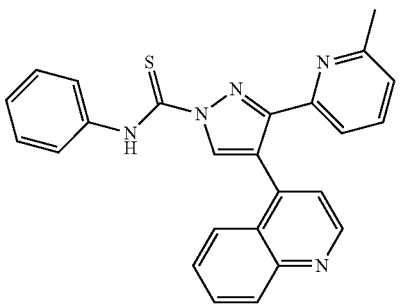

As used herein, "CHIR99021" refers to a compound having the structure of Formula XII or a pharmaceutically acceptable salt thereof. The synthesis of CHIR99021 as well as the structure and synthesis of related compounds, e.g., derivatives, including those with similar biological activity are known in the art, see, e.g. WO 1999/065897; WO 2002/020495; WO 2005/003948; WO 2006/001863; WO 2006/117212; WO 2007/016485; WO 2007/075911; WO 2007/083978; and US 2002/156087; each of which is incorporated by reference herein in its entirety.

Formula XII

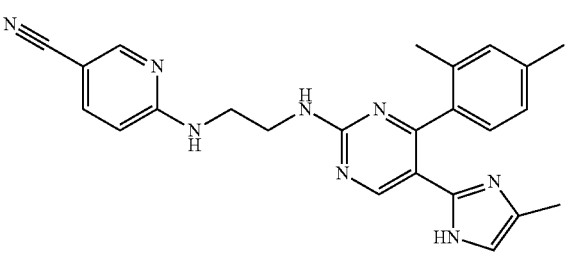

As used herein, "DMH1" refers to a compound having the structure of Formula XIII or a pharmaceutically acceptable salt thereof. The synthesis of DMH1 as well as the structure and synthesis of related compounds, e.g., derivatives, including those with similar biological activity are known in the art, see, e.g. WO 2012/115120; WO 2013/016452; WO 2013/163228; WO 2013/166488; WO2014/138088; WO 2014/176606; WO 2014/200115; WO2014/062138; US 2014/0248696; and U.S. Pat. No. 8,822,684; each of which is incorporated by reference herein in its entirety.

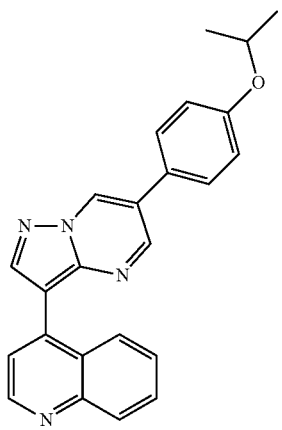

Formula XIII

As used herein, "istodax" or "romidepsin" refers to a compound having the structure of Formula XIV or a pharmaceutically acceptable salt thereof. The synthesis of istodax as well as the structure and synthesis of related compounds, e.g., derivatives, including those with similar biological activity are known in the art, see, e.g., WO14/102731; WO12/009336; WO13/106696; WO02/20817; U.S. Pat. Nos. 4,977,138; 7,611,721; 7,608,280; and US 2012/046442; and J. Am. Chem. Soc. 1 18:7237-7238, 1996; each of which is incorporated by reference herein in its entirety.

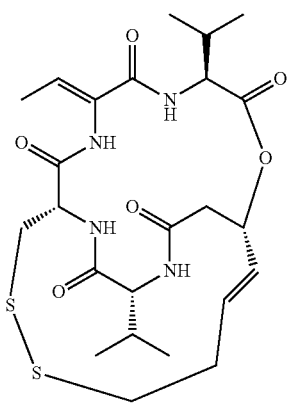

Formula XIV

Other terms are defined herein within the description of the various aspects of the invention.

BRIEF DESCRIPTION OF THE DRAWINGS

FIG. 3A depicts an overview: Fgd5·ZsGr+ HSCs were isolated from reporter mice and cultured in S-clone+IL12/SCF/TPO+0.75% BSA for 4 days. On day four, 300 ZsGr+ and 300 ZsGr− cells were sorted and competitively transplanted into lethally irradiated mice showing that all HSC activity was retained in the ZsGr+ fraction as detailed in FIG. 3B. FIG. 3B depicts peripheral blood chimerism and peripheral blood granulocyte chimerism of mice transplanted with ZsGr+ and ZsGr− cells. Lineage contribution of ZsGr+ and ZsGr− cells. Data shows that only ZsGr+ cells retain HSC activity.

FIG. 4 shows a schematic representation of a small molecule screen for compounds that support HSC ex vivo maintenance and expansion. 1) Fgd5·ZsGr+ HSC reporter mouse marrow was used to isolate ZsGr+ HSCs. 2) Isolation of HSCs marked by ZsGr reporter. 3) Development of assay where hit is defined by the maintenance of HSC reporter expression in the cultured HSCs above DMSO control following 6 days ex vivo culture. 4) Hit compounds were then functionally validated in in vitro assays and in vivo transplantation assays.

FIG. 5A demonstrates that a total of 200 ZsGr+ HSCs (derived from the Fgd5·ZsGreen HSC reporter mouse) and ZsGr−HSCs (derived from wild type mice not bearing the Fgd5Zs+ reporter) were seeded/well in various ratios (1:0; 1:1; 1:10; 1:20, 1:100, 0:1—shown as percentage ZsGr+) and imaged using the Operetta (Perkin Elmer) following 2 days ex vivo culture with individual cells plotted as being above or below the threshold of ZsGreen detection. FIG. 5B demonstrates that after 2 days of culture, the percentage of ZsGreen+ cells was determined. This established the analysis parameters and sensitivity for robust detection of ZsGr+ signal after 2 days of culturing.

FIG. 6 shows a breakdown of pathways targeted in the primary small molecule screens.

FIG. 7A demonstrates the number of compounds screened, initial hits (that showed dose response), and validated hits (by flow cytometry to quantify ZSGr+) from each of 4 different libraries of small molecules targeting kinases, epigenetic regulators, and G-protein coupled receptors (GPCR), as well as a peptide library of growth factors. FIG. 7B depicts representative results from 6-point dose response (10 uM, 5 uM, 1 uM, 0.5 uM, 0.1 uM, 0.05 uM). * indicates a hit.

FIG. 8 shows the ex vivo culture of 20 murine HSCs (Lineage−Sca1+ckit+CD34-Flk2-CD150+Fgd5·ZsGr+) for 7 or 14 days in the presence of DMSO, LSD1 inhibitor IV (LS), Tgfbeta inhibitor (RepSox) or the combination of both (C2). Images taken at 4× magnification. Note that the cultures in the presence of LS and C2 are more homogenous and less differentiated.

FIG. 9A depicts representative FACS plots of HSCs cultured for 14 days ex vivo in the presence of DMSO and the combination of LSD1 inhibitor (LS), Tgfbeta inhibitor RepSox (RS) (C2) showing increased levels of phenotypic HSCs in the presence of C2. FIG. 9B depicts the number of Lineage−Sca1+ckit+CD34-Flk2-CD150+Fgd5·ZsGr+ HSCs in each condition after 14 days of ex vivo culture.

FIG. 10A depicts bright-field and ZsGr images of 20 Fgd5·ZsGr+ HSCs cultured for 4.5 days ex vivo in the presence of LSD1 inhibitor IV (LS), Tgfbeta inhibitor RepSox (RS), and the combination of both (C2). FIG. 10B demonstrates the frequency of ZsGr+ cells remaining following 4.5 days of ex vivo culture. FIG. 10C depicts the number of ZsGr+ and ZsGr− cells after 4.5 day cultures.

FIG. 11A depicts colony number and composition. FIG. 11B depicts the total number of cells generated by HSCs cultured for 14 days.

FIG. 12A depicts a graph of peripheral blood donor chimerism, and FIG. 12B depicts a graph of peripheral blood donor (CD45.2) granulocyte chimerism. FIG. 12C depicts a graph of individual recipient mouse donor chimerism, and FIG. 12D depicts a graph of lineage contribution of donor reconstitution showing B-cell (B220+), T-cell (CD3+) and myeloid cell (Mac1+) at week 24 post-transplant is shown.

FIG. 13A depicts peripheral blood donor chimerism. FIG. 13B depicts peripheral blood donor (CD45.2) granulocyte Chimerism. FIG. 13C depicts the lineage contribution of donor reconstitution showing B-cell (B220+), T-cell (CD3+) and myeloid cell (Mac1+), FIG. 13D depicts donor chimerism of individual recipients, and FIG. 13E depicts granulocyte chimerism of individual recipients at 20 weeks post-transplant. FIG. 13F depicts calculation of limit dilution frequency bioinf.wehi.edu.au/software/elda/Hu, Y, and Smyth, G K (2009). ELDA: Extreme limiting dilution analysis for comparing depleted and enriched populations in stem cell and other assays. *Journal of Immunological Methods* 347, 70-78.

FIG. 15A depicts an overview of two strategies used to identify hits in secondary small molecule screen (C2 is combination of LSD1 inhibitor IV and the Tgfbeta inhibitor RepSox). FIG. 15B depicts hits found by following a strategy based on ZsGreen+ HSC percentage (strategy 1). FIG. 15C depicts hits found by following a strategy based on number of ZsGreen+ HSCs (strategy 2).

FIG. 16A depicts hits found by following a strategy based on ZsGreen+ HSC percentage. FIG. 16B depicts hits found by following a strategy based on number of ZsGreen+ HSCs.

FIGS. 18A-18B show a hypothesis driven strategy for modulating candidate pathways towards HSC ex vivo maintenance and expansion. FIG. 18A depicts selection of candidate target pathways via comparison of intestinal stem cell and hematopoietic stem cell maintenance and proliferation signals. FIG. 18B depicts selection of agents/pathway modulators.

FIG. 19 shows a schematic for assessing the activity of pathway modulators on HSC maintenance and expansion. Fgd5-ZsGreen+immunophenotypic HSCs (Lineage−cKit+Sca1+CD150+CD48-Fgd5·ZsGreen+) were sorted and cultured in the presence of cytokines only (Standard media) or additionally supplemented with 7 candidate pathway modulators (W7 media). Compounds modulating the 7 pathways are: A83-01, Tranylcypromine, Trichostatin A, SB203580, CHIR99021, DMH1, Sodium acetate (called here Supplements). Multiparametric analysis of cellular immunophenotype was performed by flow cytometry after 14 days of culture.

FIG. 21B depicts absolute HSC numbers after 14 days culture from 50 starting HSCs in the indicated conditions.

FIG. 22A depicts day 7 flow cytometric analysis and FIG. 22B depicts the proportion of Fgd5-ZsGreen+Sca1+ cells for each replicate.

FIG. 25A depicts peripheral blood and FIG. 25B depicts granulocyte donor chimerism at indicated time points post-transplantation are shown. FIG. 25C depicts donor HSC chimerism in the bone marrow of transplant recipients transplanted with HSCs cultured for 14 days in the indicated conditions is shown.

FIG. 28A depicts a schematic of experimental design. FIG. 28B depicts flow cytometry of cultured cord blood HSCs (CD34+CD45RA-CD90+CD38-, initially seeded at 50 cells per well) 14 days post-plating in the presence of DMSO, Stem Regenin 1 (SR1), LSD1 inhibitor (LS), Tgfbeta inhibitor RepSox (RS) and the combination of LSD1 inhibitor IV and RepSox (C2) showing percentages of CD34+CD45RA- cells (contour plots) and CD90+ cells (histogram) (+/- standard deviation).

FIG. 29A depicts the percentage of HSCs (as defined as CD34+CD45RA-CD90+) of total live cells and FIG. 29B depicts absolute numbers of HSCs, post culturing 50 cord blood HSCs (CD34+ CD45RA-CD90+CD38-) in the presence of DMSO, Stem Regenin 1 (SR1), LSD1 inhibitor IV (LS), Tgfbeta inhibitor RepSox (RS) and the combination of LSD1 IV inhibitor and RepSox (C2). *p<0.05 unpaired t-test.

FIGS. 30A-30B show that the combination (C2) of LSD1 inhibitor IV (LS) and the Tgfbeta inhibitor RepSox (RS) maintains and expands primitive in vitro colony forming potential of human cord blood HSCs following 14 days of ex vivo culture. FIG. 30A depicts colony counts and composition adjusted to represent the entire well following 14 days of ex vivo culture (Note: only a fraction of the well was added to methocult for colony formation). FIG. 30B depicts the frequency of myeloid colony types from 14 day cord blood HSC cultures. Note elevated frequency of most primitive GEMM colonies (colonies comprised of granulocytes, macrophages, erythroid and megakaryocytic lineages) after culturing in RS, LS or C2.

FIG. 31A depicts flow cytometry of cultured bone marrow derived HSCs (FACS purified as CD34+CD45RA-CD90+CD38-, 80 cells per well) 14 days post-plating in the presence of DMSO, Stem Regenin 1 (SR1), LSD1 inhibitor IV (LS), Tgfbeta inhibitor RepSox (RS) and the combination (C2) of LSD1 inhibitor IV and RepSox showing percentages of CD34+CD45RA- cells (dot plots) and CD90+ cells (histogram) (+/− Standard deviation). FIG. 31B depicts the percentage of immunophenotypic HSCs (CD34+CD45RA-CD90+CD38-) post culturing in the presence of DMSO, Stem Regenin 1 (SR1), LSD1 inhibitor IV (LS), Tgfbeta inhibitor RepSox (RS) and the combination (C2) of LSD1 inhibitor IV and RepSox. *p<0.05, ** p<0.005 unpaired t-test.

FIG. 32A depicts flow cytometry of cultured mobilized peripheral blood HSCs (FACS purified as CD34+CD45RA-CD90+ CD38-, 50 cells per well) 14 days post-plating in the presence of DMSO, Stem Regenin 1 (SR1), LSD1 inhibitor IV (LS), Tgfbeta inhibitor RepSox (RS) and the combination (C2) of LSD1 inhibitor IV and RepSox showing percentages of CD34+CD45RA-cells (contour plots) and CD90+ cells (histogram) (+/− Standard deviation). FIG. 32B depicts the percentage of immunophenotypic HSCs (CD34+CD45RA-CD90+) and stem and progenitors (CD34+CD45RA-) post 14 days culture in the presence of DMSO, Stem Regenin 1 (SR1), LSD1 inhibitor IV (LS), Tgfbeta inhibitor RepSox (RS) and the combination (C2) of LSD1 inhibitor IV and RepSox.

FIG. 34A depicts the immunophenotype of the cells post-culturing, and FIG. 34B depicts quantification of immunophenotypic HSCs (Lineage−CD34+CD45RA-CD38−CD90+) cultured in the indicated conditions.

FIG. 35A depicts the immunophenotype of the cells post-culturing, and FIG. 35B depicts quantification of immunophenotypic HSCs (Lineage−CD34+CD45RA-CD38−CD90+CD49F+) cultured in the indicated conditions.

FIGS. 37A-37C show a comparison of chemical combination with compounds previously reported to expand cord blood HSCs. 200 cord blood HSCs (FACS purified as Lineage-CD34+CD45RA-CD90+CD38-) cultured for 12 days in serum free media supplemented with cytokines (SCF, TPO, FLT3L, IL3) in the presence of StemRegenin1 (SR1), UM171, or chemical combination (W3: Tgfbeta inhibitor (A83-01), HDAC inhibitor (Trichostatin A), and LSD1 inhibitor (Tranylcypromine)) and analyzed by flow cytometry. FIG. 37A depicts the immunophenotype of the cells post-culturing, FIG. 37B depicts the percentage of indicated populations, and FIG. 37C depicts quantification of immunophenotypic HSCs (Lineage−CD34+CD45RA-CD38−CD90+) 12 days post-culturing in the indicated conditions.

FIGS. 38A-38C show the ex vivo maintenance and expansion of human mobilized peripheral blood CD34+ cells using compounds identified using murine cells. 3000 CD34+ enriched mobilized peripheral blood cells were cultured for 7 days in serum free media supplemented with cytokines (SCF, TPO, FLT3L, IL3) in the presence of the indicated individual chemicals or chemical combinations (Tgfbeta inhibitor (A, A83-01), HDAC inhibitor (TSA, Trichostatin A), LSD1 inhibitor (TC, Tranylcypromine), and p38 inhibitor (p38i, SB203580)) and analyzed by flow cytometry. FIG. 38A depicts the immunophenotype of the cells post-culturing, FIG. 38B depicts the percentage of indicated populations, and FIG. 38C depicts the quantification of immunophenotypic HSCs (Lineage−CD34+CD45RA-CD38−CD90+CD49F+) post-culturing in the indicated conditions for 7 days. (W7: A83-01 (A), Tranylcypromine, (TC) Trichostatin A (TSA), SB203580 (p38i), CHIR99021 (Chir), DMH1 (DMH), Sodium acetate (OAC), and W3: A83-01 (A), Tranylcypromine, (TC) Trichostatin A (TSA))

FIGS. 40A-40C show a comparison of chemical combination with compounds previously reported to expand cord blood HSCs for their ability to maintain/expand human mobilized peripheral blood HSCs. 50 mobilized peripheral blood HSCs (FACS purified as Lineage-CD34+CD45RA−CD90+CD38−) were cultured for 12 days in serum free media supplemented with cytokines (SCF, TPO, FLT3L, IL3) in the presence of StemRegenin1 (SR1), UM171, or chemical combination (W3: Tgfbeta inhibitor (A83-01), HDAC inhibitor (Trichostatin A), and LSD1 inhibitor (Tranylcypromine)) or additionally supplemented with p38 inhibitor (p38i, SB203580) and analyzed by flow cytometry. FIG. 40A depicts the immunophenotype of the cells post-culturing, FIG. 40B depicts the percentage of indicated populations, and FIG. 40C depicts quantification of immunophenotypic HSCs (Lineage−CD34+CD45RA-CD38−CD90+CD49F+) post culturing in the indicated conditions for 12 days.

FIGS. 41A-41C show that Romidepsin, a HDAC1/2 specific inhibitor, can replace the pan HDAC inhibitor Trichostatin A for efficient ex vivo maintenance/expansion of human HSCs. 3000 CD34+ enriched mobilized peripheral blood cells were cultured for 7 days in serum free media supplemented with cytokines (SCF, TPO, FLT3L, IL3) in the presence of the indicated chemical combinations (Tgfbeta inhibitor (A, A83-01), pan-HDAC inhibitor (TSA, Trichostatin A), LSD1 inhibitor (TC, Tranylcypromine), p38 inhibitor (p38i, SB203580), HDAC1/2 inhibitor (Rom, Romidepsin)) and analyzed by flow cytometry. FIG. 41A depicts the immunophenotype of the cells, FIG. 41B depicts the percentage of indicated populations, and FIG. 41C depicts quantification of immunophenotypic HSCs (Lineage−CD34+CD45RA-CD38−CD90+CD49F+) 7 days post-culturing in the indicated conditions.

FIG. 42B depicts quantification of peripheral blood donor chimerism at weeks 24 and 30 post transplant. FIG. 42C depicts lineage contribution of transplanted cells at week 30 post-transplant.

FIGS. 48A-48C depict an experiment schematic (FIG. 48A), a graph of donor cell engraftment (FIG. 48B) and a graph of lineage contribution (FIG. 48C) 4 weeks post-transplantation of 200 starting cell (HSC) equivalents cultured for 12 days in the presence of DMSO, W7, or W3. Lineage analysis of Mac1+ myeloid cells, CD3 positive (3) T-cells and B220 positive B-cells.

DETAILED DESCRIPTION

Figure 1:
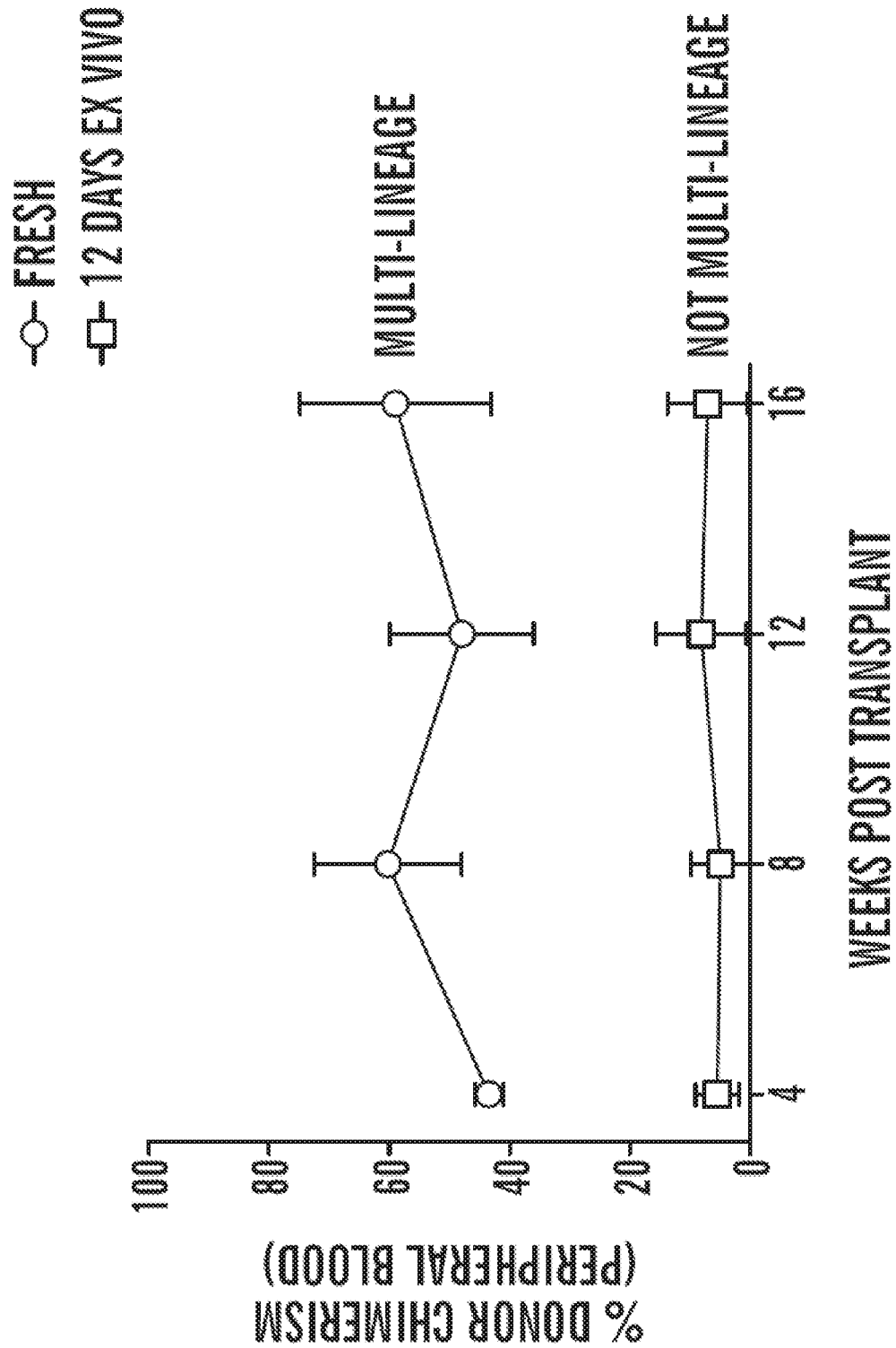
FIG. 1 shows that HSC potential is rapidly lost upon culture. Peripheral bleed analysis following transplantation into lethally irradiated hosts of freshly isolated murine HSCs or HSCs cultured for 12 days ex vivo in S-clone+IL12/SCF/TPO+0.75% BSA. Note that the cultured cells do not retain the ability to give rise to peripheral blood donor chimerism that is multi-lineage (B-cells, T-cells, myeloid cells, granulocytes) whereas freshly transplanted HSCs give rise to robust levels of donor peripheral blood chimerism comprised of all of the blood lineages analyzed including B-cells, T-cells, myeloid cells, granulocytes.
Figure 2:
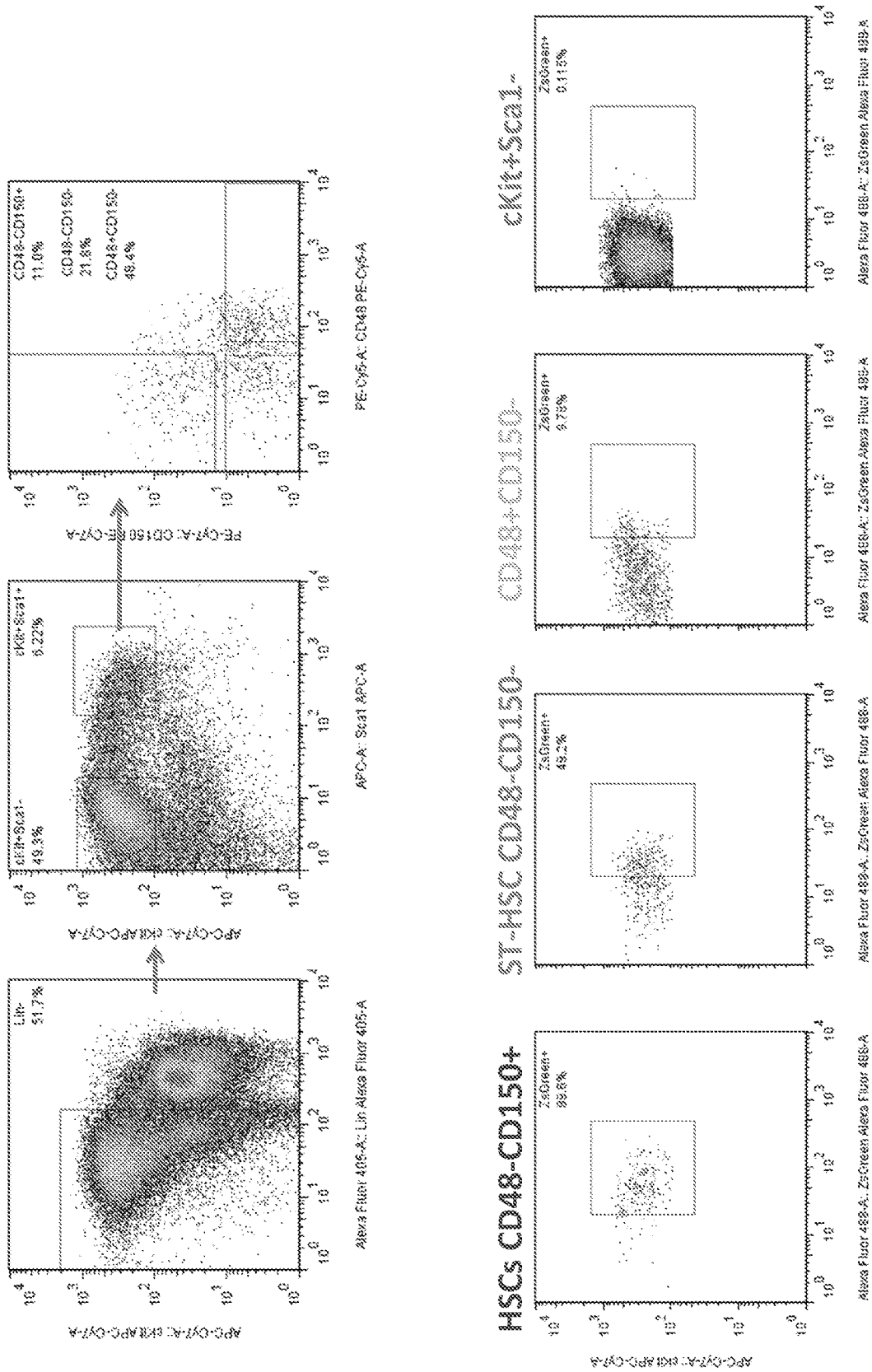
FIG. 2 shows that engineered Fgd5-ZsGreen reporter mouse faithfully labels HSCs. Bone marrow cells from Fgd5-ZsGreen reporter mouse was enriched for cKit+ cells using magnetic beads and analyzed by flow cytometry for ZsGreen expression and a panel of markers (Lineage (Ter119, CD3, CD4, CD8, B220, Mac1, Gr1, Il7RA), cKit, Sca1, CD150, CD48). ZsGreen expression is shown for the indicated stem/progenitor subpopulations. More details on the construction, characterization and specificity of the Fgd5-ZsGreen HSC reporter mouse can be found in; Gazit R, Mandal P K, Ebina W, Ben-Zvi A, Nombela-Arrieta C, Silberstein L E, Rossi D J. Journal of Experimental Medicine, 211(7):1315-31 (2014).
Figure 3A:
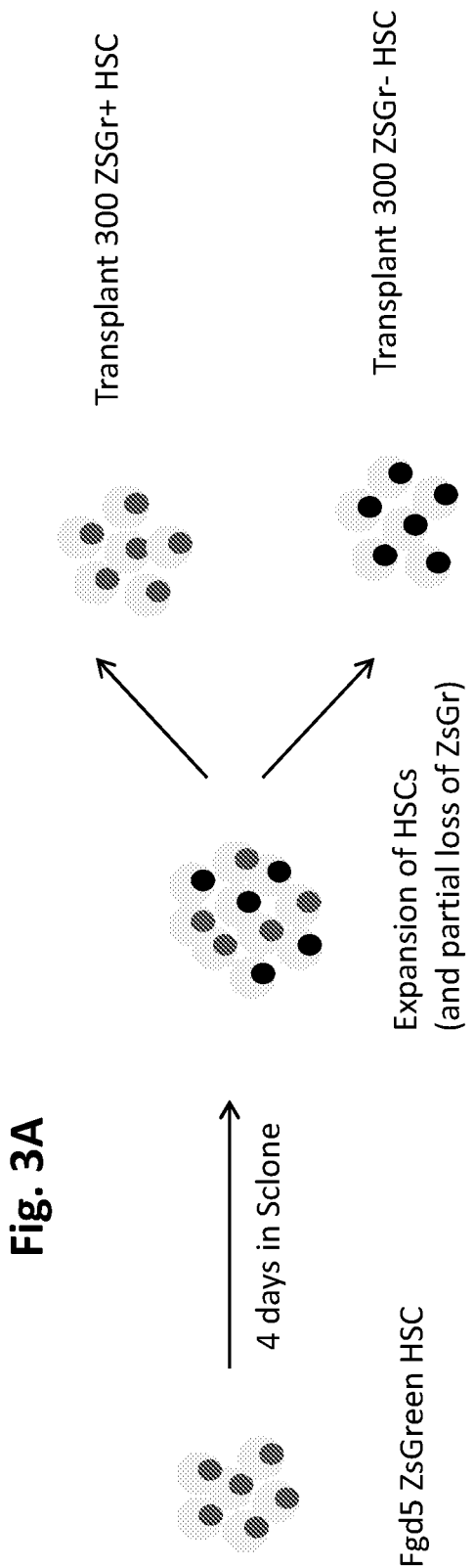
FIGS. 3A-3B show that Fgd5·ZsGr+ marks HSC potential during ex vivo culturing of HSCs.
Figure 3B:
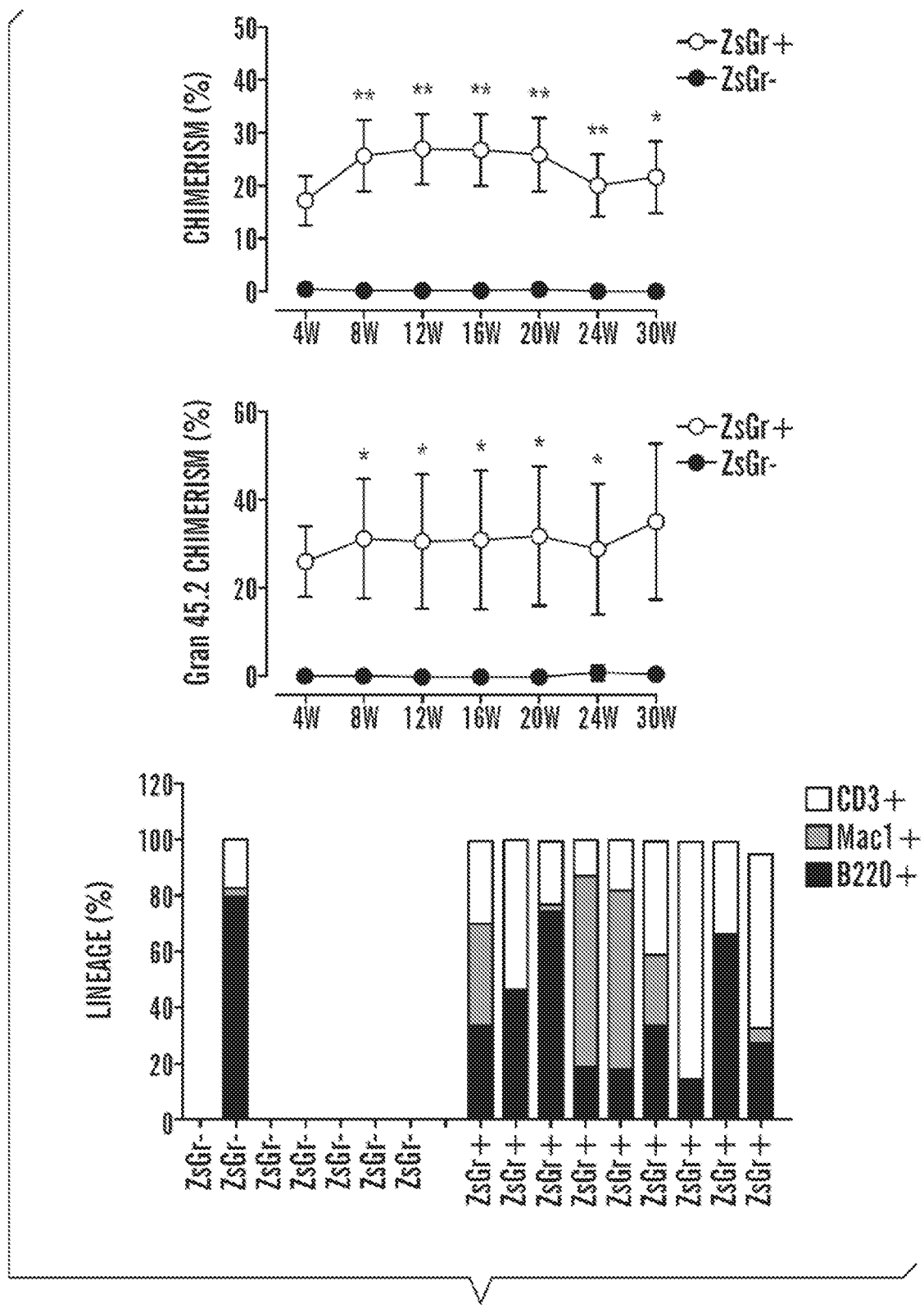

The present invention is based on the surprising discovery that the ex vivo expansion, enrichment, and maintenance of populations of hematopoietic stem cells bearing hematopoietic stem cell functional potential can be achieved by contacting these cells with one or more agents that exhibit one, two, or more activities selected from the group consisting of modulation of histone methylation, inhibition of TGFβ signaling, inhibition of p38 signaling, activation of canonical Wnt signaling, and modulation of histone acetylation. A wide variety of structurally and mechanistically distinct agents that modulate these biological events are known in the art. For instance, these agents may be small molecules capable of agonizing or antagonizing a particular event within a certain pathway (e.g., small molecules that inhibit enzymatic activity of proteins that propagate a signal transduction cascade). These agents may also be antibodies, such as monoclonal antibodies or antigen-binding fragments thereof, that disrupt a particular interaction (e.g., a ligand-receptor interaction) by virtue of competitively binding a particular protein and sterically precluding the association of the protein with its cognate binding partner. Other agents, such as therapeutic proteins and structurally constrained peptides, are topologically well-suited for antagonizing protein-protein interactions that occur over larger molecular surfaces and thus represent a class of inhibitors capable of intervening within signal transduction pathways at targets that have otherwise been intractable to disrupting with conventional small molecule therapeutics. Other classes of inhibitors include interfering RNA molecules, which are capable of attenuating the expression of a target gene by binding mRNA polynucleotides via complementary hydrogen bonding and, e.g., inducing the degradation of the target mRNA or sterically preventing the nucleation of ribosome assembly. The sections that follow provide an overview of examples of the types of agents useful with the compositions and methods of the invention so as to promote hematopoietic stem cell expansion, enrichment, and maintenance of hematopoietic stem cell functional potential.

UM171 and Structural Analogs Thereof

Additional agents that can be used in conjunction with the methods of the invention include UM171, a small molecule that has been shown to induce hematopoietic stem cell expansion. UM171 is described, e.g., in Fares et al. Science 345:1509 (2014), the disclosure of which is incorporated herein by reference. Other agents that can be used to expand, enrich, and maintain hematopoietic stem cells include UM171 analogs, such as a UM171 structural analogs according to any one of Formulas (I), (II), (III), (IV), (V), and (VI) of US 2015/0011543, the disclosure of which is incorporated herein by reference. For instance, analogs of UM171 that can be used in conjunction with the compositions and methods described herein include compounds listed in Table 11, below.

TABLE 11
UM171 and structural analogs thereof
| Compound No. | Molecular structure |
|---|---|
| 100 (UM171) | 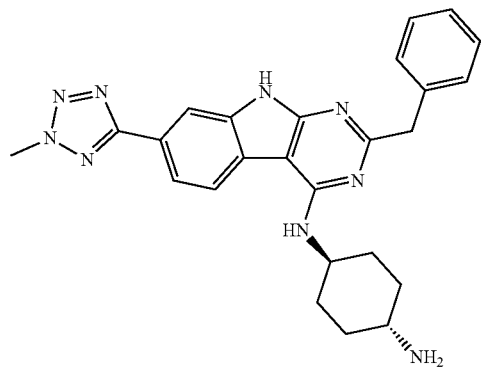 [SMILES: Cn1nnc(-c2ccc3c(c2)[nH]c2nc(Cc4ccccc4)nc(N[C@H]4CC[C@H](N)CC4)c23)n1] |
| 101 | 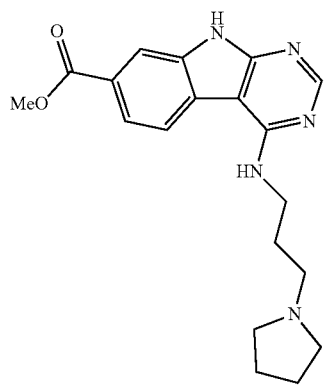 [SMILES: COC(=O)c1ccc2c(c1)[nH]c1ncnc(NCCCN3CCCC3)c12] |
| 102 | 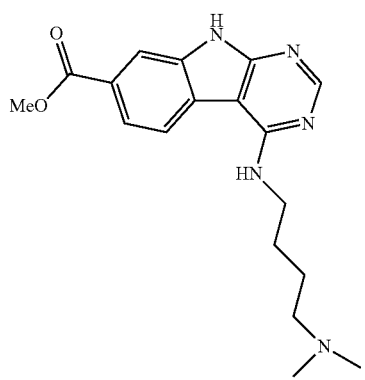 [SMILES: COC(=O)c1ccc2c(c1)[nH]c1ncnc(NCCCCN(C)C)c12] |
| 103 | 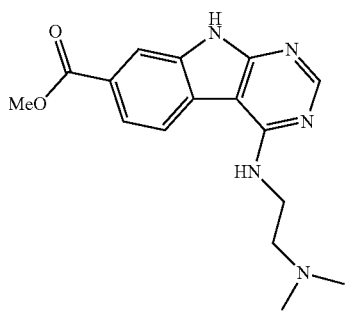 [SMILES: COC(=O)c1ccc2c(c1)[nH]c1ncnc(NCCN(C)C)c12] |

TABLE 11-continued
UM171 and structural analogs thereof
| Compound No. | Molecular structure |
|---|---|
| 104 | 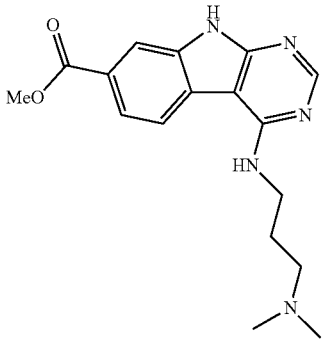 [SMILES: COC(=O)c1ccc2c(c1)[nH]c1ncnc(NCCCN(C)C)c12] |
| 105 | 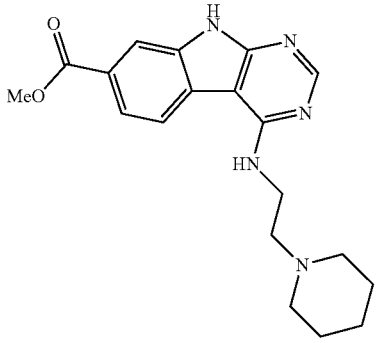 [SMILES: COC(=O)c1ccc2c(c1)[nH]c1ncnc(NCCN3CCCCC3)c12] |
| 106 | 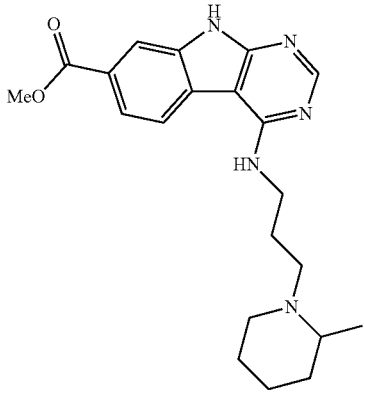 [SMILES: COC(=O)c1ccc2c(c1)[nH]c1ncnc(NCCCN3CCCCC3C)c12] |
| 107 | 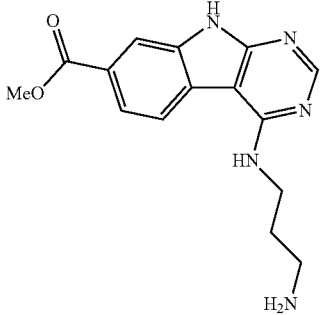 [SMILES: COC(=O)c1ccc2c(c1)[nH]c1ncnc(NCCCN)c12] |

TABLE 11-continued

UM171 and structural analogs thereof

| Compound No. | Molecular structure |
|---|---|
| 108 | 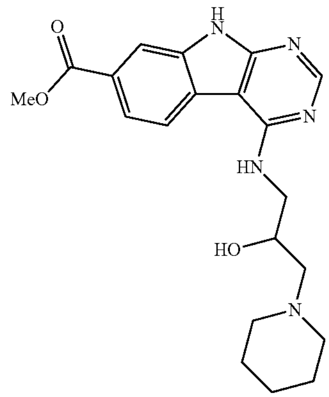 [SMILES: COC(=O)c1ccc2c(c1)[nH]c1ncnc(NCC(O)CN3CCCCC3)c12] |
| 109 | 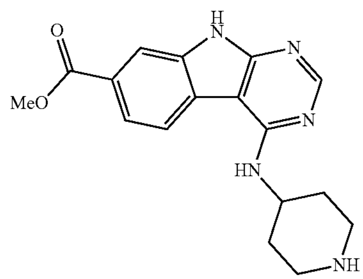 [SMILES: COC(=O)c1ccc2c(c1)[nH]c1ncnc(NC3CCNCC3)c12] |
| 110 | 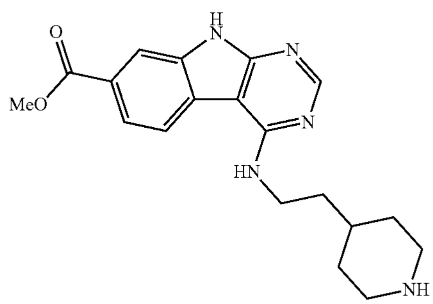 [SMILES: COC(=O)c1ccc2c(c1)[nH]c1ncnc(NCCC3CCNCC3)c12] |
| 111 | 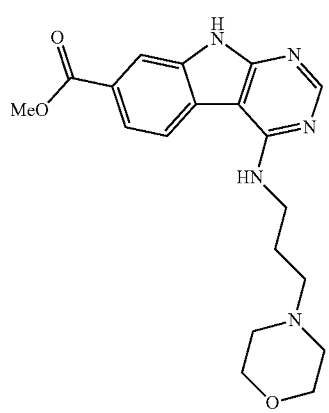 [SMILES: COC(=O)c1ccc2c(c1)[nH]c1ncnc(NCCCN3CCOCC3)c12] |

TABLE 11-continued
UM171 and structural analogs thereof
| Compound No. | Molecular structure |
|---|---|
| 112 | 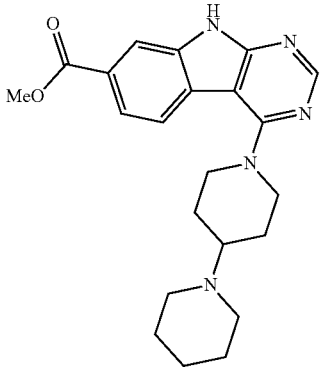 [SMILES: COC(=O)c1ccc2c(c1)[nH]c1ncnc(N3CCC(N4CCCCC4)CC3)c12] |
| 113 | 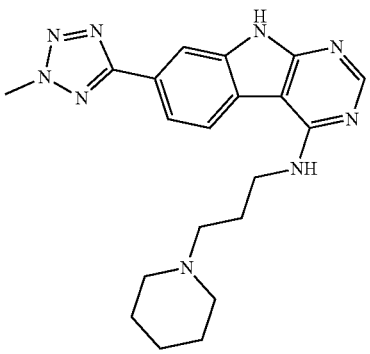 [SMILES: Cn1nnc(-c2ccc3c(c2)[nH]c2ncnc(NCCCN4CCCCC4)c23)n1] |
| 114 | 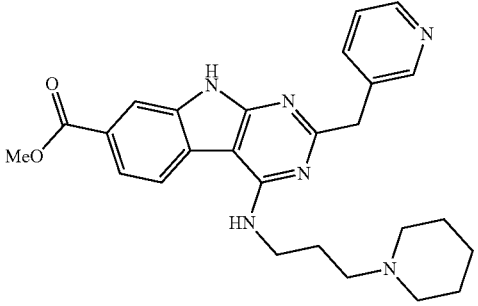 [SMILES: COC(=O)c1ccc2c(c1)[nH]c1nc(Cc3cccnc3)nc(NCCCN3CCCCC3)c12] |
| 115 | 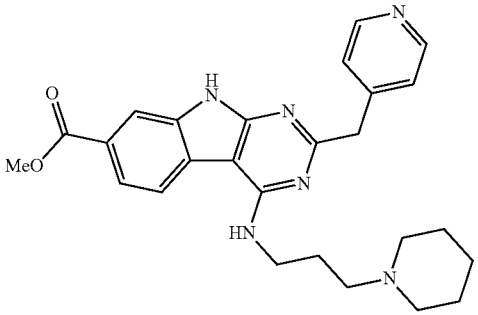 [SMILES: COC(=O)c1ccc2c(c1)[nH]c1nc(Cc3ccncc3)nc(NCCCN3CCCCC3)c12] |

TABLE 11-continued

UM171 and structural analogs thereof

| Compound No. | Molecular structure |
|---|---|
| 116 | 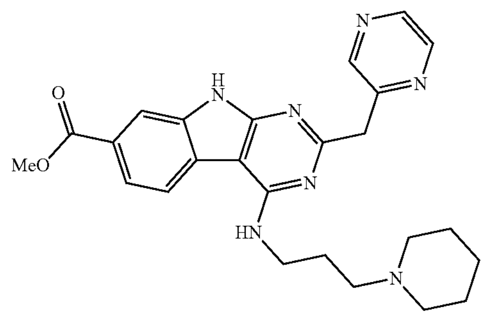 [SMILES: COC(=O)c1ccc2c(c1)[nH]c1nc(Cc3cnccn3)nc(NCCCN3CCCCC3)c12] |
| 117 | 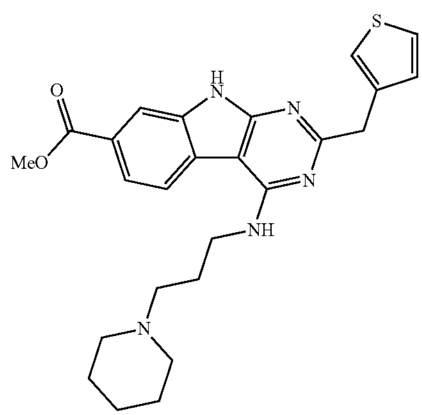 [SMILES: COC(=O)c1ccc2c(c1)[nH]c1nc(Cc3ccsc3)nc(NCCCN3CCCCC3)c12] |
| 118 | 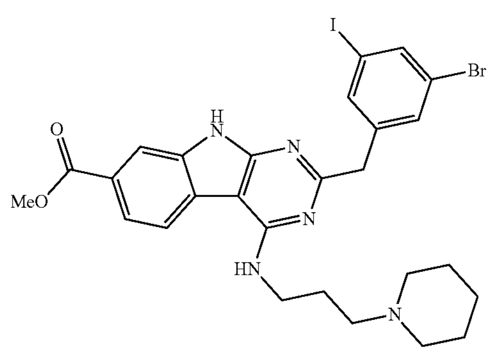 [SMILES: COC(=O)c1ccc2c(c1)[nH]c1nc(Cc3cc(Br)cc(I)c3)nc(NCCCN3CCCCC3)c12] |
| 119 | 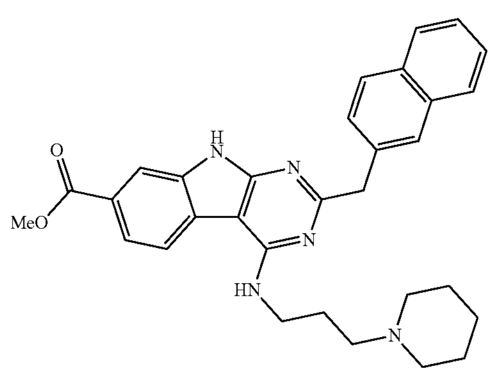 [SMILES: COC(=O)c1ccc2c(c1)[nH]c1nc(Cc3ccc4ccccc4c3)nc(NCCCN3CCCCC3)c12] |

TABLE 11-continued
UM171 and structural analogs thereof
| Compound No. | Molecular structure |
|---|---|
| 120 | 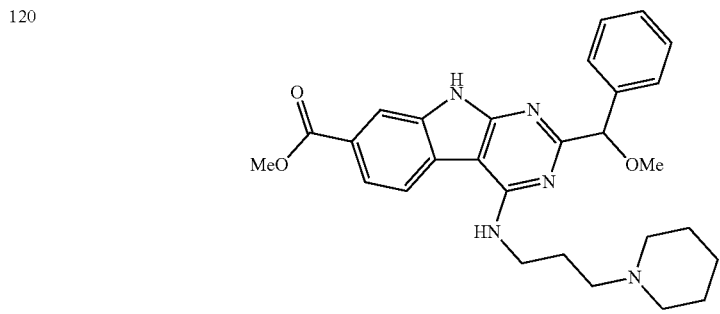 |
| 121 | 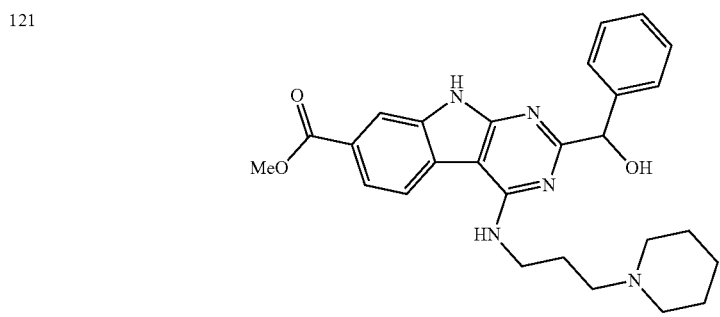 |
| 122 | 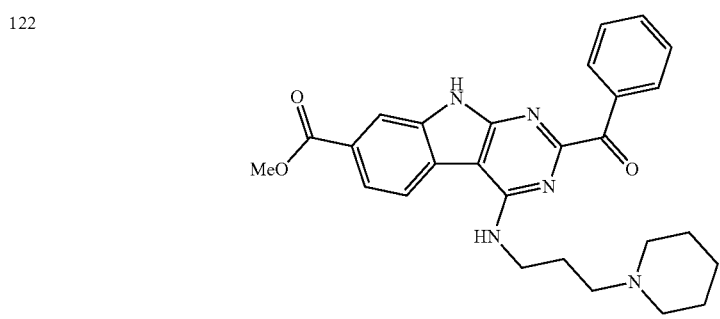 |
| 123 | 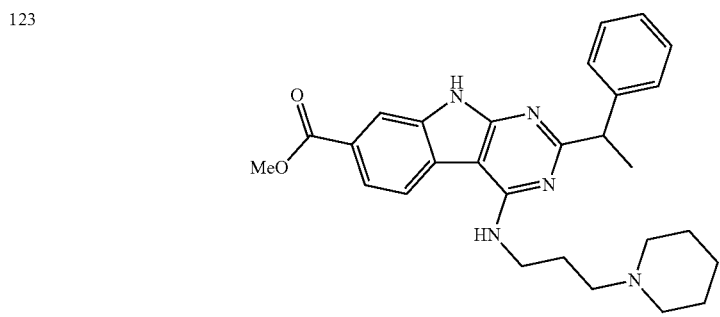 |

TABLE 11-continued

UM171 and structural analogs thereof

| Compound No. | Molecular structure |
|---|---|
| 124 | Methyl ester-substituted pyrimido-indole with 4-(3-piperidin-1-yl-propylamino) and 2-[3-(3-trifluoromethyl-3H-diazirin-3-yl)benzyl] substituents |
| 125 | Ethyl ester-substituted pyrimido-indole with 4-(3-piperidin-1-yl-propylamino) and 2-benzyl substituents |
| 126 | Methyl ester-substituted pyrimido-indole with 4-(3-piperidin-1-yl-propylamino) and 2-benzyl substituents |
| 127 | Methyl ester-substituted pyrimido-indole with 4-(3-piperidin-1-yl-propylamino) and 2-(3-bromobenzyl) substituents |

TABLE 11-continued
UM171 and structural analogs thereof
| Compound No. | Molecular structure |
|---|---|
| 128 | 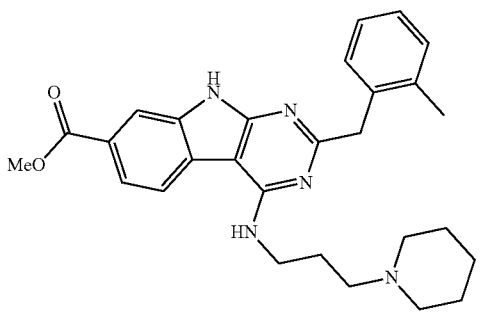 [SMILES: COC(=O)c1ccc2c(c1)[nH]c1nc(Cc3ccccc3C)nc(NCCCN3CCCCC3)c12] |
| 129 | 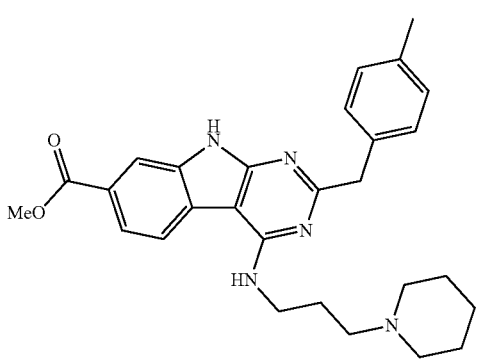 [SMILES: COC(=O)c1ccc2c(c1)[nH]c1nc(Cc3ccc(C)cc3)nc(NCCCN3CCCCC3)c12] |
| 130 | 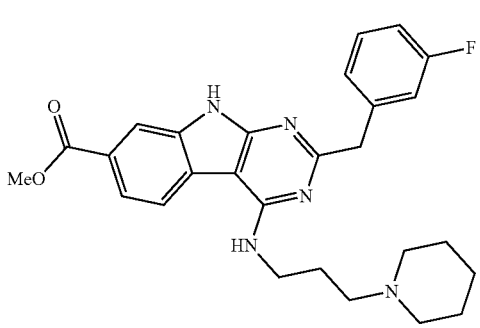 [SMILES: COC(=O)c1ccc2c(c1)[nH]c1nc(Cc3cccc(F)c3)nc(NCCCN3CCCCC3)c12] |
| 131 | 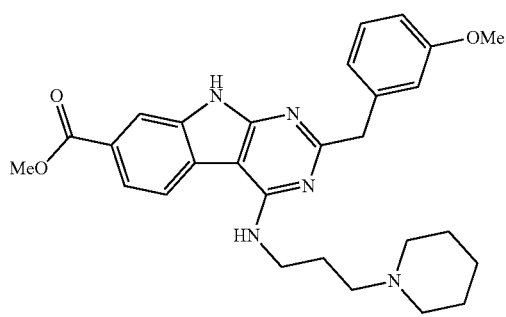 [SMILES: COC(=O)c1ccc2c(c1)[nH]c1nc(Cc3cccc(OC)c3)nc(NCCCN3CCCCC3)c12] |

TABLE 11-continued
UM171 and structural analogs thereof
| Compound No. | Molecular structure |
|---|---|
| 132 | 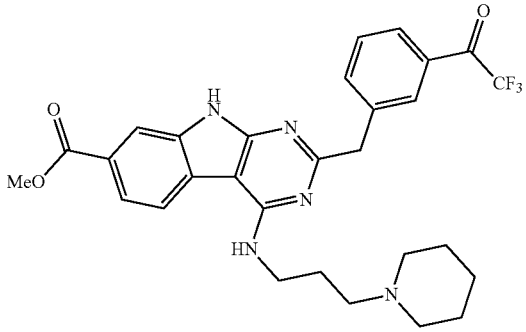 [SMILES: COC(=O)c1ccc2c(c1)[nH]c1nc(Cc3cccc(C(=O)C(F)(F)F)c3)nc(NCCCN3CCCCC3)c12] |
| 133 | 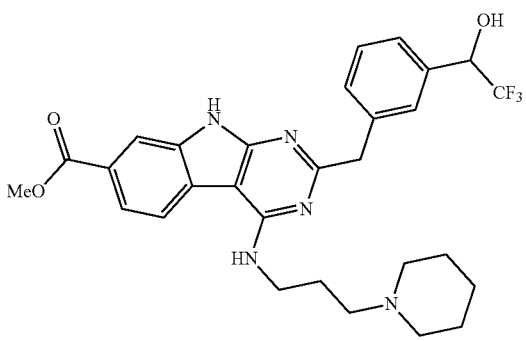 [SMILES: COC(=O)c1ccc2c(c1)[nH]c1nc(Cc3cccc(C(O)C(F)(F)F)c3)nc(NCCCN3CCCCC3)c12] |
| 134 | 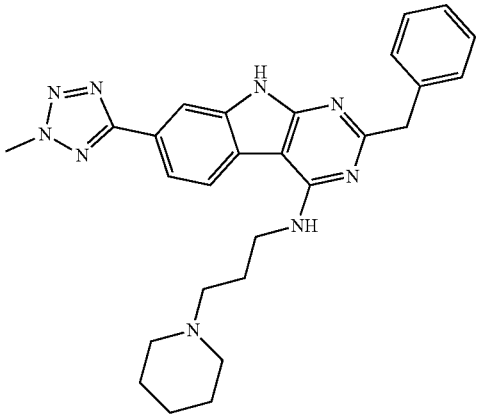 [SMILES: Cn1nnc(-c2ccc3c(c2)[nH]c2nc(Cc4ccccc4)nc(NCCCN4CCCCC4)c23)n1] |
| 135 | 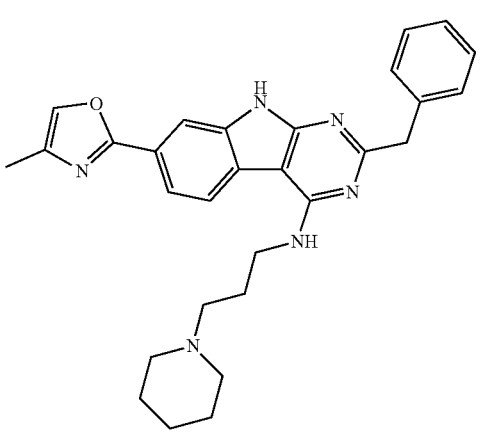 [SMILES: Cc1coc(-c2ccc3c(c2)[nH]c2nc(Cc4ccccc4)nc(NCCCN4CCCCC4)c23)n1] |

TABLE 11-continued
UM171 and structural analogs thereof
| Compound No. | Molecular structure |
| --- | --- |
| 136 | 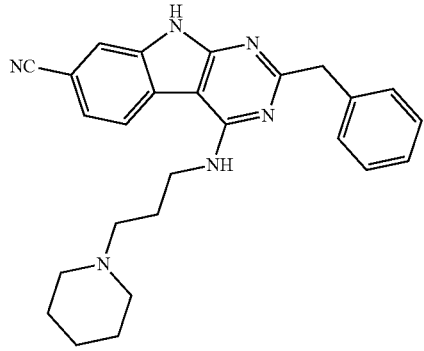 [SMILES: N#Cc1ccc2c(c1)[nH]c1nc(Cc3ccccc3)nc(NCCCN3CCCCC3)c12] |
| 137 | 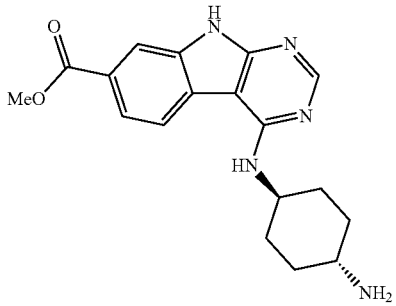 [SMILES: COC(=O)c1ccc2c(c1)[nH]c1ncnc(N[C@H]3CC[C@H](N)CC3)c12] |
| 138 | 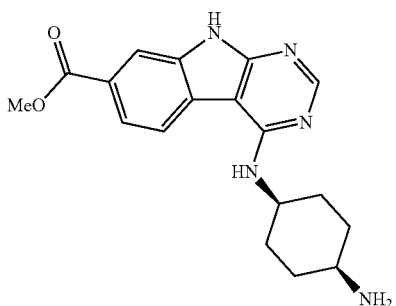 |
| 139 | 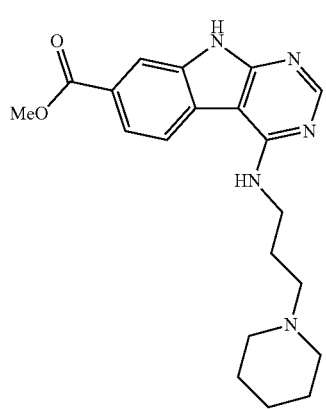 [SMILES: COC(=O)c1ccc2c(c1)[nH]c1ncnc(NCCCN3CCCCC3)c12] |

TABLE 11-continued
UM171 and structural analogs thereof
| Compound No. | Molecular structure |
| --- | --- |
| 140 | 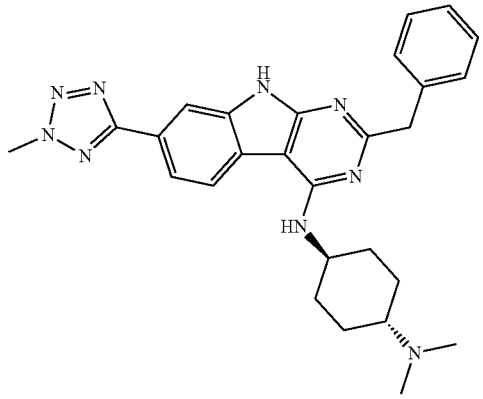 [SMILES: Cn1nnc(-c2ccc3c(c2)[nH]c2nc(Cc4ccccc4)nc(N[C@H]4CC[C@H](N(C)C)CC4)c23)n1] |
| 141 | 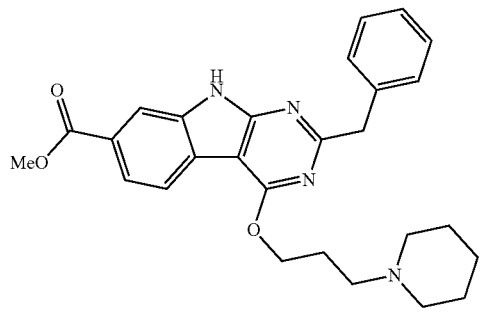 [SMILES: COC(=O)c1ccc2c(c1)[nH]c1nc(Cc3ccccc3)nc(OCCCN3CCCCC3)c12] |
| 142 | 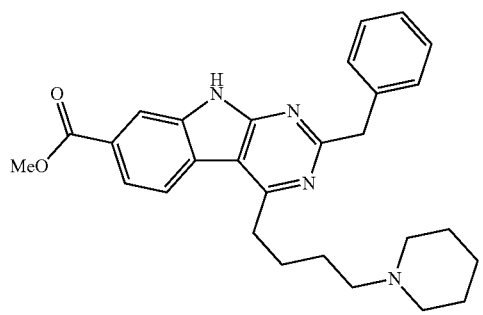 |
| 143 | 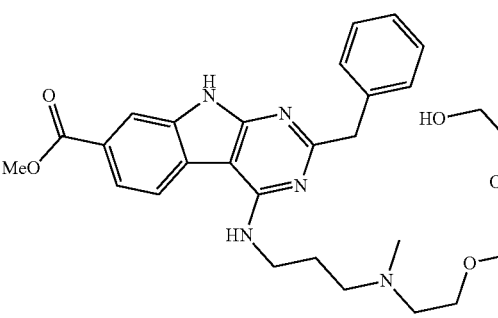 |

TABLE 11-continued

UM171 and structural analogs thereof

| Compound No. | Molecular structure |
|---|---|
| 144 | *(structure: methyl 2-benzyl-4-{[3-(methyl(3-aminopropyl)amino)propyl]amino}-9H-pyrimido[4,5-b]indole-7-carboxylate)* |
| 145 | *(structure: methyl 2-benzyl-4-{[2-hydroxy-3-(piperidin-1-yl)propyl]amino}-9H-pyrimido[4,5-b]indole-7-carboxylate)* |
| 146 | *(structure: methyl 2-benzyl-4-{[3-(piperidin-1-yl)-2-(prop-2-yn-1-yloxy)propyl]amino}-9H-pyrimido[4,5-b]indole-7-carboxylate)* |
| 147 | *(structure: methyl 2-benzyl-4-{methyl[3-(piperidin-1-yl)propyl]amino}-9H-pyrimido[4,5-b]indole-7-carboxylate)* |

TABLE 11-continued
UM171 and structural analogs thereof
| Compound No. | Molecular structure |
|---|---|
| 148 | 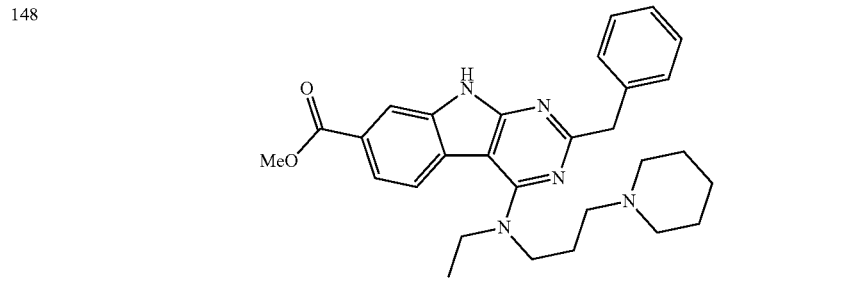 |
| 149 | 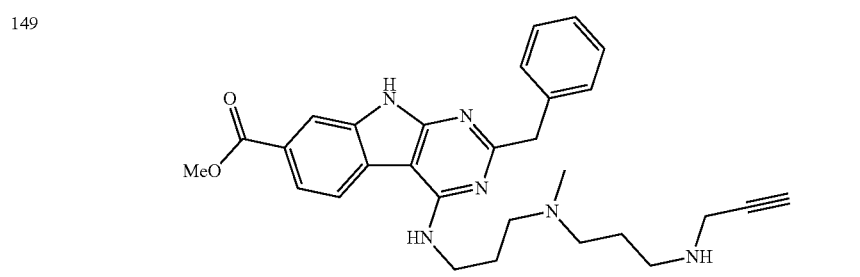 |
| 150 | 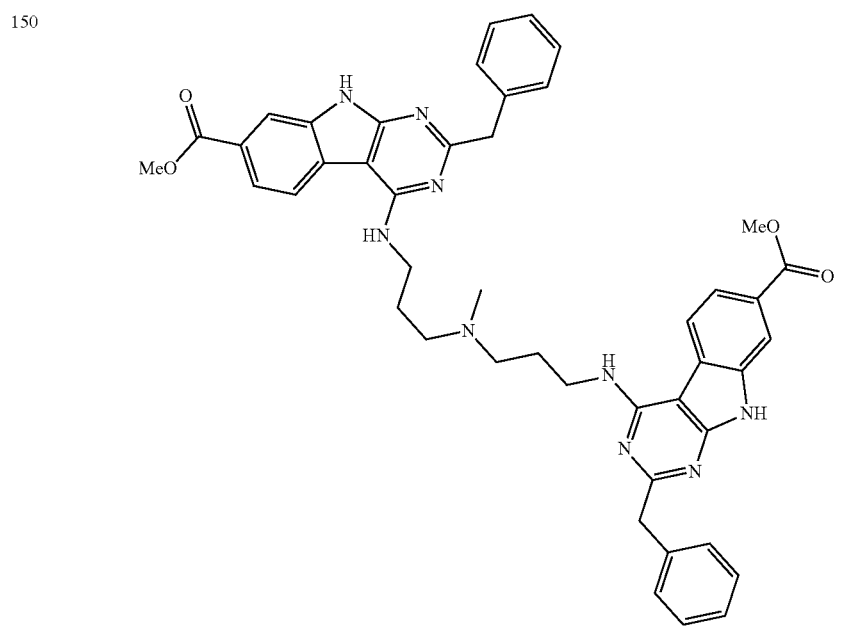 |

TABLE 11-continued
UM171 and structural analogs thereof
| Compound No. | Molecular structure |
|---|---|
| 151 | 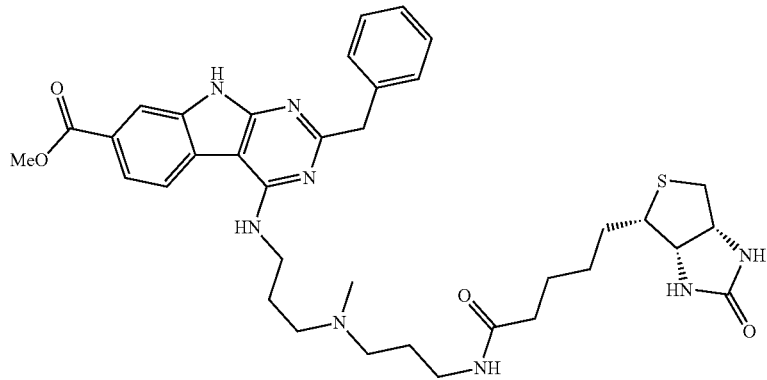 [SMILES: COC(=O)c1ccc2c(c1)[nH]c1nc(Cc3ccccc3)nc(NCCCN(C)CCCNC(=O)CCCC[C@@H]3SC[C@@H]4NC(=O)N[C@@H]43)c12] |
| 152 | 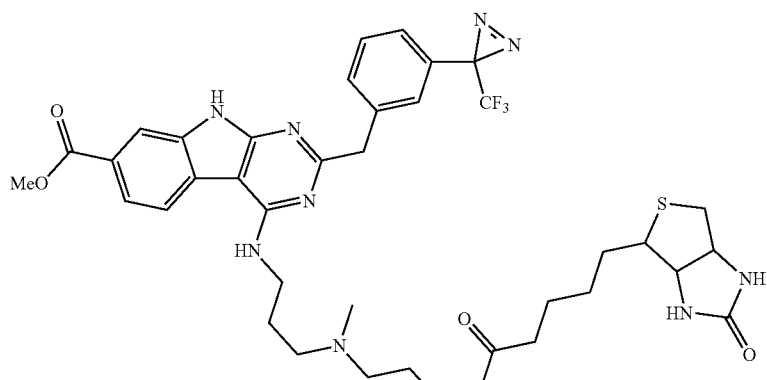 |
| 153 | 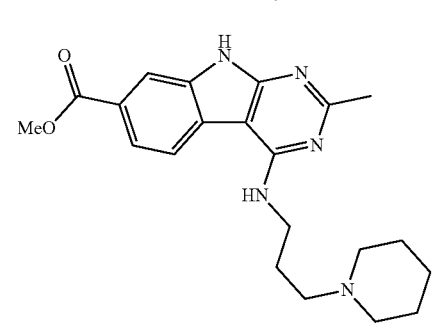 [SMILES: COC(=O)c1ccc2c(c1)[nH]c1nc(C)nc(NCCCN3CCCCC3)c12] |
| 154 | 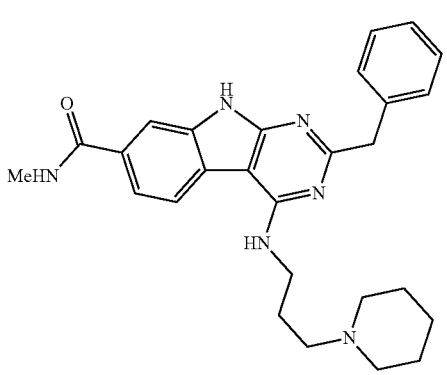 [SMILES: CNC(=O)c1ccc2c(c1)[nH]c1nc(Cc3ccccc3)nc(NCCCN3CCCCC3)c12] |

Small Molecules

A variety of small molecules may be used in conjunction with the methods described herein. Among these include modulators of enzyme-substrate interactions. A variety of small molecules have been developed in order to antagonize enzyme-substrate interactions or to intervene at distinct points within a signal transduction cascade. For instance, tranylcypromine and derivatives thereof represent a robust class of inhibitors capable of irreversibly binding to and inhibiting histone demethylases such as LSD1 by virtue of forming a covalent adduct with the isoalloxazine moiety of the FAD cofactor utilized by these enzymes to catalyze oxidative demethylation of N-methylated histone tail residues. Exemplary small molecule inhibitors of histone demethylation useful with the compositions and methods of the invention include LSD1 inhibitor IV RN-1, LSD1 inhibitor II S2101, LSD1 inhibitor LSD1-C76, LSD1 inhibitor III CBB1007, LSD1 inhibitor I (also referred to as BHC110 Inhibitor I, Histone Lysine Demethylase Inhibitor III, and/or KDM1 Inhibitor I), and tranylcypromine, described above. Examples of small molecules useful for inhibiting histone demethylases additionally include phenelzine, propargylamine, and derivatives thereof as described in US 2013/0095067, the disclosure of which is incorporated herein by reference. Other tranylcypromine derivatives have been described, e.g., in US 2014/0163041, the disclosure of which is incorporated herein by reference.

Additional examples of small molecules that can be used to modulate histone methylation include BIX01294 (a H3K9 methylation inhibitor described in, e.g., WO 2014/057997); UNC0638 (a H3K9 methylation inhibitor described in, e.g., WO 2013/050422), the disclosures of each of which are incorporated herein by reference; and CARM1 Inhibitor (PRMT Inhibitor V, 3,5-bis(3-Bromo-4-hydroxybenzylidene)-1-benzylpiperidin-4-one, a histone arginine methyltransferase inhibitor).

Several structurally distinct classes of small molecules inhibitors of TGFβ signaling have been reported. These agents can be classified on the basis of the core molecular scaffolds of these molecules. For example, TGFβ signaling inhibitors may contain a dihydropyrrlipyrazole, imidazole, pyrazolopyridine, pyrazole, imidazopyridine, triazole, pyridopyrimidine, pyrrolopyrazole, isothiazole or oxazole functionality as the core structural fragment of the molecule. Some non-limiting examples of small molecule inhibitors of TGFβ signaling include ALK5 inhibitor II (also referred to as E-616452), LY364947 (also referred to as ALK5 Inhibitor I, TbR-I Inhibitor, Transforming Growth Factor-b Type I Receptor Kinase Inhibitor), A83-01, and DMH1, described above. Other examples of small molecules that can be used to modulate TGFβ signaling in conjunction with the compositions and methods of the invention include SB431542 (4-(5-Benzol[1,3]dioxol-5-yl-4-pyrldin-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl]-benzamide hydrate, an Alk5 inhibitor), Galunisertib (LY2157299, an Alk5 inhibitor), LY2109761 (4-[2-[4-(2-pyridin-2-yl-5,6-dihydro-4H-pyrrolo[1,2-b]pyrazol-3-yl)quinolin-7-yl]oxyethyl]morpholine, an Alk5/TGFβRII inhibitor), SB525334 (6-[2-tert-butyl-5-(6-methylpyridin-2-yl)-1H-imidazol-4-yl]quinoxaline, an Alk5 inhibitor), GW788388 (N-(oxan-4-yl)-4-[4-(5-pyridin-2-yl-1H-pyrazol-4-yl)pyridin-2-yl]benzamide, an Alk5 inhibitor), K02288 (3-[6-amino-5-(3,4,5-trimethoxyphenyl)pyridin-3-yl]phenol, an Alk4/Alk5 inhibitor), SD-208 (2-(5-chloro-2-fluorophenyl)-N-pyridin-4-ylpteridin-4-amine, an Alk5 inhibitor), EW-7197 (N-((4-([1,2,4]triazolo[1,5-a]pyridin-6-yl)-5-(6-methylpyridin-2-yl)-1H-imidazol-2-yl)methyl)-2-fluoroaniline, an Alk4/Alk5 inhibitor), and LDN-212854(5-[6-[4-(1-Piperazinyl)phenyl]pyrazolo[1,5-a]pyrimidin-3-yl]-quinoline, an Alk4/Alk5 inhibitor).

Additional examples of small molecule TGFβ modulators include antagonists of TGFβ receptors, such as 2-(3-(6-Methylpyridin-2-yl)-1H-pyrazol-4-yl)-1,5 napthyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole. Other small molecule inhibitors include, but are not limited to, SB-431542, (4-[4-(1,3-Benzodioxol-5-yl)-5-(2-pyridinyl)-1H-imidazol-2-yl]-benzamide, described in Halder et al. Neoplasia 7:509 (2005)), SM16, a small molecule inhibitor of TGFβ receptor ALK5, the structure of which is shown below (Fu et al. Arteriosclerosis, Thrombosis and Vascular Biology 28:665 (2008)), SB-505124 (an Alk4/Alk5 inhibitor, structure shown below, described in Dacosta Byfield et al. Molecular Pharmacology 65:744 (2004)), and 6-bromo-indirubin-3'-oxime (described in U.S. Pat. No. 8,298,825), the disclosures of each of which are incorporated herein by reference.

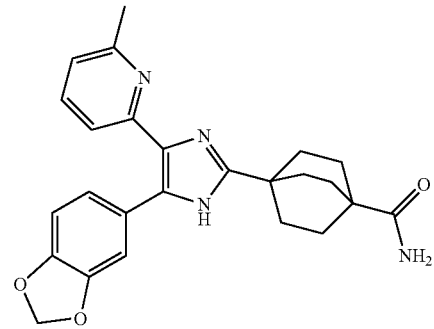

SM16

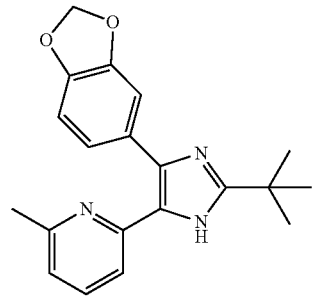

SB-505124

Additional examples of inhibitors of TGF-β signaling are described in, e.g., Callahan et al. Journal of Medicinal Chemistry 45:999 (2002); Sawyer et al. Journal of Medicinal Chemistry 46:3953 (2003); Gellibert et al. Journal of Medicinal Chemistry 47:4494 (2004); Tojo et al. Cancer Science 96:791 (2005); Petersen et al. Kidney International 73:705 (2008); Yingling et al. Nature Reviews Drug Discovery 3:1011 (2004); Byfield et al. Molecular Pharmacology 65:744 (2004); Dumont et al. Cancer Cell 3:531 (2003); WO 2002/094833; WO 2004/026865; WO 2004/067530; WO 2009/032667; WO 2004/013135; WO 2003/097639; WO 2007/048857; WO 2007/018818; WO 2006/018967; WO 2005/039570; WO 2000/031135; WO 1999/058128; U.S. Pat. Nos. 6,509,318; 6,090,383; 6,419,928; 7,223,766; 6,476,031; 6,419,928; 7,030,125; 6,943,191; US 2005/0245520; US 2004/0147574; US 2007/0066632; US 2003/

0028905; US 2005/0032835; US 2008/0108656; US 2004/015781; US 2004/0204431; US 2006/0003929; US 2007/0155722; US 2004/0138188; and US 2009/0036382, the disclosures of each which are incorporated herein by reference.

Another class of small molecules useful with the compositions and methods of the invention include modulators of bone morphogenetic protein (BMP) signaling. BMP is a member of the TGF superfamily of ligands, and modulators of BMP signaling, such as inhibitors of Alk2, Alk3, and Alk6, can be used in conjunction with the methods of the invention, e.g., to expand, enrich, and/or maintain hematopoietic stem cells in a multi-potent state. Exemplary BMP inhibitors include DMH1 (4-[6-(4-Isopropoxyphenyl) pyrazolo[1,5-a]pyrimidin-3-yl]quinoline, 4-[6-[4-(1-Methylethoxy)phenyl]pyrazolo[1,5-a]pyrimidin-3-yl]-quinoline), K02288 (3-(6-amino-5-(3,4,5-trimethoxyphenyl)pyridin-3-yl)phenol), LDN-212854 (5-[6-[4-(1-Piperazinyl)phenyl] pyrazolo[1,5-a]pyrimidin-3-yl]-quinoline), LDN-193189 (4-[6-[4-(1-Piperazinyl)phenyl]pyrazolo[1,5-a]pyrimidin-3-yl]-quinoline), LDN-214117 (1-(4-(6-Methyl-5-(3,4,5-trimethoxyphenyl)pyridin-3-yl)phenyl)piperazine), and ML347 (5-[6-(4-methoxyphenyl)pyrazolo[1,5-a]pyrimidin-3-yl]quinoline).

Inhibitors of receptor tyrosine kinases, such as vascular endothelial growth factor (VEGF) and platelet-derived growth factor (PDGF) signaling can also be used in conjunction with the compositions and methods of the invention to promote hematopoietic stem cell expansion, enrichment, and maintenance of hematopoietic stem cell functional potential. For instance, an exemplary VEGF/PDGF inhibitor useful with the methods described herein is ABT-869 (Linifanib, 1-[4-(3-amino-1H-indazol-4-yl)phenyl]-3-(2-fluoro-5-methylphenyl)urea).

Other small molecules useful with the compositions and methods of the invention include inhibitors of DNA methylation, including chemical modulators of DNMT1, DNMT3a, and DNMT3B. An exemplary inhibitor of these targets that can be used in conjunction with the compositions and methods of the invention to expand, enrich, and maintain the hematopoietic stem cell functional potential of hematopoietic stem cells is RG108 (N-Phthalyl-L-tryptophan).

A variety of small molecule inhibitors of p38 MAPK have also been reported to date, including the pyridinylimidazole compounds SB203580 (4-(4-Fluorophenyl)-2-(4-methylsulfinylphenyl)-5-(4-pyridyl)1H-imidazole) and SB202190 (4(4-Fluorophenyl)-2-(4-hydroxyphenyl)-5-(4-pyridyl) 1H-imidazole). These compounds represent a class of inhibitors that selectively antagonize p38 MAPK α- and β-isoforms without disrupting the enzymatic activity of the γ- or β-isoforms. These compounds are described in U.S. Pat. No. 6,602,896, the disclosure of which is incorporated herein by reference. Other example of p38 MAPK inhibitors include SB203580, BIRB796 (Doramapimod), VX702, SB202190, LY2228820, VX745, Vinorelbine (Navelbine), PH797804, pamapimod, CMPD-1, EO1428, JX401, ML3403, RWJ67657, SB239063, SCIO469 hydrochloride, SKF86002 dihydrochloride, SX011, and TAK715, e.g., as described in US 2014/0127231, the disclosure of which is incorporated herein by reference. Additional examples of p38 inhibitors useful with the compositions and methods of the invention include Pexmetinib (ARRY-614), PH-797804 (3-(3-Bromo-4-((2,4-difluorobenzyl)oxy)-6-methyl-2-oxopyridin-1(2H)-yl)-N,4-dimethylbenzamide), Losmapimod (GW856553X), and Skepinone-L.

Small molecule agents capable of inhibiting a protein that promotes the degradation of β-catenin include those capable of attenuating the activity of proteins that promote β-catenin phosphorylation. Such inhibitors serve to increase the nuclear concentration of this transcription factor, and a variety of examples are known in the art. Inhibitors of β-catenin phosphorylation include compounds that inhibit glycogen synthase kinase 3 (GSK3), such as CHIR99021, described above, as well as 6-bromo-indirubin-3'-oxime (Meijer et al. Chemistry and Biology 10:1255 (2003); Goessling et al. Cell 136:1136 (2009)), AR-A014418 (Bhat et al. Journal of Biological Chemistry 278:45937 (2003), and the organometallic GSK-3 inhibitor DW21 (Williams et al. Angewandte Chemie International Edition 44:1984 (2005)), the disclosures of which are incorporated herein by reference. Other small molecule modulators of Wnt signaling useful in conjunction with the compositions and methods of the invention to expand, enrich, and maintain the hematopoietic stem cell functional potential of hematopoietic stem cells include inhibitors of GSK3a and GSK3b, such as CHIR99021 and Lithium chloride.

Histone deacetylation is also amenable to targeting with small molecule therapeutics. Hydroxamic acids represent a particularly robust class of histone deacetylases that inhibit these enzymes by virtue of hydroxamate functionality that binds cationic zinc within the active sites of these enzymes. Exemplary inhibitors include trichostatin A, described above, as well as Vorinostat (N-hydroxy-N'-phenyl-octanediamide, described in Marks et al., Nature Biotechnology 25, 84 to 90 (2007); Stenger, Community Oncology 4, 384-386 (2007), the disclosures of which are incorporated by reference herein). Other histone deacetylase inhibitors include Panobinostat, described in Drugs of the Future 32(4): 315-322 (2007), the disclosure of which is incorporated herein by reference.

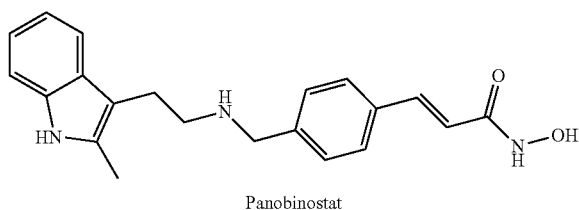 [SMILES: Cc1[nH]c2ccccc2c1CCNCc1ccc(/C=C/C(=O)NO)cc1]

Panobinostat

Additional examples of hydroxamic acid inhibitors of histone deacetylases include the compounds shown below, described in Bertrand, European Journal of Medicinal Chemistry 45:2095-2116 (2010), the disclosure of which is incorporated herein by reference:

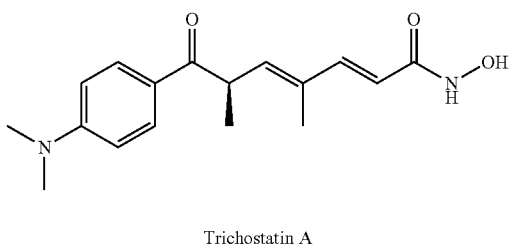

Trichostatin A

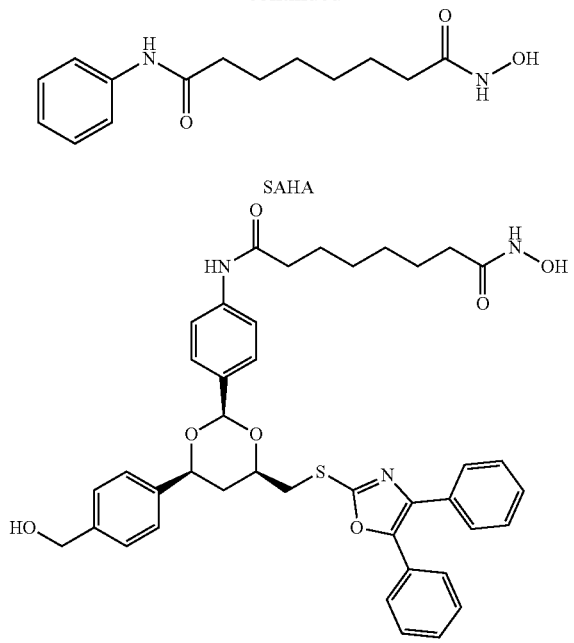

SAHA

Tubacin

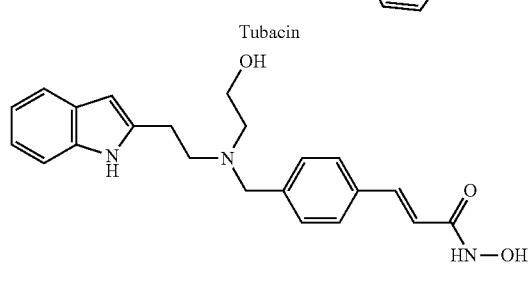

LAQ824

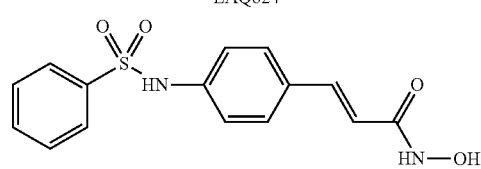

Sulfonamide

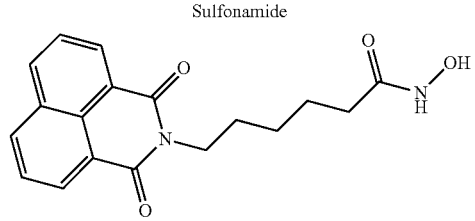

Scriptaid

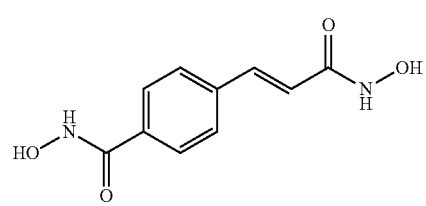

CBHA

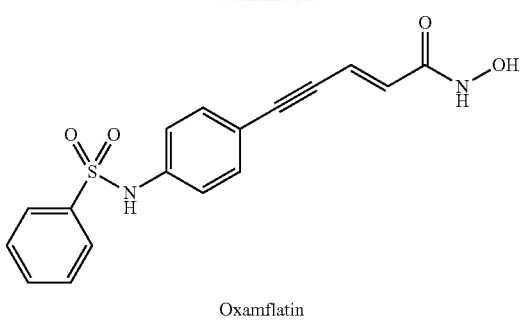

Oxamflatin

Other histone deacetylase inhibitors that do not contain a hydroxamate substituent have also been developed, including Valproic acid (Gottlicher et al. EMBO Journal 20: 6969 (2001) and Mocetinostat (N-(2-Aminophenyl)-4-[[(4-pyridin-3-ylpyrimidin-2-yl)amino]methyl]benzamide, described in Balasubramanian et al. Cancer Letters 280: 211 (2009), the disclosures of each of which are incorporated herein by reference. Other small molecule inhibitors that exploit chemical functionality distinct from a hydroxamate include those described in Bertrand, European Journal of Medicinal Chemistry 45:2095-2116 (2010), the disclosure of which is incorporated herein by reference. Other small molecule inhibitors that exploit chemical functionality distinct from a hydroxamate to inhibit histone deacetylases include those shown below.

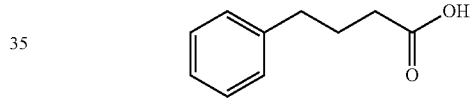

Phenylbutyric Acid

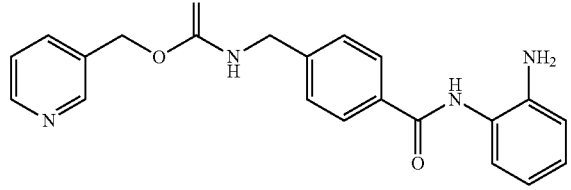

MS-275

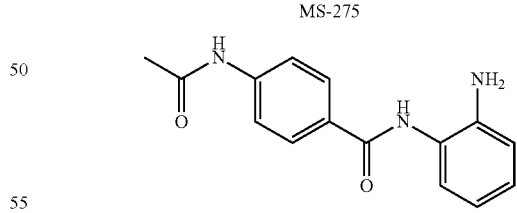

CI-994

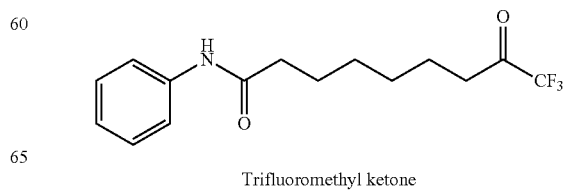

Trifluoromethyl ketone

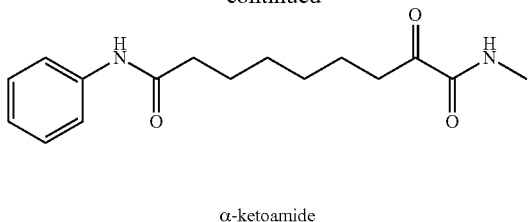

α-ketoamide

Additional examples of chemical modulators of histone acetylation useful with the compositions and methods of the invention to expand, enrich, and maintain the hematopoietic stem cell functional potential of hematopoietic stem cells include modulators of HDAC1, HDAC2, HDAC3, HDAC4, HDAC5, HDAC6, HDAC7, HDAC8, HDAC9, HDAC10, Sirt1, Sirt2, and/or HAT, such as butyrylhydroxamic acid, M344, LAQ824 (Dacinostat), AR-42, Belinostat (PXD101), CUDC-101, Scriptaid, Sodium Phenylbutyrate, Tasquinimod, Quisinostat (JNJ-26481585), Pracinostat (SB939), CUDC-907, Entinostat (MS-275), Mocetinostat (MGCD0103), Tubastatin A HCl, PCI-34051, Droxinostat, PCI-24781 (Abexinostat), RGFP966, Rocilinostat (ACY-1215), CI994 (Tacedinaline), Tubacin, RG2833 (RGFP109), Resminostat, Tubastatin A, BRD73954, BG45, 4SC-202, CAY10603, LMK-235, Nexturastat A, TMP269, HPOB, Cambinol, and Anacardic Acid.

Antibodies and Other Therapeutic Proteins

Antibodies represent a region of chemical space that is uniquely suited to target extracellular protein-protein interactions, such as receptor-ligand interactions. These agents possess the large molecular volume that is beneficial to inhibiting interactions that feature residues that contribute favorably to the free energy of the interaction dispersed over vast surfaces rather than confined to a shallow crevice. Antibody agents possess a large molecular volume that is beneficial for inhibiting interactions that occur over vast surfaces rather than within shallow crevice. Inhibitory antibodies may function by binding an extracellular receptor in such a way that sterically precludes interaction of the receptor with the cognate ligand and thus maintains the receptor in an inactive conformation. For instance, inhibitory antibodies capable of attenuating TGFβ receptor activity include Lerdelimumab, and an antibody that binds the TGFβ receptor type II. Other examples include GC-1008, an antibody that binds and antagonizes all isoforms of human TGFβ, as well as ID11, an antibody that binds all isoforms of murine TGFβ. These antibodies are described in detail, e.g., in U.S. Pat. No. 8,603,818, the disclosure of which is incorporated herein by reference.

Antagonist antibodies have also been developed that inhibit β-catenin phosphorylation by virtue of propagating the Wnt signal transduction cascade. Such antibodies may bind the Wnt receptors including Frizzled and LRP family proteins and trigger concomitant conformational changes that stimulate the propagation of the Wnt signaling pathway, which includes distinct molecular events that inhibit β-catenin phosphorylation by GKS3. For instance, the antibody 1D9 has been developed as an agonist of Wnt signal transduction, and is described in detail in US 2014/0044717, the disclosure of which is incorporated herein by reference.

Other classes of therapeutic proteins may additionally be used for inhibiting biological processes for expanding, enriching, and maintaining the hematopoietic stem cell functional potential of hematopoietic stem cells. Endogenous proteins that modulate signal transduction events may be used to attenuate these events ex vivo, thereby leveraging the natural affinity of these proteins for their cognate ligands in order to antagonize or stimulate important protein-protein interactions. For instance, a variety of proteins that antagonize the TGFβ signaling cascade can be used to this end, including Decorin, an extracellular matrix proteoglycan that negatively regulates TGFβ activity, as well as Lefty1, Lefty2, Follistatin, Noggin, Chordin, Cerberus, Germlin, Inhibin, Cystatin C, Recombinant Mouse Lefty-1 (an ACVR2B inhibitor), as well as the Smad proteins Smad6 and Smad7, which serve to prevent the phosphorylation of the R-Smad proteins or recruit ubiquitin ligases to the TGFβ receptor type I so as to promote the degradation of the receptor. These proteins are described in detail in U.S. Pat. No. 8,298,825, the disclosure of which is incorporated by reference herein.

Another modulator of TGFβ signaling that may be used in conjunction with the compositions and methods of the invention to expand, enrich, and maintain the hematopoietic stem cell functional potential of hematopoietic stem cells is Recombinant Amphibian TGF-β5 (an ACVR2A, ACVR2B, TGFβ RII activator).

In addition to the negative feedback proteins described above, proteins capable of inducing Wnt signaling so as to inhibit β-catenin phosphorylation have also been described. For instance, Rspondin (roof plate-specific spondin) proteins are also known to activate β-catenin signaling. Rspondin proteins do not bear sequence similarity to Wnt proteins and appear to potentiate Wnt signaling through a Frizzled-independent mechanism. This protein is described in detail in Kazanskaya. O., et al., Dev. Cell 7, 525-534 (2004), the disclosure of which is incorporated herein by reference.

Interfering RNA

RNA interference (RNAi) represents an inhibitory modality that exploits the ability of antagonistic RNA (e.g., double-stranded RNA containing an oligonucleotide capable of complementary hydrogen bond-mediated base pairing with an endogenous mRNA sequence) to attenuate intracellular gene expression. Mechanistically, this phenomenon often operates by way of degradation of the complementary mRNA or by steric inhibition of ribosome formation at the mRNA transcript. Long stretches of dsRNAs are often cleaved in the cytoplasm of a eukaryotic cell into short 21-25 nucleotide small interfering RNAs, known as siRNAs, by the ribonuclease known Dicer. These siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. The molecular events that underlie RISC-mediated gene silencing are described, for example, in U.S. Pat. No. 6,506,559; Fire et al., Nature 391(19):306-311 (1998); Timmons et al., Nature 395:854 (1998); Montgomery et al., TIG 14 (7):255-258 (1998); David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003), the disclosures of which are incorporated herein by reference.

Significantly, siRNA molecules useful with the compositions and methods of the invention need not be limited to those molecules containing only RNA, but may include, for example, chemically modified nucleotides and non-nucleotides that effect RNA interference, as well as molecules wherein a ribose sugar is replaced with another sugar molecule or analog thereof. Moreover, a non-natural linkage between nucleotide residues can be used, such as a phosphorothioate linkage, which is less susceptible to phosphodiesterase-mediated degradation. The RNA oligonucleotides useful with the compositions and methods of the invention may also be derivatized with a reactive functional group or a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups by standard nucleophilic substitution techniques known in the art. Other useful RNA derivatives incorporate nucleotides having modified carbohydrate moieties, such as 2'O-alkylated residues or 2'-O-methyl ribosyl derivatives and 2'-O-fluoro ribosyl derivatives that impart oligonucleotides with enhanced structural stability. The nucleobases of siRNAs may also be chemically modified. For example, halogenated bases, such as 5-bromouracil and 5-iodouracil can be incorporated into a siRNA molecule so as to modulate the strength of hydrogen bonding interactions with target mRNA. The nucleobases may also be strategically alkylated; for instance, 7-methylguanosine can be incorporated in place of a guanosine residue. Non-natural bases that promote inhibition of target gene expression may also be incorporated into interfering RNAs. Other siRNA modifications include 2'-deoxy-2'-fluorouridine or locked nucleic acid (LNA) nucleotides and RNA duplexes containing either phosphodiester or varying numbers of phosphorothioate linkages. Such modifications are described, for example, in Braasch et al., Biochemistry 42: 7967-7975 (2003), the disclosure of which is incorporated herein by reference.

Synthetic siRNA molecules, can be obtained using a number of techniques known to those of skill in the art. For example, the siRNA molecule can be chemically synthesized or recombinantly produced using methods known in the art, such as using appropriately protected ribonucleoside phosphoramidites and conventional solid-phase oligonucleotide synthesis (see, e.g., Elbashir et al. Nature 411:494 (2001); Elbashir et al. Genes & Development 15:188 (2001); Harborth. et al. Journal of Cell Science 114:4557 (2001); Masters et al. Proceeding of the National Academy of Sciences USA 98:8012 (2001); and Tuschl et al. Genes & Development 13:3191 (1999), the disclosures of which are incorporated herein by reference). In addition, dsRNAs can be expressed as stem loop structures encoded by plasmid vectors, retroviruses and lentiviruses (see, e.g., Paddison et al. Genes and Development 16:948 (2002); McManus et al. RNA 8:842 (2002); Paul et al. Nature Biotechnology 20:505 (2002); Miyagishi et al. Nature Biotechnology 20:497 (2002); Sui et al. Proceedings of the National Academy of Sciences USA 99:5515 (2002); Brummelkamp et al. Cancer Cell 2:243 (2002); Lee et al. Nature Biotechnology 20:500 (2002); Yu et al. Proceedings of the National Academy of Sciences USA 99:6047 (2002); Zeng et al. Molecular Cell 9:1327 (2002); Rubinson et al. Nature Genetics 33:401 (2003); Stewart et al. RNA 9:493 (2003), the disclosures of each of which are incorporated herein by reference).

A variety of inhibitory agents that operate by a mechanism of RNA interference have been developed to antagonize the biological processes described by the methods of the invention. For instance, TGFβ receptor type II siRNA polynucleotides have been reported that are derived from the human TGFβRII sequence (Genbank Accession Number: M85079). The siRNA duplex sequences below were developed against particular target sequences within the TGFβ receptor type II gene and have been used to knock down expression of the receptor in a variety of whole cell models. These siRNA sequences are described in detail in U.S. Pat. No. 8,067,389, the disclosure of which is incorporated herein by reference. Other oligonucleotide-based modulators of TGFβ signaling, such as siRNAs and antisense oligonucleotides, are described in U.S. Pat. Nos. 5,731,424; 6,124,449; US 2008/0015161; US 2006/0229266; US 2004/0006030; US 2005/0227936; and US 2005/0287128, the disclosures of each of which are incorporated herein by reference. siRNAs useful for targeting TGFβR or ALK5 expression can be readily designed and tested. A database of siRNA sequences and a predictor of siRNA sequences has been established (Chalk et al. (Nucleic Acids Research 33: D131 (2005). This database can be used to predict the thermodynamic parameters of a particular siRNA-target mRNA interaction, as well as to evaluate the propensity of designed siRNA sequences for off-target interactions. The database is available as an electronic resource at www.siRNA.cgb.ki.se.

| Target Sequence 5' to 3' and Nucleotide number | siRNA duplex |
|---|---|
| Nt 529 AATCCTGCATGAGCAACTGCA (SEQ ID NO: 1) | UCCUGCAUGAGCAACUGCAdTdT dTdTAGGACGUACUCGUUGACGU (SEQ ID NOS: 2 and 3) |
| Nt 1113 AAGGCCAAGCTGAAGCAGAAC (SEQ ID NO: 4) | GGCCAAGCUGAAGCAGAACdTdT dTdTCCGGUUCGACUUCGUCUUG (SEQ ID NOS: 5 and 6) |
| Nt 1253 AGCATGAGAACATACTCCAG (SEQ ID NO: 7) | GCAUGAGAACAUACUCCAGdTdT dTdTCGUACUCUUGUAUGAGGUC (SEQ ID NO: 8 and 9) |
| Nt 948 AAGACGCGGAAGCTCATGGAG (SEQ ID NO: 10) | GACGCGGAAGCUCAUGGAGdTdT dTdTCUGCGCCUUCGAGUACCUC (SEQ ID NO: 11 and 12) |

Conformationally Constrained Peptides

Peptide-based therapeutics represent an emerging class of compounds useful for the inhibition of protein-protein interactions that have often been intractable to inhibition by other means. Conformationally restricted peptides offer particular advantages for therapeutic applications, as these compounds often exhibit enhanced target affinity and selectivity by virtue of presenting structurally pre-organized epitopes in which a particular pharmacophore is spatially predisposed for interacting with a protein of interest. Constrained peptides often feature the additional benefits of enhanced protease resistivity relative to their unconstrained (e.g., linear) counterparts by restricting the access of proteases to internal amide bonds. The cell penetrating capabilities of these compounds are also frequently higher than those of linear peptides due to the sequestration of hydrogen bond donors and acceptors from aqueous solvent. Exemplary constrained peptide inhibitors useful with the compositions and methods of the invention include olefin "stapled" peptides, which often feature alpha helices that have been structurally rigidified by insertion of a covalent cross-link between residues on the same face of the helix. This class of constrained peptides is described, e.g., in Walensky et al. Journal of Medicinal Chemistry 57:6275 (2014), the disclosure of which is incorporated herein by reference. Stapled peptide inhibitors of β-catenin phosphorylation have been developed that function by disrupting the Axin/β-catenin interaction. Axin serves to anchor β-catenin to a protein complex that includes GSK3, and the association has been shown to be mediated by the insertion of an alpha helical region of Axin into a shallow pocket at the β-catenin surface. A stapled peptide of the sequence Ac-PQR$_8$ILDQHVS$_5$RVMK-NH$_2$ (SEQ ID NO: 13) has been reported that is structurally restricted to an alpha helical conformation by virtue of an olefinic cross-link at residues R$_8$ ((S)-α-(7-octenyl)alanine) and S$_5$ ((S)-α-(4-pentenyl)alanine) (see, e.g., Cui et al. Cell Research 23: 581 (2013), the disclosure of which is incorporated herein by reference). This peptide competes with Axin for binding at the surface of β-catenin and serves to liberate the protein from the GSK3-containing complex, thus increasing the nuclear concentration of this transcription factor.

Constrained peptides have also been developed by virtue of covalent cyclization between the N- and C-termini. Exemplary inhibitors of this class include the depsipeptides, which feature lactone moieties that render these peptide macrocyclic. Depsipeptide inhibitors useful with the compositions and methods of the invention include inhibitors of histone deacetylases, such as Romidepsin (also referred to as istodax; structure shown below), which is described in, e.g., Vinodhkumar et al., Biomedicine & Pharmacotherapy 62:85-93 (2008), the disclosure of which is incorporated by reference herein.

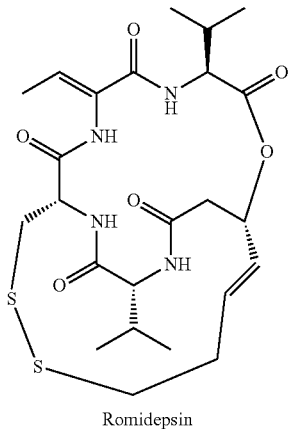 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

Romidepsin

Additional examples of depsipeptide inhibitors of histone deacetylases include Apicidin, described in Bertrand, European Journal of Medicinal Chemistry 45:2095-2116 (2010), the disclosure of which is incorporated herein by reference.

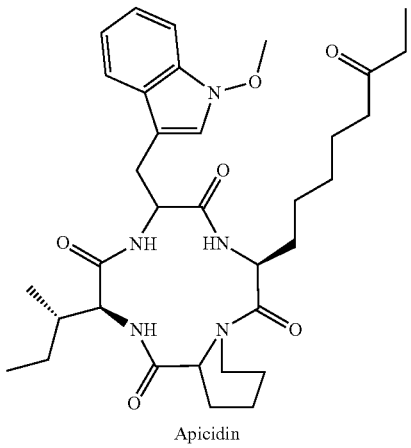 [SMILES: CCC(=O)CCCCC[C@@H]1NC(=O)C(Cc2cn(OC)c3ccccc23)NC(=O)[C@H]([C@@H](C)CC)NC(=O)C2CCCCN2C1=O]

Apicidin

Combinations of Compounds Useful with the Compositions and Methods of the Invention Embodiments of the compositions and methods of the invention may contain combinations of any of the above-described compounds may be used, e.g., for the expansion, enrichment, and maintenance of hematopoietic stem cell functional potential of a population of hematopoietic stem cells. Particular combination of compounds useful in conjunction with the compositions and methods of the inventions are specified in Tables 1-10, below.

TABLE 1

| 2-Component Combination of pathway inhibitors | | 3-Component Combination of pathway inhibitors | | |
|---|---|---|---|---|
| Histone methylation inhibitor | TGFβ signaling inhibitor | Histone methylation inhibitor | TGFβ signaling inhibitor | p38 signaling inhibitor |
| Histone methylation inhibitor | p38 signaling inhibitor | Histone methylation inhibitor | TGFβ signaling inhibitor | Wnt signaling agonist |
| Histone methylation inhibitor | Wnt signaling agonist | Histone methylation inhibitor | TGFβ signaling inhibitor | Histone acetylation inhibitor |
| Histone methylation inhibitor | Histone acetylation inhibitor | TGFβ signaling inhibitor | p38 signaling inhibitor | Wnt signaling agonist |
| TGFβ signaling inhibitor | p38 signaling inhibitor | TGFβ signaling inhibitor | p38 signaling inhibitor | Histone acetylation inhibitor |
| TGFβ signaling inhibitor | Wnt signaling agonist | p38 signaling inhibitor | Histone methylation inhibitor | Wnt signaling agonist |
| TGFβ signaling inhibitor | Histone acetylation inhibitor | p38 signaling inhibitor | Histone methylation inhibitor | Histone acetylation inhibitor |
| p38 signaling inhibitor | Wnt signaling agonist | Wnt signaling agonist | Histone methylation inhibitor | Histone acetylation inhibitor |
| p38 signaling inhibitor | Histone acetylation inhibitor | TGFβ signaling inhibitor | Wnt signaling agonist | Histone acetylation inhibitor |
| Histone acetylation inhibitor | Wnt signaling agonist | p38 signaling inhibitor | Wnt signaling agonist | Histone acetylation inhibitor |
| Histone demethylation inhibitor | TGFβ signaling inhibitor | Histone demethylation inhibitor | TGFβ signaling inhibitor | p38 signaling inhibitor |

TABLE 1-continued

| 2-Component Combination of pathway inhibitors | | 3-Component Combination of pathway inhibitors | | |
|---|---|---|---|---|
| Histone demethylation inhibitor | p38 signaling inhibitor | Histone demethylation inhibitor | TGFβ signaling inhibitor | Wnt signaling agonist |
| Histone demethylation inhibitor | Wnt signaling agonist | Histone demethylation inhibitor | TGFβ signaling inhibitor | Histone acetylation inhibitor |
| Histone demethylation inhibitor | Histone acetylation inhibitor | Histone demethylation inhibitor | TGFβ signaling inhibitor | Histone deacetylation inhibitor |
| Histone demethylation inhibitor | Histone deacetylation inhibitor | Histone demethylation inhibitor | TGFβ signaling inhibitor | Histone methylation inhibitor |
| Histone demethylation inhibitor | Histone methylation inhibitor | Histone demethylation inhibitor | p38 signaling inhibitor | Wnt signaling agonist |
| Histone deacetylation inhibitor | TGFβ signaling inhibitor | Histone demethylation inhibitor | p38 signaling inhibitor | Histone acetylation inhibitor |
| Histone deacetylation inhibitor | p38 signaling inhibitor | Histone demethylation inhibitor | p38 signaling inhibitor | Histone deacetylation inhibitor |
| Histone deacetylation inhibitor | Wnt signaling agonist | Histone demethylation inhibitor | p38 signaling inhibitor | Histone methylation inhibitor |
| Histone deacetylation inhibitor | Histone acetylation inhibitor | Histone demethylation inhibitor | Wnt signaling agonist | Histone acetylation inhibitor |
| Histone deacetylation inhibitor | Histone methylation inhibitor | Histone demethylation inhibitor | Wnt signaling agonist | Histone deacetylation inhibitor |
| | | Histone demethylation inhibitor | Wnt signaling agonist | Histone methylation inhibitor |
| | | Histone demethylation inhibitor | Histone acetylation inhibitor | Histone deacetylation inhibitor |
| | | Histone demethylation inhibitor | Histone methylation inhibitor | Histone acetylation inhibitor |
| | | Histone deacetylation inhibitor | TGFβ signaling inhibitor | p38 signaling inhibitor |
| | | Histone deacetylation inhibitor | TGFβ signaling inhibitor | Wnt signaling agonist |
| | | Histone deacetylation inhibitor | TGFβ signaling inhibitor | Histone acelylation inhibitor |
| | | Histone deacetylation inhibitor | TGFβ signaling inhibitor | Histone methylation inhibitor |
| | | Histone deacetylation inhibitor | p38 signaling inhibitor | Wnt signaling agonist |
| | | Histone deacetylation inhibitor | p38 signaling inhibitor | Histone acetylation inhibitor |
| | | Histone deacetylation inhibitor | p38 signaling inhibitor | Histone methylation inhibitor |
| | | Histone deacetylation inhibitor | Wnt signaling agonist | Histone acetylation inhibitor |
| | | Histone deacetylation inhibitor | Wnt signaling agonist | Histone methylation inhibitor |
| | | Histone deacetylation inhibitor | Histone acetylation inhibitor | Histone methylation inhibitor |
| | | Histone deacetylation inhibitor | Histone methylation inhibitor | Histone demethylation inhibitor |

TABLE 2

| 4-Component Combination of pathway inhibitors | | | |
|---|---|---|---|
| Histone methylation inhibitor | Histone demethylation inhibitor | TGFβ signaling inhibitor | p38 signaling inhibitor |
| Histone methylation inhibitor | Histone demethylation inhibitor | TGFβ signaling inhibitor | Wnt signaling agonist |
| Histone methylation inhibitor | Histone demethylation inhibitor | TGFβ signaling inhibitor | Histone acetylation inhibitor |
| Histone methylation inhibitor | Histone demethylation inhibitor | TGFβ signaling inhibitor | Histone deacetylation inhibitor |
| Histone methylation inhibitor | Histone demethylation inhibitor | p38 signaling inhibitor | Wnt signaling agonist |
| Histone methylation inhibitor | Histone demethylation inhibitor | p38 signaling inhibitor | Histone acetylation inhibitor |
| Histone methylation inhibitor | Histone demethylation inhibitor | p38 signaling inhibitor | Histone deacetylation inhibitor |
| Histone methylation inhibitor | Histone demethylation inhibitor | Wnt signaling agonist | Histone acetylation inhibitor |
| Histone methylation inhibitor | Histone demethylation inhibitor | Wnt signaling agonist | Histone deacetylation inhibitor |
| Histone methylation inhibitor | Histone demethylation inhibitor | Histone acelylation inhibitor | Histone deacetylation inhibitor |
| Histone methylation inhibitor | TGFβ signaling inhibitor | p38 signaling inhibitor | Wnt signaling agonist |

TABLE 2-continued

4-Component Combination of pathway inhibitors

| | | | |
|---|---|---|---|
| Histone methylation inhibitor | TGFβ signaling inhibitor | p38 signaling inhibitor | Histone acetylation inhibitor |
| Histone methylation inhibitor | TGFβ signaling inhibitor | p38 signaling inhibitor | Histone deacetylation inhibitor |
| Histone methylation inhibitor | TGFβ signaling inhibitor | Wnt signaling agonist | Histone acetylation inhibitor |
| Histone methylation inhibitor | TGFβ signaling inhibitor | Wnt signaling agonist | Histone deacetylation inhibitor |
| Histone methylation inhibitor | TGFβ signaling inhibitor | Histone acetylation inhibitor | Histone deacetylation inhibitor |
| Histone methylation inhibitor | p38 signaling inhibitor | Wnt signaling agonist | Histone acetylation inhibitor |
| Histone methylation inhibitor | p38 signaling inhibitor | Wnt signaling agonist | Histone deacetylation inhibitor |
| Histone methylation inhibitor | p38 signaling inhibitor | Histone acetylation inhibitor | Histone deacetylation inhibitor |
| Histone methylation inhibitor | Wnt signaling agonist | Histone acetylation inhibitor | Histone deacetylation inhibitor |
| Histone demethylation inhibitor | TGFβ signaling inhibitor | p38 signaling inhibitor | Wnt signaling agonist |
| Histone demethylation inhibitor | TGFβ signaling inhibitor | p38 signaling inhibitor | Histone acetylation inhibitor |
| Histone demethylation inhibitor | TGFβ signaling inhibitor | p38 signaling inhibitor | Histone deacetylation inhibitor |
| Histone demethylation inhibitor | TGFβ signaling inhibitor | Wnt signaling agonist | Histone acetylation inhibitor |
| Histone demethylation inhibitor | TGFβ signaling inhibitor | Wnt signaling agonist | Histone deacetylation inhibitor |
| Histone demethylation inhibitor | TGFβ signaling inhibitor | Histone acetylation inhibitor | Histone deacetylation inhibitor |
| Histone demethylation inhibitor | p38 signaling inhibitor | Wnt signaling agonist | Histone acetylation inhibitor |
| Histone demethylation inhibitor | p38 signaling inhibitor | Wnt signaling agonist | Histone deacetylation inhibitor |
| Histone demethylation inhibitor | p38 signaling inhibitor | Histone acetylation inhibitor | Histone deacetylation inhibitor |
| Histone demethylatlon inhibitor | Wnt signaling agonist | Histone acetylation inhibitor | Histone deacetylation inhibitor |
| TGFβ signaling inhibitor | p38 signaling inhibitor | Wnt signaling agonist | Histone acetylation inhibitor |
| TGFβ signaling inhibitor | p38 signaling inhibitor | Wnt signaling agonist | Histone deacetylation inhibitor |
| TGFβ signaling inhibitor | p38 signaling inhibitor | Histone acetylation inhibitor | Histone deacetylation inhibitor |
| TGFβ signaling inhibitor | Wnt signaling agonist | Histone acetylation inhibitor | Histone deacetylation inhibitor |
| p38 signaling inhibitor | Wnt signaling agonist | Histone acetylation inhibitor | Histone deacetylation inhibitor |

TABLE 3

5-Component Combination of pathway inhibitors

| | | | | |
|---|---|---|---|---|
| Histone methylation inhibitor | Histone demethylation inhibitor | TGFβ signaling inhibitor | p38 signaling inhibitor | Wnt signaling agonist |
| Histone methylation inhibitor | Histone demethylation inhibitor | TGFβ signaling inhibitor | p38 signaling inhibitor | Histone acetylation inhibitor |
| Histone methylation inhibitor | Histone demethylation inhibitor | TGFβ signaling inhibitor | p38 signaling inhibitor | Histone deacetylation inhibitor |
| Histone methylation inhibitor | Histone demethylation inhibitor | TGFβ signaling inhibitor | Wnt signaling agonist | Histone acetylation inhibitor |
| Histone methylation inhibitor | Histone demethylation inhibitor | TGFβ signaling inhibitor | Wnt signaling agonist | Histone deacetylation inhibitor |
| Histone methylation inhibitor | Histone demethylation inhibitor | TGFβ signaling inhibitor | Histone acetylation inhibitor | Histone deacetylation inhibitor |
| Histone methylation inhibitor | Histone demethylation inhibitor | p38 signaling inhibitor | Wnt signaling agonist | Histone acetylation inhibitor |
| Histone methylation inhibitor | Histone demethylation inhibitor | p38 signaling inhibitor | Wnt signaling agonist | Histone deacetylation inhibitor |
| Histone methylation inhibitor | Histone demethylation inhibitor | p38 signaling inhibitor | Histone acetylation inhibitor | Histone deacetylation inhibitor |
| Histone methylation inhibitor | Histone demethylation inhibitor | Wnt signaling agonist | Histone acetylation inhibitor | Histone deacetylation inhibitor |

TABLE 3-continued

5-Component Combination of pathway inhibitors

| | | | | |
|---|---|---|---|---|
| Histone methylation inhibitor | TGFβ signaling inhibitor | p38 signaling inhibitor | Wnt signaling agonist | Histone acetylation inhibitor |
| Histone methylation inhibitor | TGFβ signaling inhibitor | p38 signaling inhibitor | Wnt signaling agonist | Histone deacetylation inhibitor |
| Histone methylation inhibitor | TGFβ signaling inhibitor | p38 signaling inhibitor | Histone acetylation inhibitor | Histone deacetylation inhibitor |
| Histone methylation inhibitor | TGFβ signaling inhibitor | Wnt signaling agonist | Histone acetylation inhibitor | Histone deacetylation inhibitor |
| Histone methylation inhibitor | p38 signaling inhibitor | Wnt signaling agonist | Histone acetylation inhibitor | Histone deacetylation inhibitor |
| Histone demethylation inhibitor | TGFβ signaling inhibitor | p38 signaling inhibitor | Wnt signaling agonist | Histone acetylation inhibitor |
| Histone demethylation inhibitor | TGFβ signaling inhibitor | p38 signaling inhibitor | Wnt signaling agonist | Histone deacetylation inhibitor |
| Histone demethylation inhibitor | TGFβ signaling inhibitor | p38 signaling inhibitor | Histone acetylation inhibitor | Histone deacetylation inhibitor |
| Histone demethylation inhibitor | TGFβ signaling inhibitor | Wnt signaling agonist | Histone acetylation inhibitor | Histone deacetylation inhibitor |
| Histone demethylation inhibitor | p38 signaling inhibitor | Wnt signaling agonist | Histone acetylation inhibitor | Histone deacetylation inhibitor |
| TGFβ signaling inhibitor | p38 signaling inhibitor | Wnt signaling agonist | Histone acetylation inhibitor | Histone deacetylation inhibitor |

TABLE 4

| 2-Component Combination | | 3-Component Combination | | |
|---|---|---|---|---|
| LSD1 inhibitor | TGFβ inhibitor | LSD1 inhibitor | TGFβ inhibitor | p38 inhibitor |
| LSD1 inhibitor | p38 inhibitor | LSD1 inhibitor | TGFβ inhibitor | Wnt agonist |
| LSD1 inhibitor | Wnt agonist | LSD1 inhibitor | TGFβ inhibitor | HDAC inhibitor |
| LSD1 inhibitor | HDAC inhibitor | TGFβ inhibitor | p38 inhibitor | Wnt agonist |
| TGFβ inhibitor | p38 inhibitor | TGFβ inhibitor | p38 inhibitor | HDAC inhibitor |
| TGFβ inhibitor | Wnt agonist | p38 inhibitor | LSD1 inhibitor | Wnt agonist |
| TGFβ inhibitor | HDAC inhibitor | p38 inhibitor | LSD1 inhibitor | HDAC inhibitor |
| p38 inhibitor | Wnt agonist | Wnt agonist | LSD1 inhibitor | HDAC inhibitor |
| p38 inhibitor | HDAC inhibitor | TGFβ inhibitor | Wnt agonist | HDAC inhibitor |
| HDAC inhibitor | Wnt agonist | p38 inhibitor | Wnt agonist | HDAC inhibitor |

TABLE 5

4-Component Combination of Target Inhibitors

| | | | |
|---|---|---|---|
| LSD1 inhibitor | TGFβ inhibitor | p38 inhibitor | Wnt agonist |
| LSD1 inhibitor | TGFβ inhibitor | p38 inhibitor | HDAC inhibitor |
| TGFβ inhibitor | Wnt agonist | p38 inhibitor | HDAC inhibitor |
| p38 inhibitor | LSD1 inhibitor | Wnt agonist | HDAC inhibitor |
| Wnt agonist | LSD1 inhibitor | TGFβ inhibitor | HDAC inhibitor |

TABLE 6

5-Component Combination of Target Inhibitors

| | | | | |
|---|---|---|---|---|
| LSD1 inhibitor | TGFβ inhibitor | p38 inhibitor | Wnt agonist | HDAC inhibitor |

TABLE 7

| No. | 2-Component Combination | |
|---|---|---|
| 1 | LSD1 inhibitor IV RN | ALK5 inhibitor II |
| 2 | LSD1 inhibitor IV RN | LY364947 |
| 3 | LSD1 inhibitor IV RN | A83-01 |
| 4 | LSD1 inhibitor IV RN | DMH1 |
| 5 | LSD1 inhibitor II S2101 | ALK5 inhibitor II |
| 6 | LSD1 inhibitor II S2101 | LY364947 |
| 7 | LSD1 inhibitor II S2101 | A83-01 |
| 8 | LSD1 inhibitor II S2101 | DMH1 |
| 9 | LSD1 inhibitor LSD1-C76 | ALK5 inhibitor II |
| 10 | LSD1 inhibitor LSD1-C76 | LY364947 |
| 11 | LSD1 inhibitor LSD1-C76 | A83-01 |
| 12 | LSD1 inhibitor LSD1-C76 | DMH1 |
| 13 | LSD1 inhibitor III CBB1007 | ALK5 inhibitor II |
| 14 | LSD1 inhibitor III CBB1007 | LY364947 |
| 15 | LSD1 inhibitor III CBB1007 | A83-01 |
| 16 | LSD1 inhibitor III CBB1007 | DMH1 |
| 17 | LSD1 inhibitor I | ALK5 inhibitor II |
| 18 | LSD1 inhibitor I | LY364947 |
| 19 | LSD1 inhibitor I | A83-01 |
| 20 | LSD1 inhibitor I | DMH1 |
| 21 | Tranylcypromine | ALK5 inhibitor II |
| 22 | Tranylcypromine | LY364947 |
| 23 | Tranylcypromine | A83-01 |
| 24 | Tranylcypromine | DMH1 |
| 25 | LSD1 inhibitor IV RN | SB203580 |
| 26 | LSD1 inhibitor II S2101 | SB203580 |
| 27 | LSD1 inhibitor LSD1-C76 | SB203580 |
| 28 | LSD1 inhibitor III CBB1007 | SB203580 |
| 29 | LSD1 inhibitor I | SB203580 |
| 30 | Tranylcypromine | SB203580 |
| 31 | LSD1 inhibitor IV RN | CHIR99021 |
| 32 | LSD1 inhibitor II S2101 | CHIR99021 |
| 33 | LSD1 inhibitor LSD1-C76 | CHIR99021 |
| 34 | LSD1 inhibitor III CBB1007 | CHIR99021 |
| 35 | LSD1 inhibitor I | CHIR99021 |
| 36 | Tranylcypromine | CHIR99021 |
| 37 | LSD1 inhibitor IV RN | Trichostatin A |
| 38 | LSD1 inhibitor IV RN | Istodax |
| 39 | LSD1 inhibitor II S2101 | Trichostatin A |
| 40 | LSD1 inhibitor II S2101 | Istodax |
| 41 | LSD1 inhibitor LSD1-C76 | Trichostatin A |
| 42 | LSD1 inhibitor LSD1-C76 | Istodax |
| 43 | LSD1 inhibitor III CBB1007 | Trichostatin A |
| 44 | LSD1 inhibitor III CBB1007 | Istodax |
| 45 | LSD1 inhibitor I | Trichostatin A |
| 46 | LSD1 inhibitor I | Istodax |
| 47 | Tranylcypromine | Trichostatin A |
| 48 | Tranylcypromine | Istodax |

TABLE 7-continued

| No. | 2-Component Combination | |
|---|---|---|
| 49 | ALK5 inhibitor II | SB203580 |
| 50 | LY364947 | SB203580 |
| 51 | A83-01 | SB203580 |
| 52 | DMH1 | SB203580 |
| 53 | ALK5 inhibitor II | CHIR99021 |
| 54 | LY364947 | CHIR99021 |
| 55 | A83-01 | CHIR99021 |
| 56 | DMH1 | CHIR99021 |
| 57 | ALK5 inhibitor II | Trichostatin A |
| 58 | ALK5 inhibitor II | istodax |
| 59 | LY364947 | Trichostatin A |
| 60 | LY364947 | istodax |
| 61 | A83-01 | Trichostatin A |
| 62 | A83-01 | istodax |
| 63 | DMH1 | Trichostatin A |
| 64 | DMH1 | istodax |
| 65 | SB203580 | CHIR99021 |
| 66 | Trichostatin A | SB203580 |
| 67 | istodax | SB203580 |
| 68 | Trichostatin A | CHIR99021 |
| 69 | istodax | CHIR99021 |

TABLE 8

| No. | 3-Component Combination | | |
|---|---|---|---|
| 1 | LSD1 inhibitor IV RN | ALK5 inhibitor II | SB203580 |
| 2 | LSD1 inhibitor IV RN | LY364947 | SB203580 |
| 3 | LSD1 inhibitor IV RN | A83-01 | SB203580 |
| 4 | LSD1 inhibitor IV RN | DMH1 | SB203580 |
| 5 | LSD1 inhibitor II S2101 | ALK5 inhibitor II | SB203580 |
| 6 | LSD1 inhibitor II S2101 | LY364947 | SB203580 |
| 7 | LSD1 inhibitor II S2101 | A83-01 | SB203580 |
| 8 | LSD1 inhibitor II S2101 | DMH1 | SB203580 |
| 9 | LSD1 inhibitor LSD1-C76 | ALK5 inhibitor II | SB203580 |
| 10 | LSD1 inhibitor LSD1-C76 | LY364947 | SB203580 |
| 11 | LSD1 inhibitor LSD1-C76 | A83-01 | SB203580 |
| 12 | LSD1 inhibitor LSD1-C76 | DMH1 | SB203580 |
| 13 | LSD1 inhibitor III CBB1007 | ALK5 inhibitor II | SB203580 |
| 14 | LSD1 inhibitor III CBB1007 | LY364947 | SB203580 |
| 15 | LSD1 inhibitor III CBB1007 | A83-01 | SB203580 |
| 16 | LSD1 inhibitor III CBB1007 | DMH1 | SB203580 |
| 17 | LSD1 inhibitor I | ALK5 inhibitor II | SB203580 |
| 18 | LSD1 inhibitor I | LY364947 | SB203580 |
| 19 | LSD1 inhibitor I | A83-01 | SB203580 |
| 20 | LSD1 inhibitor I | DMH1 | SB203580 |
| 21 | Tranylcypromine | ALK5 inhibitor II | SB203580 |
| 22 | Tranylcypromine | LY364947 | SB203580 |
| 23 | Tranylcypromine | A83-01 | SB203580 |
| 24 | Tranylcypromine | DMH1 | SB203580 |
| 25 | LSD1 inhibitor IV RN | ALK5 inhibitor II | CHIR99021 |
| 26 | LSD1 inhibitor IV RN | LY364947 | CHIR99021 |
| 27 | LSD1 inhibitor IV RN | A83-01 | CHIR99021 |
| 28 | LSD1 inhibitor IV RN | DMH1 | CHIR99021 |
| 29 | LSD1 inhibitor II S2101 | ALK5 inhibitor II | CHIR99021 |
| 30 | LSD1 inhibitor II S2101 | LY364947 | CHIR99021 |
| 31 | LSD1 inhibitor II S2101 | A83-01 | CHIR99021 |
| 32 | LSD1 inhibitor II S2101 | DMH1 | CHIR99021 |
| 33 | LSD1 inhibitor LSD1-C76 | ALK5 inhibitor II | CHIR99021 |
| 34 | LSD1 inhibitor LSD1-C76 | LY364947 | CHIR99021 |
| 35 | LSD1 inhibitor LSD1-C76 | A83-01 | CHIR99021 |
| 36 | LSD1 inhibitor LSD1-C76 | DMH1 | CHIR99021 |
| 37 | LSD1 inhibitor III CBB1007 | ALK5 inhibitor II | CHIR99021 |
| 38 | LSD1 inhibitor III CBB1007 | LY364947 | CHIR99021 |
| 39 | LSD1 inhibitor III CBB1007 | A83-01 | CHIR99021 |
| 40 | LSD1 inhibitor III CBB1007 | DMH1 | CHIR99021 |
| 41 | LSD1 inhibitor I | ALK5 inhibitor II | CHIR99021 |
| 42 | LSD1 inhibitor I | LY364947 | CHIR99021 |
| 43 | LSD1 inhibitor I | A83-01 | CHIR99021 |
| 44 | LSD1 inhibitor I | DMH1 | CHIR99021 |
| 45 | Tranylcypromine | ALK5 inhibitor II | CHIR99021 |
| 46 | Tranylcypromine | LY364947 | CHIR99021 |
| 47 | Tranylcypromine | A83-01 | CHIR99021 |
| 48 | Tranylcypromine | DMH1 | CHIR99021 |
| 49 | LSD1 inhibitor IV RN | ALK5 inhibitor II | Trichostatin A |
| 50 | LSD1 inhibitor IV RN | LY364947 | Trichostatin A |
| 51 | LSD1 inhibitor IV RN | A83-01 | Trichostatin A |
| 52 | LSD1 inhibitor IV RN | DMH1 | Trichostatin A |
| 53 | LSD1 inhibitor II S2101 | ALK5 inhibitor II | Trichostatin A |
| 54 | LSD1 inhibitor II S2101 | LY364947 | Trichostatin A |
| 55 | LSD1 inhibitor II S2101 | A83-01 | Trichostatin A |
| 56 | LSD1 inhibitor II S2101 | DMH1 | Trichostatin A |
| 57 | LSD1 inhibitor LSD1-C76 | ALK5 inhibitor II | Trichostatin A |
| 58 | LSD1 inhibitor LSD1-C76 | LY364947 | Trichostatin A |
| 59 | LSD1 inhibitor LSD1-C76 | A83-01 | Trichostatin A |
| 60 | LSD1 inhibitor LSD1-C76 | DMH1 | Trichostatin A |
| 61 | LSD1 inhibitor III CBB1007 | ALK5 inhibitor II | Trichostatin A |
| 62 | LSD1 inhibitor III CBB1007 | LY364947 | Trichostatin A |
| 63 | LSD1 inhibitor III CBB1007 | A83-01 | Trichostatin A |
| 64 | LSD1 inhibitor III CBB1007 | DMH1 | Trichostatin A |
| 65 | LSD1 inhibitor I | ALK5 inhibitor II | Trichostatin A |
| 66 | LSD1 inhibitor I | LY364947 | Trichostatin A |
| 67 | LSD1 inhibitor I | A83-01 | Trichostatin A |
| 68 | LSD1 inhibitor I | DMH1 | Trichostatin A |
| 69 | Tranylcypromine | ALK5 inhibitor II | Trichostatin A |
| 70 | Tranylcypromine | LY364947 | Trichostatin A |
| 71 | Tranylcypromine | A83-01 | Trichostatin A |
| 72 | Tranylcypromine | DMH1 | Trichostatin A |
| 73 | LSD1 inhibitor IV RN | ALK5 inhibitor II | Istodax |
| 74 | LSD1 inhibitor IV RN | LY364947 | Istodax |
| 75 | LSD1 inhibitor IV RN | A83-01 | Istodax |
| 76 | LSD1 inhibitor IV RN | DMH1 | Istodax |
| 77 | LSD1 inhibitor II S2101 | ALK5 inhibitor II | Istodax |
| 78 | LSD1 inhibitor II S2101 | LY364947 | Istodax |
| 79 | LSD1 inhibitor II S2101 | A83-01 | Istodax |
| 80 | LSD1 inhibitor II S2101 | DMH1 | Istodax |
| 81 | LSD1 inhibitor LSD1-C76 | ALK5 inhibitor II | Istodax |
| 82 | LSD1 inhibitor LSD1-C76 | LY364947 | Istodax |
| 83 | LSD1 inhibitor LSD1-C76 | A83-01 | Istodax |
| 84 | LSD1 inhibitor LSD1-C76 | DMH1 | Istodax |
| 85 | LSD1 inhibitor III CBB1007 | ALK5 inhibitor II | Istodax |
| 86 | LSD1 inhibitor III CBB1007 | LY364947 | Istodax |
| 87 | LSD1 inhibitor III CBB1007 | A83-01 | Istodax |
| 88 | LSD1 inhibitor III CBB1007 | DMH1 | Istodax |
| 89 | LSD1 inhibitor I | ALK5 inhibitor II | Istodax |
| 90 | LSD1 inhibitor I | LY364947 | Istodax |
| 91 | LSD1 inhibitor I | A83-01 | Istodax |
| 92 | LSD1 inhibitor I | DMH1 | Istodax |
| 93 | Tranylcypromine | ALK5 inhibitor II | Istodax |
| 94 | Tranylcypromine | LY364947 | Istodax |
| 95 | Tranylcypromine | A83-01 | Istodax |
| 96 | Tranylcypromine | DMH1 | istodax |
| 97 | ALK5 inhibitor II | SB203580 | CHIR99021 |
| 98 | LY364947 | SB203580 | CHIR99021 |
| 99 | A83-01 | SB203580 | CHIR99021 |
| 100 | DMH1 | SB203580 | CHIR99021 |
| 101 | ALK5 inhibitor II | SB203580 | Trichostatin A |
| 102 | LY364947 | SB203580 | Trichostatin A |
| 103 | A83-01 | SB203580 | Trichostatin A |
| 104 | DMH1 | SB203580 | Trichostatin A |
| 105 | ALK5 inhibitor II | SB203580 | istodax |
| 106 | LY364947 | SB203580 | istodax |
| 107 | A83-01 | SB203580 | istodax |
| 108 | DMH1 | SB203580 | istodax |
| 109 | LSD1 inhibitor IV RN | SB203580 | CHIR99021 |
| 110 | LSD1 inhibitor II S2101 | SB203580 | CHIR99021 |
| 111 | LSD1 inhibitor LSD1-C76 | SB203580 | CHIR99021 |
| 112 | LSD1 inhibitor III CBB1007 | SB203580 | CHIR99021 |
| 113 | LSD1 inhibitor I | SB203580 | CHIR99021 |
| 114 | Tranylcypromine | SB203580 | CHIR99021 |
| 115 | LSD1 inhibitor IV RN | SB203580 | Trichostatin A |
| 116 | LSD1 inhibitor II S2101 | SB203580 | Trichostatin A |
| 117 | LSD1 inhibitor LSD1-C76 | SB203580 | Trichostatin A |
| 118 | LSD1 inhibitor III CBB1007 | SB203580 | Trichostatin A |
| 119 | LSD1 inhibitor I | SB203580 | Trichostatin A |
| 120 | Tranylcypromine | SB203580 | Trichostatin A |
| 121 | LSD1 inhibitor IV RN | SB203580 | istodax |
| 122 | LSD1 inhibitor II S2101 | SB203580 | istodax |
| 123 | LSD1 inhibitor LSD1-C76 | SB203580 | istodax |
| 124 | LSD1 inhibitor II CBB1007 | SB203580 | istodax |
| 125 | LSD1 inhibitor I | SB203580 | istodax |
| 126 | Tranylcypromine | SB203580 | istodax |
| 127 | LSD1 inhibitor IV RN | CHIR99021 | Trichostatin A |

TABLE 8-continued

| No. | 3-Component Combination | | |
|---|---|---|---|
| 128 | LSD1 inhibitor II S2101 | CHIR99021 | Trichostatin A |
| 129 | LSD1 inhibitor LSD1-C76 | CHIR99021 | Trichostatin A |
| 130 | LSD1 inhibitor III CBB1007 | CHIR99021 | Trichostatin A |
| 131 | LSD1 inhibitor I | CHIR99021 | Trichostatin A |
| 132 | Tranylcypromine | CHIR99021 | Trichostatin A |
| 133 | LSD1 inhibitor IV RN | CHIR99021 | istodax |
| 134 | LSD1 inhibitor II S2101 | CHIR99021 | istodax |
| 135 | LSD1 inhibitor LSD1-C76 | CHIR99021 | istodax |
| 136 | LSD1 inhibitor III CBB1007 | CHIR99021 | istodax |
| 137 | LSD1 inhibitor I | CHIR99021 | istodax |
| 138 | Tranylcypromine | CHIR99021 | istodax |
| 139 | ALK5 inhibitor II | CHIR99021 | Trichostatin A |
| 140 | LY364947 | CHIR99021 | Trichostatin A |
| 141 | A83-01 | CHIR99021 | Trichostatin A |
| 142 | DMH1 | CHIR99021 | Trichostatin A |
| 143 | ALK5 inhibitor II | CHIR99021 | istodax |
| 144 | LY364947 | CHIR99021 | istodax |
| 145 | A83-01 | CHIR99021 | istodax |
| 146 | DMH1 | CHIR99021 | istodax |
| 147 | SB203580 | CHIR99021 | Trichostatin A |
| 148 | SB203580 | CHIR99021 | istodax |

TABLE 9

| No. | 4-Component Combination | | | |
|---|---|---|---|---|
| 1 | LSD1 inhibitor IV RN | ALK5 inhibitor II | SB203580 | CHIR99021 |
| 2 | LSD1 inhibitor IV RN | LY364947 | SB203580 | CHIR99021 |
| 3 | LSD1 inhibitor IV RN | A83-01 | SB203580 | CHIR99021 |
| 4 | LSD1 inhibitor IV RN | DMH1 | SB203580 | CHIR99021 |
| 5 | LSD1 inhibitor II S2101 | ALK5 inhibitor II | SB203580 | CHIR99021 |
| 6 | LSD1 inhibitor II S2101 | LY364947 | SB203580 | CHIR99021 |
| 7 | LSD1 inhibitor II S2101 | A83-01 | SB203580 | CHIR99021 |
| 8 | LSD1 inhibitor II S2101 | DMH1 | SB203580 | CHIR99021 |
| 9 | LSD1 inhibitor LSD1-C76 | ALK5 inhibitor II | SB203580 | CHIR99021 |
| 10 | LSD1 inhibitor LSD1-C76 | LY364947 | SB203580 | CHIR99021 |
| 11 | LSD1 inhibitor LSD1-C76 | A83-01 | SB203580 | CHIR99021 |
| 12 | LSD1 inhibitor LSD1-C76 | DMH1 | SB203580 | CHIR99021 |
| 13 | LSD1 inhibitor III CBB1007 | ALK5 inhibitor II | SB203580 | CHIR99021 |
| 14 | LSD1 inhibitor III CBB1007 | LY364947 | SB203580 | CHIR99021 |
| 15 | LSD1 inhibitor III CBB1007 | A83-01 | SB203580 | CHIR99021 |
| 16 | LSD1 inhibitor III CBB1007 | DMH1 | SB203580 | CHIR99021 |
| 17 | LSD1 inhibitor I | ALK5 inhibitor II | SB203580 | CHIR99021 |
| 18 | LSD1 inhibitor I | LY364947 | SB203580 | CHIR99021 |
| 19 | LSD1 inhibitor I | A83-01 | SB203580 | CHIR99021 |
| 20 | LSD1 inhibitor I | DMH1 | SB203580 | CHIR99021 |
| 21 | Tranylcypromine | ALK5 inhibitor II | SB203580 | CHIR99021 |
| 22 | Tranylcypromine | LY364947 | SB203580 | CHIR99021 |
| 23 | Tranylcypromine | A83-01 | SB203580 | CHIR99021 |
| 24 | Tranylcypromine | DMH1 | SB203580 | CHIR99021 |
| 25 | LSD1 inhibitor IV RN | ALK5 inhibitor II | SB203580 | Trichostatin A |
| 26 | LSD1 inhibitor IV RN | LY364947 | SB203580 | Trichostatin A |
| 27 | LSD1 inhibitor IV RN | A83-01 | SB203580 | Trichostatin A |
| 28 | LSD1 inhibitor IV RN | DMH1 | SB203580 | Trichostatin A |
| 29 | LSD1 inhibitor II S2101 | ALK5 inhibitor II | SB203580 | Trichostatin A |
| 30 | LSD1 inhibitor II S2101 | LY364947 | SB203580 | Trichostatin A |
| 31 | LSD1 inhibitor II S2101 | A83-01 | SB203580 | Trichostatin A |
| 32 | LSD1 inhibitor II S2101 | DMH1 | SB203580 | Trichostatin A |
| 33 | LSD1 inhibitor LSD1-C76 | ALK5 inhibitor II | SB203580 | Trichostatin A |
| 34 | LSD1 inhibitor LSD1-C76 | LY364947 | SB203580 | Trichostatin A |
| 35 | LSD1 inhibitor LSD1-C76 | A83-01 | SB203580 | Trichostatin A |
| 36 | LSD1 inhibitor LSD1-C76 | DMH1 | SB203580 | Trichostatin A |
| 37 | LSD1 inhibitor III CBB1007 | ALK5 inhibitor II | SB203580 | Trichostatin A |
| 38 | LSD1 inhibitor III CBB1007 | LY364947 | SB203580 | Trichostatin A |
| 39 | LSD1 inhibitor III CBB1007 | A83-01 | SB203580 | Trichostatin A |
| 40 | LSD1 inhibitor III CBB1007 | DMH1 | SB203580 | Trichostatin A |
| 41 | LSD1 inhibitor I | ALK5 inhibitor II | SB203580 | Trichostatin A |
| 42 | LSD1 inhibitor I | LY364947 | SB203580 | Trichostatin A |
| 43 | LSD1 inhibitor I | A83-01 | SB203580 | Trichostatin A |
| 44 | LSD1 inhibitor I | DMH1 | SB203580 | Trichostatin A |
| 45 | Tranylcypromine | ALK5 inhibitor II | SB203580 | Trichostatin A |
| 46 | Tranylcypromine | LY364947 | SB203580 | Trichostatin A |
| 47 | Tranylcypromine | A83-01 | SB203580 | Trichostatin A |
| 48 | Tranylcypromine | DMH1 | SB203580 | Trichostatin A |
| 49 | LSD1 inhibitor IV RN | ALK5 inhibitor II | SB203580 | istodax |
| 50 | LSD1 inhibitor IV RN | LY364947 | SB203580 | istodax |
| 51 | LSD1 inhibitor IV RN | A83-01 | SB203580 | istodax |
| 52 | LSD1 inhibitor IV RN | DMH1 | SB203580 | istodax |
| 53 | LSD1 inhibitor II S2101 | ALK5 inhibitor II | SB203580 | istodax |
| 54 | LSD1 inhibitor II S2101 | LY364947 | SB203580 | istodax |
| 55 | LSD1 inhibitor II S2101 | A83-01 | SB203580 | istodax |
| 56 | LSD1 inhibitor II S2101 | DMH1 | SB203580 | istodax |
| 57 | LSD1 inhibitor LSD1-C76 | ALK5 inhibitor II | SB203580 | istodax |
| 58 | LSD1 inhibitor LSD1-C76 | LY364947 | SB203580 | istodax |
| 59 | LSD1 inhibitor LSD1-C76 | A83-01 | SB203580 | istodax |
| 60 | LSD1 inhibitor LSD1-C76 | DMH1 | SB203580 | istodax |

TABLE 9-continued

| No. | 4-Component Combination | | | |
|---|---|---|---|---|
| 61 | LSD1 inhibitor III CBB1007 | ALK5 inhibitor II | SB203580 | istodax |
| 62 | LSD1 inhibitor III CBB1007 | LY364947 | SB203580 | istodax |
| 63 | LSD1 inhibitor III CBB1007 | A83-01 | SB203580 | istodax |
| 64 | LSD1 inhibitor III CBB1007 | DMH1 | SB203580 | istodax |
| 65 | LSD1 inhibitor I | ALK5 inhibitor II | SB203580 | istodax |
| 66 | LSD1 inhibitor I | LY364947 | SB203580 | istodax |
| 67 | LSD1 inhibitor I | A83-01 | SB203580 | istodax |
| 68 | LSD1 inhibitor I | DMH1 | SB203580 | istodax |
| 66 | Tranylcypromine | ALK5 inhibitor II | SB203580 | istodax |
| 70 | Tranylcypromine | LY364947 | SB203580 | istodax |
| 71 | Tranylcypromine | A83-01 | SB203580 | istodax |
| 72 | Tranylcypromine | DMH1 | SB203580 | istodax |
| 73 | ALK5 inhibitor II | SB203580 | CHIR99021 | Trichostatin A |
| 74 | LY364947 | SB203580 | CHIR99021 | Trichostatin A |
| 75 | A83-01 | SB203580 | CHIR99021 | Trichostatin A |
| 76 | DMH1 | SB203580 | CHIR99021 | Trichostatin A |
| 77 | ALK5 inhibitor II | SB203580 | CHIR99021 | istodax |
| 78 | LY364947 | SB203580 | CHIR99021 | istodax |
| 79 | A83-01 | SB203580 | CHIR99021 | istodax |
| 80 | DMH1 | SB203580 | CHIR99021 | istodax |
| 81 | LSD1 inhibitor IV RN | SB203580 | CHIR99021 | Trichostatin A |
| 82 | LSD1 inhibitor II S2101 | SB203580 | CHIR99021 | Trichostatin A |
| 83 | LSD1 inhibitor LSD1-C76 | SB203580 | CHIR99021 | Trichostatin A |
| 84 | LSD1 inhibitor III CBB1007 | SB203580 | CHIR99021 | Trichostatin A |
| 85 | LSD1 inhibitor I | SB203580 | CHIR99021 | Trichostatin A |
| 86 | Tranylcypromine | SB203580 | CHIR99021 | Trichostatin A |
| 87 | LSD1 inhibitor IV RN | SB203580 | CHIR99021 | istodax |
| 88 | LSD1 inhibitor II S2101 | SB203580 | CHIR99021 | istodax |
| 89 | LSD1 inhibitor LSD1-C76 | SB203580 | CHIR99021 | istodax |
| 90 | LSD1 inhibitor III CBB1007 | SB203580 | CHIR99021 | istodax |
| 91 | LSD1 inhibitor I | SB203580 | CHIR99021 | istodax |
| 92 | Tranylcypromine | SB203580 | CHIR99021 | istodax |
| 93 | LSD1 inhibitor IV RN | ALK5 inhibitor II | CHIR99021 | Trichostatin A |
| 94 | LSD1 inhibitor IV RN | LY364947 | CHIR99021 | Trichostatin A |
| 95 | LSD1 inhibitor IV RN | A83-01 | CHIR99021 | Trichostatin A |
| 96 | LSD1 inhibitor IV RN | DMH1 | CHIR99021 | Trichostatin A |
| 97 | LSD1 inhibitor II S2101 | ALK5 inhibitor II | CHIR99021 | Trichostatin A |
| 98 | LSD1 inhibitor II S2101 | LY364947 | CHIR99021 | Trichostatin A |
| 99 | LSD1 inhibitor II S2101 | A83-01 | CHIR99021 | Trichostatin A |
| 100 | LSD1 inhibitor II S2101 | DMH1 | CHIR99021 | Trichostatin A |
| 101 | LSD1 inhibitor LSD1-C76 | ALK5 inhibitor II | CHIR99021 | Trichostatin A |
| 102 | LSD1 inhibitor LSD1-C76 | LY364947 | CHIR99021 | Trichostatin A |
| 103 | LSD1 inhibitor LSD1-C76 | A83-01 | CHIR99021 | Trichostatin A |
| 104 | LSD1 inhibitor LSD1-C76 | DMH1 | CHIR99021 | Trichostatin A |
| 105 | LSD1 inhibitor III CBB1007 | ALK5 inhibitor II | CHIR99021 | Trichostatin A |
| 106 | LSD1 inhibitor III CBB1007 | LY364947 | CHIR99021 | Trichostatin A |
| 107 | LSD1 inhibitor III CBB1007 | A83-01 | CHIR99021 | Trichostatin A |
| 108 | LSD1 inhibitor III CBB1007 | DMH1 | CHIR99021 | Trichostatin A |
| 109 | LSD1 inhibitor I | ALK5 inhibitor II | CHIR99021 | Trichostatin A |
| 110 | LSD1 inhibitor I | LY364947 | CHIR99021 | Trichostatin A |
| 111 | LSD1 inhibitor I | A83-01 | CHIR99021 | Trichostatin A |
| 112 | LSD1 inhibitor I | DMH1 | CHIR99021 | Trichostatin A |
| 113 | Tranylcypromine | ALK5 inhibitor II | CHIR99021 | Trichostatin A |
| 114 | Tranylcypromine | LY364947 | CHIR99021 | Trichostatin A |
| 115 | Tranylcypromine | A83-01 | CHIR99021 | Trichostatin A |
| 116 | Tranylcypromine | DMH1 | CHIR99021 | Trichostatin A |
| 117 | LSD1 inhibitor IV RN | ALK5 inhibitor II | CHIR99021 | istodax |
| 118 | LSD1 inhibitor IV RN | LY364947 | CHIR99021 | istodax |
| 119 | LSD1 inhibitor IV RN | A83-01 | CHIR99021 | istodax |
| 120 | LSD1 inhibitor IV RN | DMH1 | CHIR99021 | istodax |
| 121 | LSD1 inhibitor II S2101 | ALK5 inhibitor II | CHIR99021 | istodax |
| 122 | LSD1 inhibitor II S2101 | LY364947 | CHIR99021 | istodax |
| 123 | LSD1 inhibitor II S2101 | A83-01 | CHIR99021 | istodax |
| 124 | LSD1 inhibitor II S2101 | DMH1 | CHIR99021 | istodax |
| 125 | LSD1 inhibitor LSD1-C76 | ALK5 inhibitor II | CHIR99021 | istodax |
| 126 | LSD1 inhibitor LSD1-C76 | LY364947 | CHIR99021 | istodax |
| 127 | LSD1 inhibitor LSD1-C76 | A83-01 | CHIR99021 | istodax |
| 128 | LSD1 inhibitor LSD1-C76 | DMH1 | CHIR99021 | istodax |
| 129 | LSD1 inhibitor III CBB1007 | ALK5 inhibitor II | CHIR99021 | istodax |
| 130 | LSD1 inhibitor III CBB1007 | LY364947 | CHIR99021 | istodax |
| 131 | LSD1 inhibitor III CBB1007 | A83-01 | CHIR99021 | istodax |
| 132 | LSD1 inhibitor III CBB1007 | DMH1 | CHIR99021 | istodax |
| 133 | LSD1 inhibitor I | ALK5 inhibitor II | CHIR99021 | istodax |
| 134 | LSD1 inhibitor I | LY364947 | CHIR99021 | istodax |
| 135 | LSD1 inhibitor I | A83-01 | CHIR99021 | istodax |
| 136 | LSD1 inhibitor I | DMH1 | CHIR99021 | istodax |
| 137 | Tranylcypromine | ALK5 inhibitor II | CHIR99021 | istodax |
| 138 | Tranylcypromine | LY364947 | CHIR99021 | istodax |

TABLE 9-continued

| No. | 4-Component Combination | | | |
|---|---|---|---|---|
| 139 | Tranylcypromine | A83-01 | CHIR99021 | istodax |
| 140 | Tranylcypromine | DMH1 | CHIR99021 | istodax |

TABLE 10

| No. | 5-Component Combination | | | | |
|---|---|---|---|---|---|
| 1 | LSD1 inhibitor IV RN | ALK5 inhibitor II | SB203580 | CHIR99021 | Trichostatin A |
| 2 | LSD1 inhibitor IV RN | LY364947 | SB203580 | CHIR99021 | Trichostatin A |
| 3 | LSD1 inhibitor IV RN | A83-01 | SB203580 | CHIR99021 | Trichostatin A |
| 4 | LSD1 inhibitor IV RN | DMH1 | SB203580 | CHIR99021 | Trichostatin A |
| 5 | LSD1 inhibitor II S2101 | ALK5 inhibitor II | SB203580 | CHIR99021 | Trichostatin A |
| 6 | LSD1 inhibitor II S2101 | LY364947 | SB203580 | CHIR99021 | Trichostatin A |
| 7 | LSD1 inhibitor II S2101 | A83-01 | SB203580 | CHIR99021 | Trichostatin A |
| 8 | LSD1 inhibitor II S2101 | DMH1 | SB203580 | CHIR99021 | Trichostatin A |
| 9 | LSD1 inhibitor LSD1-C76 | ALK5 inhibitor II | SB203580 | CHIR99021 | Trichostatin A |
| 10 | LSD1 inhibitor LSD1-C76 | LY364947 | SB203580 | CHIR99021 | Trichostatin A |
| 11 | LSD1 inhibitor LSD1-C76 | A83-01 | SB203580 | CHIR99021 | Trichostatin A |
| 12 | LSD1 inhibitor LSD1-C76 | DMH1 | SB203580 | CHIR99021 | Trichostatin A |
| 13 | LSD1 inhibitor III CBB1007 | ALK5 inhibitor II | SB203580 | CHIR99021 | Trichostatin A |
| 14 | LSD1 inhibitor III CBB1007 | LY364947 | SB203580 | CHIR99021 | Trichostatin A |
| 15 | LSD1 inhibitor III CBB1007 | A83-01 | SB203580 | CHIRP9021 | Trichostatin A |
| 16 | LSD1 inhibitor III CBB1007 | DMH1 | SB203580 | CHIR99021 | Trichostatin A |
| 17 | LSD1 inhibitor I | ALK5 inhibitor II | SB203580 | CHIR99021 | Trichostatin A |
| 18 | LSD1 inhibitor I | LY364947 | SB203580 | CHIR99021 | Trichostatin A |
| 19 | LSD1 inhibitor I | A83-01 | SB203580 | CHIR99021 | Trichostatin A |
| 20 | LSD1 inhibitor I | DMH1 | SB203580 | CHIR99021 | Trichostatin A |
| 21 | Tranylcypromine | ALK5 inhibitor II | SB203580 | CHIR99021 | Trichostatin A |
| 22 | Tranylcypromine | LY364947 | SB203580 | CHIR99021 | Trichostatin A |
| 23 | Tranylcypromine | A83-01 | SB203580 | CHIR99021 | Trichostatin A |
| 24 | Tranylcypromine | DMH1 | SB203580 | CHIR99021 | Trichostatin A |
| 25 | LSD1 inhibitor IV RN | ALK5 inhibitor II | SB203580 | CHIR99021 | istodax |
| 26 | LSD1 inhibitor IV RN | LY364947 | SB203580 | CHIR99021 | istodax |
| 27 | LSD1 inhibitor IV RN | A83-01 | SB203580 | CHIR99021 | istodax |
| 28 | LSD1 inhibitor IV RN | DMH1 | SB203580 | CHIR99021 | istodax |
| 29 | LSD1 inhibitor II S2101 | ALK5 inhibitor II | SB203580 | CHIR99021 | istodax |
| 30 | LSD1 inhibitor II S2101 | LY364947 | SB203580 | CHIR99021 | istodax |
| 31 | LSD1 inhibitor II S2101 | A83-01 | SB203580 | CHIR99021 | istodax |
| 32 | LSD1 inhibitor II S2101 | DMH1 | SB203580 | CHIR99021 | istodax |
| 33 | LSD1 inhibitor LSD1-C76 | ALK5 inhibitor II | SB203580 | CHIR99021 | istodax |
| 34 | LSD1 inhibitor LSD1-C76 | LY364947 | SB203580 | CHIR99021 | istodax |
| 35 | LSD1 inhibitor LSD1-C76 | A83-01 | SB203580 | CHIR99021 | istodax |
| 36 | LSD1 inhibitor LSD1-C76 | DMH1 | SB203580 | CHIR99021 | istodax |
| 37 | LSD1 inhibitor III CBB1007 | ALK5 inhibitor II | SB203580 | CHIR99021 | istodax |
| 38 | LSD1 inhibitor III CBB1007 | LY364947 | SB203580 | CHIR99021 | istodax |
| 39 | LSD1 inhibitor III CBB1007 | A83-01 | SB203580 | CHIR99021 | istodax |
| 40 | LSD1 inhibitor III CBB1007 | DMH1 | SB203580 | CHIR99021 | istodax |
| 41 | LSD1 inhibitor I | ALK5 inhibitor II | SB203580 | CHIR99021 | istodax |
| 42 | LSD1 inhibitor I | LY364947 | SB203580 | CHIR99021 | istodax |
| 43 | LSD1 inhibitor I | A83-01 | SB203580 | CHIR99021 | istodax |
| 44 | LSD1 inhibitor I | DMH1 | SB203580 | CHIR99021 | istodax |
| 45 | Tranylcypromine | ALK5 inhibitor II | SB203580 | CHIR99021 | istodax |
| 46 | Tranylcypromine | LY364947 | SB203580 | CHIR99021 | istodax |
| 47 | Tranylcypromine | A83-01 | SB203580 | CHIR99021 | istodax |
| 48 | Tranylcypromine | DMH1 | SB203580 | CHIR99021 | istodax |

Additional Agents that can be Used to Induce Expansion, Enrichment, and Maintenance of Hematopoietic Stem Cells During Ex Vivo Culturing Other compounds may additionally be used in conjunction with the compositions and methods of the present invention in order to expand, enrich, and/or maintain hematopoietic stem cells during ex vivo culturing. Examples of these compounds include antagonists of the aryl hydrocarbon receptor (AHR), such as StemRegenin 1 (SR1), a small molecule that promotes expansion and self-renewal of human CD34+ peripheral blood and cord blood hematopoietic stem cells. SR1 has been described, e.g., in US 2014/0369973; Boitano et al. Science 1345 (2010); and Smith et al. Journal of Pharmacology and Experimental Therapeutics 338:318 (2011), the disclosures of each of which are incorporated herein by reference. Other AHR inhibitors that may be used in conjunction with the compositions and methods of the invention include SR1 analogs, such as those that contain various aryl and aliphatic substituents about the 6-aminopurine core (e.g., those described in US 2014/0369973, the disclosure of which is incorporated herein by reference). Additional examples of AHR antagonists include the stilbene derivatives (E)-1-(4'-trifluoromethylphenyl)-2-(3,5-ditrifluoromethylphenyl)-ethene, (E)-1-(4'-methoxyphenyl)-2-(3,5-dichlorophenyl)-ethene, and (E)-1-(4'-chlorophenyl)-2-(3,5-dichlorophenyl)-ethene, as described in, e.g., WO 2004/041758, the disclosure of which is incorporated herein by reference. Additional stilbene derivatives useful for the inhibition of the AHR include 3,5,4'-trihydroxystilbenes (e.g., resveratrols and, in particular, transresveratrol); 3,4,3',5-tetrahydroxystilbene (also referred to as piceatannol); 2,3',4',5'-tetrahydrostilbene (also referred to as oxyresveratrol); as well as 4,4'-dihydroxystilbenes and glycosides (e.g., galactosides, lactosides, mannosides, piceosides, and fructosides thereof) as described in, e.g., WO 1999/056737, the disclosure of which is incorporated herein by reference. Another exemplary AHR antagonist is 2-methyl-2H-pyrazole-3-carboxylic acid-(2-methyl-4-o-tolylazophenyl)-amide (also referred to as CH-223191, described in detail in, e.g., Kim et al. Molecular Pharmacology 69:1871 (2006); as well as in WO 2009/115807; the disclosures of each of which are incorporated herein by reference).

Additional agents that can be used in conjunction with the methods of the invention include UM171, another small molecule that has been shown to induce hematopoietic stem cell expansion. UM171 is described, e.g., in Fares, et al., Science, 345(6203):1509-1512 (2014), the disclosure of which is incorporated herein by reference. Other agents that can be used with the compositions and methods of the invention include UM171 analogs, such as those described in WO 2013/110198, the disclosure of which is incorporated herein by reference. Particularly useful analogs of UM171 that can be used in conjunction with the compositions and methods of the invention include compound Nos. 1-55 recited in WO 2013/110198 and the compounds disclosed in Table 11 herein. A further example of a class of compound that can additionally be used in conjunction with the compositions and methods of the present invention includes prostaglandins. Particularly useful prostaglandins include prostaglandin dmPGE2, described, e.g., in U.S. Pat. Nos. 8,551,782 and 8,168,428, the disclosures of each of which are incorporated herein by reference. Additional compounds that can be used in conjunction with the compositions and methods described herein include inhibitors of the Sirtuin 1 (SIRT1) protein, such as nicotinamide (described, e.g., in Peled et al. Experimental Hematology 40:342 (2012)) and cambinol (described, e.g., in Lugrin et al. Biochimica Biophysica Acta 1833:1498 (2013)), the disclosures of each of which are incorporated herein by reference.

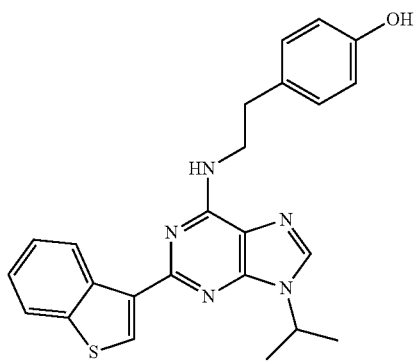
SR1

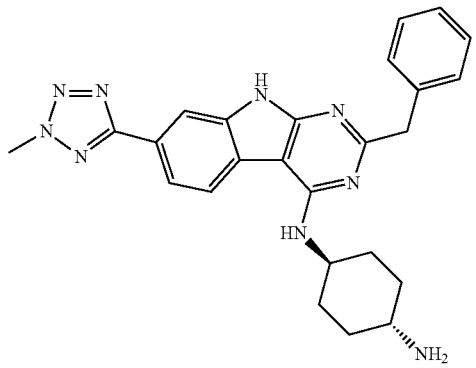
UM171

Additional agents that can be contacted with hematopoietic stem cells in combination with one or more agents that together exhibit two or more activities selected from the group consisting of modulation of histone methylation, inhibition of TGFβ signaling, inhibition of p38 signaling, activation of canonical Wnt signaling, and modulation of histone acetylation include activators of the Notch signal transduction pathway. Agonists of Notch signaling include but are not limited to proteins that contain portions of toporythmic proteins such as Delta, Serrate or Jagged (see, e.g., Lindsell et al., Cell 80: 909-917 (1995), the disclosure of which is incorporated herein by reference) that mediate binding to Notch and/or mediate Notch activity, and nucleic acids encoding the foregoing, as well as proteins, nucleic acids, small molecules, or derivatives thereof that regulate activity or gene expression of these proteins. Notch signaling agonists also include a protein or derivative or fragment thereof comprising a functionally active fragment such as a fragment of a Notch ligand that mediates binding to a Notch protein.

Notch activity is promoted by the binding of Notch ligands (e.g., Delta ligands and Serrate ligands) to the extracellular portion of the Notch receptor. Endogenous Notch ligands are typically membrane-bound on adjacent cells. As such, Notch ligands for use with the compositions and methods of the invention may be incubated with hematopoietic stem cells in solution as soluble protein factors or immobilized on a solid surface (e.g., a tissue culture plate, bead, or nanomatrix). For example, full length Notch ligands expressed on the surface of a cell induces the activation of the Notch signaling cascade in a neighboring cell upon contact of the ligand with the Notch receptor. Notch signaling agonists for use with the compositions and methods of the invention thus include soluble, optionally truncated Delta or Serrate (e.g., Jagged) molecules that contain the extracellular domains or Notch-binding portions, as well as forms of these proteins immobilized on a surface, such as the solid surface of a tissue culture plate, water-miscible bead, or nanomatrix. Such soluble proteins can be immobilized on a solid surface by an antibody or interacting protein, for example an antibody directed to an epitope tag with which a Delta or a Serrate is expressed as a fusion protein (e.g., a myc epitope tag, which is recognized by the antibody 9E10) or a protein which interacts with an epitope tag with which a Delta or a Serrate is expressed as a fusion protein (e.g., an immunoglobulin epitope tag, which is bound by Protein A) as described in US 2014/0369973, the disclosure of which is incorporated herein by reference. Exemplary agonists of Notch signaling additionally include a notch polypeptide, deltex polypeptide, mastermind polypeptide, split polypeptide, hairless polypeptide, RBP-Jκ polypeptide, or hes1 polypeptide as described in US 2011/0091448, the disclosure of which is incorporated herein by reference.

Agents such as those described above (for example, an AHR antagonist, such as SR1, optionally in combination with UM171, dmPGE2, a Notch signaling agonist, and/or a SIRT1 inhibitor, such as nicotinamide or cambinol) may be included as additional compounds that contact hematopoietic stem cells and that are in contact with one or more agents that together exhibit two or more activities selected from the group consisting of modulation of histone methylation, inhibition of TGFβ signaling, inhibition of p38 signaling, activation of canonical Wnt signaling, and modulation of histone acetylation. For instance, hematopoietic stem cells in contact with one or more of these agents may additionally be contacted with an AHR antagonist, UM171, dmPGE2, a Notch signaling agonist, and/or a SIRT1 inhibitor, such as nicotinamide or cambinol, according to distinct incubation regimens, such that one or more of these compounds are introduced to hematopoietic stem cells at various times during a culture period. Alternatively, these agents may be incubated with hematopoietic stem cells simultaneously when desired.

Hematopoietic Stem Cell Mobilization

Hematopoietic stem cells for use with the compositions and methods of the invention may arise from a variety of cell types. For instance, hematopoietic cells for methods of expansion, enrichment, and maintenance of hematopoietic stem cell functional potential as recited herein may are derived from mononuclear cells prior to the treatment of these cells with one or more agents that together exhibit two or more activities selected from the group consisting of modulation of histone methylation, inhibition of TGFβ signaling, inhibition of p38 signaling, activation of canonical Wnt signaling, and modulation of histone acetylation. Human hematopoietic stem cells may optionally be CD34+ cells prior to the treatment with one or more of these agents. For instance, human hematopoietic stem cells may be within populations with cell surface phenotypes including CD34+, CD34+CD38-, CD34+CD38-CD90+, CD34+CD38-CD90+ CD45RA-, or CD34+CD38-CD90+CD45RA-CD49F+ cells prior to the treatment with one or more of these agents.

Hematopoietic stem cells may additionally are derived from human bone marrow. Alternatively, hematopoietic stem cells may be derived from human cord blood or mobilized peripheral blood. Hematopoietic stem cells obtained from human peripheral blood may be mobilized by one of a variety of strategies. Exemplary agents that can be used to induce mobilization of hematopoietic stem cells from the bone marrow into peripheral blood include chemokine (C—X—C motif) receptor 4 (CXCR4) antagonists, such as AMD3100 (also known as Plerixafor and MOZOBIL™ (Genzyme, Boston, Mass.)) and granulocyte colony-stimulating factor (GCSF), the combination of which has been shown to rapidly mobilize CD34+ cells in clinical experiments. Additionally, chemokine (C—X—C motif) ligand 2 (CXCL2, also referred to as GROβ) represents another agent capable of inducing hematopoietic stem cell mobilization to from bone marrow to peripheral blood. Agents capable of inducing mobilization of hematopoietic stem cells for use with the compositions and methods of the invention may be used in combination with one another. For instance, CXCR4 antagonists (e.g., AMD3100), CXCL2, and/or GCSF may be administered to a subject sequentially or simultaneously in a single mixture in order to induce mobilization of hematopoietic stem cells from bone marrow into peripheral blood. The use of these agents as inducers of hematopoietic stem cell mobilization is described, e.g., in Pelus, Current Opinion in Hematology 15:285 (2008), the disclosure of which is incorporated herein by reference.

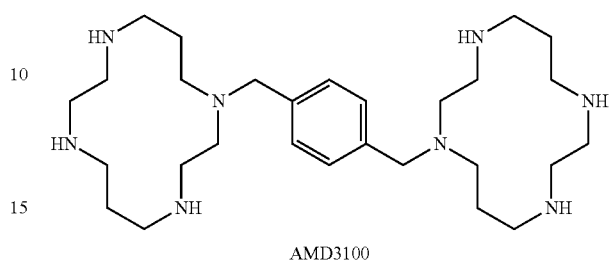

AMD3100

Modulating Target Gene Expression in Hematopoietic Stem Cells

The compositions and methods of the invention further provide strategies for regulating the expression of target genes in populations of hematopoietic stem cells. For instance, a population of hematopoietic stem cells may be expanded, enriched or maintained ex vivo according to the methods of the invention and may additionally be genetically modified so as to exhibit an altered gene expression pattern. Alternatively, a population of cells may be enriched with hematopoietic stem cells, or a population of hematopoietic stem cells may be maintained in a multi-potent state, and the cells may further be modified using established genome editing techniques known in the art. For instance, one may use a genome editing procedure to promote the expression of an exogenous gene or inhibit the expression of an endogenous gene within a hematopoietic stem cell. Importantly, populations of hematopoietic stem cells may be expanded, enriched, or maintained in a multi-potent state according to the methods of the invention recited herein and subsequently genetically modified so as to express a desired target gene, or populations of these cells may be genetically modified first and then expanded, enriched, or maintained in a multi-potent state. A wide array of methods has been established for the incorporation of target genes into the genome of a cell (e.g., a mammalian cell, such as a murine or human cell) so as to facilitate the expression of such genes.

Polynucleotides Encoding Target Genes

One example of a platform that can be used to facilitate the expression of a target gene in a hematopoietic stem cell is by the integration of the polynucleotide encoding a target gene into the nuclear genome of the cell. A variety of techniques have been developed for the introduction of exogenous genes into a eukaryotic genome. One such technique involves the insertion of a target gene into a vector, such as a viral vector. Vectors for use with the compositions and methods of the invention can be introduced into a cell by a variety of methods, including transformation, transfection, direct uptake, projectile bombardment, and by encapsulation of the vector in a liposome. Examples of suitable methods of transfecting or transforming cells include calcium phosphate precipitation, electroporation, microinjection, infection, lipofection and direct uptake. Such methods are, described in more detail, for example, in Green, et al., *Molecular Cloning: A Laboratory Manual*, Fourth Edition, Cold Spring Harbor University Press, New York (2014); and Ausubel, et al., *Current Protocols in Molecular Biology*, John Wiley & Sons, New York (2015), the disclosures of each of which are incorporated herein by reference.

Exogenous genes can also be introduced into a mammalian cell through the use of a vector containing the gene of interest to cell membrane phospholipids. For example, vectors can be targeted to the phospholipids on the extracellular surface of the cell membrane by linking the vector molecule to a VSV-G protein, a viral protein with affinity for all cell membrane phospholipids. Viral vectors containing the VSV-G protein are described in further detail, e.g., in U.S. Pat. No. 5,512,421; and in U.S. Pat. No. 5,670,354, the disclosures of each of which are incorporated by reference herein.

Recognition and binding of the polynucleotide encoding a target gene by mammalian RNA polymerase is an important molecular event for gene expression to occur. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase. Alternatively, promoters derived from viral genomes can be used for the stable expression of target genes in mammalian cells. Examples of functional viral promoters that can be used to promote mammalian expression of these enzymes include adenovirus late promoter, vaccinia virus 7.5K promoter, SV40 promoter, cytomegalovirus promoter, mouse mammary tumor virus (MMTV) promoter, LTR promoter of HIV, promoter of moloney virus, Epstein barr virus (EBV) promoter, Rous sarcoma virus (RSV) promoter, and the cytomegalovirus (CMV) promoter. Additional viral promoters include the SV40 late promoter from simian virus 40, the Baculovirus polyhedron enhancer/promoter element, Herpes Simplex Virus thymidine kinase (HSV tk) promoter, and the 35S promoter from Cauliflower Mosaic Virus. Suitable phage promoters for use with the compositions and methods of the invention include, but are not limited to, the *E. coli* T7 and T3 phage promoters, the *S. typhimurium* phage SP6 promoter, *B. subtilis* SP01 phage and *B. subtilis* phage phi 29 promoters, and N4 phage and K11 phage promoters as described in U.S. Pat. No. 5,547,892, the disclosure of which is incorporated herein by reference.

Upon incorporation of a polynucleotide encoding a target gene has been incorporated into the genome of a cell (e.g., the nuclear genome of a hematopoietic stem cell), the transcription of this polynucleotide can be induced by methods known in the art. For example expression can be induced by exposing the mammalian cell to an external chemical reagent, such as an agent that modulates the binding of a transcription factor and/or RNA polymerase to the mammalian promoter and thus regulate gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms include tetracycline and doxycycline. These reagents are commercially available (Life Technologies, Carlsbad, Calif.) and can be administered to a mammalian cell in order to promote gene expression according to established protocols.

Other DNA sequence elements that may be included in polynucleotides for use with the compositions and methods of the invention include enhancer sequences. Enhancers represent another class of regulatory elements that induce a conformational change in the polynucleotide comprising the gene of interest such that the DNA adopts a three-dimensional orientation that is favorable for binding of transcription factors and RNA polymerase at the transcription initiation site. Thus, polynucleotides for use with the compositions and methods of the invention include those that encode a target gene and additionally include a mammalian enhancer sequence. Many enhancer sequences are now known from mammalian genes, and examples include enhancers from the genes that encode mammalian globin, elastase, albumin, α-fetoprotein, and insulin. Enhancers for use with the compositions and methods of the invention also include those that are derived from the genetic material of a virus capable of infecting a eukaryotic cell. Examples include the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription are disclosed in Yaniv, et al., Nature, 297:17-18 (1982), the disclosure of which is incorporated herein by reference. An enhancer may be spliced into a vector containing a polynucleotide encoding a target gene, for example, at a position 5' or 3' to this gene. In a preferred orientation, the enhancer is positioned at the 5' side of the promoter, which in turn is located 5' relative to the polynucleotide encoding the target gene.

In addition to promoting high rates of transcription and translation, stable expression of an exogenous gene in a hematopoietic stem cell can be achieved by integration of the polynucleotide comprising the gene into the nuclear DNA of the cell. A variety of vectors for the delivery and integration of polynucleotides encoding exogenous proteins into the nuclear DNA of a mammalian cell have been developed. Examples of expression vectors are disclosed in, e.g., WO 1994/11026, the disclosure of which is incorporated herein by reference. Expression vectors for use with the compositions and methods of the invention contain a polynucleotide sequence that encodes a target gene, as well as, e.g., additional sequence elements used for the expression of these enzymes and/or the integration of these polynucleotide sequences into the genome of a mammalian cell. Certain vectors that can be used for the expression of target genes include plasmids that contain regulatory sequences, such as promoter and enhancer regions, which direct gene transcription. Other useful vectors for expression of target genes contain polynucleotide sequences that enhance the rate of translation of these genes or improve the stability or nuclear export of the mRNA that results from gene transcription. These sequence elements often encode features within RNA transcripts that enhance the nuclear export, cytosolic half-life, and ribosomal affinity of these molecules, e.g., 5' and 3' untranslated regions, an internal ribosomal entry site (IRES), and polyadenylation signal site in order to direct efficient transcription of the gene carried on the expression vector. Exemplary expression vectors may also contain a polynucleotide encoding a marker for selection of cells that contain such a vector. Non-limiting examples of a suitable marker include genes that encode resistance to antibiotics, such as ampicillin, chloramphenicol, kanamycin, or nourseothricin.

Vectors for the Expression of Target Genes

Viral genomes provide a rich source of vectors that can be used for the efficient delivery of exogenous genes into a mammalian cell. Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and often do not require added proteins or reagents in order to induce gene integration. Examples of viral vectors include a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including herpes virus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology*, Third Edition, B. N. Fields, et al., Eds., Lippincott-Raven Publishers, Philadelphia, 1996, the disclosure of which is incorporated herein by reference). Other examples of viral vectors include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described in, e.g., U.S. Pat. No. 5,801,030, the disclosure of which is incorporated herein by reference.

Additional Transfection Methods

Other techniques that can be used to introduce a polynucleotide, such as DNA or RNA (e.g., mRNA, tRNA, siRNA, miRNA, shRNA, chemically modified RNA) into a mammalian cell are well known in the art. For instance, electroporation can be used to permeabilize mammalian cells by the application of an electrostatic potential. Mammalian cells, such as hematopoietic stem cells, subjected to an external electric field in this manner are subsequently predisposed to the uptake of exogenous nucleic acids. Electroporation of mammalian cells is described in detail, e.g., in Chu et al. Nucleic Acids Research 15:1311 (1987), the disclosure of which is incorporated herein by reference. A similar technique, Nucleofection™, utilizes an applied electric field in order to stimulate the update of exogenous polynucleotides into the nucleus of a eukaryotic cell. Nucleofection™ and protocols useful for performing this technique are described in detail, e.g., in Distler et al. Experimental Dermatology 14:315 (2005), as well as in US 2010/0317114, the disclosures of each of which are incorporated herein by reference.

Additional techniques useful for the transfection of hematopoietic stem cells include the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a hematopoietic stem cell. Squeeze-poration is described in detail, e.g., in Sharei et al. Journal of Visualized Experiments 81:e50980 (2013), the disclosure of which is incorporated herein by reference.

Lipofection represents another technique useful for transfection of hematopoietic stem cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, e.g., by direct fusion of the liposome with the cell membrane or by endocytosis of the complex. Lipofection is described in detail, e.g., in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane include activated dendrimers (described, e.g., in Dennig, Topics in Current Chemistry 228:227 (2003), the disclosure of which is incorporated herein by reference) and diethyl-aminoethyl (DEAE)-dextran, the use of which as a transfection agent is described in detail, e.g., in Gulick et al. Current Protocols in Molecular Biology 40:1:9.2:9.2.1 (1997), the disclosure of which is incorporated herein by reference. Magnetic beads are another tool that can be used to transfect hematopoietic stem cells in a mild and efficient manner, as this methodology utilizes an applied magnetic field in order to direct the uptake of nucleic acids. This technology is described in detail, e.g., in US 2010/0227406, the disclosure of which is incorporated herein by reference.

Another useful tool for inducing the uptake of exogenous nucleic acids by hematopoietic stem cells is laserfection, a technique that involves exposing a cell to electromagnetic radiation of a particular wavelength in order to gently permeabilize the cells and allow polynucleotides to penetrate the cell membrane. This technique is described in detail, e.g., in Rhodes et al. Methods in Cell Biology 82:309 (2007), the disclosure of which is incorporated herein by reference.

Microvesicles represent another potential vehicle that can be used to modify the genome of a hematopoietic stem cell according to the methods of the invention described herein. For instance, microvesicles that have been induced by the co-overexpression of the glycoprotein VSV-G with, e.g., a genome-modifying protein, such as a nuclease, can be used to efficiently deliver proteins into a cell that subsequently catalyze the site-specific cleavage of an endogenous polynucleotide sequence so as to prepare the genome of the cell for the covalent incorporation of a polynucleotide of interest, such as a gene or regulatory sequence. The use of such vesicles, also referred to as Gesicles, for the genetic modification of eukaryotic cells is described in detail, e.g., in Quinn, T P, et al. Genetic Modification of Target Cells by Direct Delivery of Active Protein [abstract]. In: Methylation changes in early embryonic genes in cancer [abstract], in: Proceedings of the 18th Annual Meeting of the American Society of Gene and Cell Therapy; 2015 May 13, Abstract No. 122.

Incorporation of Target Genes by Gene Editing Techniques

In addition to viral vectors, a variety of additional tools have been developed that can be used for the incorporation of exogenous genes into hematopoietic stem cells. One such method that can be used for incorporating polynucleotides encoding target genes into hematopoietic stem cells involves the use of transposons. Transposons are polynucleotides that encode transposase enzymes and contain a polynucleotide sequence or gene of interest flanked by 5' and 3' excision sites. Once a transposon has been delivered into a cell, expression of the transposase gene commences and results in active enzymes that cleave the gene of interest from the transposon. This activity is mediated by the site-specific recognition of transposon excision sites by the transposase. In certain cases, these excision sites may be terminal repeats or inverted terminal repeats. Once excised from the transposon, the gene of interest can be integrated into the genome of a mammalian cell by transposase-catalyzed cleavage of similar excision sites that exist within the nuclear genome of the cell. This allows the gene of interest to be inserted into the cleaved nuclear DNA at the complementary excision sites, and subsequent covalent ligation of the phosphodiester bonds that join the gene of interest to the DNA of the mammalian cell genome completes the incorporation process. In certain cases, the transposon may be a retrotransposon, such that the gene encoding the target gene is first transcribed to an RNA product and then reverse-transcribed to DNA before incorporation in the mammalian cell genome. Exemplary transposon systems include the piggybac transposon (described in detail in, e.g., WO 2010/085699) and the sleeping beauty transposon (described in detail in, e.g., US2005/0112764), the disclosures of each of which are incorporated herein by reference.

Another useful tool for the integration of target genes into the genome of a hematopoietic stem cell is the clustered regularly interspaced short palindromic repeats (CRISPR)/Cas system, a system that originally evolved as an adaptive defense mechanism in bacteria and archaea against viral infection. The CRISPR/Cas system includes palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can theoretically design a CRISPR/Cas system to cleave any target DNA molecule of interest. This technique has been exploited in order to edit eukaryotic genomes (Hwang et al. Nature Biotechnology 31:227 (2013)) and can be used as an efficient means of site-specifically editing hematopoietic stem cell genomes in order to cleave DNA prior to the incorporation of a gene encoding a target gene. The use of CRISPR/Cas to modulate gene expression has been described in, e.g., U.S. Pat. No. 8,697,359, the disclosure of which is incorporated herein by reference. Alternative methods for site-specifically cleaving genomic DNA prior to the incorporation of a gene of interest in a hematopoietic stem cell include the use of zinc finger nucleases (ZFNs) and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. The use of ZFNs and TAL-ENs in genome editing applications is described, e.g., in Urnov et al. Nature Reviews Genetics 11:636 (2010); and in Joung et al. Nature Reviews Molecular Cell Biology 14:49 (2013), the disclosure of both of which are incorporated herein by reference.

Additional genome editing techniques that can be used to incorporate polynucleotides encoding target genes into the genome of a hematopoietic stem cell include the use of ARCUS™ meganucleases that can be rationally designed so as to site-specifically cleave genomic DNA. The use of these enzymes for the incorporation of genes encoding target genes into the genome of a mammalian cell is advantageous in view of the defined structure-activity relationships that have been established for such enzymes. Single chain meganucleases can be modified at certain amino acid positions in order to create nucleases that selectively cleave DNA at desired locations, enabling the site-specific incorporation of a target gene into the nuclear DNA of a hematopoietic stem cell. These single-chain nucleases have been described extensively in, e.g., U.S. Pat. Nos. 8,021,867 and 8,445,251, the disclosures of each of which are incorporated herein by reference.

Inducing the Differentiation of Hematopoietic Stem Cells

In certain cases, it may be desirable to expand, enrich, or maintain a population of hematopoietic stem cells according to the methods of the invention and subsequently induce the differentiation of these cells into a blood cell of the hematopoietic repertoire prior to infusion of the resulting cells into a recipient. This represents a useful paradigm for administering a specific blood cell type to a recipient in need thereof. Populations of hematopoietic stem cells that have been expanded, enriched, and/or maintained according to the methods of the invention may be subjected to various conditions in order to stimulate the differentiation of these cells into cells of the hematopoietic lineage, such as conditions that are known in the art. For instance, using established protocols, hematopoietic stem cells can be induced to differentiate into one of a multitude of blood cell types, such as common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, such as NK cells, B-cells and T-cells.

Indications for Hematopoietic Stem Cell Therapy

Hematopoietic stem cells produced (e.g., expanded, enriched, or maintained in a multi-potent state) through the use of the compositions and methods of the invention can be used to treat a variety of human diseases. Hematopoietic stem cells or progeny thereof administered to a patient may be autologous, syngeneic, or allogeneic, and may be administered in conjunction with one or more agents that promote the expansion of a hematopoietic stem cell in vivo. For instance, hematopoietic stem cells or progeny thereof may be administered to a patient (e.g., a human patient) in order to treat such diseases as Acute Lymphoblastic Leukemia (ALL), Acute Myelogenous Leukemia (AML), Chronic Myelogenous Leukemia (CML), Chronic Lymphocytic Leukemia (CLL), Hodgkin Lymphoma (HL), Non-Hodgkin Lymphoma (NHL), Myelodysplastic Syndrome (MDS), Multiple myeloma, Aplastic anemia, Bone marrow failure, Myeloproliferative disorders such as Myelofibrosis, Essential thrombocytopenia or Polycythemia vera, Fanconi anemia, Dyskeratosis congenita, Common variable immune deficiency (CVID, such as CVID 1, CVID 2, CVID 3, CVID 4, CVID 5, and CVID 6), Human immunodeficiency virus (HIV), Hemophagocytic lymphohistiocystosis, Amyloidosis, Solid tumors such as Neuroblastoma, Germ cell tumors, Breast cancer, Wilms' tumor, Medulloblastoma, and Neuroectodermal tumors, Autoimmune diseases such as Scleroderma, Multiple sclerosis, Ulcerative colitis, Systemic lupus erythematosus and Type I diabetes, or protein deficiencies such as Adrenoleukodystrophy (ALD), Metachromatic leukodystrophy (MLD), Hemophilia A & B, Hurler syndrome, Hunter syndrome, Fabry disease, Gaucher disease, Epidermolysis bullosa, Globoid Cell Leukodystrophy, Sanfillipo syndrome, and Morquio syndrome.

Hematopoietic stem cells or progeny thereof can also be administered to a human patient in order to treat a genetic blood disorder, such as Sickle cell anemia, Alpha thalassemia, Beta thalassemia, Delta thalassemia, Hemoglobin E/thalassemia, Hemoglobin S/thalassemia, Hemoglobin C/thalassemia, Hemoglobin D/thalassemia, Chronic granulomatous disease (X-linked Chronic granulomatous disease, autosomal recessive (AR) chronic granulomatous disease, chronic granulomatous disease AR I NCF1, Chronic granulomatous disease AR CYBA, Chronic granulomatous disease AR II NCF2, Chronic granulomatous disease AR III NCF4), X-linked Severe Combined Immune Deficiency (SCID), ADA SCID, IL7-RA SCID, CD3 SCID, Rag1/Rag2 SCID, Artemis SCID, CD45 SCID, Jak3 SCID, Congenital agranulocytosis, Congenital agranulocytosis-congenital neutropenia-SCN1, Congenital agranulocytosis-congenital neutropenia-SCN2, Familial hemophagocytic lymphohistiocystosis (FHL), Familial hemophagocytic lymphohistiocytosis type 2 (FHL2, perforin mutation), Agammaglobulinemia (X-linked Agammaglobulinemia), Wiskott-Aldrich syndrome, Chediak-Higashi syndrome, Hemolytic anemia due to red cell pyruvate kinase deficiency, Paroxysmal nocturnal hemoglobinuria, X-linked Adrenoleukodystrophy (X-ALD), X-linked lymphoproliferative disease, Unicentric Castleman's Disease, Multicentric Castleman's Disease, Congenital amegakaryocytic thrombocytopenia (CAMT) type I, Reticular dysgenesis, Fanconi anemia, Acquired idiopathic sideroblastic anemia, Systemic mastocytosis, Von willebrand disease (VWD), Congenital dyserythropoietic anemia type 2, Cartilage-hair hypoplasia syndrome, Hereditary spherocytosis, Blackfan-Diamond syndrome, Shwachman-Diamond syndrome, Thrombocytopenia-absent radius syndrome, Osteopetrosis, Infantile osteopetrosis, Mucopolysaccharidoses, Lesch-Nyhan syndrome, Glycogen storage disease, Congenital mastocytosis, Omenn syndrome, X-linked Immunodysregulation, polyendocrinopathy, and enteropathy (IPEX), IPEX characterized by mutations in FOXP3, X-linked syndrome of polyendocrinopathy, immune dysfunction, and diarrhea (XPID), X-Linked Autoimmunity-Allergic Dysregulation Syndrome (XLAAD), IPEX-like syndrome, Hyper IgM type 1, Hyper IgM type 2, Hyper IgM type 3, Hyper IgM type 4, Hyper IgM type 5, X linked hyperimmunoglobulin M, Bare lymphocyte Syndrome type I, and Bare lymphocyte Syndrome type II (Bare lymphocyte Syndrome type II, MHC class I deficiency; Bare lymphocyte Syndrome type II, complementation group A; Bare lymphocyte Syndrome type II, complementation group C; Bare lymphocyte Syndrome type II complementation group D; Bare lymphocyte Syndrome type II, complementation group E). Populations of hematopoietic stem cells expanded, enriched, or maintained by the compositions and/or methods of the invention, as well as progeny thereof, can also be used to treat a patient suffering from a hematolymphoid malignancy, a non-hematolymphoid malignancy, or a protein deficiency. In other embodiments, the patient may be tissue or cell transplantation recipient, and the hematopoietic stem cells or progeny thereof are administered in order to induce tolerance to the transplanted tissue or cells.

All patents and other publications; including literature references, issued patents, published patent applications, and co-pending patent applications, cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A method of producing an expanded population of hematopoietic stem cells ex vivo, said method comprising contacting a population of hematopoietic stem cells with one or more agents that together exhibit two or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation, wherein the one or more agents are present in amounts that are sufficient to produce an expanded population of hematopoietic stem cells.

2. A method of enriching a population of cells with hematopoietic stem cells ex vivo, said method comprising contacting a population of hematopoietic cells that contains one or more hematopoietic stem cells with one or more agents that together exhibit two or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation,
wherein the one or more agents are present in amounts that are sufficient to produce a population of cells enriched with hematopoietic stem cells.

3. A method of maintaining the hematopoietic stem cell functional potential of a population of hematopoietic stem cells ex vivo for at least two days, said method comprising contacting a first population of hematopoietic stem cells with one or more agents that together exhibit two or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation,
wherein the first population of hematopoietic stem cells exhibits a hematopoietic stem cell functional potential after two or more days that is greater than that of a control population of hematopoietic stem cells cultured under the same conditions and for the same time as said first population of hematopoietic stem cells but not contacted with said one or more agents.

4. The method of any one of paragraphs 1-3, wherein the modulation of histone methylation is activation of histone methylation, maintenance of histone methylation, or inhibition of histone demethylation.

5. The method of any one of paragraphs 1-4, wherein the modulation of histone acetylation is activation of histone acetylation, maintenance of histone acetylation, or inhibition of histone deacetylation.

6. The method of paragraph 4, wherein said one or more agents comprise a compound that activates histone methylation, maintains histone methylation, or inhibits histone demethylation and a compound that inhibits TGFβ signaling.

7. The method of paragraph 6, wherein said compound that activates histone methylation, maintains histone methylation, or inhibits histone demethylation is a histone demethylase inhibitor and said compound that inhibits TGFβ signaling is a TGFβ receptor inhibitor.

8. The method of paragraph 7, wherein said histone demethylase inhibitor is a LSD1 inhibitor.

9. The method of paragraph 8, wherein said LSD1 inhibitor is LSD1 inhibitor IV RN-1 and said TGFβ receptor inhibitor is ALK5 inhibitor II.

10. The method of paragraph 8, wherein said LSD1 inhibitor is tranylcypromine and said TGFβ receptor inhibitor is ALK5 inhibitor II.

11. A method of producing an expanded population of hematopoietic stem cells ex vivo, said method comprising contacting a population of hematopoietic stem cells with one or more agents that together inhibit the activity of two or more proteins selected from the group consisting of:
   a. a histone demethylase;
   b. a protein that propagates TGFβ signaling;
   c. a protein that propagates p38 signaling;
   d. a protein that promotes β-catenin degradation; and
   e. a histone deacetylase,
wherein the one or more agents are present in amounts that are sufficient to produce an expanded population of hematopoietic stem cells.

12. A method of enriching a population of cells with hematopoietic stem cells ex vivo, said method comprising contacting a population of hematopoietic cells that contains one or more hematopoietic stem cells with one or more agents that together inhibit the activity of two or more proteins selected from the group consisting of:
   a. a histone demethylase;
   b. a protein that propagates TGFβ signaling;
   c. a protein that propagates p38 signaling;
   d. a protein that promotes β-catenin degradation; and
   e. a histone deacetylase,
wherein the one or more agents are present in amounts that are sufficient to produce a population of cells enriched with hematopoietic stem cells.

13. A method of maintaining the hematopoietic stem cell functional potential of a population of hematopoietic stem cells ex vivo for at least two days, said method comprising contacting a first population of hematopoietic stem cells with one or more agents that together inhibit the activity of two or more proteins selected from the group consisting of:
   a. a histone demethylase;
   b. a protein that propagates TGFβ signaling;
   c. a protein that propagates p38 signaling;
   d. a protein that promotes β-catenin degradation; and
   e. a histone deacetylase,
wherein the first population of hematopoietic stem cells exhibits a hematopoietic stem cell functional potential after two or more days that is greater than that of a control population of hematopoietic stem cells cultured under the same conditions and for the same time as said first population of hematopoietic stem cells but not contacted with said one or more agents.

14. The method of any one of paragraphs 11-13, wherein the one or more agents comprise a combination of agents selected from the combination of agents of Table 1, Table 2, Table 3, Table 4, Table 5, and Table 6.

15. The method of any one of paragraphs 11-13, wherein said histone demethylase is LSD1.

16. The method of any one of paragraphs 11-13, wherein said one or more agents comprise a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine.

17. The method of any one of paragraphs 11-16, wherein said protein that propagates TGFβ signaling is a TGFβ receptor.

18. The method of any one of paragraphs 11-17, wherein said one or more agents comprise a compound that inhibits a protein that propagates TGFβ signaling selected from the group consisting of ALK5 inhibitor II, LY364947, A83-01, and DMH1.

19. The method of any one of paragraphs 11-18, wherein said one or more agents comprise a compound that inhibits a protein that propagates p38 signaling, and wherein said compound is SB203580.

20. The method of any one of paragraphs 11-19, wherein said one or more agents comprise a compound that inhibits a protein that promotes β-catenin degradation selected from the group consisting of CHIR99021, lithium chloride, BIO, and FGF2.

21. The method of any one of paragraphs 11-20, wherein said one or more agents comprise a compound that inhibits a histone deacetylase are selected from the group consisting of Trichostatin A, valproic acid, butyrylhydroxamic acid, and istodax.

22. The method of any one of paragraphs 11-21, wherein said one or more agents together inhibit the activity of a histone demethylase and a protein that propagates TGFβ signaling.

23. The method of paragraph 22, wherein said histone demethylase is LSD1.

24. The method of paragraph 22 or 23, wherein said protein that propagates TGFβ signaling is a TGFβ receptor.

25. The method of any one of paragraphs 22-24, wherein said one or more agents comprise LSD1 inhibitor IV RN-1 and ALK5 inhibitor II.

26. The method of any one of paragraphs 22-25, wherein said one or more agents comprise a compound that inhibits p38 signaling.

27. The method of any one of paragraphs 22-26, wherein said one or more agents comprise a compound that inhibits a histone deacetylase.

28. The method of any one of paragraphs 22-27, wherein said one or more agents further comprise a compound that inhibits BMP signaling.

29. A method of producing an expanded population of hematopoietic stem cells ex vivo, said method comprising contacting a population of hematopoietic stem cells with (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax.

30. A method of enriching a population of cells with hematopoietic stem cells ex vivo, said method comprising contacting a population of hematopoietic cells that contains one or more hematopoietic stem cells with (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax.

31. A method of maintaining the hematopoietic stem cell functional potential of a population of hematopoietic stem cells ex vivo for at least two days, said method comprising contacting a first population of hematopoietic stem cells with said method comprising contacting a population of hematopoietic stem cells with (a) a first agent selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax, wherein the first population of hematopoietic stem cells exhibits a hematopoietic stem cell functional potential after two or more days that is greater than that of a control population of hematopoietic stem cells cultured under the same conditions and for the same time as said first population of hematopoietic stem cells but not contacted with said first and second agents.

32. The method of any one of paragraphs 29-31, wherein the one or more agents comprise a combination of agents selected from the combination of agents of Table 7, Table 8, Table 9, and Table 10.

33. The method of any one of paragraphs 1-32, wherein said one or more agents are present in amounts that are sufficient to stimulate expansion of said population of cells by 10% or more relative to a population of hematopoietic stem cells not contacted with said one or more agents after seven or more days of culture (e.g., after seven, ten, twelve, fourteen, fifteen, twenty, or more days of culture).

34. The method of any one of paragraphs 1-32, wherein said one or more agents are present in amounts that are sufficient to stimulate expansion of said population of cells by 10% or more relative to a population of hematopoietic stem cells that have been contacted with a substance that inhibits aryl hydrocarbon receptor signaling such as SR1 or an analog thereof, UM171 or an analog thereof, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

35. The method of any one of paragraphs 1-32, wherein said one or more agents are present in amounts that are sufficient to enrich said population of cells with hematopoietic stem cells by 10% or more relative to a population of hematopoietic stem cells not contacted with said one or more agents after seven or more days of culture (e.g., after seven, ten, twelve, fourteen, fifteen, twenty, or more days of culture).

36. The method of any one of paragraphs 1-32, wherein said one or more agents are present in amounts that are sufficient to enrich said population of cells with hematopoietic stem cells by 10% or more relative to a population of hematopoietic stem cells that have been contacted with a substance that inhibits aryl hydrocarbon receptor signaling such as SR1 or an analog thereof, UM171 or an analog thereof, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

37. The method of any one of paragraphs 3, 13, and 31, wherein said first population of hematopoietic stem cells exhibits a hematopoietic stem cell functional potential after three or more days of culture (e.g., three, five, seven, ten, twelve, fourteen, fifteen, twenty, or more days) that is greater than that of said control population of hematopoietic stem cells.

38. The method of any one of paragraphs 1-37, wherein said hematopoietic stem cells are mammalian cells.

39. The method of paragraph 38, wherein said mammalian cells are human cells.

40. The method of paragraph 39, wherein said hematopoietic stem cells are CD34+ cells.

41. The method of paragraph 40, wherein at least 10% of said CD34+ cells are CD34+CD38-, CD34+CD38-CD90+, CD34+CD38-CD90+CD45RA-, or CD34+CD38-CD90+CD45RA-CD49F+ cells.

42. The method of any one of paragraphs 38-40, wherein said hematopoietic stem cells are from human cord blood.

43. The method of any one of paragraphs 38-40, wherein said hematopoietic stem cells are from human mobilized peripheral blood.

44. The method of any one of paragraphs 38-40, wherein said hematopoietic stem cells are from human bone marrow.

45. The method of any one of paragraphs 38-44, wherein said hematopoietic stem cells are freshly isolated from said human.

46. The method of any one of paragraphs 38-44, wherein said hematopoietic stem cells have been previously cryopreserved.

47. The method of paragraph 38, wherein said mammalian cells are murine cells.

48. The method of any one of paragraphs 1-47, wherein said hematopoietic stem cells are cultured for two or more days (e.g., three, five, seven, ten, twelve, fourteen, fifteen, twenty, or more days).

49. The method of any one of paragraphs 1-48, wherein said hematopoietic stem cells contact said one or more agents for two or more days (e.g., three, five, seven, ten, twelve, fourteen, fifteen, twenty, or more days).

50. The method of any one of paragraphs 1-49, wherein said hematopoietic stem cells are contacted with said one or more agents simultaneously.

51. The method of any one of paragraphs 1-49, wherein said hematopoietic stem cells are contacted with said one or more agents at different times.

52. The method of any one of paragraphs 1-51, wherein said hematopoietic stem cells maintain hematopoietic stem cell functional potential after two days (e.g., three, five, seven, ten, twelve, fourteen, fifteen, twenty, or more days) in culture.

53. The method of paragraph 52, wherein said hematopoietic stem cells maintain hematopoietic stem cell functional potential following transplantation after two days (e.g., three, five, seven, ten, twelve, fourteen, fifteen, twenty, or more days) in culture.

54. The method of any one of paragraphs 1-53, wherein said hematopoietic stem cells maintain long term engraftment potential after two days (e.g., three, five, seven, ten, twelve, fourteen, fifteen, twenty, or more days) in culture.

55. The method of any one of paragraphs 1-54, wherein upon transplantation into a patient, said hematopoietic stem cells give rise to recovery of a population of cells selected from the group consisting of neutrophils, platelets, red blood cells, monocytes, macrophages, antigen-presenting cells, microglia, osteoclasts, dendritic cells, and lymphocytes.

56. The method of paragraph 55, wherein said lymphocytes are selected from the group consisting of natural killer cells, T cells (e.g., CD4+ or CD8+ cells), and B cells.

57. The method of any one of paragraphs 1-56, wherein said hematopoietic stem cells are capable of localizing to hematopoietic tissue to reestablish productive hematopoiesis in a transplanted recipient.

58. The method of any one of paragraphs 1-57, wherein said hematopoietic stem cells are cultured on a plastic surface or on a substrate that includes vitronectin, fibronectin, or matrigel.

59. The method of any one of paragraphs 1-58, wherein said hematopoietic stem cells are cultured in the presence of 2-20% oxygen.

60. The method of paragraph 59, wherein said hematopoietic stem cells are cultured in the presence of 2-12% oxygen.

61. The method of paragraph 60, wherein said hematopoietic stem cells are cultured in the presence of about 5% oxygen.

62. The method of any one of paragraphs 1-61, wherein said hematopoietic stem cells are originally within a mononuclear cell fraction prior to treatment with said one or more agents.

63. The method of any one of paragraphs 1-61, wherein said hematopoietic stem cells are originally within a CD34+, CD34+CD38-, CD34+CD38-CD90+, CD34+CD38-CD90+CD45RA-, or CD34+CD38-CD90+CD45RA-CD49F+ enriched cell fraction prior to contacting said one or more agents.

64. The method of any one of paragraphs 1-61, wherein said hematopoietic stem cells are originally within an un-enriched cell fraction prior to contacting said one or more agents.

65. A method of introducing a polynucleotide into a population of hematopoietic stem cells, said method comprising:
    a. inserting the polynucleotide into said population of hematopoietic stem cells; and
    b. expanding said population of hematopoietic stem cells according to the method of any one of paragraphs 1, 11, 29, or maintaining the hematopoietic stem cell functional potential of said population of hematopoietic stem cells according to the method of any one of paragraphs 3, 13, and 31-64.

66. The method of paragraph 65, wherein (a) precedes (b).

67. The method of paragraph 65, wherein (b) precedes (a).

68. The method of any one of paragraphs 65-67, wherein said method comprises providing one or more reagents that cleave a nucleic acid in said cells.

69. The method of paragraph 68, wherein the one or more reagents that cleave a nucleic acid in said cells comprise a zinc finger nuclease.

70. The method of paragraph 68, wherein the one or more reagents that cleave a nucleic acid in said cells comprise a transcription activator-like effector nuclease.

71. The method of paragraph 68, wherein the one or more reagents that cleave a nucleic acid in said cells comprise a CRISPR-associated protein.

72. The method of paragraph 68, wherein the one or more agents that cleave a nucleic acid in said cells comprise a meganuclease.

73. The method of any one of paragraphs 65-72, wherein said method comprises contacting the hematopoietic stem cells with a vector selected from the group consisting of a viral vector (such as retrovirus, adenovirus, parvovirus, coronavirus, rhabdovirus, paramyxovirus, picornavirus, alphavirus, herpes virus, or poxvirus) and a transposable element (such as a piggybac transposon or sleeping beauty transposon)

74. The method of any one of paragraphs 65-72, wherein said method comprises introducing said polynucleotide into said hematopoietic stem cells by electroporation, Nucleofection™, or squeeze-poration.

75. The method of any one of paragraphs 65-72, wherein said method comprises contacting the cells with a transformation agent selected from the group consisting of a cationic polymer (e.g., diethylaminoethyl-dextran), a cationic lipid, calcium phosphate, an activated dendrimer, and a magnetic bead.

76. The method of any one of paragraphs 65-72, wherein said method comprises introducing said polynucleotide into said hematopoietic stem cells by microinjection or laserfection.

77. The method of any one of paragraphs 65-76, wherein said polynucleotide comprises a regulatory sequence selected from the group consisting of a promoter, enhancer, or silencer sequence.

78. The method of any one of paragraphs 65-76, wherein said polynucleotide encodes a molecule selected from the group consisting of a protein and a RNA (mRNA, tRNA, siRNA, miRNA, shRNA).

79. The method of any one of paragraphs 65-76, wherein said polynucleotide is a chemically modified RNA.

80. The method of any one of paragraphs 65-79, wherein said method further comprises introducing the population of expanded hematopoietic stem cells or progeny thereof into a recipient.

81. A method of treating a recipient with hematopoietic stem cells or progeny thereof, said method comprising:
   a. providing a population of hematopoietic stem cells;
   b. expanding said population of hematopoietic stem cells according to the method of any one of paragraphs 1, 11, 29, and 32-64;
   c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing the population of expanded hematopoietic stem cells or progeny thereof into said recipient.

82. A method of treating a recipient with hematopoietic stem cells or progeny thereof, said method comprising:
   a. providing a population of hematopoietic stem cells;
   b. enriching said population of hematopoietic stem cells according to the method of any one of paragraphs 2, 12, 30, and 32-64;
   c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing the population of cells enriched with hematopoietic stem cells or progeny thereof into said recipient.

83. A method of treating a recipient with hematopoietic stem cells or progeny thereof, said method comprising:
   a. providing a population of hematopoietic stem cells;
   b. maintaining the hematopoietic stem cell functional potential of said population of hematopoietic stem cells according to the method of any one of paragraphs 3, 13, and 31-64; c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing said population of hematopoietic stem cells or progeny thereof into said recipient.

84. A method of treating a recipient with hematopoietic stem cells or progeny thereof, said method comprising:
   a. providing a population of hematopoietic stem cells produced by the method of any one of paragraphs 1-64;
   b. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   c. introducing said population of hematopoietic stem cells or progeny thereof into said recipient.

85. The method of any one of paragraphs 80-84, wherein said recipient is a human.

86. The method of paragraph 85, wherein said hematopoietic stem cells are derived from one or more hematopoietic stem cells isolated from a human donor.

87. The method of paragraph 86, wherein said hematopoietic stem cells are from mobilized peripheral blood of said donor.

88. The method of paragraph 87, wherein said donor has been previously administered one or more mobilizing agents selected from the group consisting of a CXCR4 antagonist (e.g., AMD3100), GCSF, and GROβ.

89. The method of any one of paragraphs 1-88, wherein the hematopoietic stem cells are additionally contacted with a substance that inhibits aryl hydrocarbon receptor signaling.

90. The method of any one of paragraphs 34, 36, and 89, wherein the substance that inhibits aryl hydrocarbon receptor signaling is SR1 or an analog thereof.

91. The methods of any one of paragraphs 1-90, wherein the hematopoietic stem cells are additionally contacted with UM171 or an analog thereof.

92. The method of any one of paragraphs 1-91, wherein the hematopoietic stem cells are additionally contacted with a prostaglandin 93. The method of paragraph 92, wherein said prostaglandin is dmPGE2 or an analog thereof.

94. The method of any one of paragraphs 1-93, wherein the hematopoietic stem cells are additionally contacted with an agonist of Notch signaling.

95. The method of any one of paragraphs 1-94, wherein the hematopoietic stem cells are additionally contacted with an inhibitor of SIRT1.

96. The method of paragraph 95, wherein said inhibitor or SIRT1 is selected from the group consisting of nicotinamide, cambinol, and analogs thereof.

97. The method of any one of paragraphs 80-96, wherein said recipient is a human patient suffering from a disease selected from the group consisting of Acute Lymphoblastic Leukemia (ALL), Acute Myelogenous Leukemia (AML), Chronic Myelogenous Leukemia (CML), Chronic Lymphocytic Leukemia (CLL), Hodgkin Lymphoma (HL), Non-Hodgkin Lymphoma (NHL), Myelodysplastic Syndrome (MDS), Multiple myeloma, Aplastic anemia, Bone marrow failure, Myeloproliferative disorders such as Myelofibrosis, Essential thrombocytopenia or Polycythemia vera, Fanconi anemia, Dyskeratosis congenita, Common variable immune deficiency (CVID, such as CVID 1, CVID 2, CVID 3, CVID 4, CVID 5, and CVID 6), Human immunodeficiency virus (HIV), Hemophagocytic lymphohistiocystosis, Amyloidosis, Solid tumors such as Neuroblastoma, Germ cell tumors, Breast cancer, Wilms' tumor, Medulloblastoma, and Neuroectodermal tumors, Autoimmune diseases such as Scleroderma, Multiple sclerosis, Ulcerative colitis, Systemic lupus erythematosus and Type I diabetes, or protein deficiencies such as Adrenoleukodystrophy (ALD), Metachromatic leukodystrophy (MLD), Hemophilia A & B, Hurler syndrome, Hunter syndrome, Fabry disease, Gaucher disease, Epidermolysis bullosa, Globoid Cell Leukodystrophy, Sanfillipo syndrome, and Morquio syndrome.

98. The method of any one of paragraphs 80-96, wherein said recipient is a human patient suffering from a disease selected from the group consisting of Sickle cell anemia, Alpha thalassemia, Beta thalassemia, Delta thalassemia, Hemoglobin E/thalassemia, Hemoglobin S/thalassemia, Hemoglobin C/thalassemia, Hemoglobin D/thalassemia, Chronic granulomatous disease (X-linked Chronic granulomatous disease, autosomal recessive (AR) chronic granulomatous disease, chronic granulomatous disease AR I NCF1, Chronic granulomatous disease AR CYBA, Chronic granulomatous disease AR II NCF2, Chronic granulomatous disease AR III NCF4), X-linked Severe Combined Immune Deficiency (SCID), ADA SCID, IL7-RA SCID, CD3 SCID, Rag1/Rag2 SCID, Artemis SCID, CD45 SCID, Jak3 SCID, Congenital agranulocytosis, Congenital agranulocytosis-congenital neutropenia-SCN1, Congenital agranulocytosis-congenital neutropenia-SCN2, Familial hemophagocytic lymphohistiocystosis (FHL), Familial hemophagocytic lymphohistiocytosis type 2 (FHL2, perforin mutation), Agammaglobulinemia (X-linked Agammaglobulinemia), Wiskott-Aldrich syndrome, Chediak-Higashi syndrome, Hemolytic anemia due to red cell pyruvate kinase deficiency, Paroxysmal nocturnal hemoglobinuria, X-linked Adrenoleukodystrophy (X-ALD), X-linked lymphoproliferative disease, Unicentric Castleman's Disease, Multicentric Castleman's Disease, Congenital amegakaryocytic thrombocytopenia (CAMT) type I, Reticular dysgenesis, Fanconi anemia, Acquired idiopathic sideroblastic anemia, Systemic mastocytosis, Von willebrand disease (VWD), Congenital dyserythropoietic anemia type 2, Cartilage-hair hypoplasia syndrome, Hereditary spherocytosis, Blackfan-Diamond syndrome, Shwachman-Diamond syndrome, Thrombocytopenia-absent radius syndrome, Osteopetrosis, Infantile osteopetrosis, Mucopolysaccharidoses, Lesch-Nyhan syndrome, Glycogen storage disease, Congenital mastocytosis, Omenn syndrome, X-linked Immunodysregulation, polyendocrinopathy, and enteropathy (IPEX), IPEX characterized by mutations in FOXP3, X-linked syndrome of polyendocrinopathy, immune dysfunction, and diarrhea (XPID), X-Linked Autoimmunity-Allergic Dysregulation Syndrome (XLAAD), IPEX-like syndrome, Hyper IgM type 1, Hyper IgM type 2, Hyper IgM type 3, Hyper IgM type 4, Hyper IgM type 5, X linked hyperimmunoglobulin M, Bare lymphocyte Syndrome type I, and Bare lymphocyte Syndrome type II (Bare lymphocyte Syndrome type II, MHC class I deficiency; Bare lymphocyte Syndrome type II, complementation group A; Bare lymphocyte Syndrome type II, complementation group C; Bare lymphocyte Syndrome type II complementation group D; Bare lymphocyte Syndrome type II, complementation group E).

99. The method of any one of paragraphs 80-96, wherein said recipient is a human patient suffering from a hematolymphoid malignancy, a non-hematolymphoid malignancy, or a protein deficiency, or a tissue or cell transplantation recipient (e.g., to induce tolerance to transplanted tissue or cells).

100. The method of any one of paragraphs 80-99, wherein said hematopoietic stem cells are autologous or syngeneic.

101. The method of any one of paragraphs 80-99, wherein said hematopoietic stem cells are allogeneic.

102. A composition comprising one or more agents that together exhibit two or more activities selected from the group consisting of:
 a. modulation of histone methylation;
 b. inhibition of TGFβ signaling;
 c. inhibition of p38 signaling;
 d. activation of canonical Wnt signaling; and
 e. modulation of histone acetylation.

103. The composition of paragraph 102, wherein the modulation of histone methylation is activation of histone methylation, maintenance of histone methylation, or inhibition of histone demethylation.

104. The composition of paragraph 102 or 103, wherein the modulation of histone acetylation is activation of histone acetylation, maintenance of histone acetylation, or inhibition of histone deacetylation.

105. The composition of paragraph 103, wherein said one or more agents comprise a compound that activates histone methylation, maintains histone methylation, or inhibits histone demethylation and a compound that inhibits TGFβ signaling.

106. The composition of paragraph 105, wherein said compound that activates histone methylation, maintains histone methylation, or inhibits histone demethylation a histone demethylase inhibitor and said compound that inhibits TGFβ signaling is a TGFβ receptor inhibitor.

107. The composition of paragraph 106, wherein said histone demethylase inhibitor is a LSD1 inhibitor.

108. The composition of paragraph 107, wherein said LSD1 inhibitor is LSD1 inhibitor IV RN-1 and said TGFβ receptor inhibitor is ALK5 inhibitor II.

109. The composition of paragraph 107, wherein said LSD1 inhibitor is tranylcypromine and said TGFβ receptor inhibitor is ALK5 inhibitor II.

110. A composition comprising one or more agents that together inhibit the activity of two or more proteins selected from the group consisting of:
 a. a histone demethylase;
 b. a protein that propagates TGFβ signaling;
 c. a protein that propagates p38 signaling;
 d. a protein that promotes β-catenin degradation; and
 e. a histone deacetylase.

111. The composition of paragraph 110, wherein said histone demethylase is LSD1.

112. The composition of paragraph 110, wherein said one or more agents comprise a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine.

113. The composition of any one of paragraphs 110-112, wherein said protein that propagates TGFβ signaling is a TGFβ receptor.

114. The composition of any one of paragraphs 110-113, wherein said one or more agents comprise a compound that inhibits a protein that propagates TGFβ signaling selected from the group consisting of ALK5 inhibitor II, LY364947, A83-01, and DMH1.

115. The composition of any one of paragraphs 110-114, wherein said one or more agents comprise a compound that inhibits a protein that propagates p38 signaling, and wherein said compound is SB203580.

116. The composition of any one of paragraphs 110-115, wherein said one or more agents comprise a compound that inhibits a protein that promotes β-catenin degradation selected from the group consisting of CHIR99021, lithium chloride, BIO, and FGF2.

117. The composition of any one of paragraphs 110-116, wherein said one or more agents comprise a compound that inhibits a histone deacetylase selected from the group consisting of Trichostatin A, valproic acid, butyrylhydroxamic acid, and istodax.

118. The composition of any one of paragraphs 110-117, wherein said one or more agents together inhibit the activity of a histone demethylase and a protein that propagates TGFβ signaling 119. The composition of paragraph 118, wherein said histone demethylase is LSD1.

120. The composition of paragraph 118 or 119, wherein said protein that propagates TGFβ signaling is a TGFβ receptor.

121. The composition of any one of paragraphs 118-120, wherein said one or more agents comprise LSD1 inhibitor IV RN-1 and ALK5 inhibitor II.

122. The composition of any one of paragraphs 118-121, wherein said one or more agents comprise a compound that inhibits p38 signaling.

123. The composition of any one of paragraphs 118-122, wherein said one or more agents comprise a compound that inhibits a histone deacetylase.

124. The composition of any one of paragraphs 118-123, wherein said one or more agents comprise a compound that inhibits BMP signaling.

125. A composition comprising (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax.

126. The composition of any one of paragraphs 102-125, wherein said one or more agents are present in amounts that are sufficient to produce an expanded population of hematopoietic stem cells.

127. The composition of any one of paragraphs 102-125, wherein said one or more agents are present in amounts that are sufficient to produce a population of cells enriched with hematopoietic stem cells.

128. The composition of any one of paragraphs 102-125, wherein said one or more agents are present in amounts sufficient to maintain the hematopoietic stem cell functional potential of said population of hematopoietic stem cells for at least two days.

129. The composition of any one of paragraphs 126-128, wherein said one or more agents are present in an aqueous solution.

130. The composition of any one of paragraphs 126-128, wherein said one or more agents are present as a lyophilized solid.

131. The composition of any one of paragraphs 126-130, wherein said one or more agents are present in amounts that are sufficient to stimulate expansion of said population of cells by 10% or more relative to a population of hematopoietic stem cells that have been contacted with a substance that inhibits aryl hydrocarbon receptor signaling such as SR1 or an analog thereof, UM171 or an analog thereof, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

132. The composition of any one of paragraphs 126-130, wherein said one or more agents are present in amounts that are sufficient to enrich the population of cells with hematopoietic stem cells by 10% or more relative to a population of hematopoietic stem cells that have been contacted with a substance that inhibits aryl hydrocarbon receptor signaling such as SR1 or an analog thereof, UM171 or an analog thereof, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

133. The composition of any one of paragraphs 126-130, wherein said one or more agents are present in amounts that are sufficient to maintain long term engraftment potential of said hematopoietic stem cells post-transplantation after having contacted said cells in culture for two or more days (e.g., three, five, seven, ten, twelve, fourteen, fifteen, twenty, or more days).

134. A composition comprising a combination of agents selected from the combination of agents of Table 1, Table 2, Table 3, Table 4, Table 5, Table 6, Table 7, Table 8, Table 9, and Table 10.

135. A cell culture medium comprising the composition of any one of paragraphs 102-134.

136. The cell culture medium of paragraph 135, wherein said cell culture medium is substantially free of serum.

137. The composition of any one of paragraphs 102-134, wherein said composition further comprises a population of hematopoietic stem cells in contact with said one or more agents.

138. The composition of paragraph 137, wherein said hematopoietic stem cells have been cultured in the presence of said one or more agents for two or more days (e.g., three, five, seven, ten, twelve, fourteen, fifteen, twenty, or more days).

139. A method of producing an expanded population of hematopoietic stem cells ex vivo, said method comprising contacting a population of hematopoietic stem cells with (1) a first agent that exhibits one or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation; and (2) a second agent selected from the group consisting of SR1 or an analog thereof, UM171 or an analog thereof, a prostaglandin, an agonist of Notch signaling, or an inhibitor of SIRT1, wherein the first and second agents are present in amounts that together are sufficient to produce an expanded population of hematopoietic stem cells.

140. A method of enriching a population of cells with hematopoietic stem cells ex vivo, said method comprising contacting a population of hematopoietic cells that contains one or more hematopoietic stem cells with (1) a first agent that exhibits one or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation; and (2) a second agent selected from the group consisting of SR1 or an analog thereof, UM171 or an analog thereof, a prostaglandin, an agonist of Notch signaling, or an inhibitor of SIRT1, wherein the first and second agents are present in amounts that together are sufficient to produce a population of cells enriched with hematopoietic stem cells.

141. A method of maintaining the hematopoietic stem cell functional potential of a population of hematopoietic stem cells ex vivo for at least two days, said method comprising contacting a first population of hematopoietic stem cells with (1) a first agent that exhibits one or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation; and (2) a second agent selected from the group consisting of SR1 or an analog thereof, UM171 or an analog thereof, a prostaglandin, an agonist of Notch signaling, or an inhibitor of SIRT1, wherein the population of hematopoietic stem cells exhibits a hematopoietic stem cell functional potential after two or more days that is greater than that of a control population of hematopoietic stem cells cultured under the same conditions and for the same time as said population of hematopoietic stem cells but not contacted with said one or more agents and said one or more substances.

142. A population of hematopoietic stem cells produced by the method of any one of paragraphs 1-101 and 139-141.

143. A kit comprising the composition of any one of paragraphs 102-134, 137, and 138, wherein said kit further comprises a package insert.

144. The kit of paragraph 143, wherein said package insert instructs a user of said kit to expand, enrich, or maintain the hematopoietic stem cell functional potential of a population of hematopoietic stem cells ex vivo.

145. The kit of paragraph 143, wherein said package insert instructs said user to express a polynucleotide in said hematopoietic stem cells.

146. The kit of paragraph 143, wherein said package insert instructs said user to administer said hematopoietic stem cells to a patient.

Some embodiments of the technology described herein can be defined according to any of the following numbered paragraphs:

1. A method of producing an expanded population of hematopoietic stem cells ex vivo, said method comprising contacting a population of hematopoietic stem cells with one or more agents that together exhibit two or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation,
wherein the one or more agents are present in amounts that are sufficient to produce an expanded population of hematopoietic stem cells.

2. A method of enriching a population of cells with hematopoietic stem cells ex vivo, said method comprising contacting a population of hematopoietic cells that contains one or more hematopoietic stem cells with one or more agents that together exhibit two or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation,
wherein the one or more agents are present in amounts that are sufficient to produce a population of cells enriched with hematopoietic stem cells.

3. A method of maintaining the hematopoietic stem cell functional potential of a population of hematopoietic stem cells ex vivo for at least two days, said method comprising contacting a first population of hematopoietic stem cells with one or more agents that together exhibit two or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation,
wherein the first population of hematopoietic stem cells exhibits a hematopoietic stem cell functional potential after two or more days that is greater than that of a control population of hematopoietic stem cells cultured under the same conditions and for the same time as said first population of hematopoietic stem cells but not contacted with said one or more agents.

4. The method of any one of paragraphs 1-3, wherein the modulation of histone methylation is activation of histone methylation, maintenance of histone methylation, or inhibition of histone demethylation.

5. The method of any one of paragraphs 1-4, wherein the modulation of histone acetylation is activation of histone acetylation, maintenance of histone acetylation, or inhibition of histone deacetylation.

6. The method of paragraph 4, wherein said one or more agents comprise a compound that activates histone methylation, maintains histone methylation, or inhibits histone demethylation and a compound that inhibits TGFβ signaling.

7. The method of paragraph 6, wherein said compound that activates histone methylation, maintains histone methylation, or inhibits histone demethylation is a histone demethylase inhibitor and said compound that inhibits TGFβ signaling is a TGFβ receptor inhibitor.

8. The method of paragraph 7, wherein said histone demethylase inhibitor is a LSD1 inhibitor.

9. The method of paragraph 8, wherein said LSD1 inhibitor is LSD1 inhibitor IV RN-1 and said TGFβ receptor inhibitor is ALK5 inhibitor II.

10. The method of paragraph 8, wherein said LSD1 inhibitor is tranylcypromine and said TGFβ receptor inhibitor is ALK5 inhibitor II.

11. A method of producing an expanded population of hematopoietic stem cells ex vivo, said method comprising contacting a population of hematopoietic stem cells with one or more agents that together inhibit the activity of two or more proteins selected from the group consisting of:
   a. a histone demethylase;
   b. a protein that propagates TGFβ signaling;
   c. a protein that propagates p38 signaling;
   d. a protein that promotes β-catenin degradation; and
   e. a histone deacetylase,
wherein the one or more agents are present in amounts that are sufficient to produce an expanded population of hematopoietic stem cells.

12. A method of enriching a population of cells with hematopoietic stem cells ex vivo, said method comprising contacting a population of hematopoietic cells that contains one or more hematopoietic stem cells with one or more agents that together inhibit the activity of two or more proteins selected from the group consisting of:
   a. a histone demethylase;
   b. a protein that propagates TGFβ signaling;
   c. a protein that propagates p38 signaling;
   d. a protein that promotes β-catenin degradation; and
   e. a histone deacetylase,
wherein the one or more agents are present in amounts that are sufficient to produce a population of cells enriched with hematopoietic stem cells.

13. A method of maintaining the hematopoietic stem cell functional potential of a population of hematopoietic stem cells ex vivo for at least two days, said method comprising contacting a first population of hematopoietic stem cells with one or more agents that together inhibit the activity of two or more proteins selected from the group consisting of:
   a. a histone demethylase;
   b. a protein that propagates TGFβ signaling;
   c. a protein that propagates p38 signaling;
   d. a protein that promotes β-catenin degradation; and
   e. a histone deacetylase,
wherein the first population of hematopoietic stem cells exhibits a hematopoietic stem cell functional potential after two or more days that is greater than that of a control population of hematopoietic stem cells cultured under the same conditions and for the same time as said first population of hematopoietic stem cells but not contacted with said one or more agents.

14. The method of any one of paragraphs 11-13, wherein the one or more agents comprise a combination of agents selected from the combination of agents of Table 1, Table 2, Table 3, Table 4, Table 5, and Table 6.

15. The method of any one of paragraphs 11-13, wherein said histone demethylase is LSD1.

16. The method of any one of paragraphs 11-13, wherein said one or more agents comprise a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine.

17. The method of any one of paragraphs 11-16, wherein said protein that propagates TGFβ signaling is a TGFβ receptor.

18. The method of any one of paragraphs 11-17, wherein said one or more agents comprise a compound that inhibits a protein that propagates TGFβ signaling selected from the group consisting of ALK5 inhibitor II, LY364947, A83-01, and DMH1.

19. The method of any one of paragraphs 11-18, wherein said one or more agents comprise a compound that inhibits a protein that propagates p38 signaling, and wherein said compound is SB203580.

20. The method of any one of paragraphs 11-19, wherein said one or more agents comprise a compound that inhibits a protein that promotes β-catenin degradation selected from the group consisting of CHIR99021, lithium chloride, BIO, and FGF2.

21. The method of any one of paragraphs 11-20, wherein said one or more agents comprise a compound that inhibits a histone deacetylase are selected from the group consisting of Trichostatin A, valproic acid, butyrylhydroxamic acid, and istodax.

22. The method of any one of paragraphs 11-21, wherein said one or more agents together inhibit the activity of a histone demethylase and a protein that propagates TGFβ signaling.

23. The method of paragraph 22, wherein said histone demethylase is LSD1.

24. The method of paragraph 22 or 23, wherein said protein that propagates TGFβ signaling is a TGFβ receptor.

25. The method of any one of paragraphs 22-24, wherein said one or more agents comprise LSD1 inhibitor IV RN-1 and ALK5 inhibitor II.

26. The method of any one of paragraphs 22-25, wherein said one or more agents comprise a compound that inhibits p38 signaling.

27. The method of any one of paragraphs 22-26, wherein said one or more agents comprise a compound that inhibits a histone deacetylase.

28. The method of any one of paragraphs 22-27, wherein said one or more agents further comprise a compound that inhibits BMP signaling.

29. A method of producing an expanded population of hematopoietic stem cells ex vivo, said method comprising contacting a population of hematopoietic stem cells with (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax.

30. A method of enriching a population of cells with hematopoietic stem cells ex vivo, said method comprising contacting a population of hematopoietic cells that contains one or more hematopoietic stem cells with (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax.

31. A method of maintaining the hematopoietic stem cell functional potential of a population of hematopoietic stem cells ex vivo for at least two days, said method comprising contacting a first population of hematopoietic stem cells with said method comprising contacting a population of hematopoietic stem cells with (a) a first agent selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax, wherein the first population of hematopoietic stem cells exhibits a hematopoietic stem cell functional potential after two or more days that is greater than that of a control population of hematopoietic stem cells cultured under the same conditions and for the same time as said first population of hematopoietic stem cells but not contacted with said first and second agents.

32. The method of any one of paragraphs 29-31, wherein the one or more agents comprise a combination of agents selected from the combination of agents of Table 7, Table 8, Table 9, and Table 10.

33. The method of any one of paragraphs 1-32, wherein said one or more agents are present in amounts that are sufficient to stimulate expansion of said population of cells by 10% or more relative to a population of hematopoietic stem cells not contacted with said one or more agents after seven or more days of culture (e.g., after seven, ten, twelve, fourteen, fifteen, twenty, or more days of culture).

34. The method of any one of paragraphs 1-32, wherein said one or more agents are present in amounts that are sufficient to stimulate expansion of said population of cells by 10% or more relative to a population of hematopoietic stem cells that have been contacted with a substance that inhibits aryl hydrocarbon receptor signaling such as SR1 or an analog thereof, UM171 or an analog thereof, a UM171 analog selected from Table 11, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

35. The method of any one of paragraphs 1-32, wherein said one or more agents are present in amounts that are sufficient to enrich said population of cells with hematopoietic stem cells by 10% or more relative to a population of hematopoietic stem cells not contacted with said one or more agents after seven or more days of culture (e.g., after seven, ten, twelve, fourteen, fifteen, twenty, or more days of culture).

36. The method of any one of paragraphs 1-32, wherein said one or more agents are present in amounts that are sufficient to enrich said population of cells with hematopoietic stem cells by 10% or more relative to a population of hematopoietic stem cells that have been contacted with a substance that inhibits aryl hydrocarbon receptor signaling such as SR1 or an analog thereof, UM171 or an analog thereof, a UM171 analog selected from Table 11, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

37. The method of any one of paragraphs 3, 13, and 31, wherein said first population of hematopoietic stem cells exhibits a hematopoietic stem cell functional potential after three or more days of culture (e.g., three, five, seven, ten, twelve, fourteen, fifteen, twenty, or more days) that is greater than that of said control population of hematopoietic stem cells.

38. The method of any one of paragraphs 1-37, wherein said hematopoietic stem cells are mammalian cells.

39. The method of paragraph 38, wherein said mammalian cells are human cells.

40. The method of paragraph 39, wherein said hematopoietic stem cells are CD34+ cells.

41. The method of paragraph 40, wherein at least 10% of said CD34+ cells are CD34+CD38-, CD34+CD38-CD90+, CD34+CD38-CD90+CD45RA-, or CD34+CD38-CD90+CD45RA-CD49F+ cells.

42. The method of any one of paragraphs 38-40, wherein said hematopoietic stem cells are from human cord blood.

43. The method of any one of paragraphs 38-40, wherein said hematopoietic stem cells are from human mobilized peripheral blood.

44. The method of any one of paragraphs 38-40, wherein said hematopoietic stem cells are from human bone marrow.

45. The method of any one of paragraphs 38-44, wherein said hematopoietic stem cells are freshly isolated from said human.

46. The method of any one of paragraphs 38-44, wherein said hematopoietic stem cells have been previously cryopreserved.

47. The method of paragraph 38, wherein said mammalian cells are murine cells.

48. The method of any one of paragraphs 1-47, wherein said hematopoietic stem cells are cultured for two or more days (e.g., three, five, seven, ten, twelve, fourteen, fifteen, twenty, or more days).

49. The method of any one of paragraphs 1-48, wherein said hematopoietic stem cells contact said one or more agents for two or more days (e.g., three, five, seven, ten, twelve, fourteen, fifteen, twenty, or more days).

50. The method of any one of paragraphs 1-49, wherein said hematopoietic stem cells are contacted with said one or more agents simultaneously.

51. The method of any one of paragraphs 1-49, wherein said hematopoietic stem cells are contacted with said one or more agents at different times.

52. The method of any one of paragraphs 1-51, wherein said hematopoietic stem cells maintain hematopoietic stem cell functional potential after two days (e.g., three, five, seven, ten, twelve, fourteen, fifteen, twenty, or more days) in culture.

53. The method of paragraph 52, wherein said hematopoietic stem cells maintain hematopoietic stem cell functional potential following transplantation after two days (e.g., three, five, seven, ten, twelve, fourteen, fifteen, twenty, or more days) in culture.

54. The method of any one of paragraphs 1-53, wherein said hematopoietic stem cells maintain long term engraftment potential after two days (e.g., three, five, seven, ten, twelve, fourteen, fifteen, twenty, or more days) in culture.

55. The method of any one of paragraphs 1-54, wherein upon transplantation into a patient, said hematopoietic stem cells give rise to recovery of a population of cells selected from the group consisting of neutrophils, platelets, red blood cells, monocytes, macrophages, antigen-presenting cells, microglia, osteoclasts, dendritic cells, and lymphocytes.

56. The method of paragraph 55, wherein said lymphocytes are selected from the group consisting of natural killer cells, T cells (e.g., CD4+ or CD8+ cells), and B cells.

57. The method of any one of paragraphs 1-56, wherein said hematopoietic stem cells are capable of localizing to hematopoietic tissue to reestablish productive hematopoiesis in a transplanted recipient.

58. The method of any one of paragraphs 1-57, wherein said hematopoietic stem cells are cultured on a plastic surface or on a substrate that includes vitronectin, fibronectin, or matrigel.

59. The method of any one of paragraphs 1-58, wherein said hematopoietic stem cells are cultured in the presence of 2-20% oxygen.

60. The method of paragraph 59, wherein said hematopoietic stem cells are cultured in the presence of 2-12% oxygen.

61. The method of paragraph 60, wherein said hematopoietic stem cells are cultured in the presence of about 5% oxygen.

62. The method of any one of paragraphs 1-61, wherein said hematopoietic stem cells are originally within a mononuclear cell fraction prior to treatment with said one or more agents.

63. The method of any one of paragraphs 1-61, wherein said hematopoietic stem cells are originally within a CD34+, CD34+CD38-, CD34+CD38-CD90+, CD34+CD38-CD90+CD45RA-, or CD34+CD38-CD90+CD45RA-CD49F+ enriched cell fraction prior to contacting said one or more agents.

64. The method of any one of paragraphs 1-61, wherein said hematopoietic stem cells are originally within an un-enriched cell fraction prior to contacting said one or more agents.

65. A method of introducing a polynucleotide into a population of hematopoietic stem cells, said method comprising:
  a. inserting the polynucleotide into said population of hematopoietic stem cells; and
  b. expanding said population of hematopoietic stem cells according to the method of any one of paragraphs 1, 11, 29, or maintaining the hematopoietic stem cell functional potential of said population of hematopoietic stem cells according to the method of any one of paragraphs 3, 13, and 31-64.

66. The method of paragraph 65, wherein (a) precedes (b).

67. The method of paragraph 65, wherein (b) precedes (a).

68. The method of any one of paragraphs 65-67, wherein said method comprises providing one or more reagents that cleave a nucleic acid in said cells.

69. The method of paragraph 68, wherein the one or more reagents that cleave a nucleic acid in said cells comprise a zinc finger nuclease.
70. The method of paragraph 68, wherein the one or more reagents that cleave a nucleic acid in said cells comprise a transcription activator-like effector nuclease.
71. The method of paragraph 68, wherein the one or more reagents that cleave a nucleic acid in said cells comprise a CRISPR-associated protein.
72. The method of paragraph 68, wherein the one or more agents that cleave a nucleic acid in said cells comprise a meganuclease.
73. The method of any one of paragraphs 65-72, wherein said method comprises contacting the hematopoietic stem cells with a vector selected from the group consisting of a viral vector (such as retrovirus, adenovirus, parvovirus, coronavirus, rhabdovirus, paramyxovirus, picornavirus, alphavirus, herpes virus, or poxvirus) and a transposable element (such as a piggybac transposon or sleeping beauty transposon)
74. The method of any one of paragraphs 65-72, wherein said method comprises introducing said polynucleotide into said hematopoietic stem cells by electroporation, Nucleofection™, or squeeze-poration.
75. The method of any one of paragraphs 65-72, wherein said method comprises contacting the cells with a transformation agent selected from the group consisting of a cationic polymer (e.g., diethylaminoethyl-dextran), a cationic lipid, calcium phosphate, an activated dendrimer, and a magnetic bead.
76. The method of any one of paragraphs 65-72, wherein said method comprises introducing said polynucleotide into said hematopoietic stem cells by microinjection or laserfection.
77. The method of any one of paragraphs 65-76, wherein said polynucleotide comprises a regulatory sequence selected from the group consisting of a promoter, enhancer, or silencer sequence.
78. The method of any one of paragraphs 65-76, wherein said polynucleotide encodes a molecule selected from the group consisting of a protein and a RNA (mRNA, tRNA, siRNA, miRNA, shRNA).
79. The method of any one of paragraphs 65-76, wherein said polynucleotide is a chemically modified RNA.
80. The method of any one of paragraphs 65-79, wherein said method further comprises introducing the population of expanded hematopoietic stem cells or progeny thereof into a recipient.
81. A method of treating a recipient with hematopoietic stem cells or progeny thereof, said method comprising:
   a. providing a population of hematopoietic stem cells;
   b. expanding said population of hematopoietic stem cells according to the method of any one of paragraphs 1, 11, 29, and 32-64;
   c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and d. introducing the population of expanded hematopoietic stem cells or progeny thereof into said recipient.
82. A method of treating a recipient with hematopoietic stem cells or progeny thereof, said method comprising:
   a. providing a population of hematopoietic stem cells;
   b. enriching said population of hematopoietic stem cells according to the method of any one of paragraphs 2, 12, 30, and 32-64;
   c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing the population of cells enriched with hematopoietic stem cells or progeny thereof into said recipient.
83. A method of treating a recipient with hematopoietic stem cells or progeny thereof, said method comprising:
   a. providing a population of hematopoietic stem cells;
   b. maintaining the hematopoietic stem cell functional potential of said population of hematopoietic stem cells according to the method of any one of paragraphs 3, 13, and 31-64; c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing said population of hematopoietic stem cells or progeny thereof into said recipient.
84. A method of treating a recipient with hematopoietic stem cells or progeny thereof, said method comprising:
   a. providing a population of hematopoietic stem cells produced by the method of any one of paragraphs 1-64;
   b. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   c. introducing said population of hematopoietic stem cells or progeny thereof into said recipient.
85. The method of any one of paragraphs 80-84, wherein said recipient is a human.
86. The method of paragraph 85, wherein said hematopoietic stem cells are derived from one or more hematopoietic stem cells isolated from a human donor.
87. The method of paragraph 86, wherein said hematopoietic stem cells are from mobilized peripheral blood of said donor.
88. The method of paragraph 87, wherein said donor has been previously administered one or more mobilizing agents selected from the group consisting of a CXCR4 antagonist (e.g., AMD3100), GCSF, and GROβ.
89. The method of any one of paragraphs 1-88, wherein the hematopoietic stem cells are additionally contacted with a substance that inhibits aryl hydrocarbon receptor signaling.

90. The method of any one of paragraphs 34, 36, and 89, wherein the substance that inhibits aryl hydrocarbon receptor signaling is SR1 or an analog thereof.
91. The methods of any one of paragraphs 1-90, wherein the hematopoietic stem cells are additionally contacted with UM171, an analog thereof, or a UM171 analog selected from Table 11.
92. The method of any one of paragraphs 1-91, wherein the hematopoietic stem cells are additionally contacted with a prostaglandin
93. The method of paragraph 92, wherein said prostaglandin is dmPGE2 or an analog thereof.
94. The method of any one of paragraphs 1-93, wherein the hematopoietic stem cells are additionally contacted with an agonist of Notch signaling.
95. The method of any one of paragraphs 1-94, wherein the hematopoietic stem cells are additionally contacted with an inhibitor of SIRT1.
96. The method of paragraph 95, wherein said inhibitor or SIRT1 is selected from the group consisting of nicotinamide, cambinol, and analogs thereof.
97. The method of any one of paragraphs 80-96, wherein said recipient is a human patient suffering from a disease selected from the group consisting of Acute Lymphoblastic Leukemia (ALL), Acute Myelogenous Leukemia (AML), Chronic Myelogenous Leukemia (CML), Chronic Lymphocytic Leukemia (CLL), Hodgkin Lymphoma (HL), Non-Hodgkin Lymphoma (NHL), Myelodysplastic Syndrome (MDS), Multiple myeloma, Aplastic anemia, Bone marrow failure, Myeloproliferative disorders such as Myelofibrosis, Essential thrombocytopenia or Polycythemia vera, Fanconi anemia, Dyskeratosis congenita, Common variable immune deficiency (CVID, such as CVID 1, CVID 2, CVID 3, CVID 4, CVID 5, and CVID 6), Human immunodeficiency virus (HIV), Hemophagocytic lymphohistiocystosis, Amyloidosis, Solid tumors such as Neuroblastoma, Germ cell tumors, Breast cancer, Wilms' tumor, Medulloblastoma, and Neuroectodermal tumors, Autoimmune diseases such as Scleroderma, Multiple sclerosis, Ulcerative colitis, Systemic lupus erythematosus and Type I diabetes, or protein deficiencies such as Adrenoleukodystrophy (ALD), Metachromatic leukodystrophy (MLD), Hemophilia A & B, Hurler syndrome, Hunter syndrome, Fabry disease, Gaucher disease, Epidermolysis bullosa, Globoid Cell Leukodystrophy, Sanfillipo syndrome, and Morquio syndrome.
98. The method of any one of paragraphs 80-96, wherein said recipient is a human patient suffering from a disease selected from the group consisting of Sickle cell anemia, Alpha thalassemia, Beta thalassemia, Delta thalassemia, Hemoglobin E/thalassemia, Hemoglobin S/thalassemia, Hemoglobin C/thalassemia, Hemoglobin D/thalassemia, Chronic granulomatous disease (X-linked Chronic granulomatous disease, autosomal recessive (AR) chronic granulomatous disease, chronic granulomatous disease AR I NCF1, Chronic granulomatous disease AR CYBA, Chronic granulomatous disease AR II NCF2, Chronic granulomatous disease AR III NCF4), X-linked Severe Combined Immune Deficiency (SCID), ADA SCID, IL7-RA SCID, CD3 SCID, Rag1/Rag2 SCID, Artemis SCID, CD45 SCID, Jak3 SCID, Congenital agranulocytosis, Congenital agranulocytosis-congenital neutropenia-SCN1, Congenital agranulocytosis-congenital neutropenia-SCN2, Familial hemophagocytic lymphohistiocystosis (FHL), Familial hemophagocytic lymphohistiocytosis type 2 (FHL2, perforin mutation), Agammaglobulinemia (X-linked Agammaglobulinemia), Wiskott-Aldrich syndrome, Chediak-Higashi syndrome, Hemolytic anemia due to red cell pyruvate kinase deficiency, Paroxysmal nocturnal hemoglobinuria, X-linked Adrenoleukodystrophy (X-ALD), X-linked lymphoproliferative disease, Unicentric Castleman's Disease, Multicentric Castleman's Disease, Congenital amegakaryocytic thrombocytopenia (CAMT) type I, Reticular dysgenesis, Fanconi anemia, Acquired idiopathic sideroblastic anemia, Systemic mastocytosis, Von willebrand disease (VWD), Congenital dyserythropoietic anemia type 2, Cartilage-hair hypoplasia syndrome, Hereditary spherocytosis, Blackfan-Diamond syndrome, Shwachman-Diamond syndrome, Thrombocytopenia-absent radius syndrome, Osteopetrosis, Infantile osteopetrosis, Mucopolysaccharidoses, Lesch-Nyhan syndrome, Glycogen storage disease, Congenital mastocytosis, Omenn syndrome, X-linked Immunodysregulation, polyendocrinopathy, and enteropathy (IPEX), IPEX characterized by mutations in FOXP3, X-linked syndrome of polyendocrinopathy, immune dysfunction, and diarrhea (XPID), X-Linked Autoimmunity-Allergic Dysregulation Syndrome (XLAAD), IPEX-like syndrome, Hyper IgM type 1, Hyper IgM type 2, Hyper IgM type 3, Hyper IgM type 4, Hyper IgM type 5, X linked hyperimmunoglobulin M, Bare lymphocyte Syndrome type I, and Bare lymphocyte Syndrome type II (Bare lymphocyte Syndrome type II, MHC class I deficiency; Bare lymphocyte Syndrome type II, complementation group A; Bare lymphocyte Syndrome type II, complementation group C; Bare lymphocyte Syndrome type II complementation group D; Bare lymphocyte Syndrome type II, complementation group E).
99. The method of any one of paragraphs 80-96, wherein said recipient is a human patient suffering from a hematolymphoid malignancy, a non-hematolymphoid malignancy, or a protein deficiency, or a tissue or cell transplantation recipient (e.g., to induce tolerance to transplanted tissue or cells).
100. The method of any one of paragraphs 80-99, wherein said hematopoietic stem cells are autologous or syngeneic.
101. The method of any one of paragraphs 80-99, wherein said hematopoietic stem cells are allogeneic.
102. A composition comprising one or more agents that together exhibit two or more activities selected from the group consisting of:
   a. modulation of histone methylation;
   b. inhibition of TGFβ signaling;
   c. inhibition of p38 signaling;
   d. activation of canonical Wnt signaling; and
   e. modulation of histone acetylation.
103. The composition of paragraph 102, wherein the modulation of histone methylation is activation of histone methylation, maintenance of histone methylation, or inhibition of histone demethylation.
104. The composition of paragraph 102 or 103, wherein the modulation of histone acetylation is activation of histone acetylation, maintenance of histone acetylation, or inhibition of histone deacetylation.
105. The composition of paragraph 103, wherein said one or more agents comprise a compound that activates histone methylation, maintains histone methylation, or inhibits histone demethylation and a compound that inhibits TGFβ signaling.
106. The composition of paragraph 105, wherein said compound that activates histone methylation, maintains histone methylation, or inhibits histone demethylation a histone demethylase inhibitor and said compound that inhibits TGFβ signaling is a TGFβ receptor inhibitor.
107. The composition of paragraph 106, wherein said histone demethylase inhibitor is a LSD1 inhibitor.

108. The composition of paragraph 107, wherein said LSD1 inhibitor is LSD1 inhibitor IV RN-1 and said TGFβ receptor inhibitor is ALK5 inhibitor II.

109. The composition of paragraph 107, wherein said LSD1 inhibitor is tranylcypromine and said TGFβ receptor inhibitor is ALK5 inhibitor II.

110. A composition comprising one or more agents that together inhibit the activity of two or more proteins selected from the group consisting of:
   a. a histone demethylase;
   b. a protein that propagates TGFβ signaling;
   c. a protein that propagates p38 signaling;
   d. a protein that promotes β-catenin degradation; and
   e. a histone deacetylase.

111. The composition of paragraph 110, wherein said histone demethylase is LSD1.

112. The composition of paragraph 110, wherein said one or more agents comprise a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine.

113. The composition of any one of paragraphs 110-112, wherein said protein that propagates TGFβ signaling is a TGFβ receptor.

114. The composition of any one of paragraphs 110-113, wherein said one or more agents comprise a compound that inhibits a protein that propagates TGFβ signaling selected from the group consisting of ALK5 inhibitor II, LY364947, A83-01, and DMH1.

115. The composition of any one of paragraphs 110-114, wherein said one or more agents comprise a compound that inhibits a protein that propagates p38 signaling, and wherein said compound is SB203580.

116. The composition of any one of paragraphs 110-115, wherein said one or more agents comprise a compound that inhibits a protein that promotes β-catenin degradation selected from the group consisting of CHIR99021, lithium chloride, BIO, and FGF2.

117. The composition of any one of paragraphs 110-116, wherein said one or more agents comprise a compound that inhibits a histone deacetylase selected from the group consisting of Trichostatin A, valproic acid, butyrylhydroxamic acid, and istodax.

118. The composition of any one of paragraphs 110-117, wherein said one or more agents together inhibit the activity of a histone demethylase and a protein that propagates TGFβ signaling 119. The composition of paragraph 118, wherein said histone demethylase is LSD1.

120. The composition of paragraph 118 or 119, wherein said protein that propagates TGFβ signaling is a TGFβ receptor.

121. The composition of any one of paragraphs 118-120, wherein said one or more agents comprise LSD1 inhibitor IV RN-1 and ALK5 inhibitor II.

122. The composition of any one of paragraphs 118-121, wherein said one or more agents comprise a compound that inhibits p38 signaling.

123. The composition of any one of paragraphs 118-122, wherein said one or more agents comprise a compound that inhibits a histone deacetylase.

124. The composition of any one of paragraphs 118-123, wherein said one or more agents comprise a compound that inhibits BMP signaling.

125. A composition comprising (a) a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax.

126. The composition of any one of paragraphs 102-125, wherein said one or more agents are present in amounts that are sufficient to produce an expanded population of hematopoietic stem cells.

127. The composition of any one of paragraphs 102-125, wherein said one or more agents are present in amounts that are sufficient to produce a population of cells enriched with hematopoietic stem cells.

128. The composition of any one of paragraphs 102-125, wherein said one or more agents are present in amounts sufficient to maintain the hematopoietic stem cell functional potential of said population of hematopoietic stem cells for at least two days.

129. The composition of any one of paragraphs 126-128, wherein said one or more agents are present in an aqueous solution.

130. The composition of any one of paragraphs 126-128, wherein said one or more agents are present as a lyophilized solid.

131. The composition of any one of paragraphs 126-130, wherein said one or more agents are present in amounts that are sufficient to stimulate expansion of said population of cells by 10% or more relative to a population of hematopoietic stem cells that have been contacted with a substance that inhibits aryl hydrocarbon receptor signaling such as SR1 or an analog thereof, UM171 or an analog thereof, a UM171 analog selected from Table 11, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

132. The composition of any one of paragraphs 126-130, wherein said one or more agents are present in amounts that are sufficient to enrich the population of cells with hematopoietic stem cells by 10% or more relative to a population of hematopoietic stem cells that have been contacted with a substance that inhibits aryl hydrocarbon receptor signaling such as SR1 or an analog thereof, UM171 or an analog thereof, a UM171 analog selected from Table 11, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

133. The composition of any one of paragraphs 126-130, wherein said one or more agents are present in amounts that are sufficient to maintain long term engraftment potential of said hematopoietic stem cells post-transplantation after having contacted said cells in culture for two or more days (e.g., three, five, seven, ten, twelve, fourteen, fifteen, twenty, or more days).

134. A composition comprising a combination of agents selected from the combination of agents of Table 1, Table 2, Table 3, Table 4, Table 5, Table 6, Table 7, Table 8, Table 9, and Table 10.

135. A cell culture medium comprising the composition of any one of paragraphs 102-134.

136. The cell culture medium of paragraph 135, wherein said cell culture medium is substantially free of serum.

137. The composition of any one of paragraphs 102-134, wherein said composition further comprises a population of hematopoietic stem cells in contact with said one or more agents.

138. The composition of paragraph 137, wherein said hematopoietic stem cells have been cultured in the presence of said one or more agents for two or more days (e.g., three, five, seven, ten, twelve, fourteen, fifteen, twenty, or more days).

139. A method of producing an expanded population of hematopoietic stem cells ex vivo, said method comprising contacting a population of hematopoietic stem cells with
  (1) a first agent that exhibits one or more activities selected from the group consisting of:
    a. modulation of histone methylation;
    b. inhibition of TGFβ signaling;
    c. inhibition of p38 signaling;
    d. activation of canonical Wnt signaling; and
    e. modulation of histone acetylation; and
  (2) a second agent selected from the group consisting of SR1 or an analog thereof, UM171 or an analog thereof, a UM171 analog selected from Table 11, a prostaglandin, an agonist of Notch signaling, or an inhibitor of SIRT1, wherein the first and second agents are present in amounts that together are sufficient to produce an expanded population of hematopoietic stem cells.

140. A method of enriching a population of cells with hematopoietic stem cells ex vivo, said method comprising contacting a population of hematopoietic cells that contains one or more hematopoietic stem cells with (1) a first agent that exhibits one or more activities selected from the group consisting of:
    a. modulation of histone methylation;
    b. inhibition of TGFβ signaling;
    c. inhibition of p38 signaling;
    d. activation of canonical Wnt signaling; and
    e. modulation of histone acetylation; and
(2) a second agent selected from the group consisting of SR1 or an analog thereof, UM171 or an analog thereof, a UM171 analog selected from Table 11, a prostaglandin, an agonist of Notch signaling, or an inhibitor of SIRT1, wherein the first and second agents are present in amounts that together are sufficient to produce a population of cells enriched with hematopoietic stem cells.

141. A method of maintaining the hematopoietic stem cell functional potential of a population of hematopoietic stem cells ex vivo for at least two days, said method comprising contacting a first population of hematopoietic stem cells with
  (1) a first agent that exhibits one or more activities selected from the group consisting of:
    a. modulation of histone methylation;
    b. inhibition of TGFβ signaling;
    c. inhibition of p38 signaling;
    d. activation of canonical Wnt signaling; and
    e. modulation of histone acetylation; and
  (2) a second agent selected from the group consisting of SR1 or an analog thereof, UM171 or an analog thereof, a UM171 analog selected from Table 11, a prostaglandin, an agonist of Notch signaling, or an inhibitor of SIRT1, wherein the population of hematopoietic stem cells exhibits a hematopoietic stem cell functional potential after two or more days that is greater than that of a control population of hematopoietic stem cells cultured under the same conditions and for the same time as said population of hematopoietic stem cells but not contacted with said one or more agents and said one or more substances.

142. A population of hematopoietic stem cells produced by the method of any one of paragraphs 1-101 and 139-141.

143. A kit comprising the composition of any one of paragraphs 102-134, 137, and 138, wherein said kit further comprises a package insert.

144. The kit of paragraph 143, wherein said package insert instructs a user of said kit to expand, enrich, or maintain the hematopoietic stem cell functional potential of a population of hematopoietic stem cells ex vivo.

145. The kit of paragraph 143, wherein said package insert instructs said user to express a polynucleotide in said hematopoietic stem cells.

146. The kit of paragraph 143, wherein said package insert instructs said user to administer said hematopoietic stem cells to a patient.

147. A method of producing an expanded population of hematopoietic stem cells ex vivo, said method comprising contacting a population of hematopoietic stem cells with one or more agents that together exhibit two or more activities selected from the group consisting of:
    a. modulation of histone methylation;
    b. inhibition of TGFβ signaling;
    c. inhibition of p38 signaling;
    d. activation of canonical Wnt signaling;
    e. modulation of histone acetylation; and
    f. inhibition of aryl hydrocarbon receptor signaling;
  wherein the one or more agents are present in amounts that are sufficient to produce an expanded population of hematopoietic stem cells.

148. A method of enriching a population of cells with hematopoietic stem cells ex vivo, said method comprising contacting a population of hematopoietic cells that contains one or more hematopoietic stem cells with one or more agents that together exhibit two or more activities selected from the group consisting of:
    a. modulation of histone methylation;
    b. inhibition of TGFβ signaling;
    c. inhibition of p38 signaling;
    d. activation of canonical Wnt signaling;
    e. modulation of histone acetylation, and
    f. inhibition of aryl hydrocarbon receptor signaling;
  wherein the one or more agents are present in amounts that are sufficient to produce a population of cells enriched with hematopoietic stem cells.

149. A method of maintaining the hematopoietic stem cell functional potential of a population of hematopoietic stem cells ex vivo for at least two days, said method comprising contacting a first population of hematopoietic stem cells with one or more agents that together exhibit two or more activities selected from the group consisting of:
    a. modulation of histone methylation;
    b. inhibition of TGFβ signaling;
    c. inhibition of p38 signaling;
    d. activation of canonical Wnt signaling;
    e. modulation of histone acetylation and
    f. inhibition of aryl hydrocarbon receptor signaling;
  wherein the first population of hematopoietic stem cells exhibits a hematopoietic stem cell functional potential after two or more days that is greater than that of a control population of hematopoietic stem cells cultured under the same conditions and for the same time as said first population of hematopoietic stem cells but not contacted with said one or more agents.

150. The method of any one of paragraphs 147-149, wherein the modulation of histone methylation is activation of histone methylation, maintenance of histone methylation, or inhibition of histone demethylation.

151. The method of any one of paragraphs 147-150, wherein the modulation of histone acetylation is activation of histone acetylation, maintenance of histone acetylation, or inhibition of histone deacetylation.

152. The method of paragraph 151, wherein said one or more agents comprise a compound that activates histone methylation, maintains histone methylation, or inhibits histone demethylation and a compound that inhibits TGFβ signaling.

153. The method of paragraph 152, wherein said compound that activates histone methylation, maintains histone methylation, or inhibits histone demethylation is a histone demethylase inhibitor and said compound that inhibits TGFβ signaling is a TGFβ receptor inhibitor.

154. The method of paragraph 153, wherein said histone demethylase inhibitor is a LSD1 inhibitor.

155. The method of paragraph 154, wherein said LSD1 inhibitor is LSD1 inhibitor IV RN-1 and said TGFβ receptor inhibitor is ALK5 inhibitor II.

156. The method of paragraph 155, wherein said LSD1 inhibitor is tranylcypromine and said TGFβ receptor inhibitor is ALK5 inhibitor II.

157. A method of producing an expanded population of hematopoietic stem cells ex vivo, said method comprising contacting a population of hematopoietic stem cells with one or more agents that together inhibit the activity of two or more proteins selected from the group consisting of:
 a. a histone demethylase;
 b. a protein that propagates TGFβ signaling;
 c. a protein that propagates p38 signaling;
 d. a protein that promotes β-catenin degradation;
 e. a histone deacetylase; and
 f. aryl hydrocarbon receptor;
wherein the one or more agents are present in amounts that are sufficient to produce an expanded population of hematopoietic stem cells.

158. A method of enriching a population of cells with hematopoietic stem cells ex vivo, said method comprising contacting a population of hematopoietic cells that contains one or more hematopoietic stem cells with one or more agents that together inhibit the activity of two or more proteins selected from the group consisting of:
 a. a histone demethylase;
 b. a protein that propagates TGFβ signaling;
 c. a protein that propagates p38 signaling;
 d. a protein that promotes β-catenin degradation;
 e. a histone deacetylase; and
 f. aryl hydrocarbon receptor;
wherein the one or more agents are present in amounts that are sufficient to produce a population of cells enriched with hematopoietic stem cells.

159. A method of maintaining the hematopoietic stem cell functional potential of a population of hematopoietic stem cells ex vivo for at least two days, said method comprising contacting a first population of hematopoietic stem cells with one or more agents that together inhibit the activity of two or more proteins selected from the group consisting of:
 a. a histone demethylase;
 b. a protein that propagates TGFβ signaling;
 c. a protein that propagates p38 signaling;
 d. a protein that promotes β-catenin degradation;
 e. a histone deacetylase; and
 f. aryl hydrocarbon receptor;
wherein the first population of hematopoietic stem cells exhibits a hematopoietic stem cell functional potential after two or more days that is greater than that of a control population of hematopoietic stem cells cultured under the same conditions and for the same time as said first population of hematopoietic stem cells but not contacted with said one or more agents.

160. The method of any one of paragraphs 147-159, wherein the one or more agents comprise a combination of agents selected from the combination of agents of Table 1, Table 2, Table 3, Table 4, Table 5, and Table 6.

161. The method of any one of paragraphs 147-160, wherein said histone demethylase is LSD1.

162. The method of any one of paragraphs 147-161, wherein said one or more agents comprise a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine.

163. The method of any one of paragraphs 147-162, wherein said protein that propagates TGF signaling is a TGFβ receptor.

164. The method of any one of paragraphs 147-163, wherein said one or more agents comprise a compound that inhibits a protein that propagates TGFβ signaling selected from the group consisting of ALK5 inhibitor II, LY364947, A83-01, and DMH1.

165. The method of any one of paragraphs 147-164, wherein said one or more agents comprise a compound that inhibits a protein that propagates p38 signaling, and wherein said compound is SB203580.

166. The method of any one of paragraphs 147-165, wherein said one or more agents comprise a compound that inhibits a protein that promotes β-catenin degradation selected from the group consisting of CHIR99021, lithium chloride, BIO, and FGF2.

167. The method of any one of paragraphs 147-166, wherein said one or more agents comprise a compound that inhibits a histone deacetylase are selected from the group consisting of Trichostatin A, valproic acid, butyrylhydroxamic acid, and istodax.

168. The method of any one of paragraphs 147-167, wherein said one or more agents together inhibit the activity of a histone demethylase and a protein that propagates TGFβ signaling.

169. The method of paragraph 168, wherein said histone demethylase is LSD1.

170. The method of paragraph 168-169, wherein said protein that propagates TGFβ signaling is a TGFβ receptor.

171. The method of any one of paragraphs 168-170, wherein said one or more agents comprise LSD1 inhibitor IV RN-1 and ALK5 inhibitor II.

172. The method of any one of paragraphs 147-171, wherein said one or more agents comprise a compound that inhibits p38 signaling.

173. The method of any one of paragraphs 147-172, wherein said one or more agents comprise a compound that inhibits a histone deacetylase.

174. The method of any one of paragraphs 147-173, wherein said one or more agents further comprise a compound that inhibits BMP signaling.

175. The method of any one of paragraphs 147-174, wherein the substance that inhibits aryl hydrocarbon receptor signaling is SR1 or an analog thereof.

176. A method of producing an expanded population of hematopoietic stem cells ex vivo, said method comprising contacting a population of hematopoietic stem cells with (a)

a first agent selected from the group consisting of an LSD1 inhibitor IV RN-1, LSD1 inhibitor II S2101, LSD1 inhibitor LSD1-C76, LSD1 inhibitor III CBB1007, LSD1 inhibitor I, and Tranylcypromine, and (b) a second agent selected from the group consisting of ALK5 inhibitor II, LY364947, A83-01, Trichostatin A, SB203580, CHIR99021, DMH1, sodium acetate, and istodax.

177. The method of any one of paragraphs 147-176, wherein said one or more agents are present in amounts that are sufficient to stimulate expansion of said population of cells by 10% or more relative to a population of hematopoietic stem cells not contacted with said one or more agents after seven or more days of culture (e.g., after seven, ten, twelve, fourteen, fifteen, twenty, or more days of culture).

178. The method of any one of paragraphs 147-177, wherein said one or more agents are present in amounts that are sufficient to stimulate expansion of said population of cells by 10% or more relative to a population of hematopoietic stem cells that have been contacted with a substance that inhibits aryl hydrocarbon receptor signaling such as SR1 or an analog thereof, UM171 or an analog thereof, a UM171 analog selected from Table 11, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

179. The method of any one of paragraphs 147-178, wherein said one or more agents are present in amounts that are sufficient to enrich said population of cells with hematopoietic stem cells by 10% or more relative to a population of hematopoietic stem cells not contacted with said one or more agents after seven or more days of culture (e.g., after seven, ten, twelve, fourteen, fifteen, twenty, or more days of culture).

180. The method of any one of paragraphs 147-179, wherein said one or more agents are present in amounts that are sufficient to enrich said population of cells with hematopoietic stem cells by 10% or more relative to a population of hematopoietic stem cells that have been contacted with a substance that inhibits aryl hydrocarbon receptor signaling such as SR1 or an analog thereof, UM171 or an analog thereof, a UM171 analog selected from Table 11, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

181. The method of any one of paragraphs 147-180, wherein said first population of hematopoietic stem cells exhibits a hematopoietic stem cell functional potential after three or more days of culture (e.g., three, five, seven, ten, twelve, fourteen, fifteen, twenty, or more days) that is greater than that of said control population of hematopoietic stem cells.

182. The method of any one of paragraphs 147-181, wherein said hematopoietic stem cells are mammalian cells.

183. The method of paragraph 182, wherein said mammalian cells are human cells.

184. The method of paragraph 183, wherein said hematopoietic stem cells are CD34+ cells.

185. The method of paragraph 184, wherein at least 10% of said CD34+ cells are CD34+CD38−, CD34+CD38-CD90+, CD34+CD38-CD90+CD45RA−, or CD34+CD38-CD90+CD45RA-CD49F+ cells.

186. The method of any one of paragraphs 183-185, wherein said hematopoietic stem cells are from human cord blood.

187. The method of any one of paragraphs 183-185, wherein said hematopoietic stem cells are from human mobilized peripheral blood.

188. The method of any one of paragraphs 183-185, wherein said hematopoietic stem cells are from human bone marrow.

189. The method of any one of paragraphs 183-188, wherein said hematopoietic stem cells are freshly isolated from said human.

190. The method of any one of paragraphs 183-189, wherein said hematopoietic stem cells have been previously cryopreserved.

191. The method of paragraph 182, wherein said mammalian cells are murine cells.

192. The method of any one of paragraphs 147-191, wherein said hematopoietic stem cells are cultured for two or more days (e.g., three, five, seven, ten, twelve, fourteen, fifteen, twenty, or more days).

193. The method of any one of paragraphs 147-192, wherein said hematopoietic stem cells contact said one or more agents for two or more days (e.g., three, five, seven, ten, twelve, fourteen, fifteen, twenty, or more days).

194. The method of any one of paragraphs 147-193, wherein said hematopoietic stem cells are contacted with said one or more agents simultaneously.

195. The method of any one of paragraphs 147-194, wherein said hematopoietic stem cells are contacted with said one or more agents at different times.

196. The method of any one of paragraphs 147-195, wherein said hematopoietic stem cells maintain hematopoietic stem cell functional potential after two days (e.g., three, five, seven, ten, twelve, fourteen, fifteen, twenty, or more days) in culture.

197. The method of paragraph 196, wherein said hematopoietic stem cells maintain hematopoietic stem cell functional potential following transplantation after two days (e.g., three, five, seven, ten, twelve, fourteen, fifteen, twenty, or more days) in culture.

198. The method of any one of paragraphs 47-197, wherein said hematopoietic stem cells maintain long term engraftment potential after two days (e.g., three, five, seven, ten, twelve, fourteen, fifteen, twenty, or more days) in culture.

199. The method of any one of paragraphs 147-198, wherein upon transplantation into a patient, said hematopoietic stem cells give rise to recovery of a population of cells selected from the group consisting of neutrophils, platelets, red blood cells, monocytes, macrophages, antigen-presenting cells, microglia, osteoclasts, dendritic cells, and lymphocytes.

200. The method of paragraph 199, wherein said lymphocytes are selected from the group consisting of natural killer cells, T cells (e.g., CD4+ or CD8+ cells), and B cells.

201. The method of any one of paragraphs 147-200, wherein said hematopoietic stem cells are capable of localizing to hematopoietic tissue to reestablish productive hematopoiesis in a transplanted recipient.

202. The method of any one of paragraphs 147-201, wherein said hematopoietic stem cells are cultured on a plastic surface or on a substrate that includes vitronectin, fibronectin, or matrigel.

203. The method of any one of paragraphs 147-202, wherein said hematopoietic stem cells are cultured in the presence of 2-20% oxygen.

204. The method of paragraph 203, wherein said hematopoietic stem cells are cultured in the presence of 2-12% oxygen.

204. The method of paragraph 203, wherein said hematopoietic stem cells are cultured in the presence of about 5% oxygen.

205. The method of any one of paragraphs 147-204, wherein said hematopoietic stem cells are originally within a mononuclear cell fraction prior to treatment with said one or more agents.

206. The method of any one of paragraphs 147-205, wherein said hematopoietic stem cells are originally within a CD34+, CD34+CD38-, CD34+CD38-CD90+, CD34+CD38-CD90+CD45RA-, or CD34+CD38-CD90+CD45RA-CD49F+ enriched cell fraction prior to contacting said one or more agents.

207. The method of any one of paragraphs 147-206, wherein said hematopoietic stem cells are originally within an un-enriched cell fraction prior to contacting said one or more agents.

208. A method of introducing a polynucleotide into a population of hematopoietic stem cells, said method comprising:
   a. inserting the polynucleotide into said population of hematopoietic stem cells; and
   b. expanding said population of hematopoietic stem cells according to the method of any one of paragraphs 147-207, or maintaining the hematopoietic stem cell functional potential of said population of hematopoietic stem cells according to the method of any one of paragraphs 147-207.

209. The method of paragraph 208, wherein (a) precedes (b).

210. The method of paragraph 208, wherein (b) precedes (a).

211. The method of any one of paragraphs 208-201, wherein said method comprises providing one or more reagents that cleave a nucleic acid in said cells.

212. The method of paragraph 211, wherein the one or more reagents that cleave a nucleic acid in said cells comprise a zinc finger nuclease.

213. The method of paragraph 211, wherein the one or more reagents that cleave a nucleic acid in said cells comprise a transcription activator-like effector nuclease.

214. The method of paragraph 211, wherein the one or more reagents that cleave a nucleic acid in said cells comprise a CRISPR-associated protein.

215. The method of paragraph 211, wherein the one or more agents that cleave a nucleic acid in said cells comprise a meganuclease.

216. The method of any one of paragraphs 208-215, wherein said method comprises contacting the hematopoietic stem cells with a vector selected from the group consisting of a viral vector (such as retrovirus, adenovirus, parvovirus, coronavirus, rhabdovirus, paramyxovirus, picornavirus, alphavirus, herpes virus, or poxvirus) and a transposable element (such as a piggybac transposon or sleeping beauty transposon)

217. The method of any one of paragraphs 208-216, wherein said method comprises introducing said polynucleotide into said hematopoietic stem cells by electroporation, Nucleofection™, or squeeze-poration.

218. The method of any one of paragraphs 208-217, wherein said method comprises contacting the cells with a transformation agent selected from the group consisting of a cationic polymer (e.g., diethylaminoethyl-dextran), a cationic lipid, calcium phosphate, an activated dendrimer, and a magnetic bead.

219. The method of any one of paragraphs 208-218, wherein said method comprises introducing said polynucleotide into said hematopoietic stem cells by microinjection or laserfection.

220. The method of any one of paragraphs 208-219, wherein said polynucleotide comprises a regulatory sequence selected from the group consisting of a promoter, enhancer, or silencer sequence.

221. The method of any one of paragraphs 208-220, wherein said polynucleotide encodes a molecule selected from the group consisting of a protein and a RNA (mRNA, tRNA, siRNA, miRNA, shRNA).

222. The method of any one of paragraphs 208-221, wherein said polynucleotide is a chemically modified RNA.

223. The method of any one of paragraphs 208-222, wherein said method further comprises introducing the population of expanded hematopoietic stem cells or progeny thereof into a recipient.

224. A method of treating a recipient with hematopoietic stem cells or progeny thereof, said method comprising:
   a. providing a population of hematopoietic stem cells;
   b. expanding said population of hematopoietic stem cells according to the method of any one of paragraphs 147-207;
   c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing the population of expanded hematopoietic stem cells or progeny thereof into said recipient.

225. A method of treating a recipient with hematopoietic stem cells or progeny thereof, said method comprising:
   a. providing a population of hematopoietic stem cells;
   b. enriching said population of hematopoietic stem cells according to the method of any one of paragraphs 147-207;
   c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing the population of cells enriched with hematopoietic stem cells or progeny thereof into said recipient.

226. A method of treating a recipient with hematopoietic stem cells or progeny thereof, said method comprising:
   a. providing a population of hematopoietic stem cells;
   b. maintaining the hematopoietic stem cell functional potential of said population of hematopoietic stem cells according to the method of any one of paragraphs 147-207;
   c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing said population of hematopoietic stem cells or progeny thereof into said recipient.

227. A method of treating a recipient with hematopoietic stem cells or progeny thereof, said method comprising:
   a. providing a population of hematopoietic stem cells produced by the method of any one of paragraphs 147-207;

b. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and c. introducing said population of hematopoietic stem cells or progeny thereof into said recipient.

228 The method of any one of paragraphs 224-227, wherein said recipient is a human.

229. The method of paragraph 228, wherein said hematopoietic stem cells are derived from one or more hematopoietic stem cells isolated from a human donor.

230. The method of paragraph 229, wherein said hematopoietic stem cells are from mobilized peripheral blood of said donor.

231. The method of paragraph 228-229, wherein said donor has been previously administered one or more mobilizing agents selected from the group consisting of a CXCR4 antagonist (e.g., AMD3100), GCSF, and GROβ.

232. The methods of any one of paragraphs 147-231, wherein the hematopoietic stem cells are additionally contacted with UM171, an analog thereof, or a UM171 analog selected from Table 11.

233. The methods of any one of paragraphs 147-232, wherein the hematopoietic stem cells are additionally contacted with a compound selected from Table 11.

234. The method of any one of paragraphs 147-233, wherein the hematopoietic stem cells are additionally contacted with a prostaglandin 235. The method of paragraph 234, wherein said prostaglandin is dmPGE2 or an analog thereof.

236. The method of any one of paragraphs 147-235, wherein the hematopoietic stem cells are additionally contacted with an agonist of Notch signaling.

237. The method of any one of paragraphs 147-236, wherein the hematopoietic stem cells are additionally contacted with an inhibitor of SIRT1.

238. The method of paragraph 237, wherein said inhibitor or SIRT1 is selected from the group consisting of nicotinamide, cambinol, and analogs thereof.

239. The method of any one of paragraphs 224-238, wherein said recipient is a human patient suffering from a disease selected from the group consisting of Acute Lymphoblastic Leukemia (ALL), Acute Myelogenous Leukemia (AML), Chronic Myelogenous Leukemia (CML), Chronic Lymphocytic Leukemia (CLL), Hodgkin Lymphoma (HL), Non-Hodgkin Lymphoma (NHL), Myelodysplastic Syndrome (MDS), Multiple myeloma, Aplastic anemia, Bone marrow failure, Myeloproliferative disorders such as Myelofibrosis, Essential thrombocytopenia or Polycythemia vera, Fanconi anemia, Dyskeratosis congenita, Common variable immune deficiency (CVID, such as CVID 1, CVID 2, CVID 3, CVID 4, CVID 5, and CVID 6), Human immunodeficiency virus (HIV), Hemophagocytic lymphohistiocystosis, Amyloidosis, Solid tumors such as Neuroblastoma, Germ cell tumors, Breast cancer, Wilms' tumor, Medulloblastoma, and Neuroectodermal tumors, Autoimmune diseases such as Scleroderma, Multiple sclerosis, Ulcerative colitis, Systemic lupus erythematosus and Type I diabetes, or protein deficiencies such as Adrenoleukodystrophy (ALD), Metachromatic leukodystrophy (MLD), Hemophilia A & B, Hurler syndrome, Hunter syndrome, Fabry disease, Gaucher disease, Epidermolysis bullosa, Globoid Cell Leukodystrophy, Sanfillipo syndrome, and Morquio syndrome.

240. The method of any one of paragraphs 224-238, wherein said recipient is a human patient suffering from a disease selected from the group consisting of Sickle cell anemia, Alpha thalassemia, Beta thalassemia, Delta thalassemia, Hemoglobin E/thalassemia, Hemoglobin S/thalassemia, Hemoglobin C/thalassemia, Hemoglobin D/thalassemia, Chronic granulomatous disease (X-linked Chronic granulomatous disease, autosomal recessive (AR) chronic granulomatous disease, chronic granulomatous disease AR I NCF1, Chronic granulomatous disease AR CYBA, Chronic granulomatous disease AR II NCF2, Chronic granulomatous disease AR III NCF4), X-linked Severe Combined Immune Deficiency (SCID), ADA SCID, IL7-RA SCID, CD3 SCID, Rag1/Rag2 SCID, Artemis SCID, CD45 SCID, Jak3 SCID, Congenital agranulocytosis, Congenital agranulocytosis-congenital neutropenia-SCN1, Congenital agranulocytosis-congenital neutropenia-SCN2, Familial hemophagocytic lymphohistiocystosis (FHL), Familial hemophagocytic lymphohistiocytosis type 2 (FHL2, perforin mutation), Agammaglobulinemia (X-linked Agammaglobulinemia), Wiskott-Aldrich syndrome, Chediak-Higashi syndrome, Hemolytic anemia due to red cell pyruvate kinase deficiency, Paroxysmal nocturnal hemoglobinuria, X-linked Adrenoleukodystrophy (X-ALD), X-linked lymphoproliferative disease, Unicentric Castleman's Disease, Multicentric Castleman's Disease, Congenital amegakaryocytic thrombocytopenia (CAMT) type I, Reticular dysgenesis, Fanconi anemia, Acquired idiopathic sideroblastic anemia, Systemic mastocytosis, Von willebrand disease (VWD), Congenital dyserythropoietic anemia type 2, Cartilage-hair hypoplasia syndrome, Hereditary spherocytosis, Blackfan-Diamond syndrome, Shwachman-Diamond syndrome, Thrombocytopenia-absent radius syndrome, Osteopetrosis, Infantile osteopetrosis, Mucopolysaccharidoses, Lesch-Nyhan syndrome, Glycogen storage disease, Congenital mastocytosis, Omenn syndrome, X-linked Immunodysregulation, polyendocrinopathy, and enteropathy (IPEX), IPEX characterized by mutations in FOXP3, X-linked syndrome of polyendocrinopathy, immune dysfunction, and diarrhea (XPID), X-Linked Autoimmunity-Allergic Dysregulation Syndrome (XLAAD), IPEX-like syndrome, Hyper IgM type 1, Hyper IgM type 2, Hyper IgM type 3, Hyper IgM type 4, Hyper IgM type 5, X linked hyperimmunoglobulin M, Bare lymphocyte Syndrome type I, and Bare lymphocyte Syndrome type II (Bare lymphocyte Syndrome type II, MHC class I deficiency; Bare lymphocyte Syndrome type II, complementation group A; Bare lymphocyte Syndrome type II, complementation group C; Bare lymphocyte Syndrome type II complementation group D; Bare lymphocyte Syndrome type II, complementation group E).

241. The method of any one of paragraphs 224-238, wherein said recipient is a human patient suffering from a hematolymphoid malignancy, a non-hematolymphoid malignancy, or a protein deficiency, or a tissue or cell transplantation recipient (e.g., to induce tolerance to transplanted tissue or cells).

242. The method of any one of paragraphs 224-241, wherein said hematopoietic stem cells are autologous or syngeneic.

243. The method of any one of paragraphs 224-241, wherein said hematopoietic stem cells are allogeneic.

244. A composition comprising one or more agents that together exhibit two or more activities selected from the group consisting of:

a. modulation of histone methylation;

b. inhibition of TGFβ signaling;

c. inhibition of p38 signaling;
d. activation of canonical Wnt signaling;
e. modulation of histone acetylation; and
f. inhibition of aryl hydrocarbon receptor.

245. The composition of paragraph 244, wherein the modulation of histone methylation is activation of histone methylation, maintenance of histone methylation, or inhibition of histone demethylation.

246. The composition of paragraph 244 or 245, wherein the modulation of histone acetylation is activation of histone acetylation, maintenance of histone acetylation, or inhibition of histone deacetylation.

247. The composition of any of paragraphs 244-246, wherein said one or more agents comprise a compound that activates histone methylation, maintains histone methylation, or inhibits histone demethylation and a compound that inhibits TGFβ signaling.

248. The composition of any of paragraphs 244-247, wherein said compound that activates histone methylation, maintains histone methylation, or inhibits histone demethylation a histone demethylase inhibitor and said compound that inhibits TGFβ signaling is a TGFβ receptor inhibitor.

249. The composition of any of paragraphs 244-248, wherein said histone demethylase inhibitor is a LSD1 inhibitor.

250. The composition of paragraph 249, wherein said LSD1 inhibitor is LSD1 inhibitor IV RN-1 and said TGFβ receptor inhibitor is ALK5 inhibitor II.

251. The composition of any of paragraphs 244-250, wherein said LSD1 inhibitor is tranylcypromine and said TGFβ receptor inhibitor is ALK5 inhibitor II.

252. A composition comprising one or more agents that together inhibit the activity of two or more proteins selected from the group consisting of:
   a. a histone demethylase;
   b. a protein that propagates TGFβ signaling;
   c. a protein that propagates p38 signaling;
   d. a protein that promotes β-catenin degradation; and
   e. a histone deacetylase; and
   f. aryl hydrocarbon receptor.

253. The composition of paragraph 252, wherein said histone demethylase is LSD1.

254. The composition of paragraph 252, wherein said one or more agents comprise a histone demethylase inhibitor selected from the group consisting of LSD1 inhibitor IV RN-1, LSD1 inhibitor II S2101, LSD1 inhibitor LSD1-C76, LSD1 inhibitor III CBB1007, LSD1 inhibitor I, and Tranylcypromine.

255. The composition of any one of paragraphs 252-254, wherein said protein that propagates TGFβ signaling is a TGFβ receptor.

256. The composition of any one of paragraphs 252-255, wherein said one or more agents comprise a compound that inhibits a protein that propagates TGFβ signaling selected from the group consisting of ALK5 inhibitor II, LY364947, A83-01, and DMH1.

257. The composition of any one of paragraphs 252-256, wherein said one or more agents comprise a compound that inhibits a protein that propagates p38 signaling, and wherein said compound is SB203580.

258. The composition of any one of paragraphs 252-257, wherein said one or more agents comprise a compound that inhibits a protein that promotes β-catenin degradation selected from the group consisting of CHIR99021, lithium chloride, BIO, and FGF2.

259. The composition of any one of paragraphs 252-258, wherein said one or more agents comprise a compound that inhibits a histone deacetylase selected from the group consisting of Trichostatin A, valproic acid, butyrylhydroxamic acid, and istodax.

260. The composition of any one of paragraphs 252-259, wherein said one or more agents together inhibit the activity of a histone demethylase and a protein that propagates TGFβ signaling 261. The composition of any of paragraphs 252-260, wherein said histone demethylase is LSD1.

262. The composition of paragraph 260 or 261, wherein said protein that propagates TGFβ signaling is a TGFβ receptor.

263. The composition of any one of paragraphs 260-262, wherein said one or more agents comprise LSD1 inhibitor IV RN-1 and ALK5 inhibitor II.

264. The composition of any one of paragraphs 260-263, wherein said one or more agents comprise a compound that inhibits p38 signaling.

265. The composition of any one of paragraphs 260-264, wherein said one or more agents comprise a compound that inhibits a histone deacetylase.

266. The composition of any one of paragraphs 260-265, wherein said one or more agents comprise a compound that inhibits BMP signaling.

267. The composition of any of paragraphs 244-266, wherein said one or more agents that inhibit aryl hydrocarbon receptor signaling comprise SR1.

268. The composition of any one of paragraphs 244-267, wherein said one or more agents are present in amounts that are sufficient to produce an expanded population of hematopoietic stem cells.

269. The composition of any one of paragraphs 244-268, wherein said one or more agents are present in amounts that are sufficient to produce a population of cells enriched with hematopoietic stem cells.

270. The composition of any one of paragraphs 244-269, wherein said one or more agents are present in amounts sufficient to maintain the hematopoietic stem cell functional potential of said population of hematopoietic stem cells for at least two days.

271. The composition of any one of paragraphs 244-270, wherein said one or more agents are present in an aqueous solution.

272. The composition of any one of paragraphs 244-271, wherein said one or more agents are present as a lyophilized solid.

273. The composition of any one of paragraphs 244-272, wherein said one or more agents are present in amounts that are sufficient to stimulate expansion of said population of cells by 10% or more relative to a population of hematopoietic stem cells that have been contacted with a substance that inhibits aryl hydrocarbon receptor signaling such as SR1 or an analog thereof, UM171 or an analog thereof, a UM171 analog selected from Table 11, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

274. The composition of any one of paragraphs 244-273, wherein said one or more agents are present in amounts that are sufficient to enrich the population of cells with hematopoietic stem cells by 10% or more relative to a population of hematopoietic stem cells that have been contacted with a substance that inhibits aryl hydrocarbon receptor signaling such as SR1 or an analog thereof, UM171 or an analog thereof, a UM171 analog selected from Table 11, a prostaglandin, an agonist of Notch signaling, or an inhibitor of SIRT1 such as nicotinamide, cambinol, or an analog thereof, after seven or more days of culture (e.g., after seven, ten, twelve, fourteen, fifteen, twenty, or more days of culture).

275. The composition of any one of paragraphs 244-274, wherein said one or more agents are present in amounts that are sufficient to maintain long term engraftment potential of said hematopoietic stem cells post-transplantation after having contacted said cells in culture for two or more days (e.g., three, five, seven, ten, twelve, fourteen, fifteen, twenty, or more days).

275. A composition comprising a combination of agents selected from the combination of agents of Table 1, Table 2, Table 3, Table 4, Table 5, Table 6, Table 7, Table 8, Table 9, and Table 10.

276. A cell culture medium comprising the composition of any one of paragraphs 244-275.

277. The cell culture medium of paragraph 276, wherein said cell culture medium is substantially free of serum.

278. The composition of any one of paragraphs 244-277, wherein said composition further comprises a population of hematopoietic stem cells in contact with said one or more agents.

279. The composition of paragraph 278, wherein said hematopoietic stem cells have been cultured in the presence of said one or more agents for two or more days (e.g., three, five, seven, ten, twelve, fourteen, fifteen, twenty, or more days).

280. A method of producing an expanded population of hematopoietic stem cells ex vivo, said method comprising contacting a population of hematopoietic stem cells with
(1) a first agent that exhibits one or more activities selected from the group consisting of:
 a. modulation of histone methylation;
 b. inhibition of TGFβ signaling;
 c. inhibition of p38 signaling;
 d. activation of canonical Wnt signaling;
 e. modulation of histone acetylation; and
 f. inhibition of aryl hydrocarbon receptor signaling; and
(2) a second agent selected from the group consisting of UM171 or an analog thereof, a UM171 analog selected from Table 11, a prostaglandin, an agonist of Notch signaling, or an inhibitor of SIRT1, wherein the first and second agents are present in amounts that together are sufficient to produce an expanded population of hematopoietic stem cells.

281. A method of enriching a population of cells with hematopoietic stem cells ex vivo, said method comprising contacting a population of hematopoietic cells that contains one or more hematopoietic stem cells with (1) a first agent that exhibits one or more activities selected from the group consisting of:
 a. modulation of histone methylation;
 b. inhibition of TGFβ signaling;
 c. inhibition of p38 signaling;
 d. activation of canonical Wnt signaling;
 e. modulation of histone acetylation; and
 f. inhibition of aryl hydrocarbon receptor signaling; and
(2) a second agent selected from the group consisting of UM171 or an analog thereof, a UM171 analog selected from Table 11, a prostaglandin, an agonist of Notch signaling, or an inhibitor of SIRT1, wherein the first and second agents are present in amounts that together are sufficient to produce a population of cells enriched with hematopoietic stem cells.

282. A method of maintaining the hematopoietic stem cell functional potential of a population of hematopoietic stem cells ex vivo for at least two days, said method comprising contacting a first population of hematopoietic stem cells with
(1) a first agent that exhibits one or more activities selected from the group consisting of:
 a. modulation of histone methylation;
 b. inhibition of TGFβ signaling;
 c. inhibition of p38 signaling;
 d. activation of canonical Wnt signaling;
 e. modulation of histone acetylation; and
 f. inhibition of aryl hydrocarbon receptor signaling; and
(2) a second agent selected from the group consisting of UM171 or an analog thereof, a UM171 analog selected from Table 11, a prostaglandin, an agonist of Notch signaling, or an inhibitor of SIRT1, wherein the population of hematopoietic stem cells exhibits a hematopoietic stem cell functional potential after two or more days that is greater than that of a control population of hematopoietic stem cells cultured under the same conditions and for the same time as said population of hematopoietic stem cells but not contacted with said one or more agents and said one or more substances.

283. A population of hematopoietic stem cells produced by the method of any one of paragraphs 147-243 and 280-282.

284. A kit comprising the composition of any one of paragraphs 244-279, wherein said kit further comprises a package insert.

285. The kit of paragraph 284, wherein said package insert instructs a user of said kit to expand, enrich, or maintain the hematopoietic stem cell functional potential of a population of hematopoietic stem cells ex vivo.

286. The kit of paragraph 284, wherein said package insert instructs said user to express a polynucleotide in said hematopoietic stem cells.

287. The kit of paragraph 284, wherein said package insert instructs said user to administer said hematopoietic stem cells to a patient.

EXAMPLES

Figures 5A, 5B:
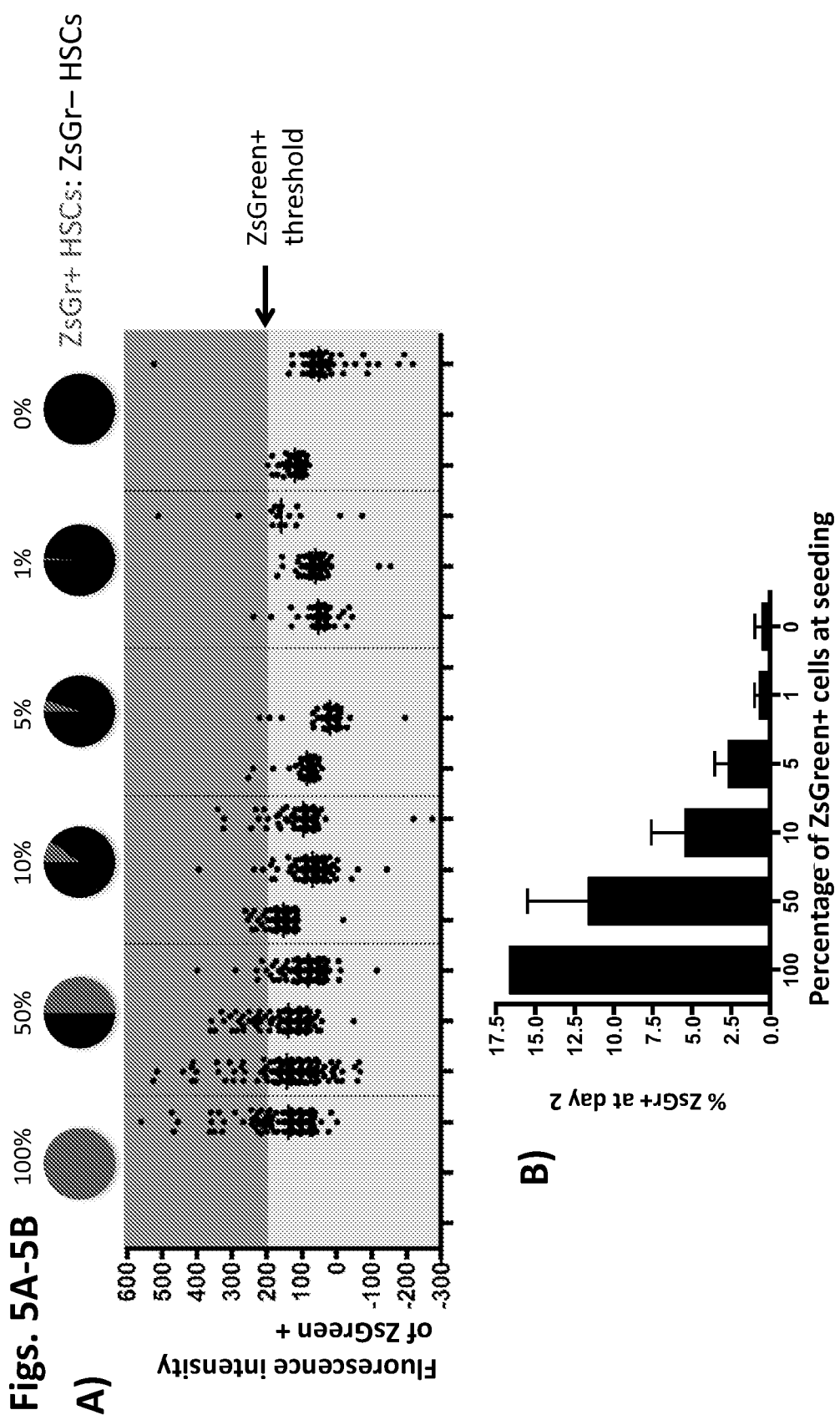
FIGS. 5A-5B show the development of a sensitivity assay.
Figure 7A:
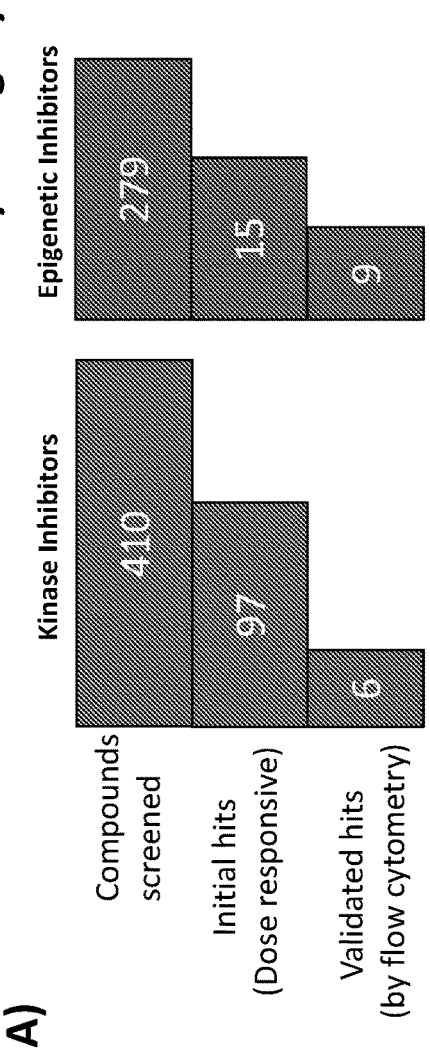
FIGS. 7A-7B show initial screen results for various small molecule and growth factor libraries.
Figure 7B:
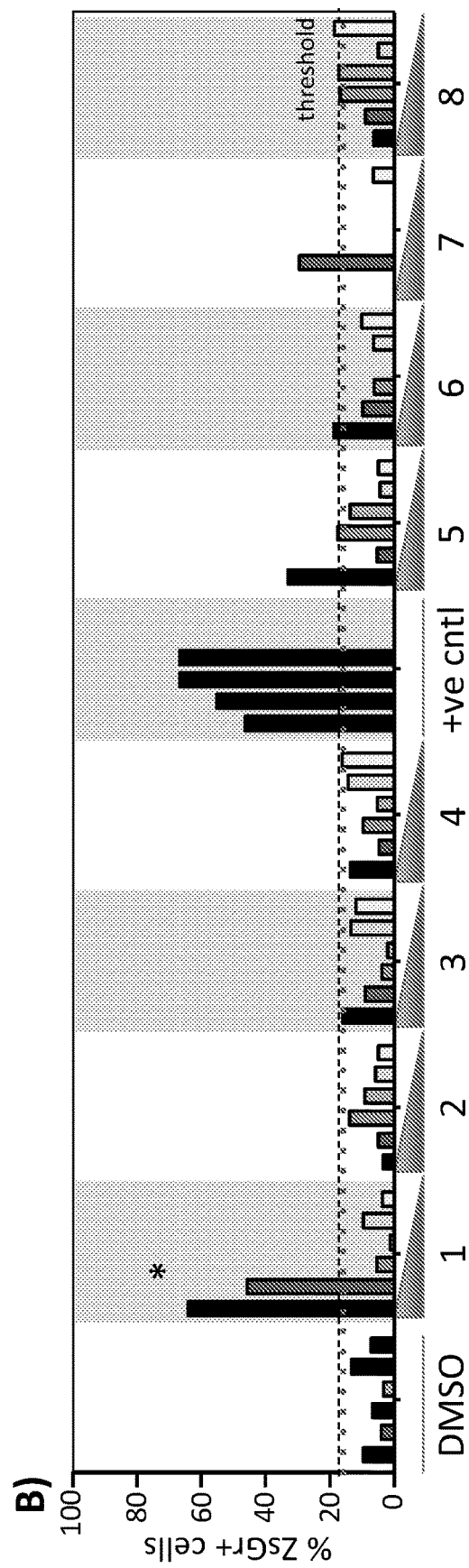
Figures 16A, 16B:
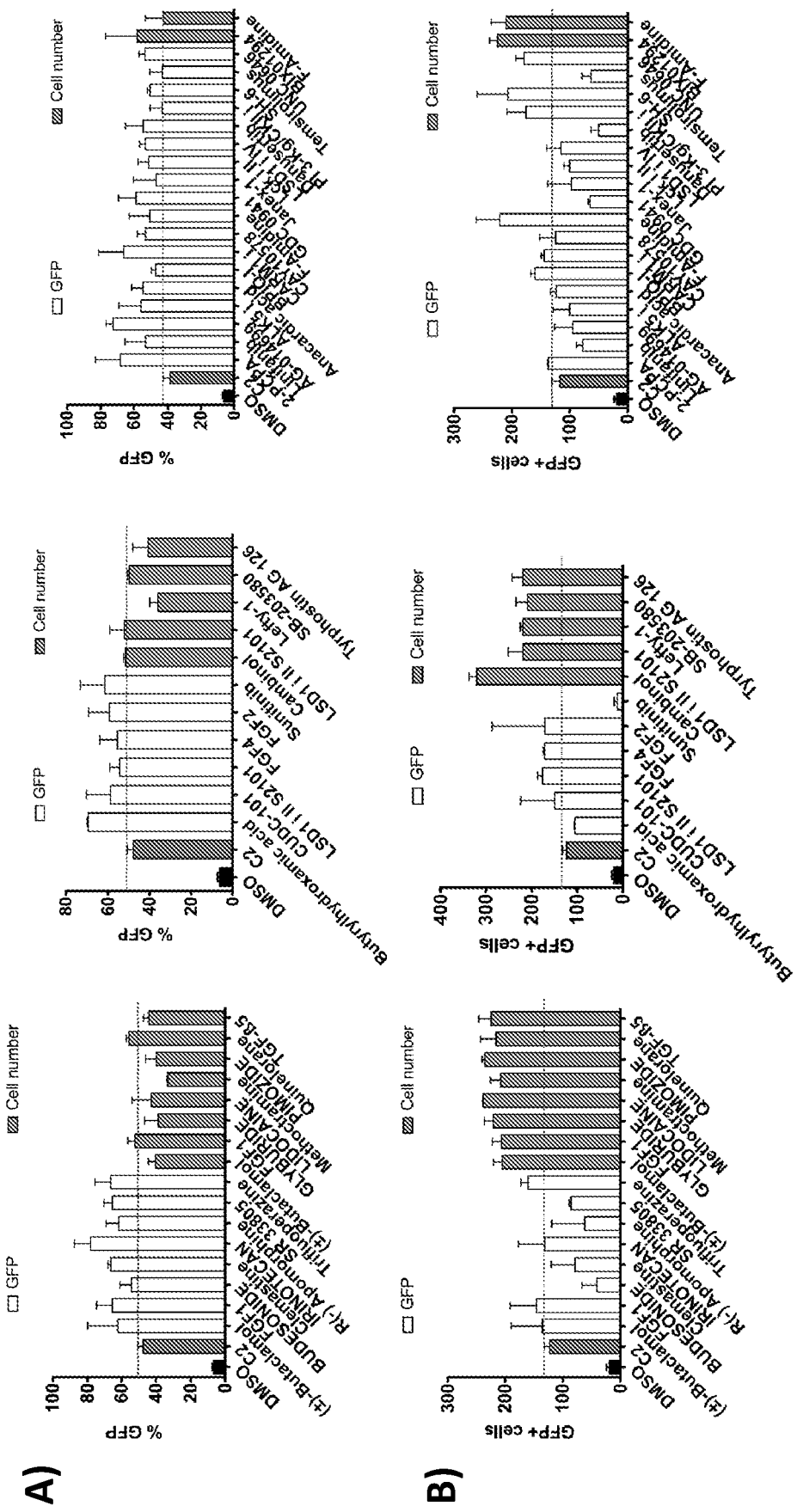
FIGS. 16A-16B show hits of a secondary screen of compounds identified in a primary screen and then re-screened in the presence of C2 (Combination of LSD1 inhibitor IV and the Tgfbeta inhibitor RepSox).

Example 1. Small Molecule Screens to Identify Combinations of Compounds that Expand, Enrich, and Maintain Cells with Hematopoietic Stem Cell Properties Upon Ex Vivo Culturing FIG. 1 shows that HSC potential is rapidly lost upon culture. Peripheral bleed analysis following transplantation into lethally irradiated hosts of freshly isolated murine HSCs (Blue line, circles) or HSCs cultured for 12 days ex vivo in S-clone+IL12/SCF/TPO+0.75% BSA (red line, squares). Various small molecule screens were conducted in order to determine optimal combinations of compounds that can be used to expand, enrich, and maintain the hematopoietic stem cell functional potential of hematopoietic stem cells. FIG. 4 shows a schematic representation of a small molecule screen for compounds that support HSC ex vivo maintenance and expansion. 1) Zs·Gr HSC reporter mouse marrow used to isolate HSCs (described in FIGS. 2 and 3A-3C). 2) Isolation of HSCs marked by ZsGr reporter. 3) Development of assay where hit is defined by the maintenance of HSC reporter expression above DMSO control following 6 days ex vivo culture. 4) Functional validation of hits in vitro and in vivo. FIGS. 5A-5B show the development of a sensitivity assay. FIG. 5A: A total of 200 ZsGr+ and ZsGr−HSCs were seeded/well in various ratios (1:0; 1:1; 1:10; 1:20, 1:100, 0:1—shown as percentage ZsGr+) and imaged using the Operetta (Perkin Elmer) following 2 days ex vivo culture with individual cells plotted as being above or below the threshold of ZsGreen detection. FIG. 5B: After 2 days of culture, the percentage of ZsGreen+ cells was determined. This established a minimum number of cells needed/well to allow for robust detection of ZsGr+ signal after 2 days of culturing. FIG. 6 shows a breakdown of pathways targeted in primary small molecule screens. FIGS. 7A-7B show initial screen results for various library screens. FIG. 7A: Number of compounds screened, initial hits (showing dose response), and validated hits (by flow cytometry to quantify ZSGr+) from each of 4 different libraries of small molecules targeting kinases, epigenetic regulators, and G-protein coupled receptors (GPCR), as well as a peptide library of growth factors. FIG. 7B: Representative results from 6-point dose response (10 uM, 5 uM, 1 uM, 0.5 uM, 0.1 uM, 0.05 uM). * indicates a hit. (See also FIGS. 16A-16B).

Figure 9A:
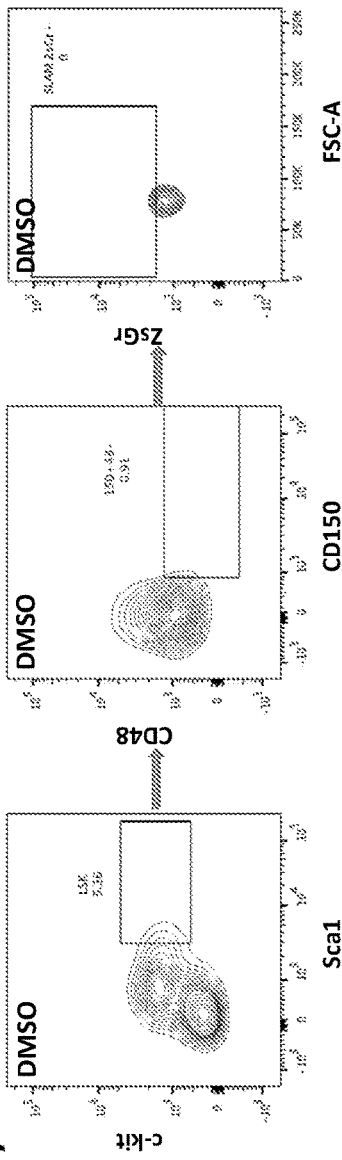
FIGS. 9A-9B show the expansion of phenotypic murine HSCs for 14 days ex vivo. 20 murine HSCs (Lineage−Sca1+ckit+CD34-Flk2-CD150+Fgd5·ZsGr+) were cultured in the presence of DMSO, LSD1 inhibitor IV (LS), Tgfbeta inhibitor RepSox (RS), and the combination of both (C2) for 14 days. This method supports maintenance and expansion of ZsGr+ HSCs.
Figure 9B:
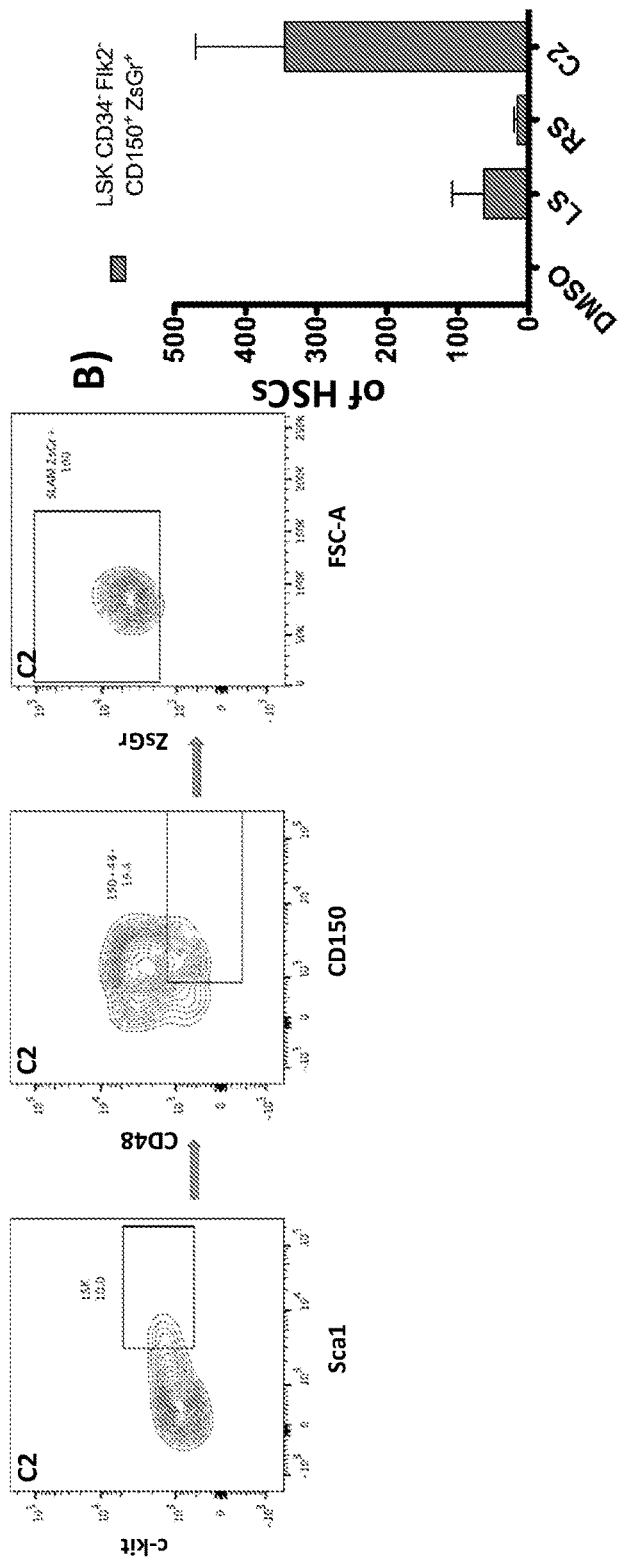
Figure 10A:
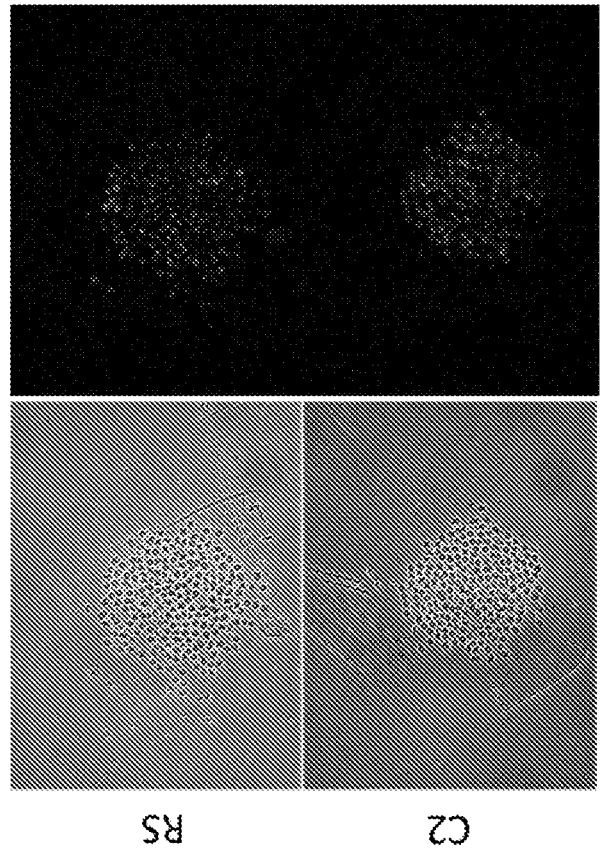
FIGS. 10A-10C show that LSD1 inhibitor (LS), Tgfbeta inhibitor RepSox (RS), and the combination of both (C2) supports maintenance and expansion of ZsGr+ murine HSCs.
Figure 10B:
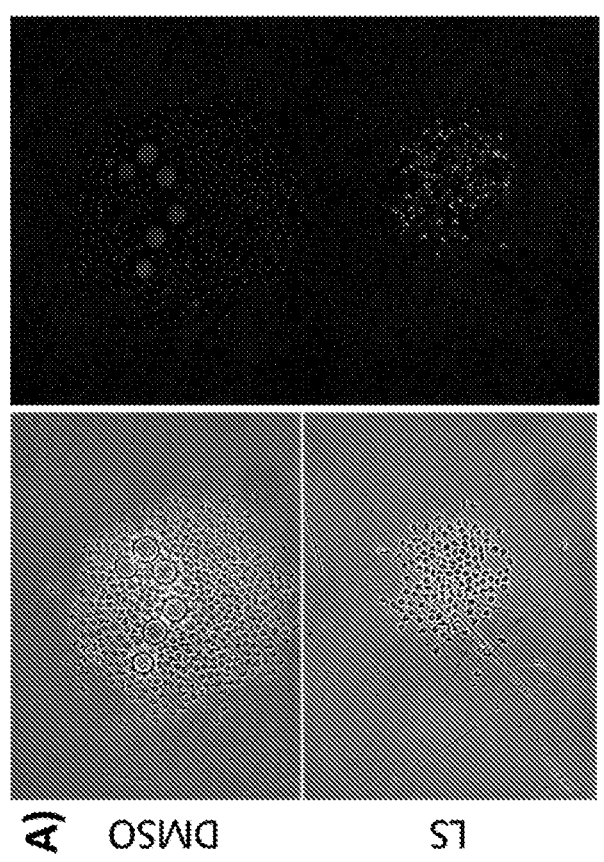
Figure 10C:
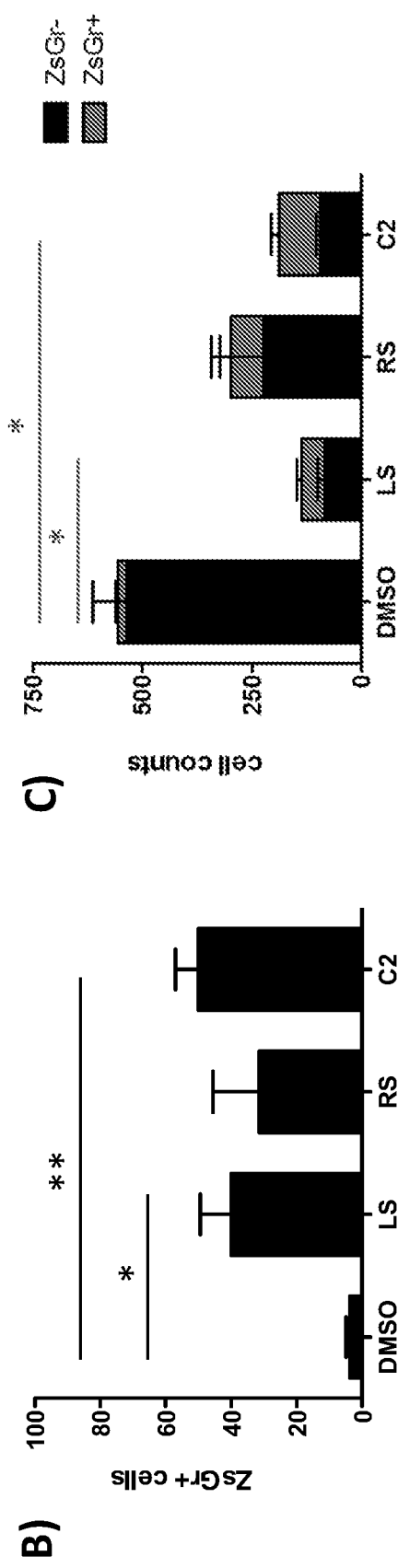
Figures 11A, 11B:
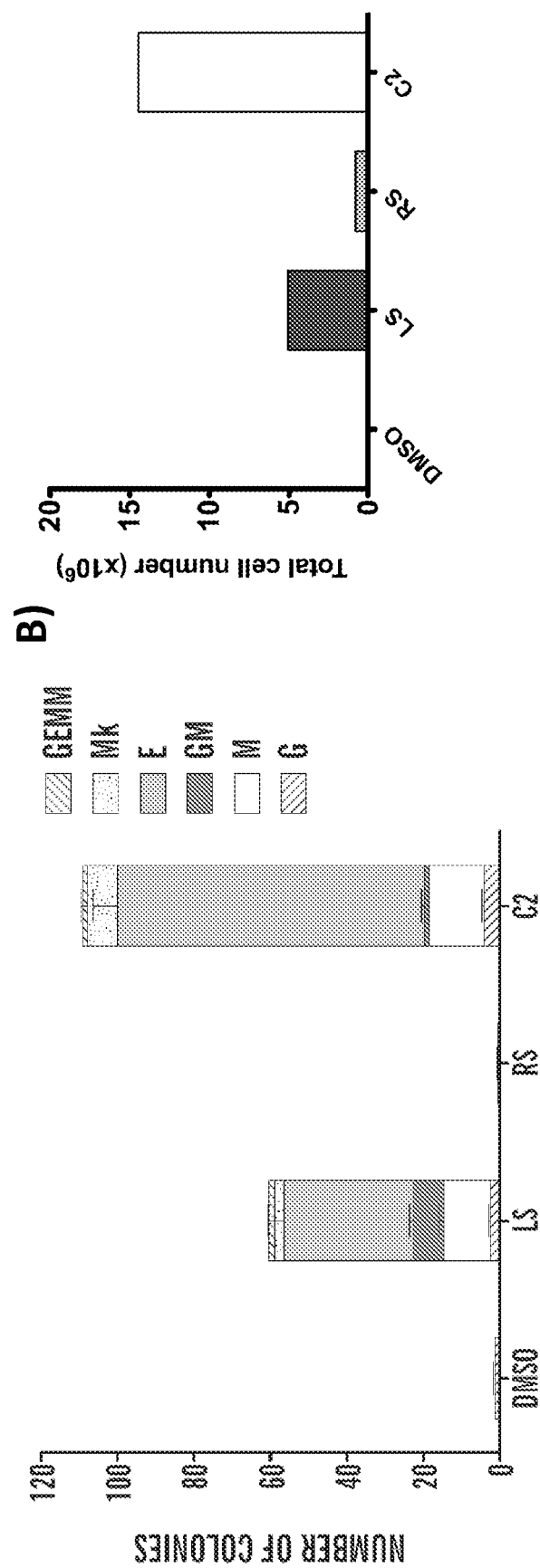
FIGS. 11A-11B show the results of a colony forming assay of purified murine HSCs exposed to DMSO, LSD1 inhibitor (LS), Tgfbeta inhibitor RepSox (RS), and the combination of both (C2) cultured for 14 days. HSCs were cultured in the presence of DMSO, LSD1 inhibitor IV (LS), Tgfbeta inhibitor RepSox (RS), and the combination of both (C2) for 14 days and then 1/300 of the culture was plated in 1 ml of MethoCult 3434. Arising colonies were scored 10 days post-plating into methylcellulose.
Figure 12A:
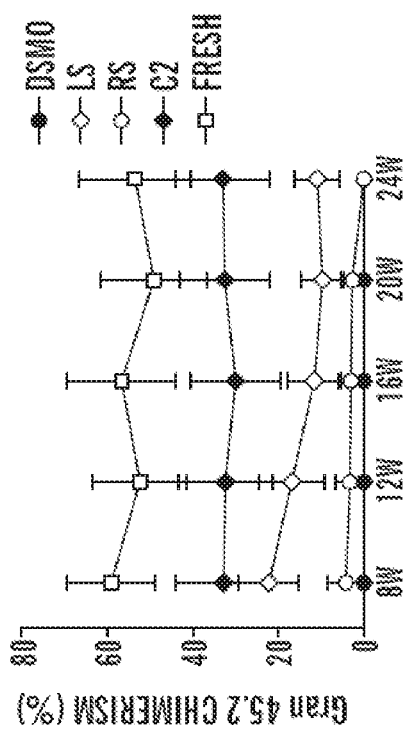
FIGS. 12A-12D show the results of competitive transplantation of purified murine HSCs (lineage-Sca1+ckit+CD150+CD48−CD34−Fgd5ZsGr+) exposed to DMSO, LSD1 inhibitor (LS), Tgfbeta inhibitor RepSox (RS), and the combination of both (C2) cultured for 14 days. The cultures arising from 100 starting murine HSC were competitively transplanted into lethally irradiated recipients following 14 days of ex vivo culture DMSO, LSD1 inhibitor IV (LS), Tgfbeta inhibitor RepSox (RS), and the combination of both (C2) showing
Figure 12B:
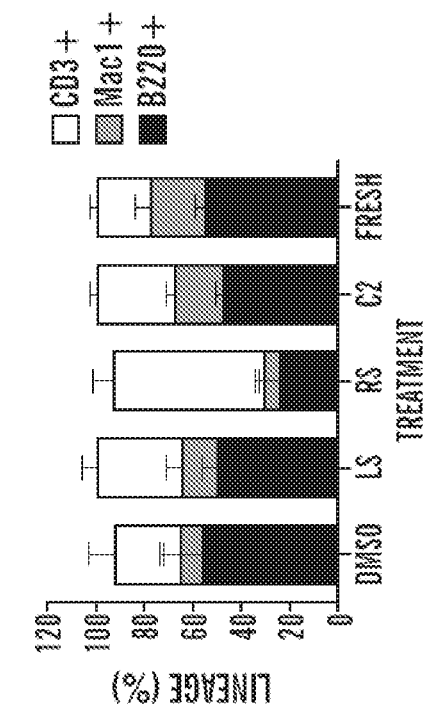
Figure 12C:
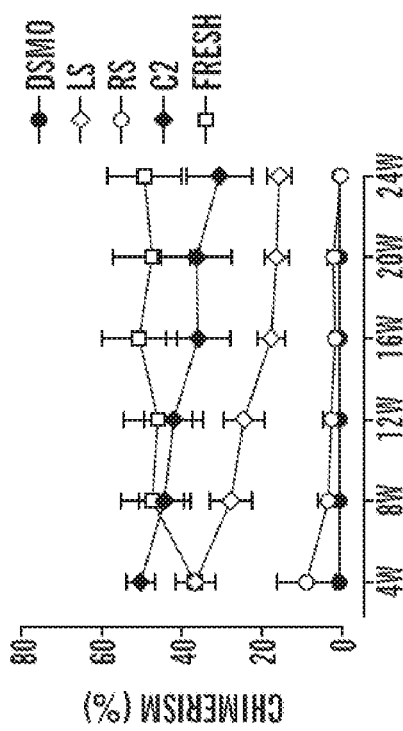
Figure 12D:
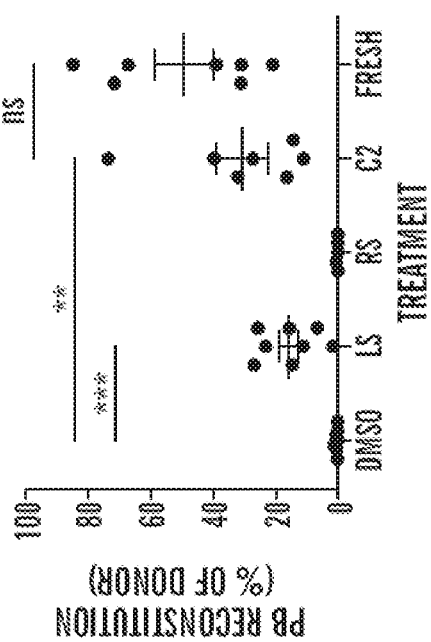
Figure 13A:
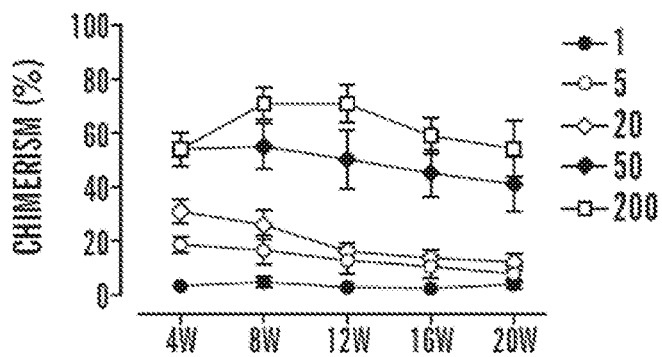
FIGS. 13A-13F show the results of a limit dilution assay of purified murine HSCs (lineage−Sca1+ckit+CD150+CD48−CD34−Fgd5ZsGr+) cultured for 14 days with the combination (C2) of LSD1 inhibitor IV (LS) and the Tgfbeta inhibitor RepSox (RS). The cultures arising from 1, 5, 20, 50 or 200 starting murine HSCs were competitively transplanted following 14 days of ex vivo culture in the presence of C2.
Figure 13B:
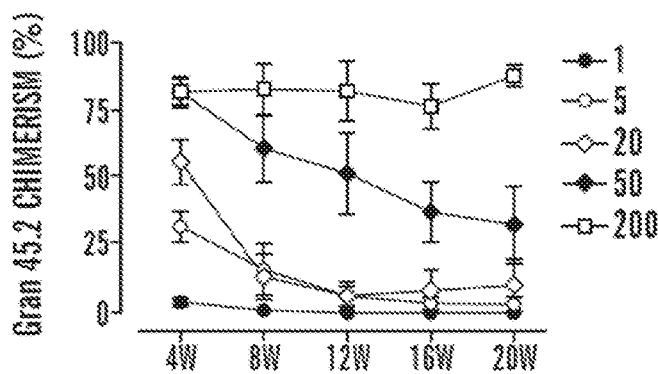
Figure 13C:
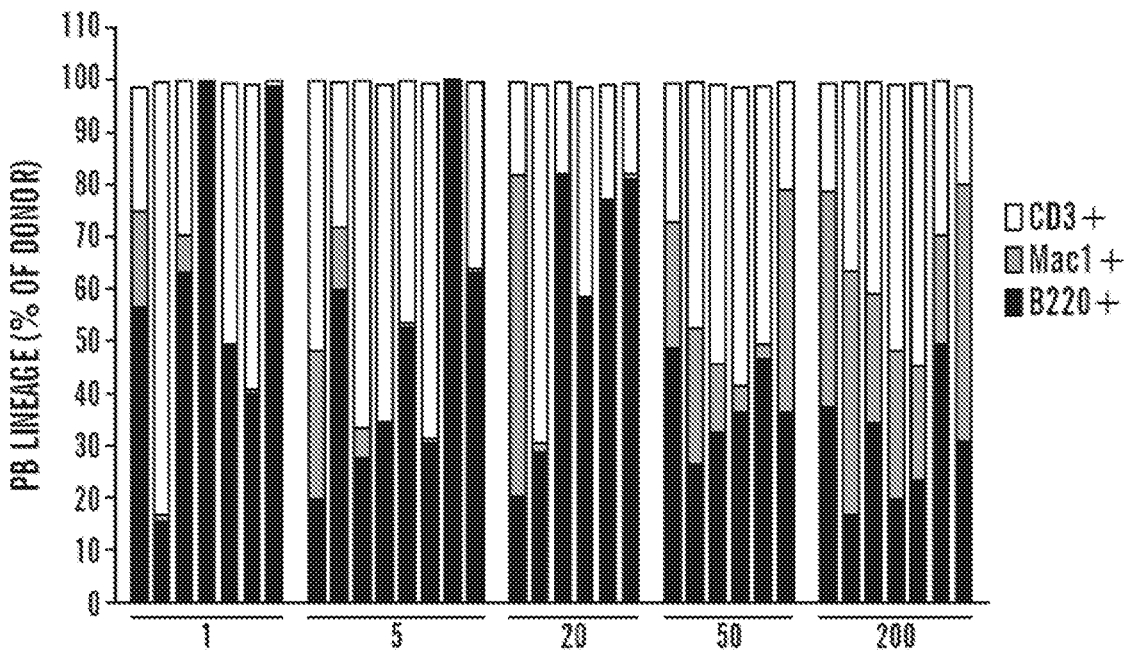
Figure 13D:
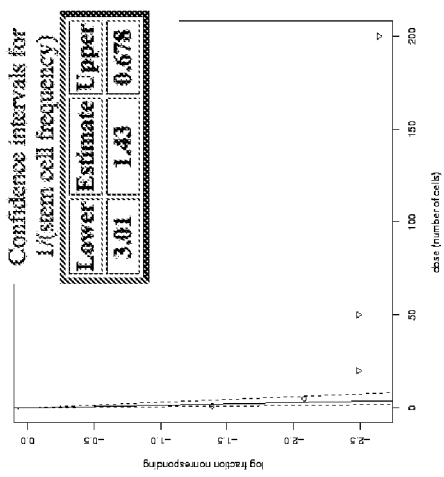
Figure 13E:
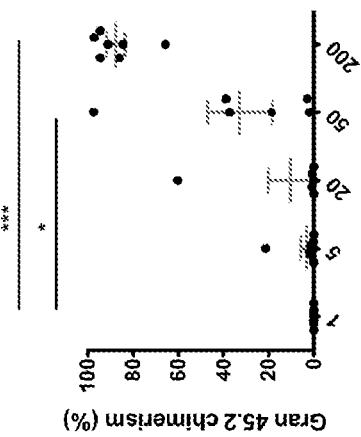
Figure 13F:
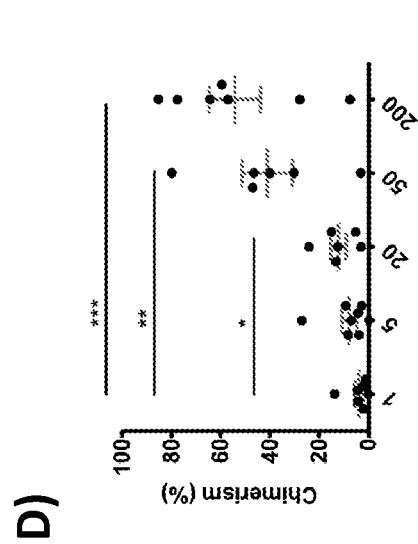

Example 2. Inhibition of Histone Demethylation and TGFβ Signaling During Ex Vivo Culturing of HSCs Promotes Expansion, Enrichment, and Maintenance Cells with Hematopoietic Stem Cell Properties An optimal combination of compounds that can be used to expand, enrich, and maintain the hematopoietic stem cell functional potential of hematopoietic stem cells includes a histone demethylase inhibitor and an inhibitor of the TGFβ receptor Alk5. FIG. 8 shows the ex vivo culture of 20 murine HSCs (LSK34-Flk2-150+ZsGr+) for 7 or 14 days in the presence of DMSO, LSD1 inhibitor IV (LS), Tgfbeta inhibitor (RepSox) or the combination of both (C2). Images taken at 4× magnification. Note that the cultures in the presence of C2 or LS are more homogenous and less differentiated. FIGS. 9A-9B show the expansion of phenotypic HSCs for 14 days ex vivo. 20 murine HSCs (LSK34-Flk2-150+ ZsGr+) were cultured in the presence of DMSO, LSD1 inhibitor IV (LS), Tgfbeta inhibitor RepSox (RS), and the combination of both (C2) for 14 days. This method supports maintenance and expansion of ZsGr+ HSCs. FIG. 9A: Representative FACS plots of HSCs cultured for 14 days ex vivo in the presence of DMSO and the combination of LSD1 inhibitor (LS), Tgfbeta inhibitor RepSox (RS) (C2) showing increased levels of phenotypic HSCs in the presence of C2. FIG. 9B: Number of ZsGr+ HSCs in each condition after 14 days of ex vivo culture. FIGS. 10A-10C show that LSD1 inhibitor (LS), Tgfbeta inhibitor RepSox (RS), and the combination of both (C2) supports maintenance and expansion of ZsGr+ HSCs. A) Bright-field and ZsGr images of 20 HSCs cultured for 4.5 days ex vivo in the presence of LSD1 inhibitor IV (LS), Tgfbeta inhibitor RepSox (RS), and the combination of both (C2). FIG. 10B: Frequency of ZsGr+ cells remaining following 4.5 days of ex vivo culture. FIG. 10C: Number of ZsGr+(Green) and ZsGr− (Black) cells within 4.5 day cultures (See also FIGS. 11A-13F and 28A-32B).

Figures 22A, 22B:
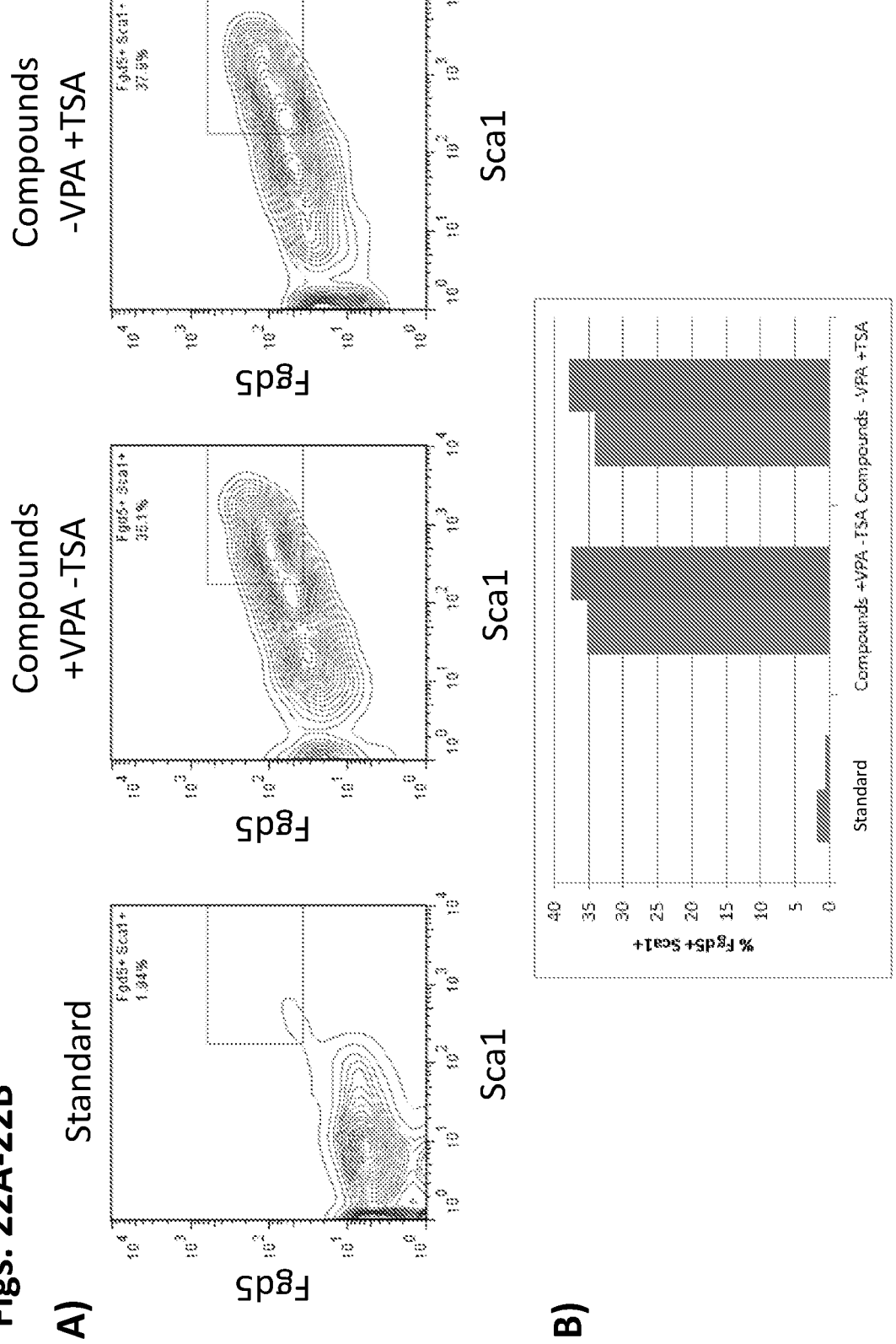
FIGS. 22A-22B show that structurally distinct HDAC inhibitors function equivalently to maintain immunophenotypic HSCs. 100 murine HSCs (lineage-, ckit+, Sca1+, CD150+, CD48-, Fgd5ZsGr+) were cultured in the presence of cytokines only (SCF, TPO, and IL12) in the absence of compounds (Standard), or additionally supplemented with a cocktail of compounds (Lithium chloride, nicotinamide, N-acetylcysteine, ascorbic acid, A83-01, and SB203580) plus either valproic acid (VPA) or trichostatin A (TSA), which are structurally distinct HDAC inhibitors.

Example 3. Ex Vivo Culturing HSCs in the Presence of HDAC Inhibitors Promotes Expansion, Enrichment, and Maintenance of Cells with Hematopoietic Stem Cell Properties In addition to inhibitors of histone demethylation and TGFβ signaling, histone deacetylase inhibitors also promote the expansion, enrichment, and maintenance of hematopoietic stem cells ex vivo. FIGS. 22A-22B shows that structurally distinct HDAC inhibitors function equivalently to maintain immunophenotypic HSCs. 100 murine HSCs were cultured in the presence of cytokines only (SCF, TPO, and IL12) in the absence of compounds (Standard), or additionally supplemented with a cocktail of compounds (Lithium chloride, nicotinamide, N-acetylcysteine, ascorbic acid, A83-01, and SB203580) plus either valproic acid (VPA) or trichostatin A (TSA), which are structurally distinct HDAC inhibitors. FIG. 22A: Day 7 flow cytometry analysis and FIG. 22B: proportion of Fgd5-ZsGreen+Sca1+ cells for each replicate. FIGS. 41A-41C show that Romidepsin, a HDAC1/2 specific inhibitor, can replace Trichostatin A, a pan HDAC inhibitor, for efficient ex vivo maintenance/ expansion of human HSCs. 3000 CD34+ enriched mobilized peripheral blood cells were cultured for 7 days in serum free media supplemented with cytokines (SCF, TPO, FLT3L, IL3) in the presence of the indicated chemical combinations (Tgfbeta inhibitor (A, A83-01), pan-HDAC inhibitor (TSA, Trichostatin A), LSD1 inhibitor (TC, Tranylcypromine), p38 inhibitor (p38i, SB203580), HDAC1/2 inhibitor (Rom, Romidepsin)) and analyzed by flow cytometry. FIG. 41A: immunophenotype of the cells, FIG. 41B: percentage of indicated populations, and FIG. 41C: quantification of immunophenotypic HSCs (Lineage−CD34+CD45RA-CD38-CD90+CD49F+) 7 days post-culturing in the indicated conditions.

Figures 14A, 14B:
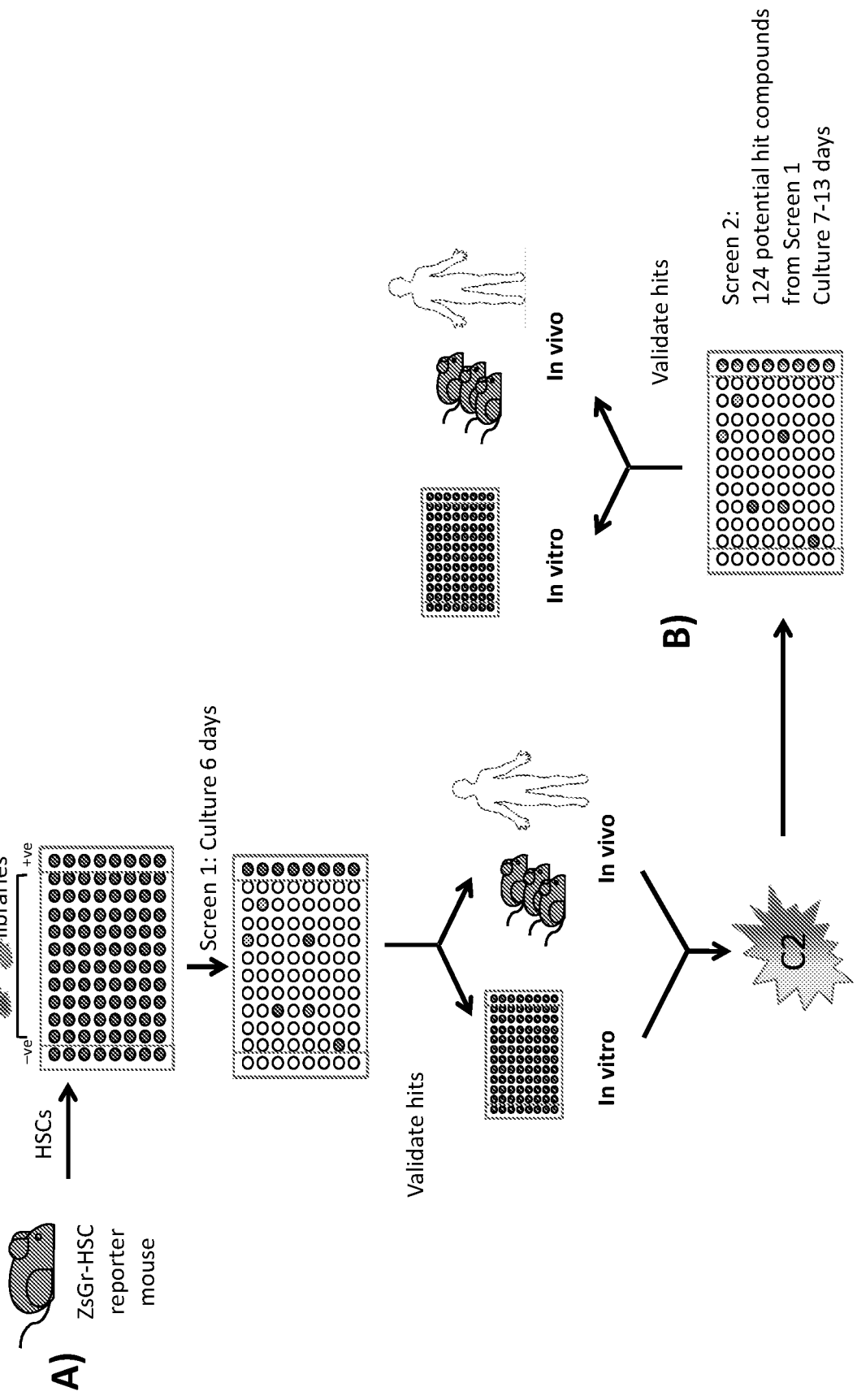
FIGS. 14A-14B show secondary small molecule screen for compounds that synergize with C2 (LSD1 inhibitor IV and Tgfbeta inhibitor) to support HSC ex vivo maintenance and expansion. Schematic of primary (FIG. 14A) and (FIG. 14B) secondary screen in which 124 potential hit compounds identified in primary screen were rescreened (screen 2) in the presence of C2.
Figures 15A, 15B, 15C:
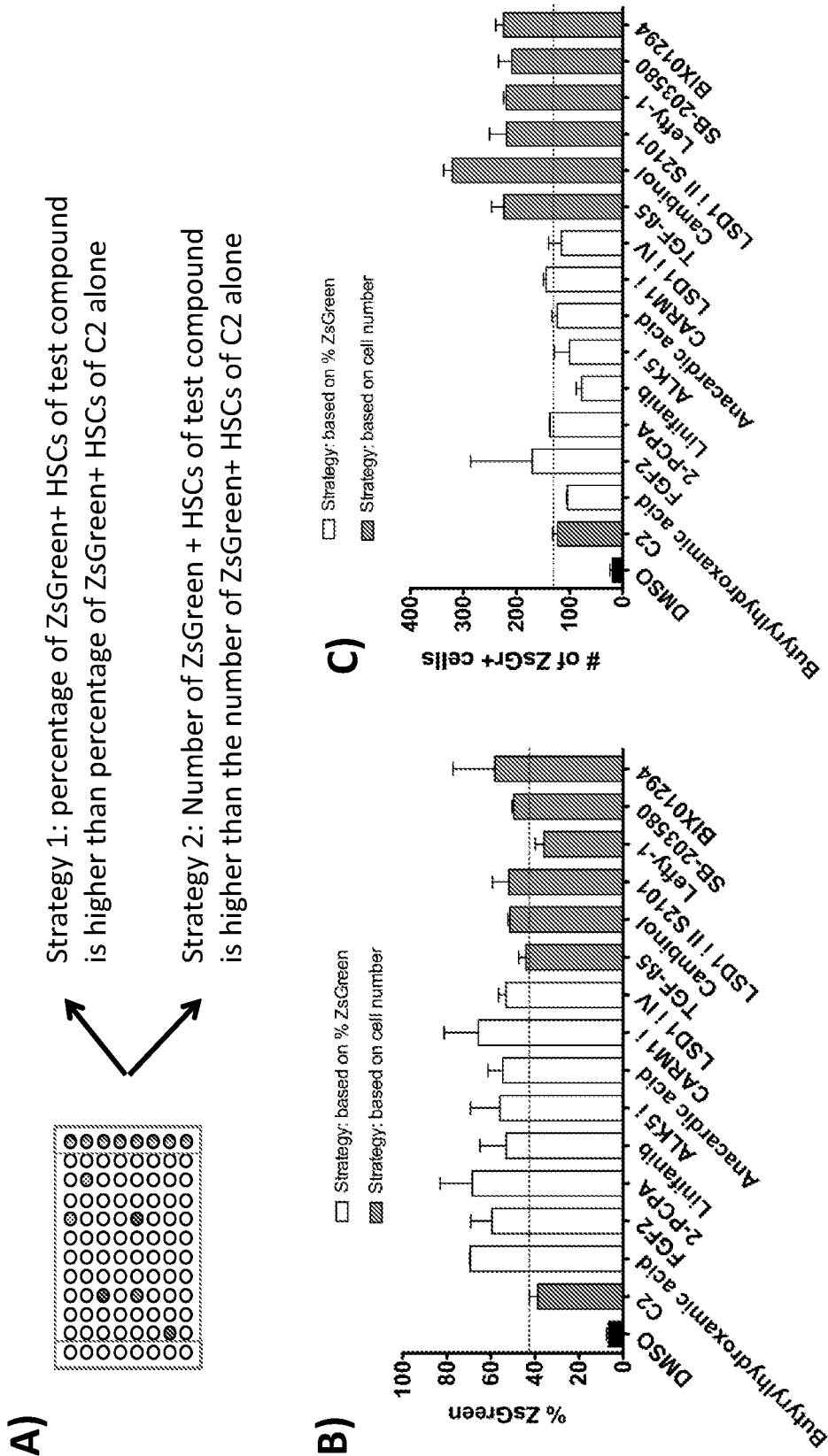
FIGS. 15A-15C show potential hits of secondary screen that target pathways of interest including Tgfbeta, histone methylation, histone acetylation, p38 signaling and Wnt signaling.
Figure 17:
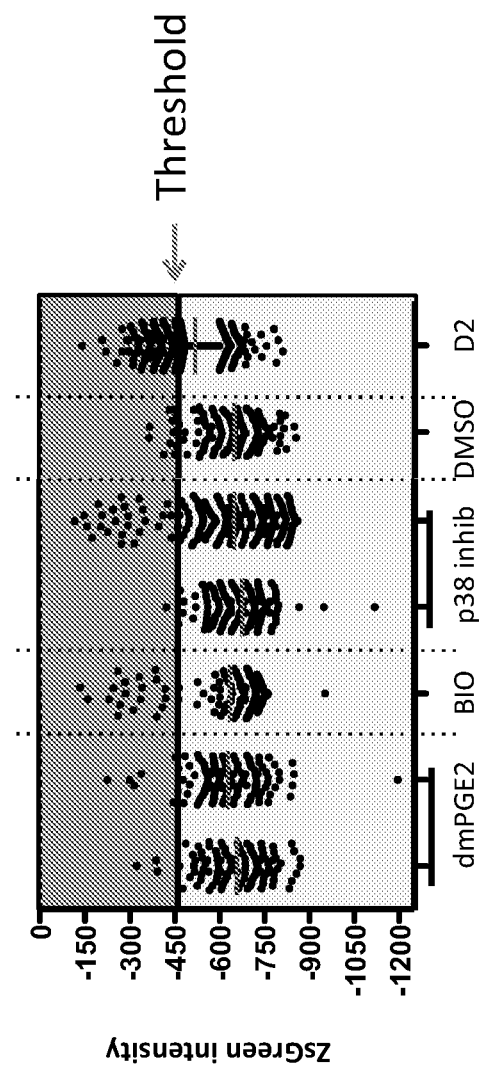
FIG. 17 shows the results of experiments testing compounds previously reported to maintain murine HSCs. Culturing ZsGreen positive HSCs for 6 days in the presence of: dmPGE2 (North, Zon, *Nature*. 2007), BIO (Ko et al, *Stem Cells*. 2011), p38 inhibitor (Wang et al, *Stem Cells Dev.* 2011), DMSO: negative control. D2 is ZsGr+ HSCs maintained for 2 days ex vivo. Threshold of cells identified as ZsGreen+(i.e., HSCs) is shown with arrow.
Figure 20:
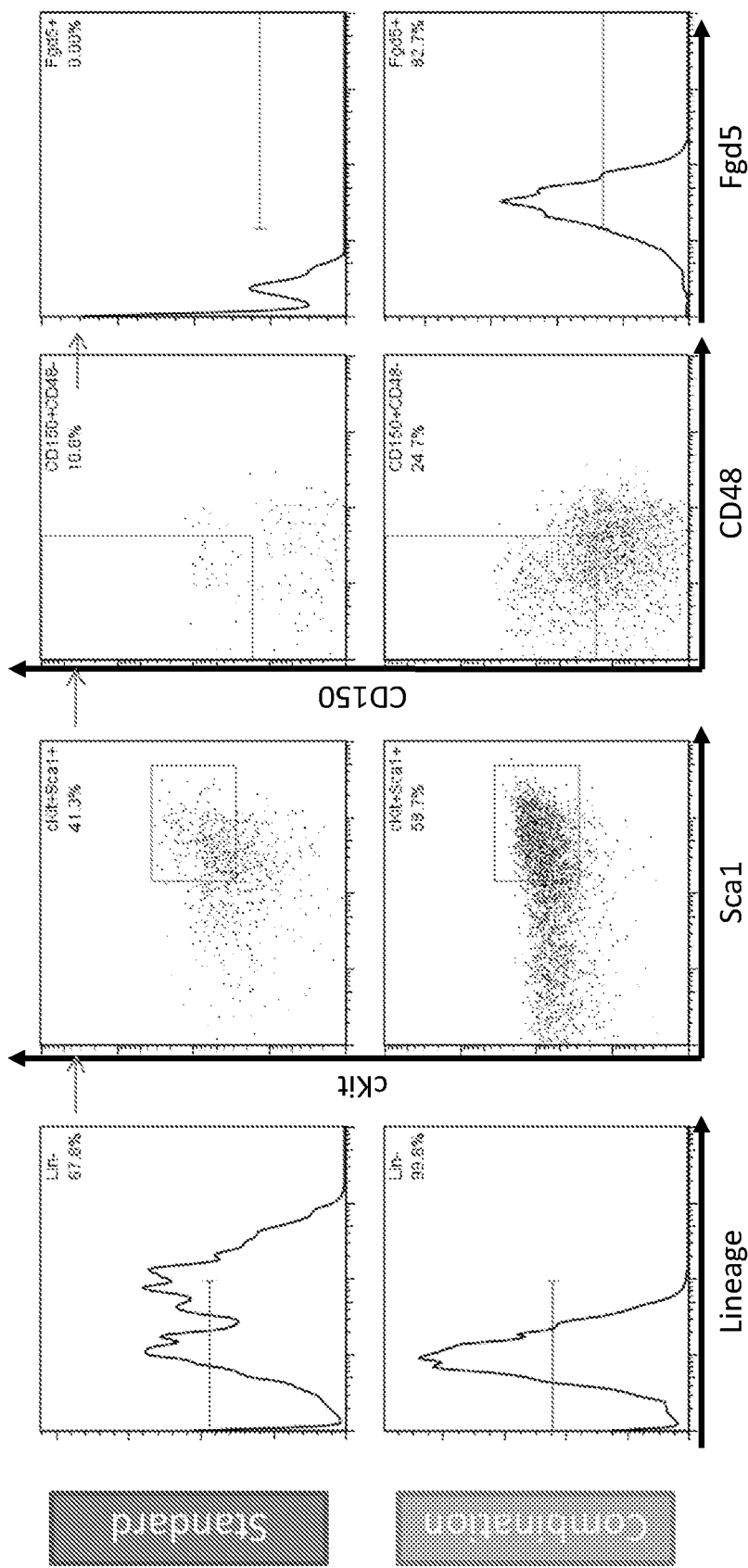
FIG. 20 shows the combinatorial modulation of 7 candidate pathways maintains and expands immunophenotypic HSCs during ex vivo culturing. 50 mouse HSCs were cultured in a serum free media supplemented with SCF, TPO, and IL12, plus or minus the seven candidate pathway modulators. Flow cytometric analysis was performed on Day 15. Compounds modulating the 7 pathways are: A83-01, Tranylcypromine, Trichostatin A, SB203580, CHIR99021, DMH1, and Sodium acetate.
Figure 27:
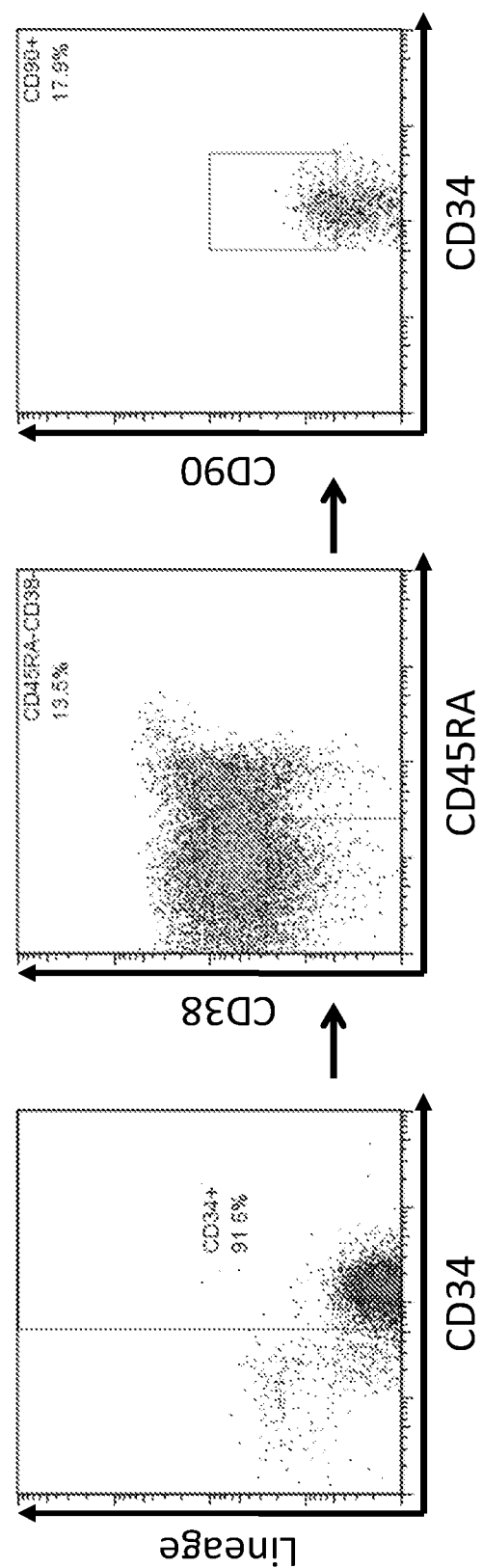
FIG. 27 shows a sorting strategy for primary human HSCs from CD34+ enriched cord blood. Sorted HSCs have the immunophenotype of CD34+lineage-CD38-CD45RA-CD90+.
Figures 28A, 28B:
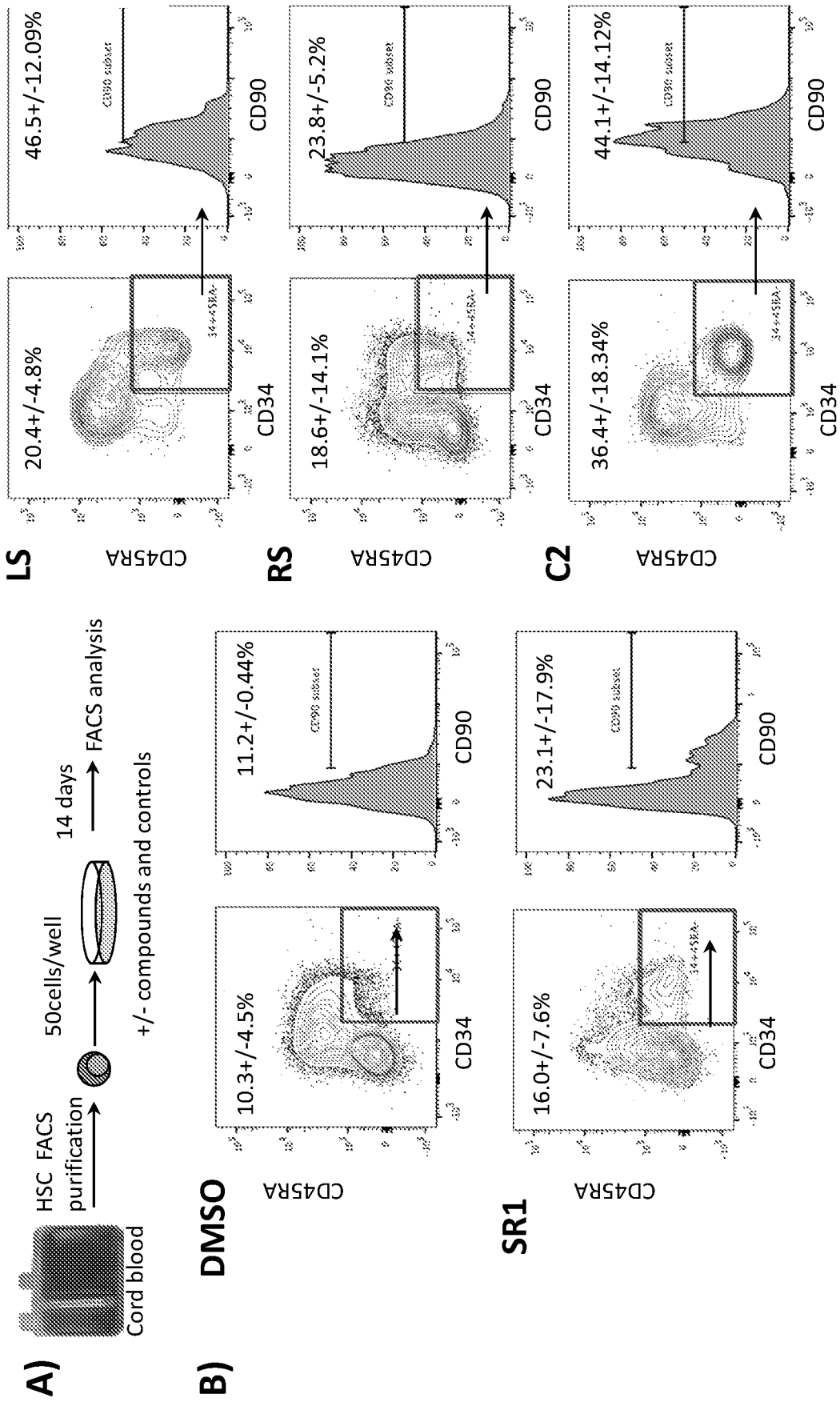
FIGS. 28A-28B show that the combination (C2) of LSD1 inhibitor IV (LS) and the Tgfbeta inhibitor RepSox (RS) can maintain and expand phenotypic human cord blood (CB) HSCs following 14 days ex vivo culturing.
Figures 29A, 29B:
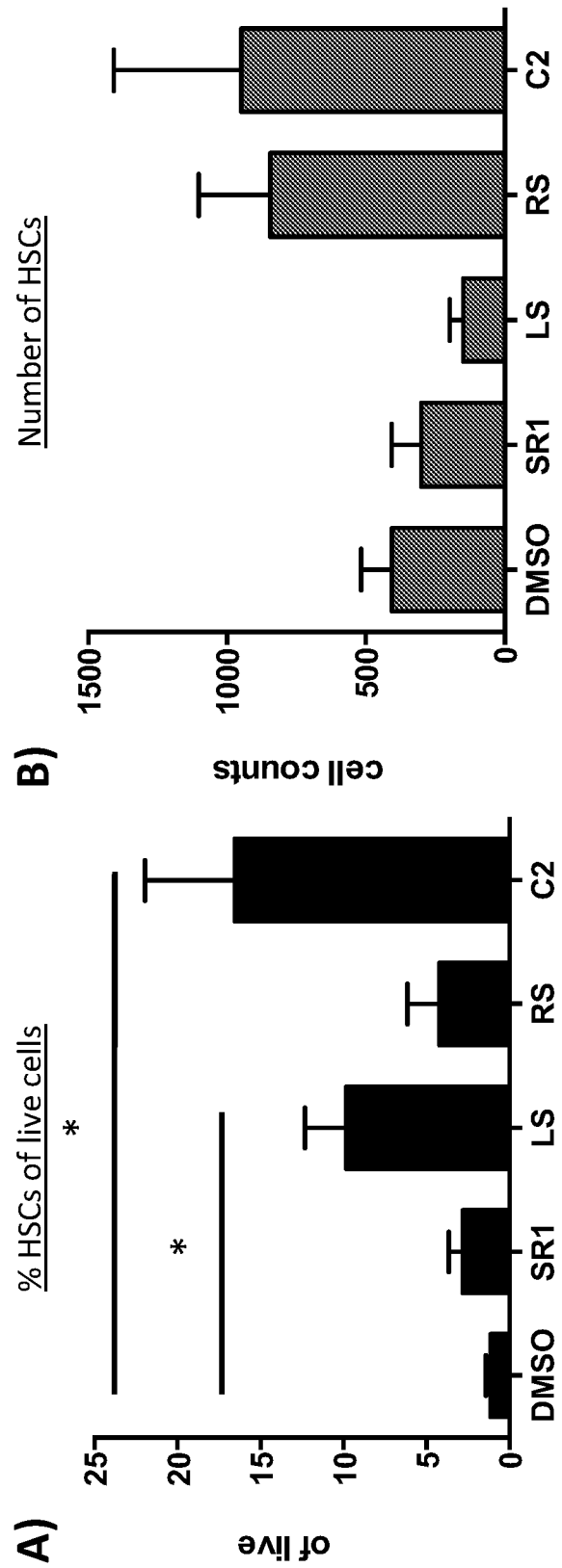
FIGS. 29A-29B show that the combination (C2) of LSD1 inhibitor IV (LS) and the Tgfbeta inhibitor RepSox (RS) can maintain and expand phenotypic human cord blood HSCs following 14 days ex vivo culturing.
Figures 31A, 31B:
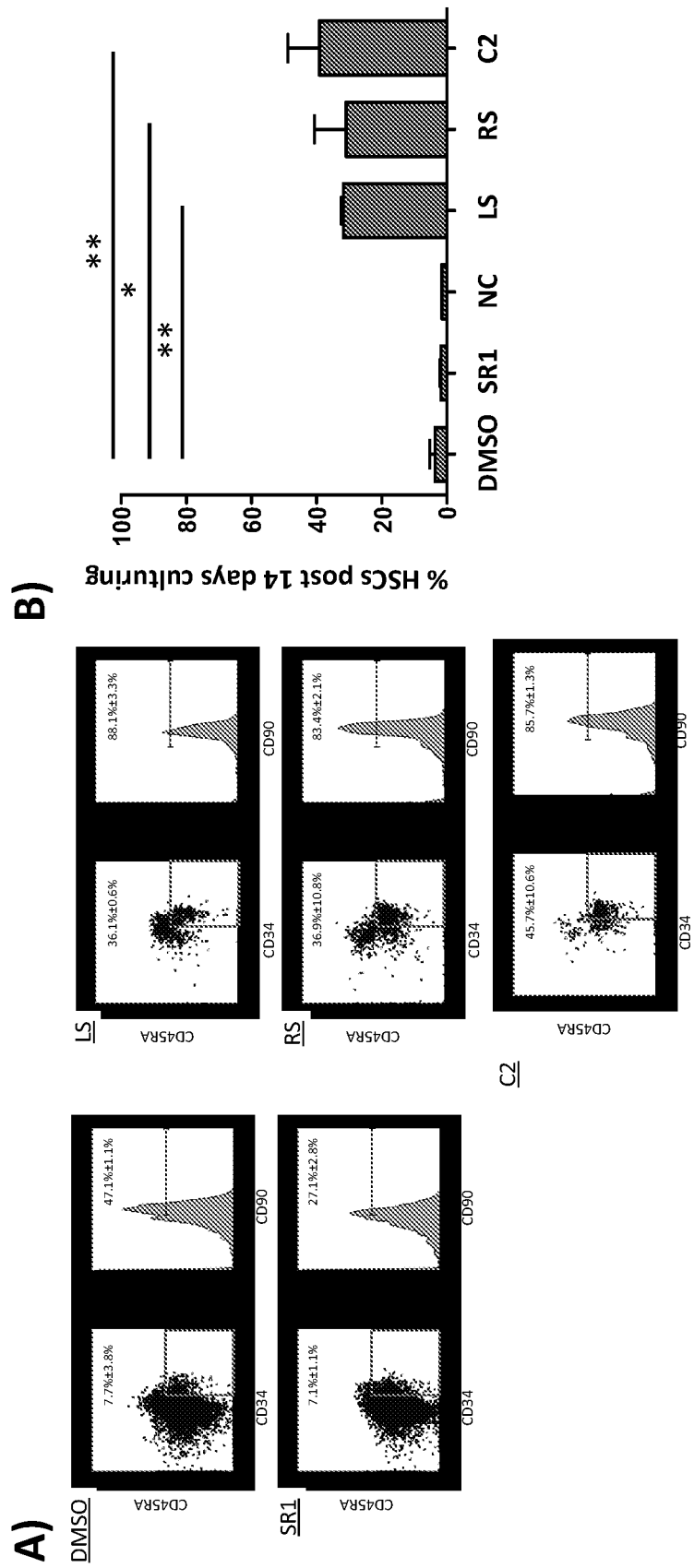
FIGS. 31A-31B show that the combination (C2) of LSD1 inhibitor IV (LS) and the Tgfbeta inhibitor RepSox (RS) can maintain and expand phenotypic human bone marrow HSCs following 14 days ex vivo culturing.
Figure 32A:
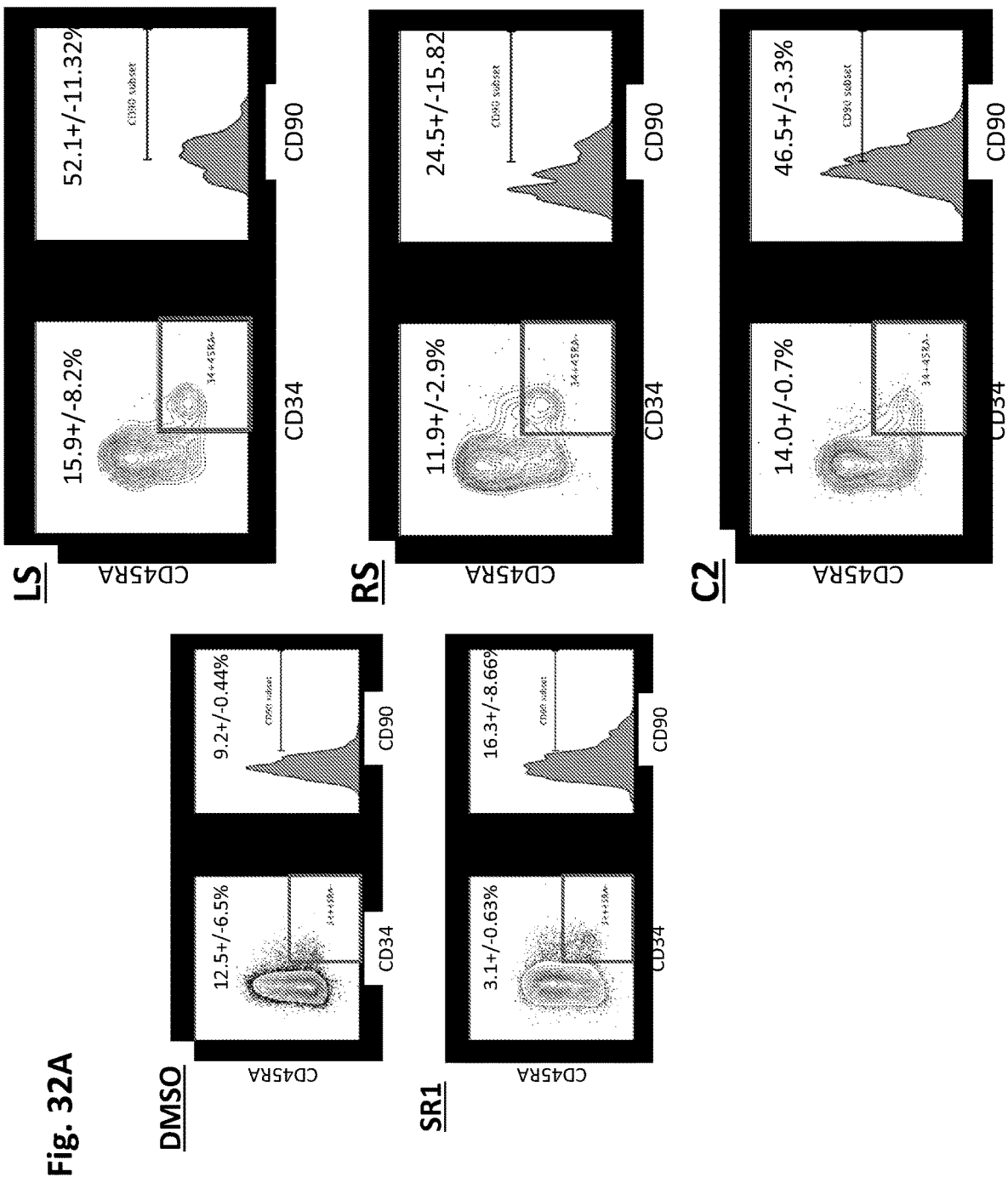
FIGS. 32A-32B show that the combination (C2) of LSD1 inhibitor IV (LS) and the Tgfbeta inhibitor RepSox (RS) can maintain and expand phenotypic human mobilized peripheral blood HSCs following 14 days ex vivo culturing.
Figure 32B:
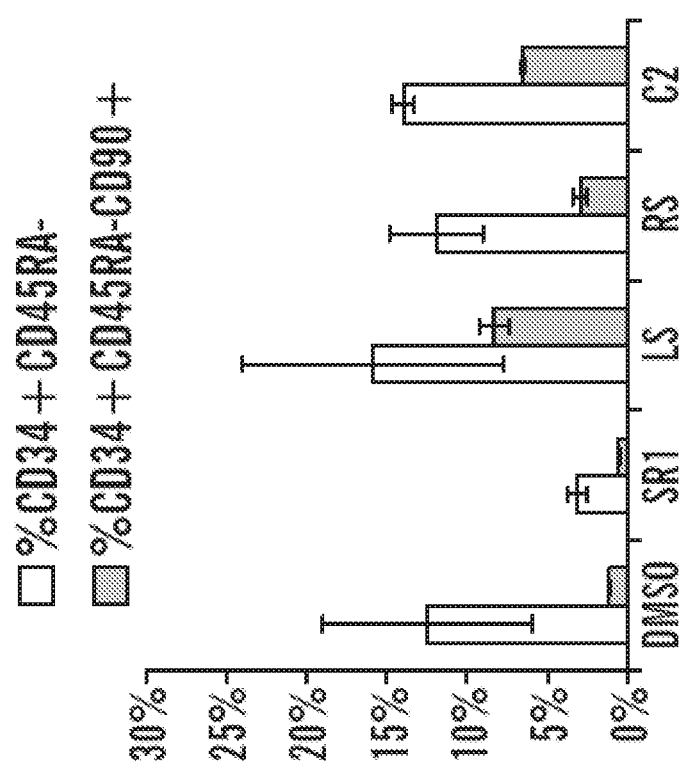

Example 4. Secondary Screens to Identify Compounds that Promote Expansion, Enrichment, and Maintenance of Cells with Hematopoietic Stem Cell Properties Ex Vivo A variety of secondary screens were conducted in order to identify additional compounds that can be used to expand, enrich, and maintain the hematopoietic stem cell functional potential of hematopoietic stem cells. FIGS. 14A-14B show secondary small molecule screen for compounds that synergize with C2 (LSD1 inhibitor IV and Tgfbeta inhibitor) to support HSC ex vivo maintenance and expansion. Schematic of FIG. 14A: primary and FIG. 14B: secondary screen in which 124 potential hit compounds identified in primary screen were rescreened in the presence of C2. FIGS. 15A-15C show potential hits of secondary screen that target pathways of interest including Tgfbeta, histone methylation, histone acetylation, p38 signaling and Wnt signaling. FIG. 15A: Overview of two strategies used to identify hits in secondary small molecule screen. FIG. 15B: Hits found by following a strategy based on ZsGreen+ HSC percentage (strategy 1). FIG. 15C: Hits found by following a strategy based on number of ZsGreen+ HSCs (strategy 2). FIG. 17 shows the results of experiments testing compounds reported to maintain murine HSCs: Culturing ZsGreen positive HSCs for 6 days in the presence of; dmPGE2 (North, Zon, Nature. 2007), BIO (Ko et al, Stem Cells. 2011), p38 inhibitor (Wang et al, Stem Cells Dev. 2011), DMSO: negative control. D2 is ZsGr+ HSCs maintained for 2 days ex vivo. Threshold of cells identified as ZsGreen+(i.e., HSCs) is shown with arrow. FIGS. 18A-18B show a hypothesis driven strategy for modulating candidate pathways towards HSC maintenance/expansion. FIG. 18A: Selection of candidate target pathways via comparison of intestinal stem cell and hematopoietic stem cell maintenance/proliferation signals. FIG. 18B: Selection of agents/pathway modulators. FIG. 19 shows a schematic for assessing the activity of pathway modulators on HSC maintenance/expansion. Fgd5-ZsGreen+immunophenotypic HSCs (Lineage-cKit+Sca1+CD150+CD48-Fgd5-ZsGreen+) were sorted and cultured in the presence of cytokines only (Standard media) or additionally supplemented with 7 candidate pathway modulators (W7 media). Multiparametric analysis of cellular immunophenotype was performed by flow cytometry after 14 days of culture. FIG. 20 shows the combinatorial modulation of 7 candidate pathways maintains and expands immunophenotypic HSCs. 50 mouse HSCs were cultured in a serum free media supplemented with SCF, TPO, and IL12, plus or minus the seven candidate pathway modulators. Flow cytometric analysis was performed on Day 15. For a description of an example sorting strategy used for flow cytometry analyses of human cord blood, see FIG. 27.

Example 5. In Vivo Function of Ex Vivo Cultured HSCs

Figure 24:
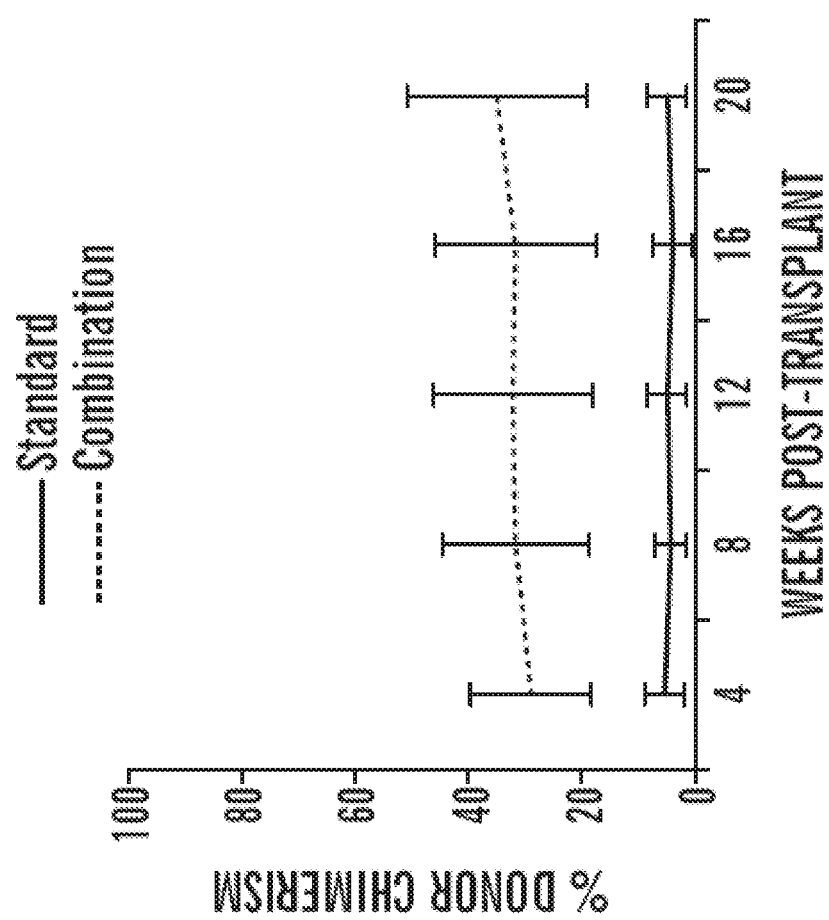
FIG. 24 shows the in vivo function of murine HSCs cultured for 14 days in the presence of DMSO (Standard) or compounds targeting 7 pathways (Combination) consisting of Tgfbeta inhibitor A83-01, Lsd1 inhibitor Tranylcypromine, HDAC inhibitor Trichostatin A, the p38 kinase inhibitor SB203580, BMP inhibitor DMH1, Gsk3beta inhibitor Chir99021, and sodium acetate. 10 HSCs were cultured for 14 days in the indicated conditions followed by in vivo competitive transplantation into lethally irradiated hosts (against $2 \times 10^5$ congenically marked bone marrow cells). Peripheral blood donor chimerism at indicated time points post-transplantation are shown.
Figure 25A:
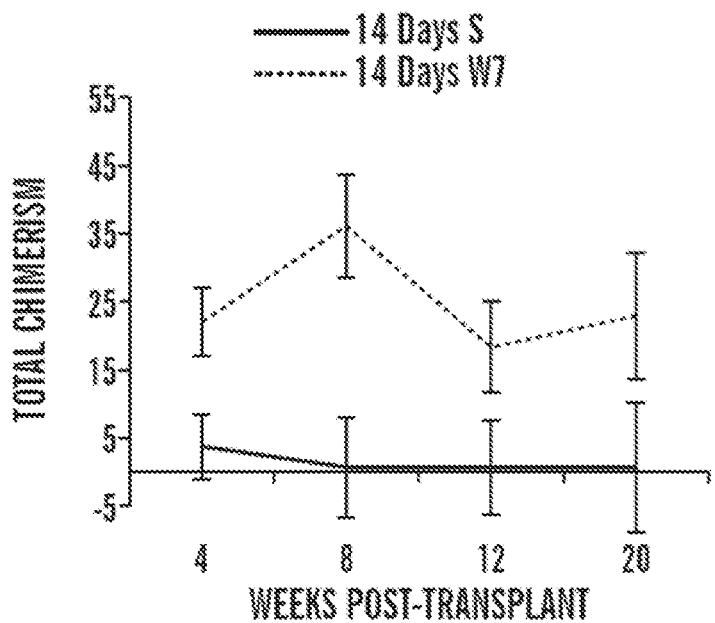
FIGS. 25A-25C show the in vivo function of murine HSCs cultured for 14 days in the presence of DMSO (S: Standard), or compounds targeting 7 pathways (W7: Tgfbeta inhibitor A83-01, Lsd1 inhibitor Tranylcypromine, HDAC inhibitor Trichostatin A, the p38 kinase inhibitor SB203580, BMP inhibitor DMH1, Gsk3beta inhibitor Chir99021, and sodium acetate). 100 HSCs (lineage-, ckit+, Sca1+, CD150+, CD48-, Fgd5ZsGr+) were cultured for 14 days in the indicated conditions followed by in vivo competitive transplantation (against $2 \times 10^5$ congenically marked bone marrow cells).
Figure 25B:
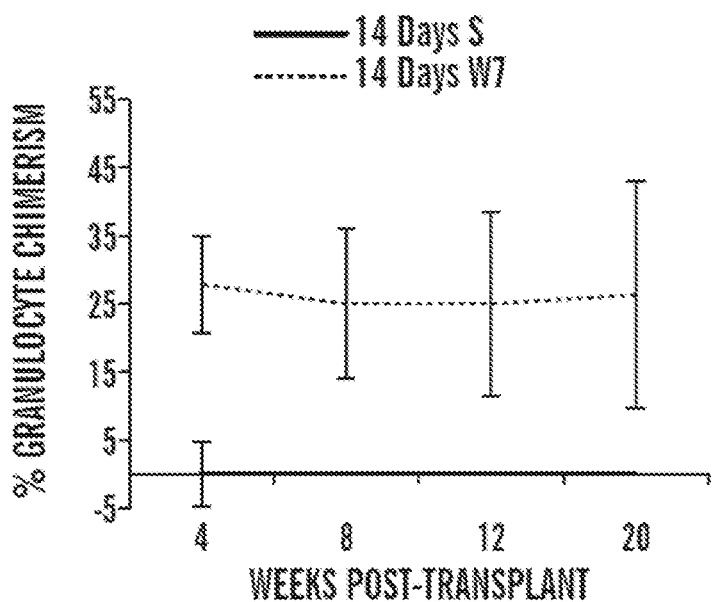
Figure 25C:
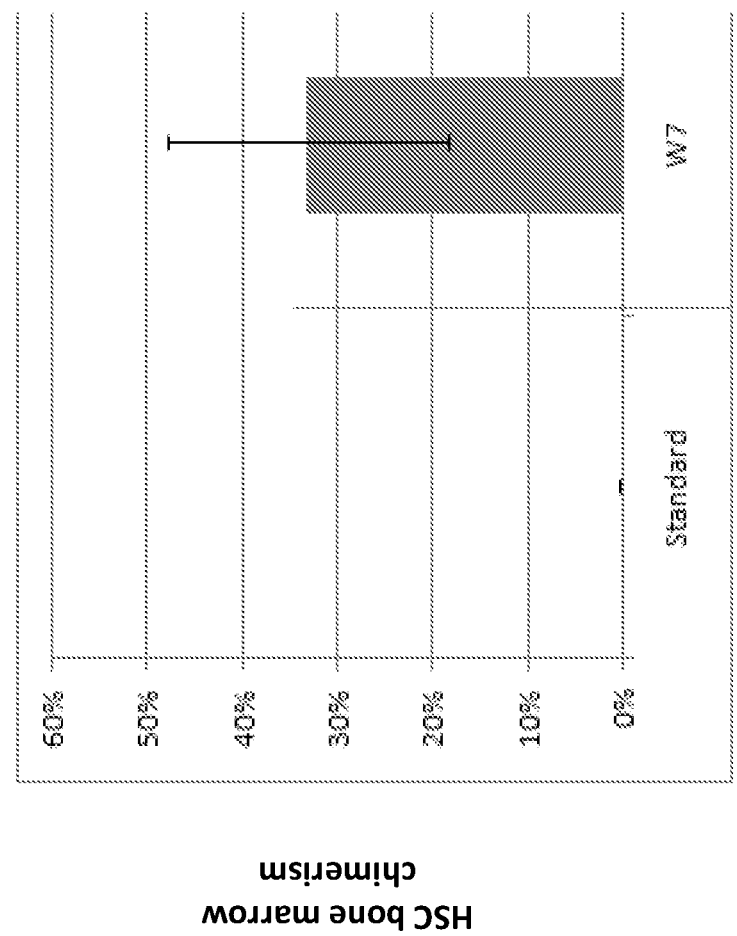

A series of experiments was conducted in order to probe the activity of ex vivo cultured hematopoietic stem cells in in vivo transplantation assays. FIG. 24 shows the in vivo function of murine HSCs cultured for 14 days in the presence DMSO (Standard), or compounds targeting 7 pathways (Combination) (Tgfbeta inhibitor A83-01, Lsd1 inhibitor Tranylcypromine, HDAC inhibitor Trichostatin A, the p38 kinase inhibitor SB203580, BMP inhibitor DMH1, Gsk3beta inhibitor Chir99021, and sodium acetate). 10 HSCs were cultured for 14 days in the indicated conditions followed by in vivo competitive transplantation into lethally irradiated hosts (against $2 \times 10^5$ congenically marked bone marrow cells). Peripheral blood donor chimerism at indicated time points post-transplantation are shown. FIGS. 25A-25C show the in vivo function of murine HSCs cultured for 14 days in the presence DMSO (S-Standard), or compounds targeting 7 pathways (W) (Tgfbeta inhibitor A83-01, Lsd1 inhibitor Tranylcypromine, HDAC inhibitor Trichostatin A, the p38 kinase inhibitor SB203580, BMP inhibitor DMH1, Gsk3beta inhibitor Chir99021, and sodium acetate). 100 HSCs were cultured for 14 days in the indicated conditions followed by in vivo competitive transplantation (against $2 \times 10^5$ congenically marked bone marrow cells). FIG. 25A: Peripheral blood and FIG. 25B: granulocyte donor chimerism at indicated time points post-transplantation are shown. FIG. 25C: Donor HSC chimerism in the bone marrow of transplant recipients transplanted with HSCs cultured for 14 days in the indicated conditions is shown.

Figure 21A:
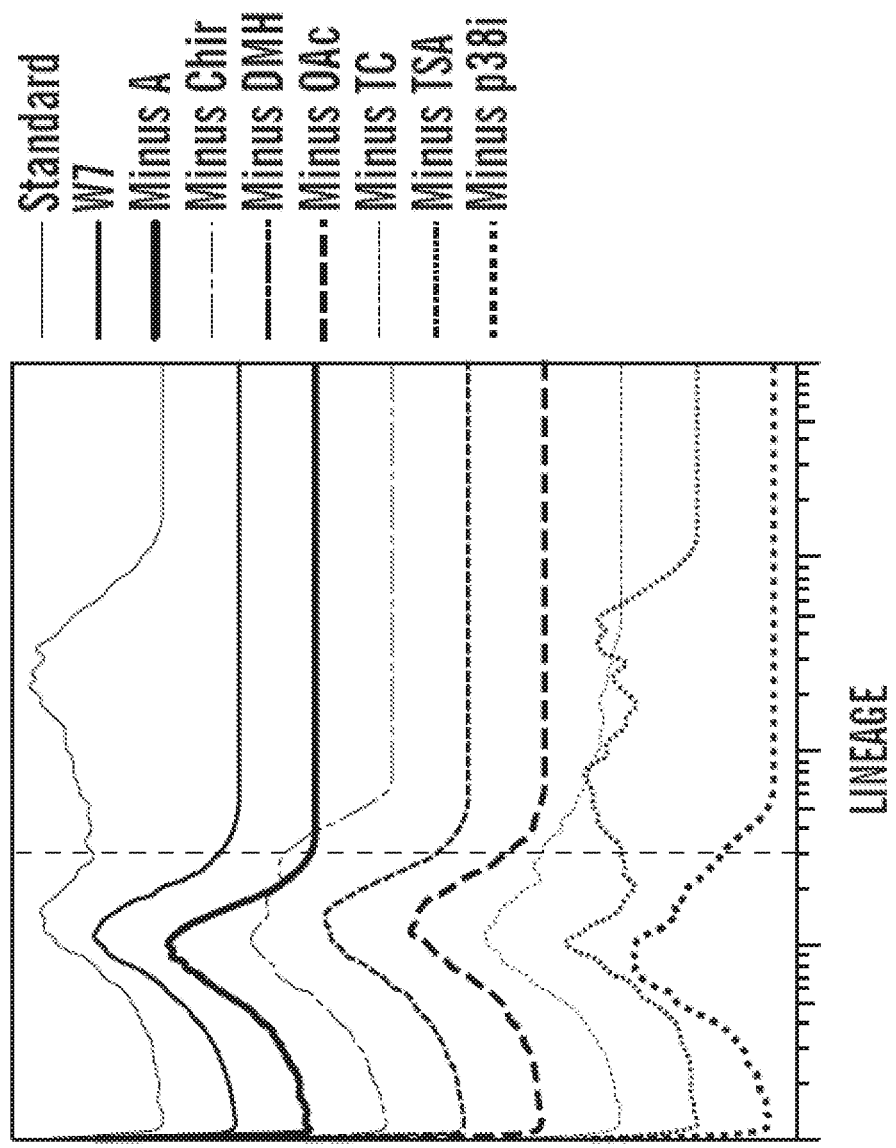
FIGS. 21A-21B show the contribution of each compound/pathway in ability to maintain and expand phenotypic HSCs during ex vivo culture. 50 murine HSCs (lineage-, ckit+, Sca1+, CD150+, CD48-, Fgd5ZsGr+) were cultured in the presence of cytokines only (SCF, TPO, and IL12) in the absence of compounds (standard), or with all 7 compounds (W7), or with subtraction of each individual compound (A83-01 (A), Tranylcypromine (TC), Trichostatin A (TSA), SB203580 (p38i), CHIR99021 (Chir), DMH1 (DMH), Sodium acetate (OAC)). Flow cytometry analysis was performed on Day 14 showing (FIG. 21A) differentiation to lineage+ cells (stained by antibody cocktail against antigens for: B-cells, T-cells, myeloid cells, erythrocytes, and granulocytes), where lineage positive is to the right of the dashed line.
Figure 21B:
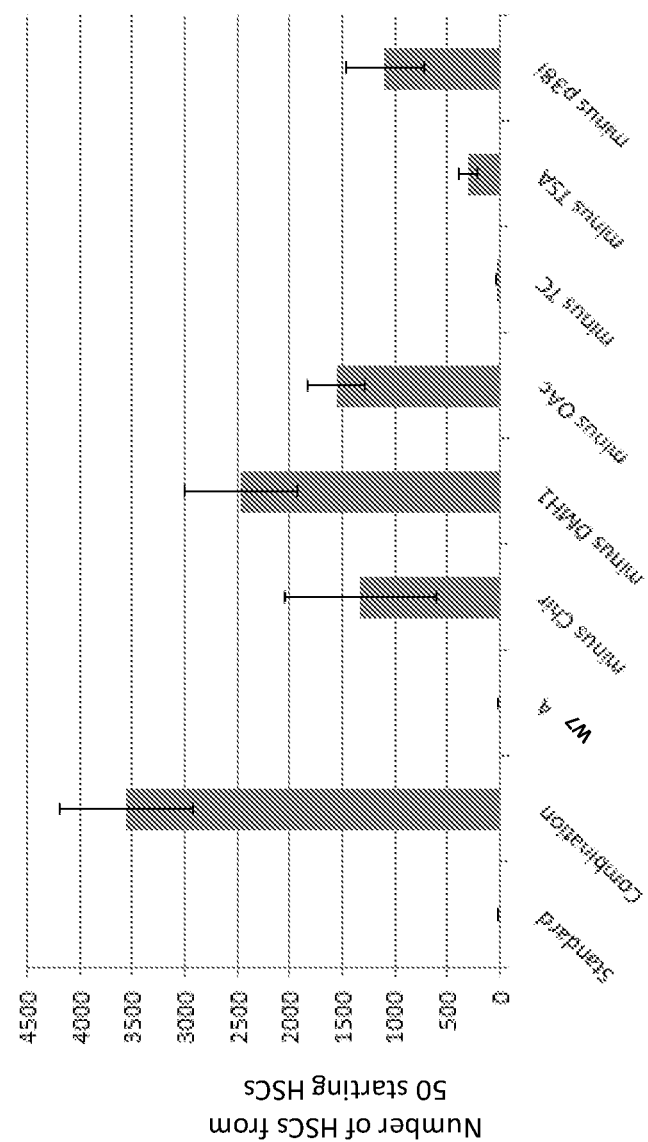
Figure 23:
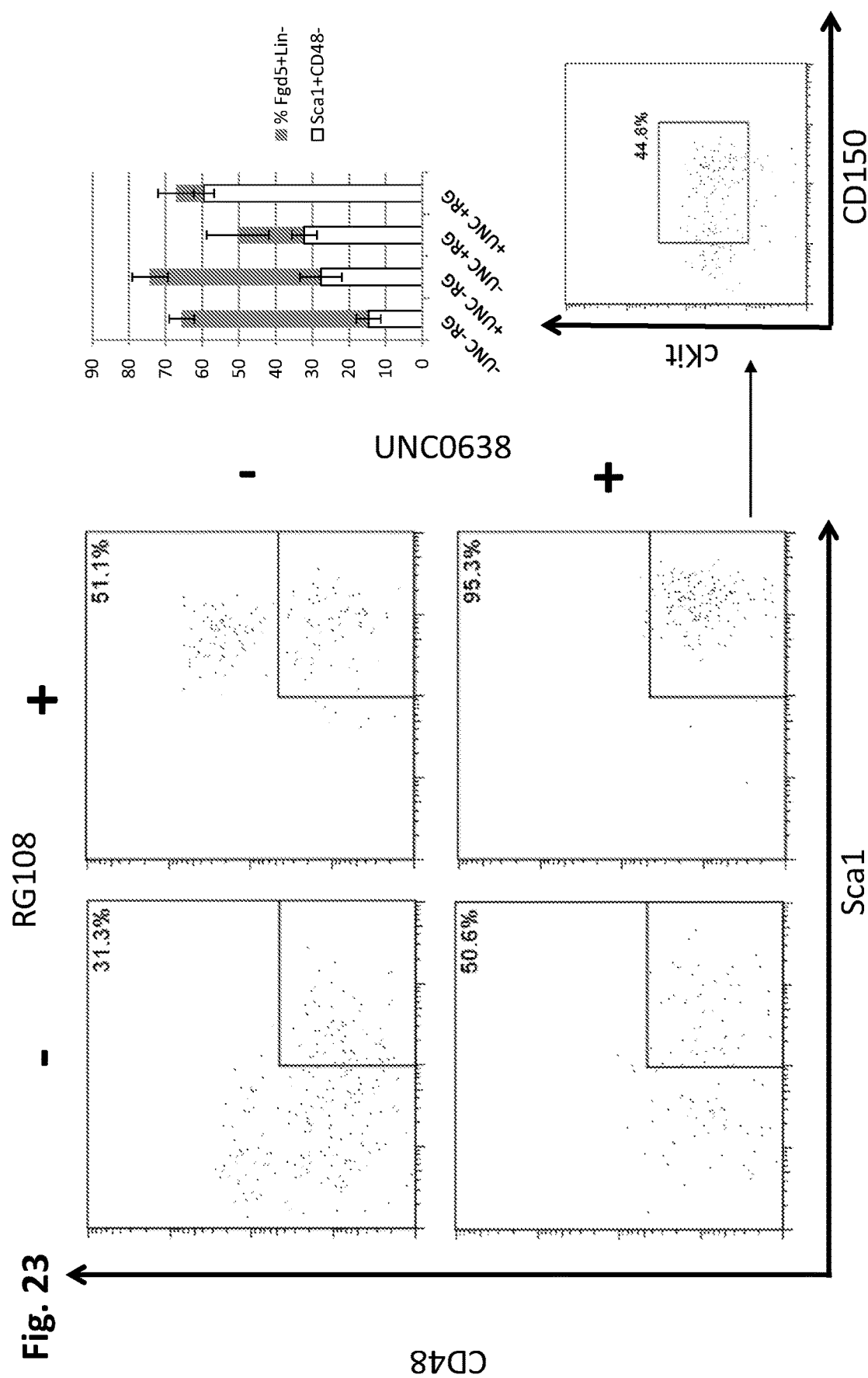
FIG. 23 shows that the supplementation with additional compounds during ex vivo culturing reduces heterogeneity of Fgd5·ZsGr+ HSCs cells with respect to CD48 and Sca1 expression. 40 murine HSCs (lineage-, ckit+, Sca1+, CD150+, CD48-, Fgd5ZsGr+) were cultured for 12 days in the presence of cytokines (SCF, TPO, and IL12) and a cocktail of compounds (Lithium chloride, nicotinamide, N-acetylcysteine, ascorbic acid, A83-01, and SB203580, trichostatin A) plus either or both DNA methyltransferase inhibitor (RG108) and G9a inhibitor (UNC0638). Flow cytometry plots of Fgd5+Lineage– cells from the indicated culture conditions are shown. The histogram shows the proportions of the indicated subpopulations.
Figure 35A:
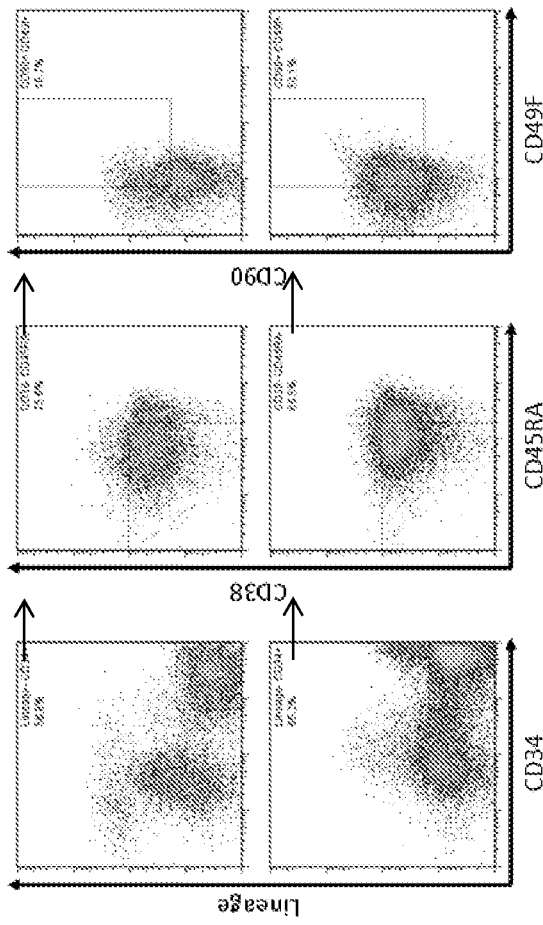
FIGS. 35A-35B show that supplementation of minimal chemical combination with p38 inhibitor improves the yield of human cord blood HSCs. 200 cord blood HSCs (FACS purified as Lineage-CD34+CD45RA-CD90+CD38-) were cultured for 12 days in serum free media supplemented with cytokines (SCF, TPO, FLT3L, IL3) in the presence of the indicated chemical combinations (Tgfbeta inhibitor (A, A83-01), HDAC inhibitor (TSA, Trichostatin A), and LSD1 inhibitor (TC, Tranylcypromine)) or additionally supplemented with p38 inhibitor (p38i, SB203580) and analyzed by flow cytometry.
Figure 35B:
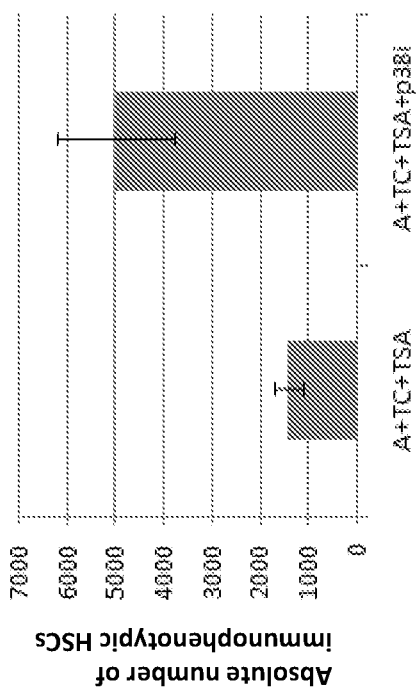

Example 6. Relative Contributions of Compounds to HSC Expansion, Maintenance and Enrichment A series of experiments was conducted in order to determine the relative contribution of compounds that modulate particular pathways to the expansion of hematopoietic stem cells. FIGS. 21A-21B show the contribution of each compound/pathway in ability to maintain and expand phenotypic HSCs during ex vivo culture. 50 murine HSCs (lineage-, ckit+, Sca1+, CD150+, CD48-, Fgd5ZsGr+) were cultured in the presence of cytokines only (SCF, TPO, and IL12) in the absence of compounds (standard), or with all 7 compounds (W7), or with subtraction of each individual compound (A83-01 (A), Tranylcypromine (TC), Trichostatin A (TSA), SB203580 (p38i), CHIR99021 (Chir), DMH1 (DMH), Sodium acetate (OAC)). Flow cytometry analysis was performed on Day 14 showing FIG. 21A: differentiation to lineage+ cells (stained by antibody cocktail against antigens for: B-cells, T-cells, myeloid cells, erythrocyte, granulocyte), where lineage positive is to the right of the dashed line. FIG. 21B: Absolute HSC numbers after 14 days culture in the indicated conditions from 50 starting HSCs. FIG. 23 shows that the supplementation with additional compounds reduces heterogeneity of Fgd5+ cells with respect to CD48 and Sca1 expression. 40 murine HSCs were cultured for 12 days in the presence of cytokines (SCF, TPO, and IL12)) and a cocktail of compounds (Lithium chloride, nicotinamide, N-acetylcysteine, ascorbic acid, A83-01, and SB203580, trichostatin A) plus either or both DNA methyltransferase inhibitor (RG108) and G9a inhibitor (UNC0638). Flow cytometry plots of Fgd5+Lineage– cells from the indicated culture conditions are shown. The histogram shows the proportions of the indicated subpopulations. FIGS. 35A-35B show that supplementation of minimal chemical combination with p38 inhibitor improves the yield of human cord blood HSCs. 200 cord blood HSCs were cultured for 12 days in serum free media supplemented with cytokines (SCF, TPO, FLT3L, IL3) in the presence of the indicated chemical combinations (Tgfbeta inhibitor (A, A83-01), HDAC inhibitor (TSA, Trichostatin A), and LSD1 inhibitor (TC, Tranylcypromine)) or additionally supplemented with p38 inhibitor (p38i, SB203580) and analyzed by flow cytometry. FIG. 35A: Immunophenotype of the cells post-culturing, and FIG. 35B: quantification of immunophenotypic HSCs (Lineage–CD34+CD45RA-CD38-CD90+CD49F+) cultured in the indicated conditions.

Figure 26:
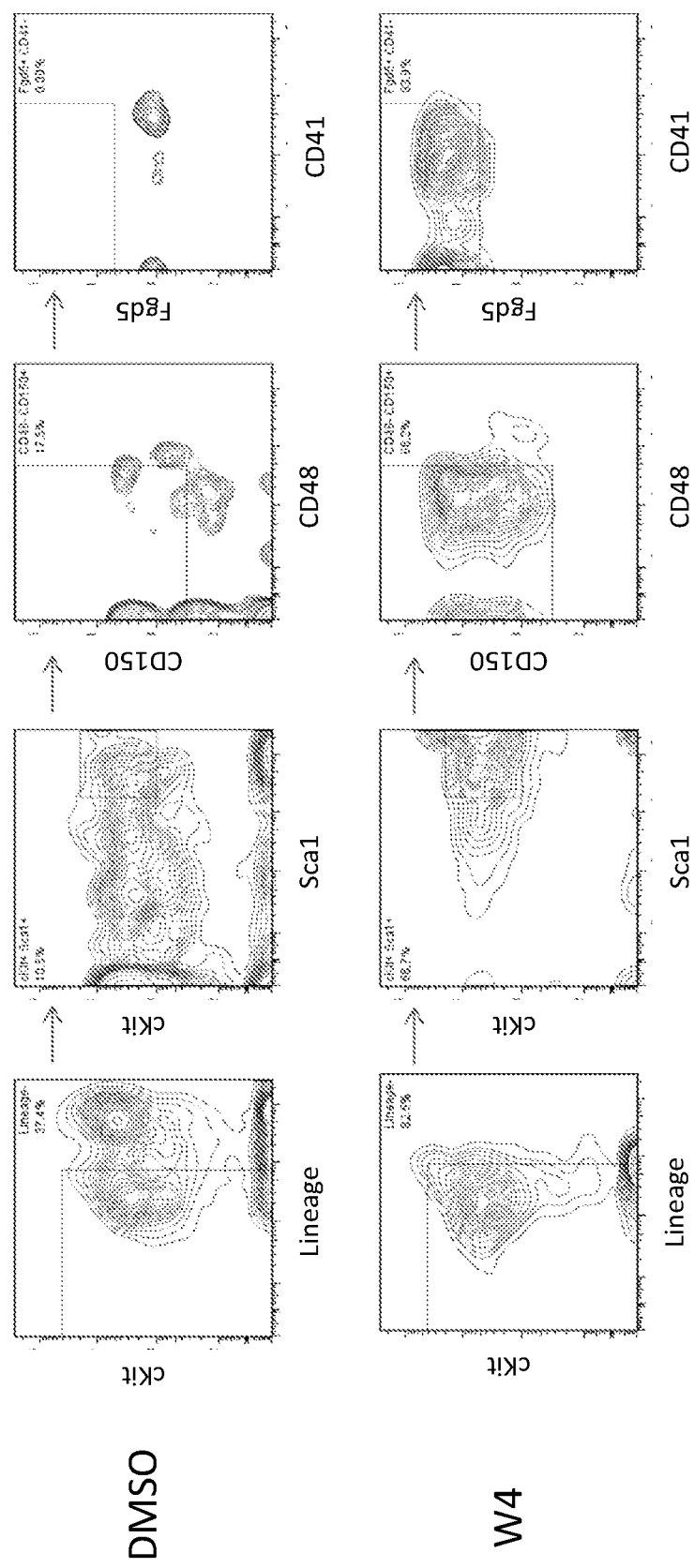
FIG. 26 shows that the modulation of four pathways is sufficient to maintain/expand immunophenotypic murine HSCs. 50 HSCs (lineage-, ckit+, Sca1+, CD150+, CD48-, Fgd5ZsGr+) were cultured for 14 days in serum free media supplemented with cytokines in the presence of DMSO, or compounds targeting 4 pathways (W4: Tgfbeta inhibitor A83-01, Lsd1 inhibitor Tranylcypromine, HDAC inhibitor Trichostatin A, and the p38 kinase inhibitor SB203580) identified from the initial set of 7 compounds (Tgfbeta inhibitor A83-01, Lsd1 inhibitor Tranylcypromine, HDAC inhibitor Trichostatin A, the p38 kinase inhibitor SB203580, BMP inhibitor DMH1, Gsk3beta inhibitor Chir99021, and sodium acetate) Immunophenotypic HSCs (Lineage–cKit+ Sca1+CD48–CD150+Fgd5ZsGreen+CD41-) were analyzed by flow cytometry.
Figures 33A, 33B:
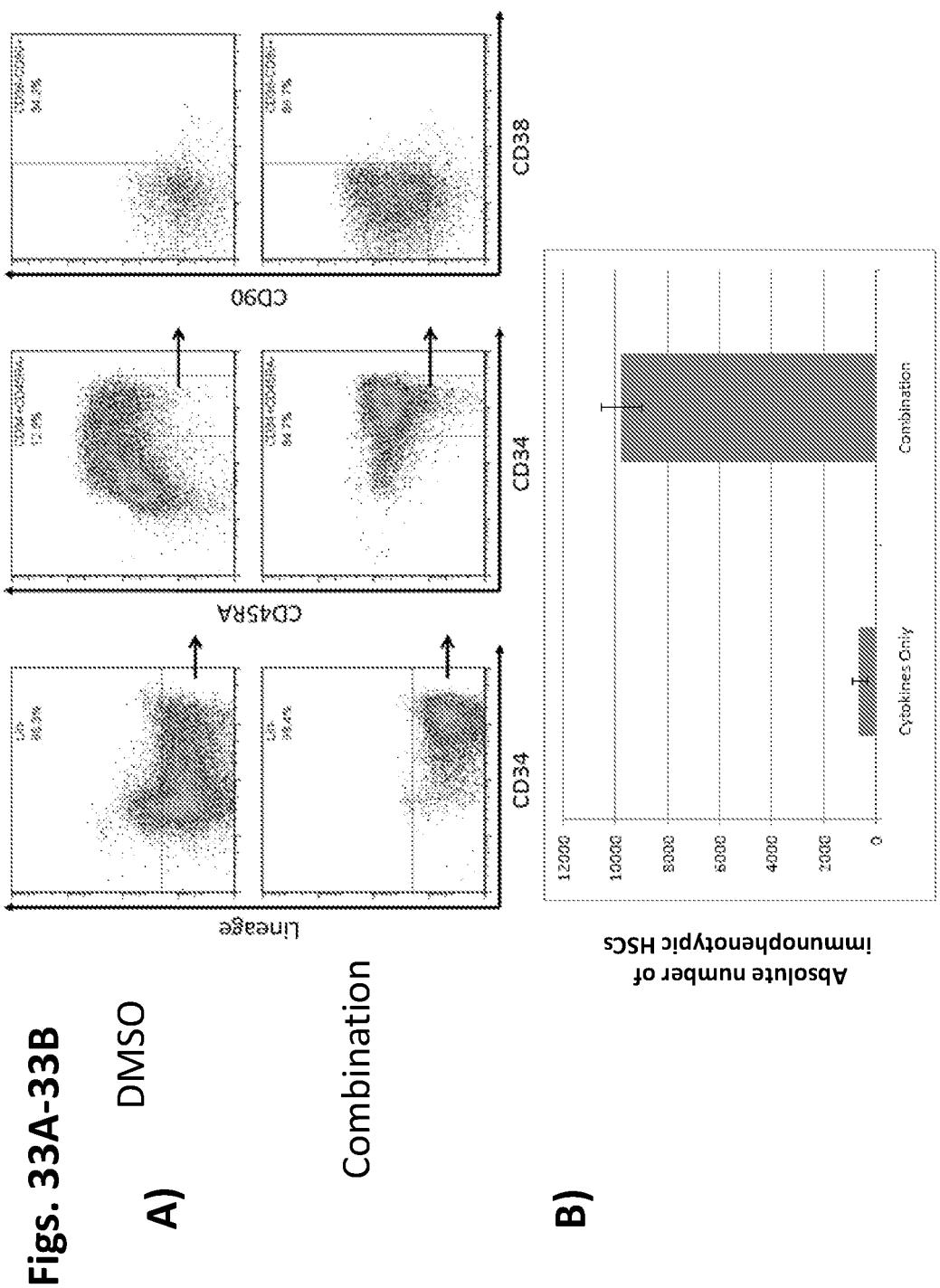
FIGS. 33A-33B show that compounds targeting 7 pathways identified in murine system enable maintenance and expansion of immunophenotypic cord blood HSCs. 200 cord blood HSCs (FACS purified as Lineage-CD34+CD45RA-CD90+CD38-) were cultured for 12 days in serum free media supplemented with cytokines (SCF, TPO, FLT3L, IL3) in the presence of DMSO, or compounds targeting 7 pathways (Combination: Tgfbeta inhibitor A83-01, Lsd1 inhibitor Tranylcypromine, HDAC inhibitor Trichostatin A, the p38 kinase inhibitor SB203580, BMP inhibitor DMH1, Gsk3beta inhibitor Chir99021, and sodium acetate) showing (FIG. 33A) Immunophenotype of the cells post-culturing analyzed by flow cytometry and (FIG. 33B) quantification of immunophenotypic HSCs (Lineage−CD34+CD45RA-CD38−CD90+).
Figures 34A, 34B:
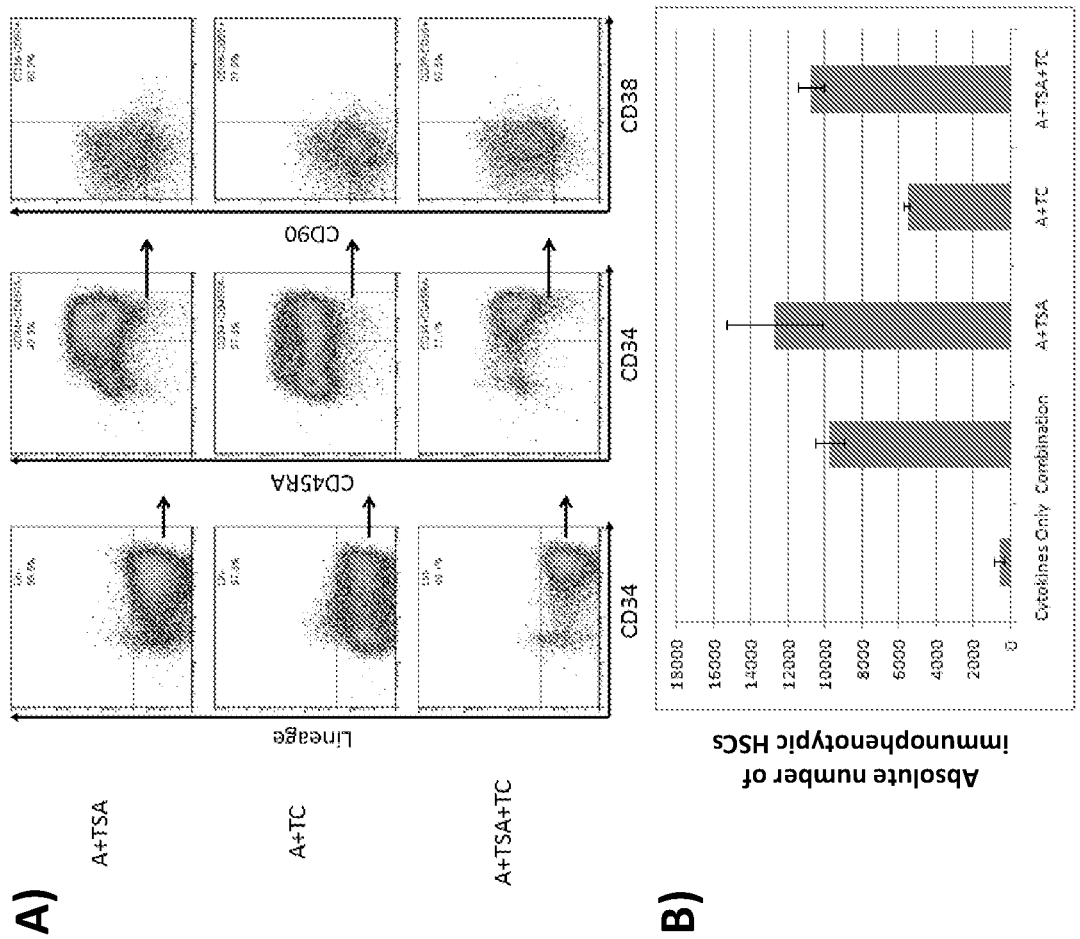
FIGS. 34A-34B show that targeting 3 pathways is sufficient for maintenance and expansion of immunophenotypic human cord blood HSCs. 200 cord blood HSCs (FACS purified as Lineage-CD34+CD45RA-CD90+CD38-) were cultured for 12 days in serum free media supplemented with cytokines (SCF, TPO, FLT3L, IL3) in the presence of the indicated chemical combinations (Tgfbeta inhibitor (A, A83-01), HDAC inhibitor (TSA, Trichostatin A), and LSD1 inhibitor (TC, Tranylcypromine)) and analyzed by flow cytometry.

Example 7. Modulation of Multiple Pathways During Ex Vivo Culturing Promotes HSC Expansion, Enrichment, and Maintenance of Cells with Hematopoietic Stem Cell Properties In addition to histone demethylation, TGFβ signaling, and histone deacetylation, modulation of other pathways additionally promotes HSC expansion, enrichment, and maintenance of hematopoietic stem cell functional potential. FIG. 26 shows that the modulation of four pathways is sufficient to maintain/expand immunophenotypic murine HSCs. 50 HSCs were cultured for 14 days in serum free media supplemented with cytokines in the presence of DMSO, or compounds targeting 4 pathways (W4) (Tgfbeta inhibitor A83-01, Lsd1 inhibitor Tranylcypromine, HDAC inhibitor Trichostatin A, and the p38 kinase inhibitor SB203580) identified from the initial set of 7 compounds (Tgfbeta inhibitor A83-01, Lsd1 inhibitor Tranylcypromine, HDAC inhibitor Trichostatin A, the p38 kinase inhibitor SB203580, BMP inhibitor DMH1, Gsk3beta inhibitor Chir99021, and sodium acetate). Immunophenotypic HSCs (Lineage–cKit+Sca1+CD48-CD150+Fgd5ZsGreen+CD41-) were analyzed by flow cytometry. FIGS. 33A-33B show that compounds targeting 7 pathways identified in murine system enable maintenance/expansion of immunophenotypic cord blood HSCs. 200 cord blood HSCs were cultured for 12 days in serum free media supplemented with cytokines (SCF, TPO, FLT3L, IL3) in the presence of DMSO, or compounds targeting 7 pathways (Combination: Tgfbeta inhibitor A83-01, Lsd1 inhibitor Tranylcypromine, HDAC inhibitor Trichostatin A, the p38 kinase inhibitor SB203580, BMP inhibitor DMH1, Gsk3beta inhibitor Chir99021, and sodium acetate) showing FIG. 33A: Immunophenotype of the cells post-culturing analyzed by flow cytometry, and FIG. 33B: quantification of immunophenotypic HSCs (Lineage–CD34+CD45RA-CD38-CD90+). See also FIGS. 34A-34B, 37A-37C, and 40A-40C.

Figure 38A:
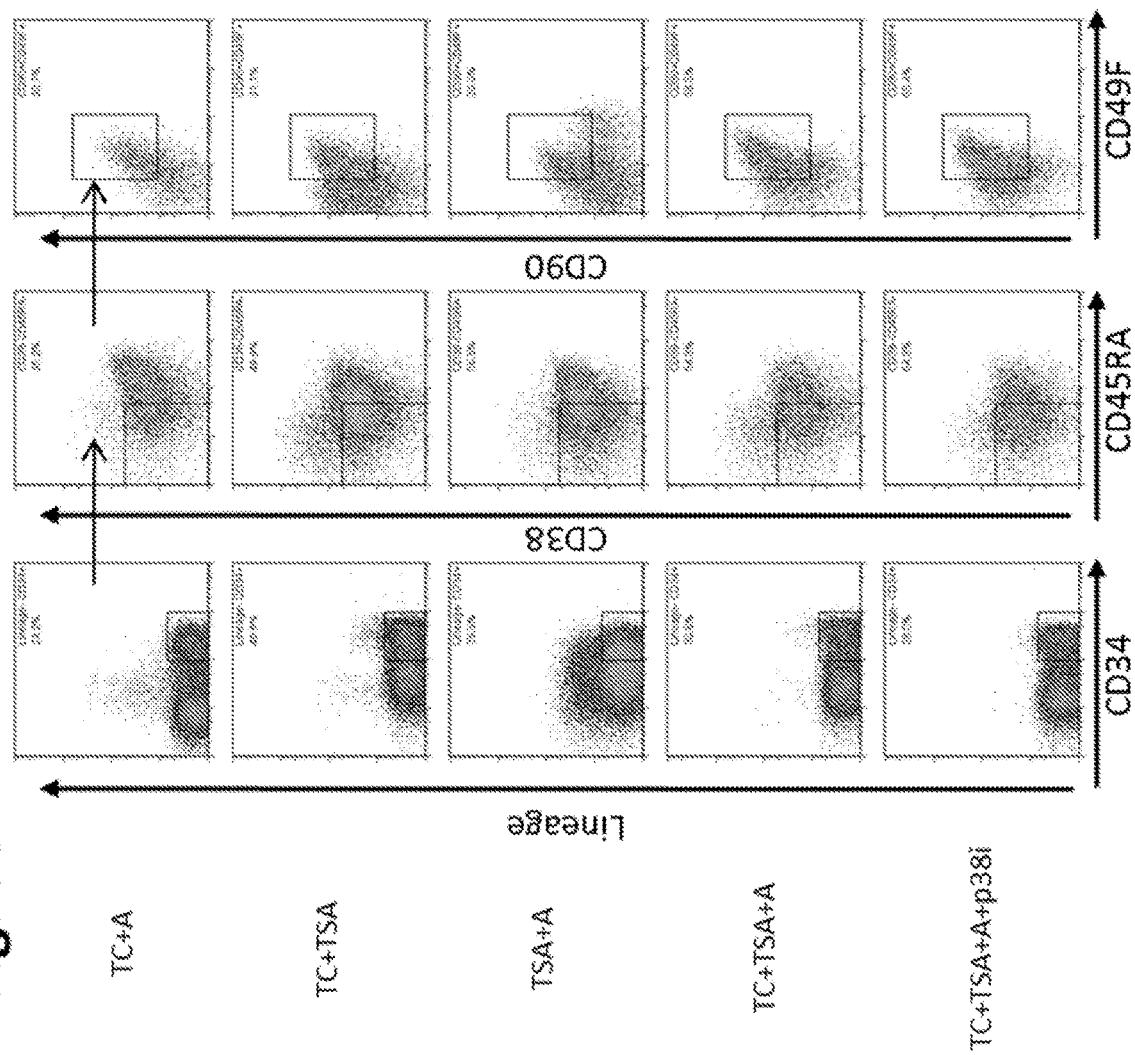
Figure 39:
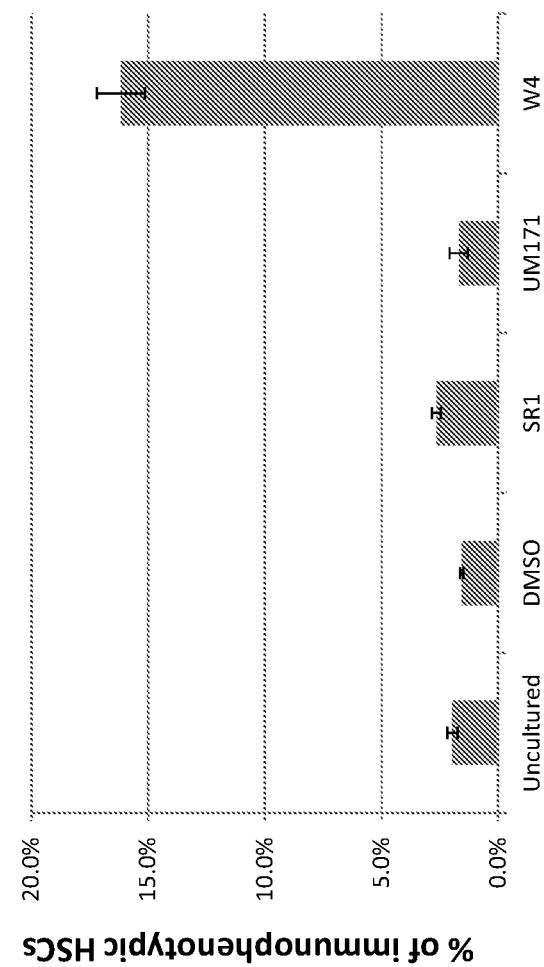
FIG. 39 shows that the ex vivo culture of human mobilized peripheral blood CD34+ cells using chemical combination enriches immunophenotypic HSCs. 3000 CD34+ enriched mobilized peripheral blood cells were cultured for 7 days in serum free media supplemented with cytokines (SCF, TPO, FLT3L, IL3) in the presence of DMSO, the indicated individual chemicals (StemRegenin (SR1), UM171) or combination of four compounds (W4: Tgfbeta inhibitor (A83-01), HDAC inhibitor (Trichostatin A), LSD1 inhibitor (Tranylcypromine), and p38 inhibitor (SB203580)) and analyzed by flow cytometry. Quantification of the fraction of immunophenotypic HSCs (Lineage−CD34+ CD45RA-CD38−CD90+) in CD34+ enriched mobilized peripheral blood prior to ex vivo culture (Uncultured) and post-culturing in the indicated conditions for 7 days showing a 8-fold enrichment of HSCs post-culturing.

FIGS. 38A-38C show the ex vivo maintenance/proliferation of human mobilized peripheral blood CD34+ cells using compounds identified using murine cells. 3000 CD34+ enriched mobilized peripheral blood cells were cultured for 7 days in serum free media supplemented with cytokines (SCF, TPO, FLT3L, IL3) in the presence of the indicated individual chemicals or chemical combinations (Tgfbeta inhibitor (A, A83-01), HDAC inhibitor (TSA, Trichostatin A), LSD1 inhibitor (TC, Tranylcypromine), and p38 inhibitor (p38i, SB203580)) and analyzed by flow cytometry. FIG. 38A: Immunophenotype of the cells post-culturing, FIG. 38B: percentage of indicated populations, and FIG. 38C: quantification of immunophenotypic HSCs (Lineage–CD34+CD45RA-CD38-CD90+CD49F+) post-culturing in the indicated conditions for 7 days. (W7: A83-01 (A), Tranylcypromine, (TC) Trichostatin A (TSA), SB203580 (p38i), CHIR99021 (Chir), DMH1 (DMH), Sodium acetate (OAC), and W3: A83-01 (A), Tranylcypromine, (TC) Trichostatin A (TSA)) FIG. 39 shows that the ex vivo culture of human mobilized peripheral blood CD34+ cells using chemical combination enriches immunophenotypic HSCs. 3000 CD34+ enriched mobilized peripheral blood cells were cultured for 7 days in serum free media supplemented with cytokines (SCF, TPO, FLT3L, IL3) in the presence of the indicated individual chemicals (StemRegenin (SR1), UM171) or combination of four compounds (W4: Tgfbeta inhibitor (A83-01), HDAC inhibitor (Trichostatin A), LSD1 inhibitor (Tranylcypromine), and p38 inhibitor (SB203580)) and analyzed by flow cytometry. Quantification of the fraction of immunophenotypic HSCs (Lineage–CD34+CD45RA-CD38-CD90+) in CD34+ enriched mobilized peripheral blood prior to ex vivo culture (Uncultured) and post-culturing in the indicated conditions for 7 days.

Example 8. Culturing HSCs Under Low Ambient Oxygen

Figure 36:
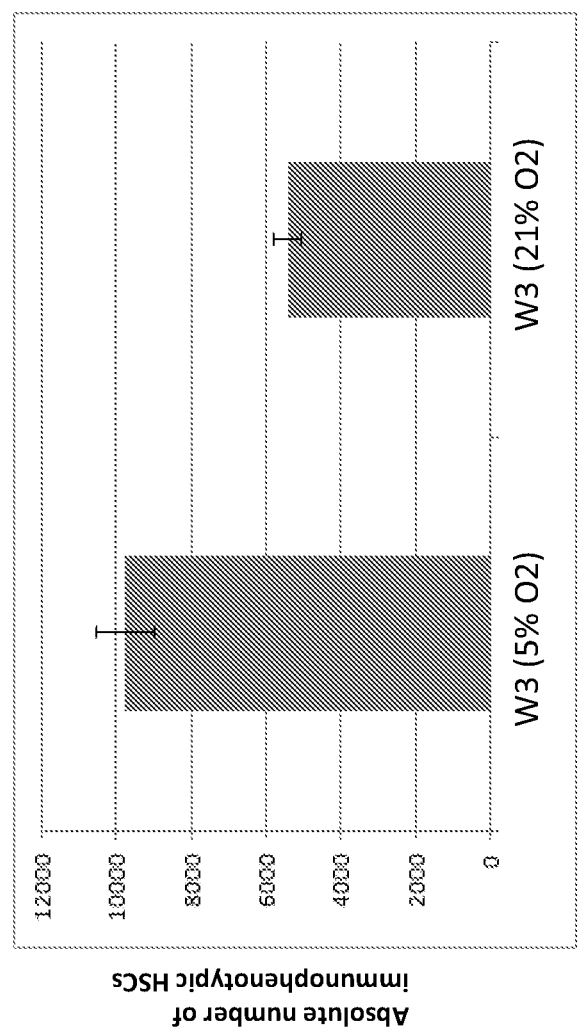
FIG. 36 shows the cultivation under low oxygen tension improves the yield of human cord blood HSCs. 200 cord blood HSCs (FACS purified as Lineage-CD34+CD45RA-CD90+CD38-) were cultured in serum free media supplemented with cytokines (SCF, TPO, FLT3L, IL3) and compounds targeting 3 pathways (W3: Tgfbeta inhibitor (A83-01), HDAC inhibitor (Trichostatin A), and LSD1 inhibitor (Tranylcypromine)) for 12 days in either standard tissue culture incubator (atmospheric oxygen, 21% O2) or low oxygen incubator (5% O2). Immunophenotypic HSCs (Lineage−CD34+CD45RA-CD38−CD90+) cultured in the indicated conditions were quantified post-culturing.

Culturing hematopoietic stem cells under conditions of reduced oxygen relative to physiologic levels can be advantageous for hematopoietic stem cell expansion. FIG. 36 shows the cultivation under low oxygen tension improves the yield of human cord blood HSCs. 200 cord blood HSCs were cultured in serum free media supplemented with cytokines (SCF, TPO, FLT3L, IL3) and compounds targeting 3 pathways (W3: Tgfbeta inhibitor (A83-01), HDAC inhibitor (Trichostatin A), and LSD1 inhibitor (Tranylcypromine)) for 12 days in either standard tissue culture incubator (atmospheric oxygen, 21% O2) or low oxygen incubator (5% O2) Immunophenotypic HSCs (Lineage–CD34+CD45RA-CD38-CD90+) cultured in the indicated conditions were quantified post-culturing.

Example 9. Transplanted HSCs

Figure 42A:
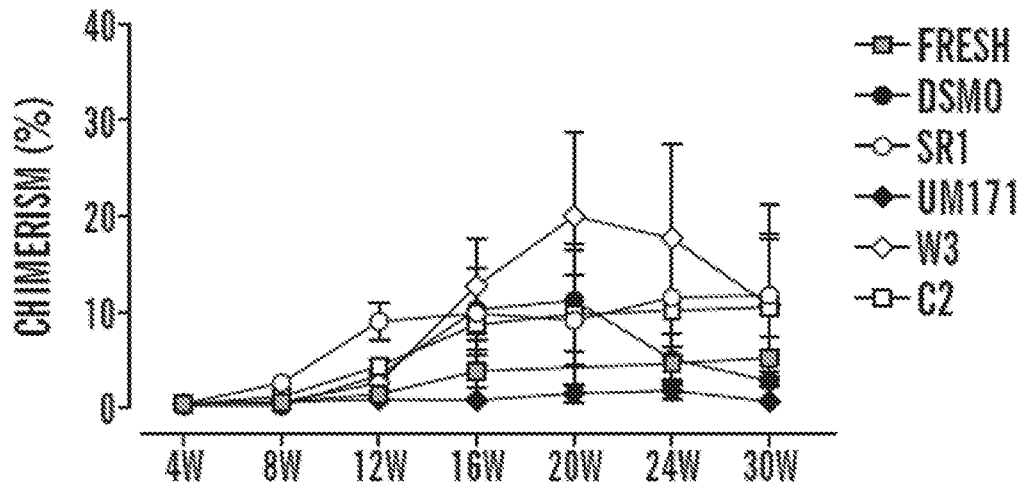
FIGS. 42A-42C show transplantation results of human CD34+ cord blood cells cultured for 14 days ex vivo. The cultures of 10,000 starting CD34+ cord blood cells were transplanted into sublethally irradiated immunocompromised NSG (Nod-Scid-gamma) mice following 14 days of ex vivo culture in the presence of DMSO, W3 (Tgfbeta inhibitor A83-01, LSD1 inhibitor tranylcypromine, HDAC inhibitor trichostatin A), the combination of LSD1 inhibitor IV and the Tgfbeta inhibitor RepSox (C2), Stem Regenin 1 (SR1) and UM171; or 10,000 uncultured CD34+ cord blood cells (fresh) showing (FIG. 42A) peripheral blood donor chimerism.
Figure 42B:
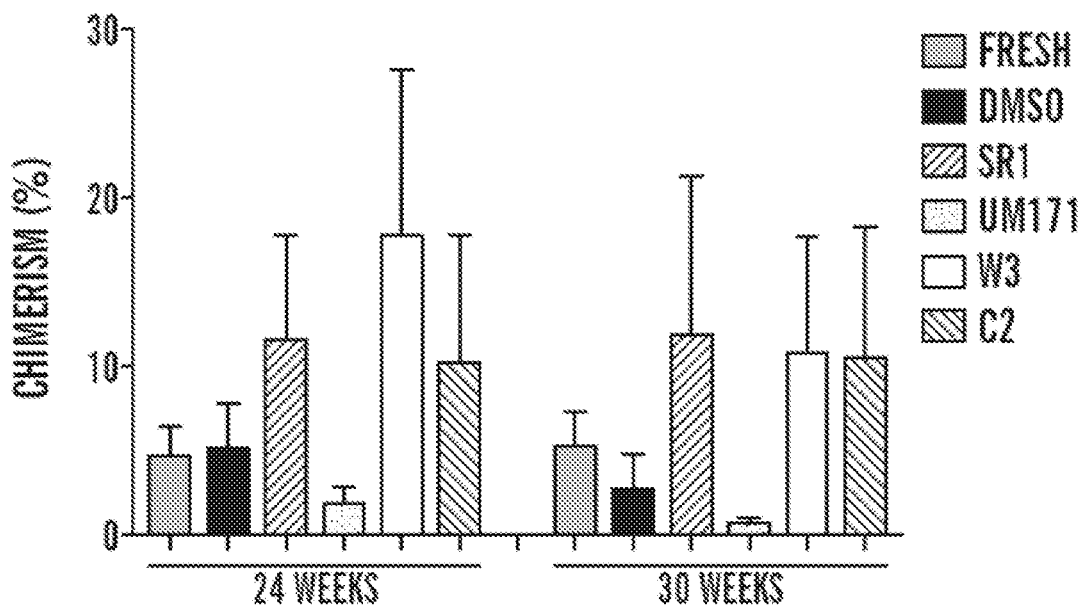
Figure 42C:
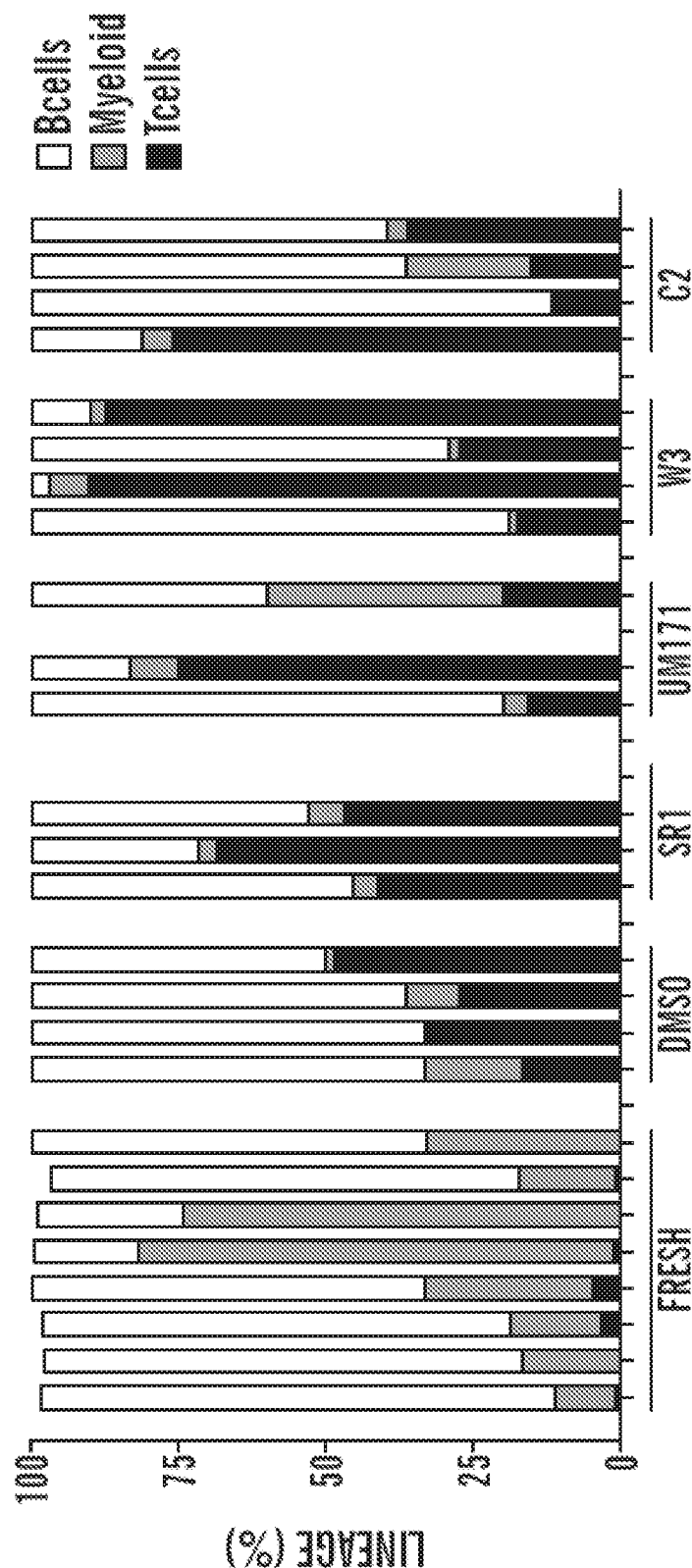

A series of experiments was conducted in order to probe the functionality of ex vivo cultured hematopoietic stem cells post-transplantation. FIGS. 42A-42C show the results of experiments in which transplanted human CD34+ cord blood cultured for 14 days ex vivo: The cultures of 10,000 starting CD34+ cord blood cells were transplanted into sublethally irradiated immunocompromised NSG (Nod-Scid-gamma) mice following 14 days of ex vivo culture in the presence of DMSO, W3 (Tgfbeta inhibitor A83-01, LSD1 inhibitor tranylcypromine, HDAC inhibitor trichostatin A), the combination of LSD1 inhibitor IV and the Tgfbeta inhibitor RepSox (C2), Stem Regenin 1 (SR1) and UM171; or 10,000 uncultured CD34+ cord blood cells (Fresh) showing FIG. 42A: Peripheral blood donor chimerism. FIG. 42B: Quantification of peripheral blood donor chimerism at weeks 24 and 30 post transplant, and FIG. 42C: Lineage contribution of transplanted cells at week 30 post-transplant.

Example 10. Transplanted HSCs

Figure 43:
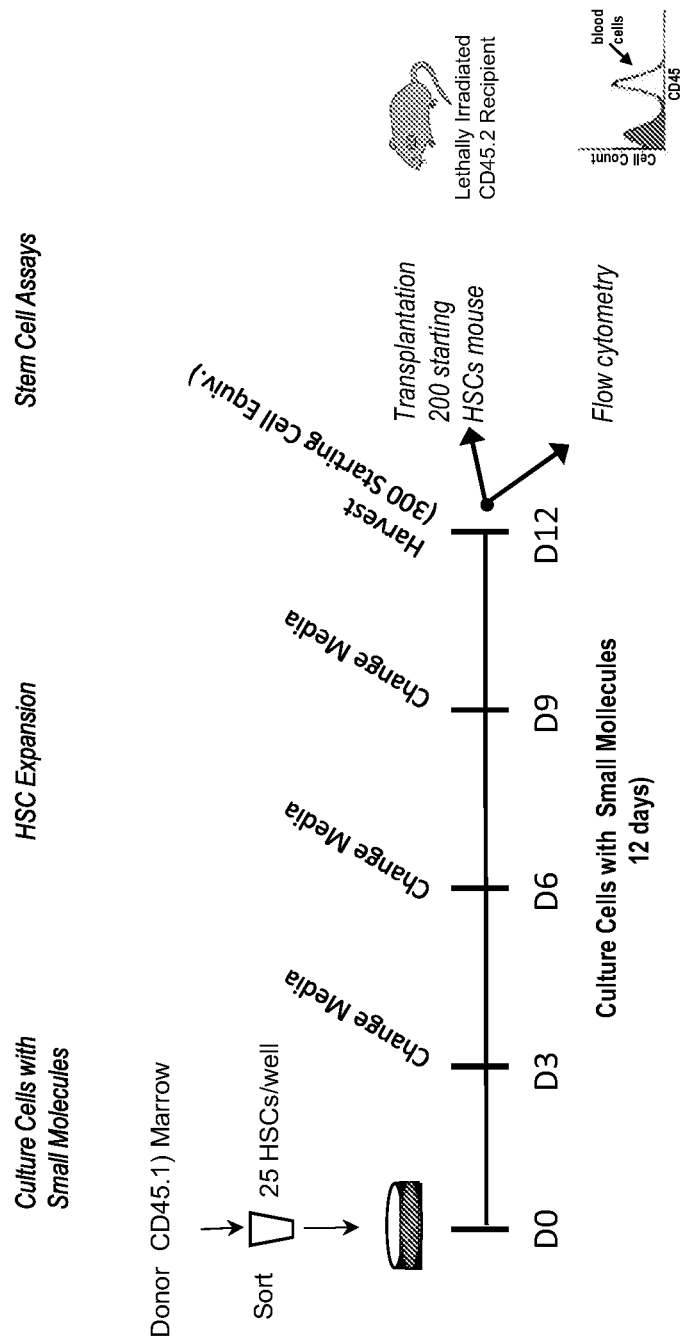
FIG. 43 depicts a schematic of the experimental procedure for the results depicted in FIGS. 44-48C.
Figure 44:
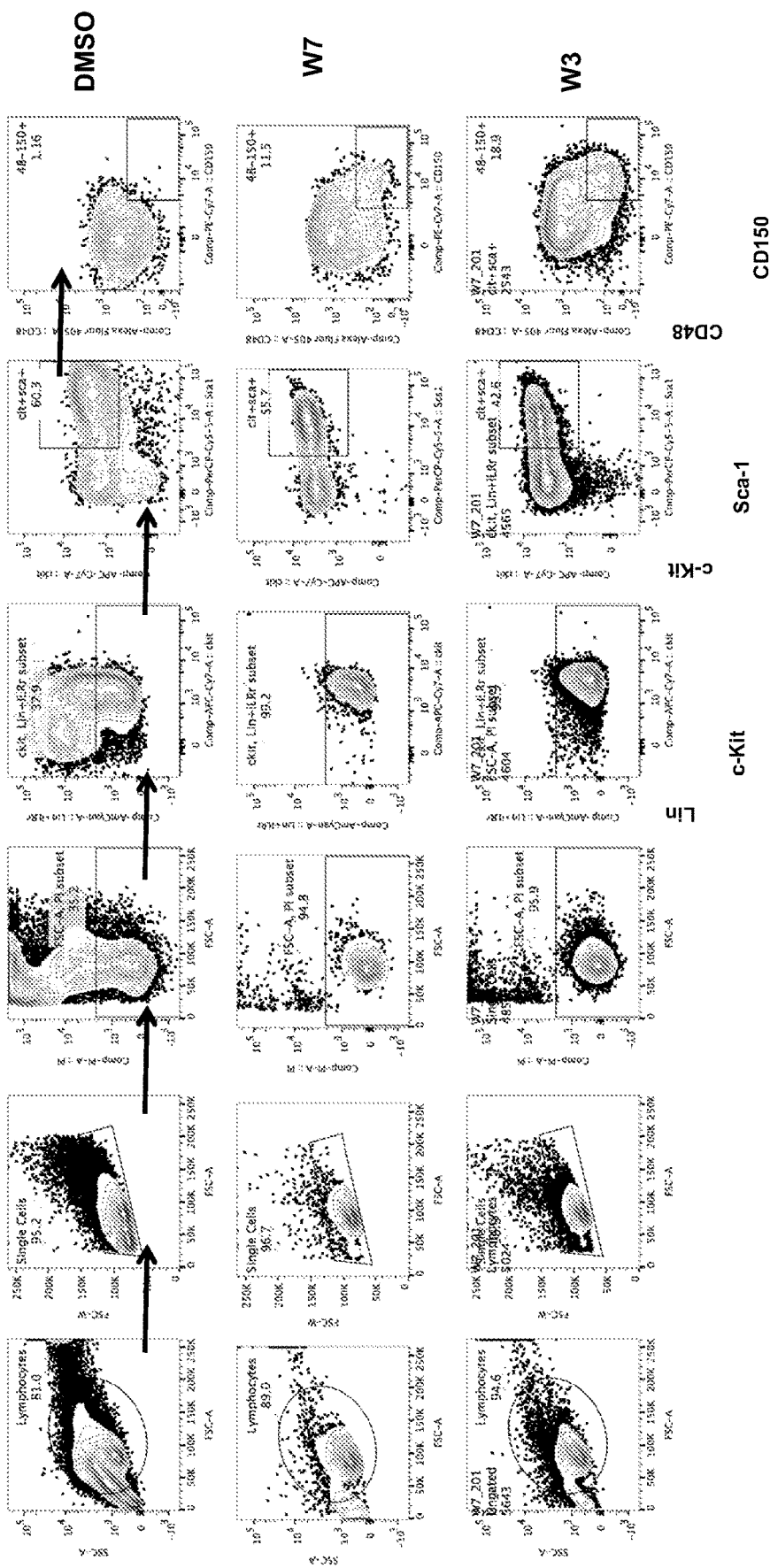
FIG. 44 depicts the results of FACS analysis 12 days post culturing.
Figure 45:
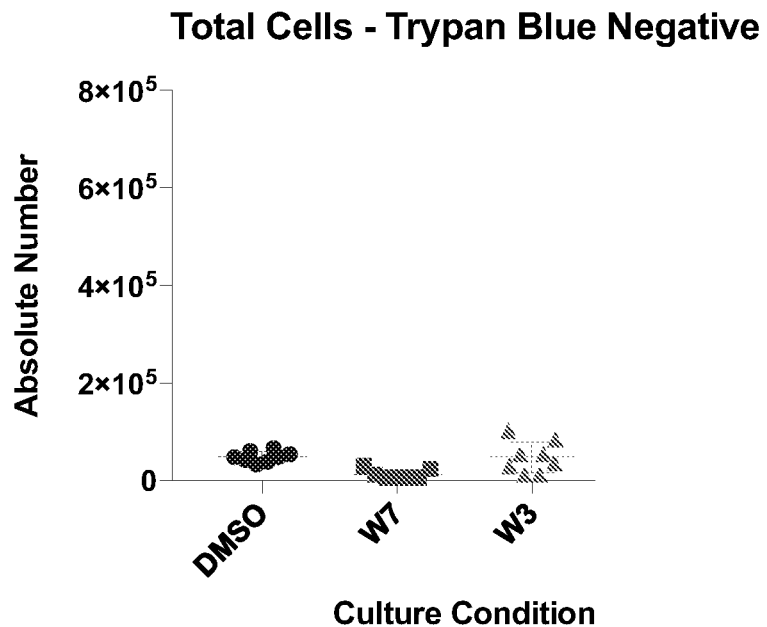
FIG. 45 depicts a graph of total live cell output 12 days post-culturing from 300 starting cell HSC equivalents in the presence of DMSO, W7, or W3.
Figure 46A:
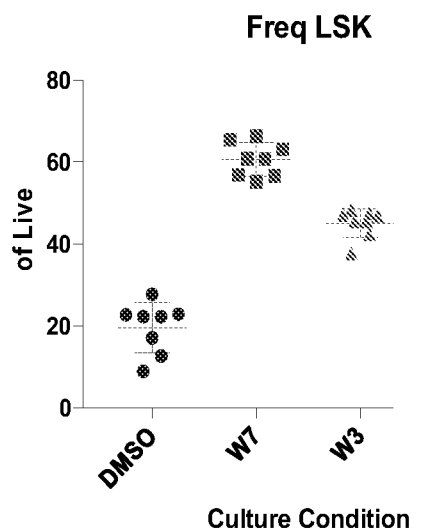
FIGS. 46A-46B depict graphs of the frequency (FIG. 46A) and absolute number (FIG. 46B) of lineage-IL7R-ckit+Sca1+(LSK) cells 12 days post-culturing in the presence of DMSO, W7, or W3.
Figure 46B:
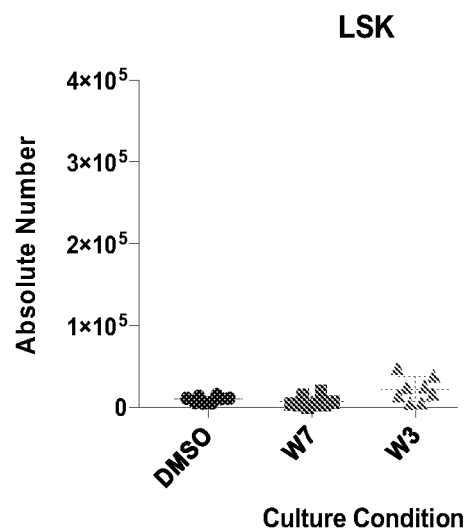
Figure 47B:
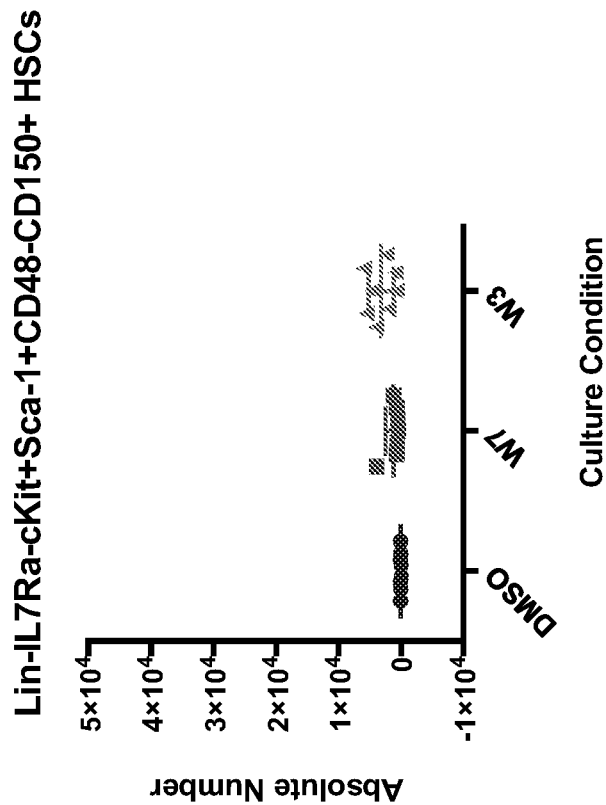
FIGS. 47A-47B depicts graphs of the frequency (FIG. 47A) and absolute number (FIG. 47B) of lineage-IL7R-ckit+Sca1+CD48-CD150+ HSCs 12 days post-culturing in the presence of DMSO, W7, or W3.
Figure 47A:
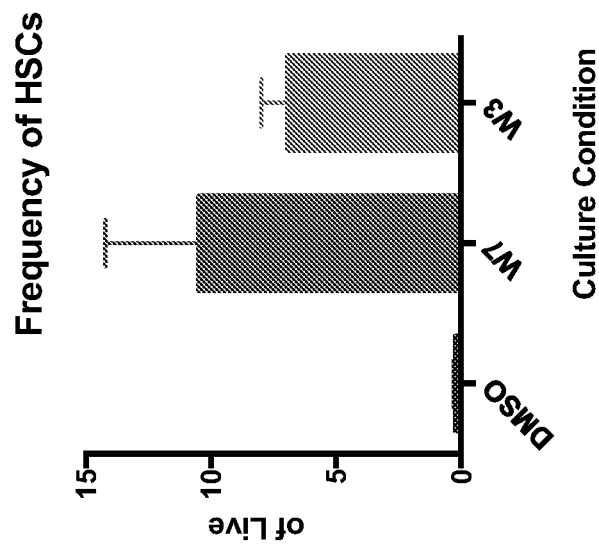

A series of experiments was conducted to assess the functionality of ex vivo cultured hematopoietic stem cells post-transplantation. FIG. 43 depicts the experimental procedure. FIGS. 44-47B depict the characterization of the cells after 12 days of culturing in the presence of either DMSO, W7, or W3. Lineage analysis was conducted for both lineage-IL7R-ckit+Sca1+(LSK) (FIGS. 46A-46B) and lineage-IL7R-ckit+Sca1+CD48-CD150+ HSCs (FIGS. 47A-47B). 12 days post-culturing in the presence of DMSO, W7, or W3. Donor cells obtained by this ex vivo culturing protocol were transplanted into irradiated recipients (FIG. 48A) and donor cell engraftment (FIG. 48B) and lineage contribution (FIG. 48C) were analyzed 4 weeks post-transplantation of 200 starting cell (HSC) equivalents.

What is claimed herein is:

1. A method of producing an expanded population of hematopoietic stem cells ex vivo, said method comprising contacting a population of hematopoietic stem cells with one or more agents that together exhibit the activities of:
   a. modulation of histone methylation;
   b. inhibition of TGFβ signaling; and
   c. modulation of histone acetylation,
wherein the one or more agents are present in amounts that are sufficient to produce an expanded population of hematopoietic stem cells.

2. The method of claim 1 wherein the population of hematopoietic stem cells exhibits a hematopoietic stem cell functional potential after two or more days that is greater than that of a control population of hematopoietic stem cells cultured under the same conditions and for the same time as said population of hematopoietic stem cells but not contacted with said one or more agents.

3. The method of claim 1, wherein said agent that modulates histone methylation is a histone demethylase inhibitor and said agent that inhibits TGFβ signaling is a TGFβ receptor inhibitor.

4. The method of claim 3, wherein said histone demethylase inhibitor is a LSD1 inhibitor.

5. The method of claim 4, wherein said LSD1 inhibitor is LSD1 inhibitor IV RN-1 and said TGFβ receptor inhibitor is ALK5 inhibitor II.

6. The method of claim 4, wherein said LSD1 inhibitor is tranylcypromine and said TGFβ receptor inhibitor is ALK5 inhibitor II.

7. The method of claim 1, wherein the one or more agents comprise a combination of agents selected from the combination of agents of Table 1, Table 2, Table 3, Table 4, Table 5, and Table 6.

8. The method of claim 1, wherein said histone demethylase is LSD1.

9. The method of claim 8, wherein said one or more agents comprise a histone demethylase inhibitor selected from the group consisting of LSD1 inhibitor IV RN-1, LSD1 inhibitor II S2101, LSD1 inhibitor LSD1-C76, LSD1 inhibitor III CBB1007, and LSD1 inhibitor I Tranylcypromine.

10. The method of claim 1, wherein said one or more agents comprise a compound that inhibits a histone deacetylase are selected from the group consisting of Trichostatin A, valproic acid, butyrylhydroxamic acid, and istodax.

11. The method of claim 1, wherein said one or more agents further comprise a compound that inhibits BMP signaling.

12. The method of claim 1, wherein said hematopoietic stem cells are from human cord blood, mobilized peripheral blood, or bone marrow.

13. A method of introducing a polynucleotide into a population of hematopoietic stem cells, said method comprising:
   a. inserting the polynucleotide into said population of hematopoietic stem cells; and
   b. expanding said population of hematopoietic stem cells according to the method of claim 1.

14. A method of treating a recipient with hematopoietic stem cells or progeny thereof, said method comprising:
   a. providing a population of hematopoietic stem cells;
   b. expanding said population of hematopoietic stem cells according to the method of claim 1;
   c. optionally differentiating said hematopoietic stem cells into common lymphoid progenitor cells, common myeloid progenitor cells, megakaryocyte-erythroid progenitor cells, granulocyte-megakaryocyte progenitor cells, granulocytes, promyelocytes, neutrophils, eosinophils, basophils, erythrocytes, reticulocytes, thrombocytes, megakaryoblasts, platelet-producing megakaryocytes, platelets, monocytes, macrophages, dendritic cells, microglia, osteoclasts, and lymphocytes, NK cells, B-cells and/or T-cells; and
   d. introducing the population of expanded hematopoietic stem cells or progeny thereof into said recipient.

15. The method of claim 1, wherein the hematopoietic stem cells are additionally contacted with a substance that inhibits aryl hydrocarbon receptor signaling, a prostaglandin, an agonist of Notch signaling, or an inhibitor of SIRT1.

16. The methods of claim 1, wherein the hematopoietic stem cells are additionally contacted with UM171, an analog thereof, or a UM171 analog selected from Table 11.

17. The method of claim 1, wherein the a population of hematopoietic stem cells is further contacted with one or more agents that together exhibit the activities of:
   inhibition of p38 signaling; or
   activation of canonical Wnt signaling or promotion of β-catenin degradation.

18. The method of claim 17, wherein said one or more agents comprise an agent that inhibits p38 signaling, and wherein said compound is SB203580.

19. The method of claim 17, wherein said one or more agents comprise a compound that promotes β-catenin degradation selected from the group consisting of CHIR99021, lithium chloride, BIO, and FGF2.

20. The method of claim 1, wherein the cells are contacted with the one or more agents simultaneously.

21. A composition comprising one or more agents that together exhibit the activities of:
   a. modulation of histone methylation;
   b. inhibition of TGFβ signaling; and
   c. modulation of histone acetylation.

* * * * *

UNITED STATES PATENT AND TRADEMARK OFFICE
CERTIFICATE OF CORRECTION

PATENT NO. : 10,669,528 B2  
APPLICATION NO. : 15/738638  
DATED : June 2, 2020  
INVENTOR(S) : Rossi et al.

Page 1 of 1

It is certified that error appears in the above-identified patent and that said Letters Patent is hereby corrected as shown below:

In the Claims

At Column 166, Claim 17, Line 42, "a" should be deleted.

Signed and Sealed this  
Eighteenth Day of August, 2020

Andrei Iancu  
*Director of the United States Patent and Trademark Office*